(12) United States Patent
Ando et al.

(10) Patent No.: US 6,608,095 B2
(45) Date of Patent: Aug. 19, 2003

(54) SULFONYLBENZENE COMPOUNDS AS ANTI-INFLAMMATORY/ANALGESIC AGENTS

(75) Inventors: Kazuo Ando, Chita-gun (JP); Tomoki Kato, Chita-gun (JP); Akiyoshi Kawai, Chita-gun (JP); Tomomi Nonomura, Chita-gun (JP)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/841,348

(22) Filed: Apr. 24, 2001

(65) Prior Publication Data

US 2002/0045654 A1 Apr. 18, 2002

Related U.S. Application Data

(62) Division of application No. 09/446,049, filed as application No. PCT/IB99/00970 on May 31, 1999, now Pat. No. 6,294,558.

(30) Foreign Application Priority Data

Jun. 11, 1998 (CA) .................................. PCT/IB98/00912

(51) Int. Cl.$^7$ ................ A61K 31/41; A61K 31/38; C07D 277/00; C07D 233/00; C07D 207/00
(52) U.S. Cl. ................ 514/365; 514/341; 514/374; 514/378; 514/401; 514/427; 514/429; 548/203; 548/215; 548/240; 548/205; 548/300.1; 548/356.1; 548/401; 548/373.1; 548/565; 548/577
(58) Field of Search .................. 514/374, 378, 514/365, 406, 427, 429, 341, 420; 548/203, 215, 240, 205, 300.1, 356.1, 401, 373.1, 565, 577

(56) References Cited

U.S. PATENT DOCUMENTS

| | | | |
|---|---|---|---|
| 3,839,325 A | 10/1974 | Hoffstadt | 260/239 |
| 3,896,145 A | 7/1975 | Berger, et al. | 260/315 |
| 4,071,466 A | 1/1978 | Schroeder et al. | 252/301.22 |
| 4,259,504 A | 3/1981 | Lang, Jr. et al. | 548/262 |
| 4,329,463 A | 5/1982 | Lang, Jr. et al. | 544/405 |
| 5,134,142 A | 7/1992 | Matsuo et al. | 514/255 |
| 5,466,823 A * | 11/1995 | Talley et al. | 548/377.1 |
| 5,474,995 A | 12/1995 | Ducharme et al. | 514/241 |
| 5,504,215 A | 4/1996 | Talley et al. | 548/377.1 |
| 5,508,426 A | 4/1996 | Talley et al. | 548/359.1 |
| 5,516,907 A | 5/1996 | Talley et al. | 548/365.7 |
| 5,521,207 A * | 5/1996 | Graneto | 514/406 |
| 5,550,142 A * | 8/1996 | Ducharme et al. | 514/365 |
| 5,585,504 A * | 12/1996 | Desmond et al. | 549/323 |
| 5,668,161 A * | 9/1997 | Talley et al. | 514/365 |
| 5,710,140 A * | 1/1998 | Ducharme et al. | 514/91 |
| 5,756,350 A | 5/1998 | Lee et al. | 514/406 |
| 5,756,529 A | 5/1998 | Isakson et al. | 514/406 |
| 5,756,530 A | 5/1998 | Lee et al. | 514/406 |
| 5,760,068 A | 6/1998 | Talley et al. | 514/403 |
| 5,792,778 A | 8/1998 | de Laszlo et al. | 514/318 |
| 5,840,746 A | 11/1998 | Ducharme et al. | 514/438 |
| 5,866,596 A | 2/1999 | Sartori et al. | 514/376 |
| 5,869,516 A | 2/1999 | Arlt et al. | 514/404 |
| 5,892,053 A | 4/1999 | Zhi et al. | 548/377.1 |
| 5,994,381 A | 11/1999 | Haruta et al. | 514/374 |

FOREIGN PATENT DOCUMENTS

| | | |
|---|---|---|
| EP | 0418845 | 9/1990 |
| EP | 0554829 | 8/1993 |
| GB | 1377247 | 12/1974 |
| WO | 9500501 | 1/1995 |
| WO | 9515315 | 6/1995 |
| WO | 9515316 | 6/1995 |
| WO | 9515317 | 6/1995 |

(List continued on next page.)

OTHER PUBLICATIONS

PubMed Abstr. 12195419, Galli G. et al;G Ital Nefrol 19/2, 199–203(2002).*
PubMed Abstr. 12110513,Hocherl et al;Am. J. Physiol. Renal Physiol, 283/2,F294–301(2002).*
PubMed Abstr. 12086293,Konstam et al;Cleve Clin J Med., 69/1,147–52(2002).*

(List continued on next page.)

Primary Examiner—Richard L. Raymond
Assistant Examiner—Sudhaker B Patel
(74) Attorney, Agent, or Firm—Peter C. Richardson; Gregg C. Benson; Martha G. Munchhof

(57) ABSTRACT

This invention provides a compound of the formula:

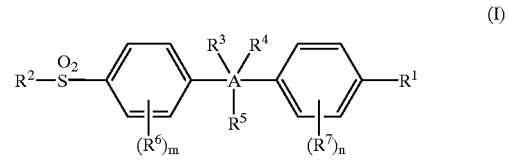

(I)

or its pharmaceutically acceptable salt thereof, wherein A is partially unsaturated or unsaturated five membered heterocyclic, or partially unsaturated or unsaturated five membered carbocyclic, wherein the 4-(sulfonyl)phenyl and the 4-substituted phenyl in the formula (I) are attached to ring atoms of Ring A, which are adjacent to each other; $R^1$ is optionally substituted aryl or heteroaryl, with the proviso that when A is pyrazole, $R^1$ is heteroaryl; $R^2$ is $C_{1-4}$ alkyl, halo-substituted $C_{1-4}$ alkyl, $C_{1-4}$ alkylamino, $C_{1-4}$ dialkylamino or amino; $R^3$, $R^4$ and $R^5$ are independently hydrogen, halo, $C_{1-4}$ alkyl, halo-substituted $C_{1-4}$ alkyl or the like; or two of $R^3$, $R^4$ and $R^5$ are taken together with atoms to which they are attached and form a 4–7 membered ring; $R^6$ and $R^7$ are independently hydrogen, halo, $C_{1-4}$ alkyl, halo-substituted $C_{1-4}$ alkyl, $C_{1-4}$ alkoxy, $C_{1-4}$ alkylthio, $C_{1-4}$ alkylamino or N,N-di $C_{1-4}$ alkylamino; and m and n are independently 1, 2, 3 or 4.

This invention also provides a pharmaceutical composition useful for the treatment of a medical condition in which prostaglandins are implicated as pathogens.

10 Claims, No Drawings

FOREIGN PATENT DOCUMENTS

| | | |
|---|---|---|
| WO | 9515318 | 6/1995 |
| WO | 9619469 | 6/1996 |
| WO | 9636617 | 11/1996 |
| WO | 9711701 | 4/1997 |
| WO | 9711704 | 4/1997 |
| WO | 9713755 | 4/1997 |
| WO | 9727181 | 7/1997 |
| WO | 9816227 | 4/1998 |
| WO | 9822442 | 5/1998 |
| WO | 9843648 | 10/1998 |
| WO | 9850075 | 11/1998 |

OTHER PUBLICATIONS

PubMed.Abstr. 12075734,Davies et al;Ann Oncol, 13/5, 669–78(2002).*

PubMed.Abstr. 12055598,Sigthorsson et al;Gastroenerology, 122/7, 1913–23(2002).*

PubMed Abstr. 12032335,Rocca et al;Proc Natl Acad Sci USA, 99/11,7634–9(2002).*

Prasti, et al., Selective Cyclooxygenase–2–Inhibitors, Ann. Reports Med. Chem. 32, pp. 211–220 (1997).

Cecil Textbook of Medicine, 19$^{th}$ Edition, vol. 2, p. 2075 (1996).

Callaghan, Patrick D., et al.; Synthesis of 1H–4, 1,2–benzothiadiazines from substituted N–acetyl–N–aryl–N'thioaroylhydrazines; J. Chem. Soc., Perkin Trans. 1 (14), pp. 1286–90 (1975).

Bulletin De La Societe Chimique De France; Societe Francaise De Chimie, Paris, Fr. pp. 490–494 (1960).

* cited by examiner

SULFONYLBENZENE COMPOUNDS AS ANTI-INFLAMMATORY/ANALGESIC AGENTS

This application is a divisional application of U.S. patent application Ser. No. 09/446,049, filed Dec. 15, 1999, which has issued as U.S. Pat. No. 6,294,558, on Sep. 25, 2001, which is a 35 U.S.C. §371 application of PCT/IB99/00970, filed May 31, 1999, which claims priority to PCT/IB98/00912, filed Jun. 11, 1998.

TECHNICAL FIELD

This invention relates to compound and pharmaceutical compositions for the treatment of cyclooxygenase mediated diseases. The compounds of this invention inhibit the biosynthesis of prostaglandins by intervention of the action of the enzyme cyclooxygenase on arachidonic acid, and are therefore useful in the treatment or alleviation of inflammation and other inflammation associated disorders, such as arthritis, in mammals. This invention also relates to pharmaceutical compositions comprising such compounds.

BACKGROUND ART

Nonsteroidal anti-inflammatory drugs (NSAIDs) are widely used in treating pain and the signs and symptoms of arthritis because of their analgesic and anti-inflammatory activity. It is accepted that common NSAIDs work by blocking the activity of cyclooxygenase (COX), also known as prostaglandin G/H synthase (PGHS), the enzyme that converts arachidonic acid into prostanoids. Prostaglandins, especially prostaglandin $E_2$ ($PGE_2$). which is the predominant eicosanoid detected in inflammation conditions, are mediators of pain. fever and other symptoms associated with inflammation. Inhibition of the biosynthesis of prostaglandins has been a therapeutic target of anti-inflammatory drug discosvery. The therapeutic use of conventional NSAIDs is, however. limited due to drug associated side effects, including life threatening ulceration and renal toxicity. An alternative to NSAIDs is the use of corticosteriods, however, long term therapy can also result in severe side effects.

Recently, two forms of COX were identified, a constitutive isoform (COX-1) and an inducible isoform (COX-2) of which expression is upregulated at sites of inflammation (Vane, J. R.; Mitchell, J. A.; Appleton, I.; Tomlinson, A.; Bishop-Bailey, D.; Croxtoll, J.; Willoughby, D. A. Proc. Natl. Acad. Sci. USA, 1994, 91, 2046). COX-1 is thought to play a physiological role and to be responsible for gastrointestinal and renal protection. On the other hand, COX-2 appears to play a pathological role and to be the predominant isoform present in inflammation conditions. A pathological role for prostaglandins has been implicated in a number of human disease states including rheumatoid and osteoarthritis, pyrexia, asthma, bone resorption, cardiovascular diseases, dysmenorrhea, premature labour. nephritis, nephrosis, atherosclerosis, hypotension, shock, pain, cancer, and Alzheimer disease. The NSAIDs currently on market inhibit both isoforms of COX with little variation for selectivity, explaining their beneficial (inhibition of COX-2) and deleterious effects (inhibition of COX-1). It is believed that compounds that would selectively inhibit the biosynthesis of prostaglandins by intervention of the induction phase of the inducible enzyme COX-2 and/or by intervention of the activity of the enzyme COX-2 on arachidonic acid would provide alternate therapy to the use of NSAIDs or corticosteriods in that such compounds would exert anti-inflammatory effects without the adverse side effects associated with COX-1 inhibition.

A variety of sulfonylbenzene compounds which inhibit COX have been disclosed in patents publications (WO 97/16435, WO 97/14691, WO 96/19469, WO 96/36623, WO 96/03392, WO 96/03387, WO 97/727181, WO 96/936617, WO 96/19469, WO 96/08482, WO 95/00501, WO 95/15315, WO 95/15316, WO 95/15317, WO 95/15318, WO 97/13755, EP 0799523, EP 418845, and EP 554829). Especially, International Publication Number WO 97/11704 discloses pyrazole compounds substituted by optionally substituted aryl.

BRIEF DISCLOSURE OF THE INVENTION

The present invention provides a compound of the following formula:

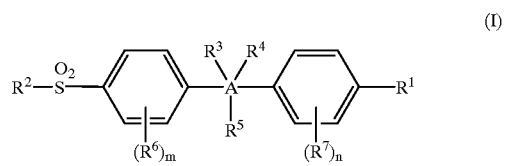

or its pharmaceutically acceptable salt thereof, wherein

A is partially unsaturated or unsaturated five membered heterocyclic, or partially unsaturated or unsaturated five membered carbocyclic, wherein the 4-(sulfonyl) phenyl and the 4-substituted phenyl in the formula (I) are attached to ring atoms of Ring A adjacent to each other;

$R^1$ is aryl or heteroaryl, and the aryl or heteroaryl being optionally substituted by one to four substituents selected from halo, $C_{1-4}$alkyl, halo-substituted $C_{1-4}$ alkyl, $C_{1-4}$ alkoxy, $C_{1-4}$ alkyl carbonyl, hydroxy, nitro, cyano and amino, with the proviso that when A is pyrazole, $R^1$ is heteroaryl;

$R^2$ is $C_{1-4}$ alkyl, halo-substituted $C_{1-4}$ alkyl, $C_{1-4}$ alkylamino. $C_{1-4}$ dialkylamino or amino;

$R^3$, $R^4$ and $R^5$ are independently hydrogen, halo, $C_{1-4}$ alkyl, halo-substituted $C_{1-4}$ alkyl, $C_{2-5}$ alkenyl, $C_{2-5}$ alkynyl, $C_{1-4}$ alkoxy, hydroxy-$C_{1-4}$ alkyl, $C_{1-4}$ alkoxy $C_{1-4}$ alkyl, $C_{1-4}$ alkanoyl, cyano, nitro, cyano $C_{1-4}$ alkyl, carboxy. $C_{1-4}$ alkoxycarbonyl, aminocarbonyl, N—$C_{1-4}$ alkylaminocarbonyl, N,N-di-$C_{1-4}$ alkylaminocarbonyl, N-arylaminocarbonyl, N,N-diarylaminocarbonyl, N—$C_{1-4}$ alkyl-N-arylaminocarbonyl, aryl, aryloxy, aryloxy-$C_{1-4}$alkyl, heteroaryl, heteroaryloxy, heteroaryloxy-$C_{1-4}$ alkyl, morpholino-carbonyl, $C_{1-4}$ alkoxyaminocarbonyl or $C_{1-4}$ alkyl-carbonylamino; or two of $R^3$, $R^4$ and $R^5$ are taken together with atoms to which they are attached and form a 4–7 membered ring;

$R^6$ and $R^7$ are independently hydrogen, halo, $C_{1-4}$ alkyl, halo-substituted $C_{1-4}$ alkyl, $C_{1-4}$ alkoxy, $C_{1-4}$ alkylthio, $C_{1-4}$ alkylamino, N,N-di $C_{1-4}$ alkylamnino, hydroxyl-$C_{1-4}$ alkyl, $C_{1-4}$ alkoxy-$C_{1-4}$ alkyl, $C_{1-4}$ alkyl-$C_{1-4}$ alkoxy, $C_{1-4}$ alkylamino-$C_{1-4}$ alkyl, hydroxy, amino-$C_{1-4}$ alkyl and N,N-di $C_{1-4}$ alkylamino-$C_{1-4}$ alkyl; and m and n are independently 1, 2, 3 or 4.

The sulfonylbenzene compounds of the present invention exhibit inhibition of COX activity. Preferable compounds of this invention exhibit inhibitory activity against COX-2, with more preferable compounds having COX-2 selectivity.

Accordingly, the present invention also provides a pharmaceutical composition, usefull for the treatment of a medical condition in which prostaglandins are implicated as pathogens, which comprises a compound of the formula (I) and the pharmaceutically acceptable salts thereof.

Further, the present invention provides a method for the treatment of a medical condition in which prostaglandins are implicated as pathogens, in a mammalian subject, which comprises administering to said subject a therapeutically effective amount of said pharmaceutical composition.

The medical conditions in which prostaglandins are implicated as pathogens, include the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis including rheumatoid arthritis, degenerative joint disease (osteoarthritis), gout, ankylosing spondylitis, systemic lumpus erythematosus and juvenile arthritis, bursitis, burns injuries following surgical and dental procedures.

The compounds and pharmaceutical composition of this invention may inhibit cellular neoplastic transformations and metastatic tumor growth and thus may be used in the treatment and/or prevention of cancers in the colon, breast, skin, esophagus, stomach, urinary bladder, lung and liver. The compounds and pharmaceutical composition of this invention were used in the treatment and/or prevention of cyclooxygenase-mediated proliferation disorders such as which occur in diabetic retinopathy and tumor angiogenesis.

The compounds and pharmaceutical composition of this invention may inhibit prostaniod-induced smooth muscle contraction by preventing the synthesis of contractile prostanoids, and thus may be of use in the treatment of dysmenorrhea, premature labor, asthma and eosinophil related disorders and in the treatment of neurodegenerative diseases such as Alzheimer's and Parkinson's disease, and for the treatment of bone loss (treatment of osteoarthritis), stroke, seizures, migraine, multiple sclevosis, AIDS and encephaloathy.

By virtue of the COX-2 activity and/or specificity for COX-2 over COX-1, such compounds will prove useful as an alternative to conventional NSAIDs particularly where such NSAIDs may be contra-indicated such as in patients with ulcers (such as peptic ulcers and gastric ulcers), gastritis, regional enterotis, ulcerative colitis, diverticulitis or with a recurrent history of GI lesions, GI bleeding, coagulation disorders including anemia such as hypoprothrombinemia, haemophilia and other bleeding problems; kidney disease; prior to surgery of taking of anticoagulants.

This invention also provides a compound of formula:

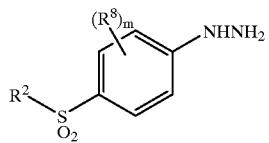

or its salt thereof, wherein $R^2$ is $C_{1-4}$ alkyl, halo-substituted $C_{1-4}$ alkyl, $C_{1-4}$ alkylamino, $C_{1-4}$ dialkylamino or amino; $R^8$ is independently hydrogen, halo, $C_{1-4}$ alkyl, halo-substituted $C_{1-4}$ alkyl, $C_{1-4}$ alkoxy, $C_{1-4}$ alkylthio, $C_{1-4}$ alkylamino, N,N-di $C_{1-4}$ alkylamino, $C_{1-4}$ alkylamino-$C_{1-4}$ alkyl, N,N-di $C_{1-4}$ alkylamino-$C_{1-4}$ alkyl, $C_{1-4}$ alkoxy-$C_{1-4}$ alkyl or hydroxy-$C_{1-4}$ alkyl and m is 2, 3 or 4, with the proviso that $R^8$ is not chloro nor trifluoromethyl.

DETAILED DESCRIPTION OF THE INVENTION

As used herein, the term "halo" is fluoro, chloro, bromo or iodo.

As used herein, the term "$C_{1-4}$" alkyl means straight or branched chain saturated radicals of 1 to 4 carbon atoms, including, but not limited to methyl, ethyl, n-propyl, isopropyl, n-butyl, iso-butyl, secondary-butyl, tertiary-butyl.

As used herein, the term "halo-substituted alkyl" refers to an alkyl radical as described above substituted with one or more halogens included, but not limited to, chloromethyl, dichloromethyl, fluoromethyl, difluoromethyl, trifluoromethyl, 2,2,2-trichloroethyl, and the like.

As used herein, the term "$C_{2-5}$" alkenyl means straight or branched chain unsaturated radicals of 2 to 5 carbon atoms, including, but not limited to ethenyl,1-propenyl, 2-propenyl (allyl), iso-propenyl, 2-methyl-1-propenyl, 1-butenyl, 2-butenyl, and the like.

As used herein, the term "$C_{2-5}$" alkynyl is used herein to mean straight or branched hydrocarbon chain radicals having one triple bond including, but not limited to, ethynyl, propynyl, butynyl, and the like.

As used herein the term "aryl" means aromatic radicals such as phenyl, naphthyl, tetrahydronaphthyl, indanyl, biphenyl and the like.

As used herein "heteroaryl" group usually has one heteroatom selected from O, S and N in the ring. In addition to said heteroatom, the aromatic group may optionally have up to four N atoms in the ring. For example, heteroaryl group includes pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), tetrazole, quinolyl, isoquinolyl, benzothienyl, benzofuryl, indolyl, and the like.

As used herein, the term partially unsaturated or unsaturated five membered carbocyclic means aromatic or non-aromatic ring-shaped radicals, for example, cyclopentenyl, cyclopent-1,3-dienyl, oxocyclopentenyl, and the like.

Examples of "partially unsaturated or unsaturated five membered heterocyclic" are thienyl, oxazolyl, furyl pyrrolyl, thiazolyl, imidazolyl, isoxazolyl, isothiazolyl, pyrazolyl, oxolinyl, thiolinyl, pyrazolinyl, imidazolinyl, pyrrolinyl, furanone, and the like.

Preferred compounds of this invention are those of the formula (I) wherein A is partially unsaturated or unsaturated five membered heterocyclic.

Further preferred compounds of this inv-ention are those of the formula (I) wherein A is thienyl, oxazolyl, furyl, pyrrolinyl, thiazolyl, imidazolyl, isoxazolyl, isothiazolyl, pyrazolyl, oxolinyl, thiolinyl, pyrazolinyl, imidazolinyl, pyrrolinyl or furanone.

Much preferred compounds of this invention are those of the formnula (I) wherein A is thienyl, oxazolyl, furyl, pyrrolyl, thiazolyl, imidazolyl, isoxazolyl, isothiazolyl, pyrazolyl or furanone; and $R^3$, $R^4$ and $R^5$ are independently hydrogen, halo, $C_{1-4}$ alkyl, halo-substituted $C_{1-4}$ alkyl, $C_{2-5}$ alkenyl, $C_{2-5}$ alkynyl, $C_{1-4}$ alkoxy, hydroxy-$C_{1-4}$ alkyl, $C_{1-4}$ alkoxy $C_{1-4}$ alkyl, $C_{1-4}$ alkanoyl, cyano, nitro, cyano $C_{1-4}$ alkyl, carboxyl, $C_{1-4}$ alkoxycarbonyl, aminocarbonyl, N—$C_{1-4}$ alkylaminocarbonyl, N,N-di-$C_{1-4}$ alkylaminocarbonyl, morpholino-carbonyl, $C_{1-4}$ alkoxyaminocarbonyl or $C_{1-4}$ alkyl-carbonylamino.

Among these, preferred compounds of this invention are those of the formula (I) wherein A is thienyl, oxazolyl, furyl, pyrrolyl, thiazolyl, imidazolyl, isoxazolyl, pyrazolyl or furanone;

R$^1$ is phenyl or heteroaryl selected from pyridyl, pyrazinyl, pyrimidinyl, pyridazinyl, thienyl, furyl, imidazolyl, pyrrolyl, oxazolyl, thiazolyl, isothiazolyl, pyrazolyl, tetrazolyl, triazolyl, oxadiazolyl, thiadiazolyl, tetrazole, quinolyl, isoquinolyl, benzo[b] thienyl, benzo[b]furyl and indolyl, and the phenyl or heteroaryl being optionally substituted by one to three substituents selected from halo, C$_{1-4}$ alkyl, halo-substituted C$_{1-4}$ alkyl, C$_{1-4}$ alkoxy, C$_{1-4}$ alkyl carbonyl, C$_{1-5}$ alkoxycarbonyl, hydroxy, nitro, cyano and amino;

R$^2$ is C$_{1-4}$ alkyl, halo-substituted C$_{1-4}$ alkyl or amino;

R$^3$, R$^4$ and R$^5$ are independently hydrogen, halo, C$_{1-4}$ alkyl, halo-substituted C$_{1-4}$ alkyl, C$_{2-5}$ alkenyl, C$_{1-4}$ alkoxy, hydroxy-C$_{1-4}$ alkyl, C$_{1-4}$ alkoxy C$_{1-4}$ alkyl, C$_{1-4}$ alkanoyl, cyano, nitro, cyano C$_{1-4}$ alkyl, carboxy, C$_{1-4}$ alkoxycarbonyl, aminocarbonyl, morpholinocarbonyl, C$_{1-4}$ alkoxyaminocarbonyl or C$_{1-4}$ alkylcarbonylamino; and R$^6$ and R$^7$ are independently hydrogen, halo, C$_{1-4}$ alkyl, halo-substituted C$_{1-4}$ alkyl, C$_{1-4}$ alkoxy, C$_{1-4}$ alkylthio, hydroxyl-C$_{1-4}$ alkyl, C$_{1-4}$ alkoxy-C$_{1-4}$ alkyl, C$_{1-4}$ alkyl-C$_{1-4}$ alkoxy, C$_{1-4}$ alkylamino-C$_{1-4}$ alkyl or hydroxy; and m and n are independently 1 or 2.

Further preferred compounds of this invention are those of the formula (I) wherein A is thienyl, oxazolyl, furyl, pyrrolyl, thiazolyl, imidazolyl, isooxazolyl, pyrazolyl or furanone;

R$^1$ is phenyl or heteroaryl selected from pyridyl, pyrazinyl, pyrimidinyl, pyridazinyl, thienyl, furyl, imidazolyl, pyrrolyl, oxazolyl, thiazolyl, isothiazolyl, pyrazolyl, benzo[b]thienyl, benzo[b]furyl and indolyl, and the phenyl or heteroaryl being optionally substituted by halo, C$_{1-4}$ alkyl, C$_{1-4}$ alkyl carbonyl or C$_{1-4}$ alkoxy carbonyl;

R$^2$ is methyl, ethyl, fluoromethyl, difluoromethyl or amino:

R$^3$, R$^4$ and R$^5$ are independently hydrogen, halo, C$_{1-4}$ alkyl, fluoro-substituted C$_{1-4}$ alkyl, C$_{1-4}$ alkoxy, hydroxy-C$_{1-4}$ alkyl, C$_{1-4}$ alkanoyl, cyano, nitro, cyano C$_{1-4}$ alkyl, carboxy, C$_{1-4}$ alkoxycarbonyl, morpholinocarbonyl, C$_{1-4}$ alkoxyaminocarbonyl or C$_{1-4}$ alkylcarbonylamino; and R$^6$ and R$^7$ are independently hydrogen, halo, C$_{1-4}$ alkyl, halo-substituted C$_{1-4}$ alkyl, C$_{1-4}$ alkoxy, hydroxyl-C$_{1-4}$ alkyl, C$_{1-4}$ alkoxy-C$_{1-4}$ alkyl, C$_{1-4}$ alkyl-C$_{1-4}$ alkoxy, C$_{1-4}$ alkylamino-C$_{1-4}$ alkyl or hydroxy.

Also, further preferred compounds of this invention are those of the formula (I) wherein A is thienyl, oxazolyl, furyl, pyrrolyl, thiazolyl, imidazolyl, isooxazolyl, pyrazolyl or furanone;

R$^1$ is phenyl or heteroaryl selected from pyridyl, pyrimidinyl, thienyl, furyl, imidazolyl, pyrrolyl, oxazolyl, thiazolyl, benzo[b]thienyl and benzo[b]furyl, and the phenyl or heteroaryl being optionally substituted by one to three substituents selected from fluoro, chloro, methyl, ethyl, propyl, fluoromethyl, difluoromethyl, trifluoromethyl, chloromethyl, methoxyl, acetyl, ethylcarbonyl, methoxycarbonyl, ethoxycarbonyl and butoxycarbonyl;

R$^2$ is methyl, fluoromethyl or amino;

R$^3$, R$^4$ and R$^5$ are independently hydrogen, fluoro, chloro, methyl, ethyl, propyl, fluoromethyl, difluoromethyl, trifluoromethyl, methoxy, ethoxyl, hydroxymethyl, hydroxyethyl, methylcarbonyl, cyano, nitro, cyanomethyl, cyanoethyl, carboxy, methoxylcarbonyl, ethoxycarbonyl, morpholinocarbonyl, methoxyaminocarbonyl or methylcarbonylamino; and R$^6$ and R$^7$ are independently hydrogen, fluoro, chloro, methyl, ethyl, propyl, fluoromethyl, difluoromethyl, trifluoromethyl, methoxy, ethoxy, hydroxymethyl, hydroxyethyl, methoxymethyl, methoxyethyl, ethoxymethyl, methylaminomethyl, methylaminoethyl, ethylaminomethyl, aminomethyl, aminoethyl or hydroxy.

Among these, preferred compounds of this invention are those of the formula (I) wherein A is oxazolyl, pyrrolyl, imidazolyl, isoxazolyl, pyrazolyl or furanone;

R$^1$ is phenyl or heteroaryl selected from pyridyl, pyrimidinyl, thienyl, furyl, imidazolyl, pyrrolyl, oxazolyl, thiazolyl, benzothienyl and benzofuryl, and the heteroaryl being optionally substituted by chloro or methyl;

R$^2$ is methyl, fluoromethyl or amino;

R$^3$, R$^4$ and R$^5$ are independently hydrogen, methyl, trifluoromethyl, hydroxymethyl, cyano, cyanomethyl, carboxy, ethoxycarbonyl, morpholinocarbonyl, methoxyaminocarbonyl or methylcarbonylamino; and R$^6$ and R$^7$ are independently hydrogen, fluoro, chloro, methyl, methoxy, hydroxymethyl, hydroxymethyl, ethoxy, trifluoromethyl, methoxymethyl, methylaminomethyl, Also, preferred compounds of this invention are those of the formula (I) wherein A is pyrazolyl or furanone;

R$^1$ is heteroaryl selected from thienyl, furyl, oxazolyl and thiazolyl;

R$^2$ is methyl or amino;

R$^3$, R$^4$ and R$^5$ are independently hydrogen, methyl or trifluoromethyl;

R$^6$ and R$^7$ are independently hydrogen, fluoro, chloro, methyl or methoxy; and m and n are 1.

Preferred individual compounds of this invention are:

1-[4-(methylsulfonyl)phenyl]-5-[4-(2-thienyl)phenyl]-3-trifluoromethyl-1H-pyrazole;

1-[4-(methylsulfonyl)phenyl]-5-[4-(3-thienyl)phenyl]-3-trifluoromethyl-1H-pyrazole;

1-[4-(methylsulfonyl)phenyl]-5-[4-(2-furyl)phenyl]-3-trifluoromethyl-1H-pyrazole;

1-[4-(methylsulfonyl)phenyl]-5-[4-(benzo[b]furan-2-yl)phenyl]-3-trifluoromethyl-1H-pyrazole;

4-[5-[4-(3-thienyl)phenyl]-3-(trifluoromethyl)-1H-pyrazol-1-yl]-1-phenylsulfonamide;

4-[5-[4-(3-thienyl)phenyl]-4-cyano-1H-pyrazol-1-yl]-1-phenylsulfonamide;

4-[5-[4-(4-pyridyl)phenyl]-3-(trifluoromethyl)-1H-pyrazol-1-yl]-1-phenylsulfonamide;

4-[5-[4-(3-pyridyl)phenyl]-3-(trifluoromethyl)-1H-pyrazol-1-yl]-1-phenylsulfonamide;

4-[5-[4-(5-methyl-2-thienyl)phenyl]-3-(trifluoromethyl)-1H-pyrazol-1-yl]-1-phenylsulfonamide;

4-[5-[4-(3-furyl)phenyl]-3-(trifluoromethyl)-1H-pyrazol-1-yl]-1-phenylsulfonamide;

4-[5-[4-(5-pyrimidinyl)phenyl]-3-(trifluoromethyl)-1H-pyrazol-1-yl]-1-phenylsulfonamide;

4-[5-[4-(2-pyrrolyl)phenyl]-3-(trifluoromethyl)-1H-pyrazol-1-yl]-1-phenylsulfonamide;

4-[5-[4-(2-benzothienyl)phenyl]-3-(trifluoromethyl)-1H-pyrazol-1-yl]-1-phenylsulfonamide;

4-[5-[4-(5-acetylthiophene-2-yl)phenyl]-3-(trifluoromethyl)-1H-pyrazol-1-yl]-1-phenylsulfanamide;
4-[5-[4-(3-pyrrolyl)phenyl]-3-(trifluoromethyl)-1H-pyrazol-1-yl]-1-phenylsulfonamide;
4-[5-[4-(3-methyl-2-thienyl)phenyl]-3-(trifluoromethyl)-1H-pyrazol-1-yl]-1-phenylsulfonamide;
methyl 1-[4-(sulfamoylphenyl]-5-[4-(3-thienyl)phenyl]-1H-pyrazole-3-carboxylate;
4-[3-(cyanomethyl)-5-[4-(3-thienyl)phenyl]-1H-pyrazol-1-yl]-1-phenylsulfonamide;
4-[3-(hydroxymethyl)-5-[4-(3-thienyl)phenyl]-1H-pyrazol-1-yl]-1-phenylsulfonamide;
1-[4-(methylsulfonyl)phenyl]-5-[4-(3-furyl)phenyl]-3-trifluoromethyl-1H-pyrazole;
4-[5-[4-(2-thiazolyl)phenyl]-3-(trifluoromethyl)-1H-pyrazol-1-yl]-1-phenylsulfonamide;
1-[4-(methylsulfonyl)phenyl]-5-[4-(2-thiazolyl)phenyl]-3-trifluoromethyl-1H-pyrazole;
4-[5-[4-(5-thiazolyl)phenyl]-3-(trifluoromethyl)-1H-pyrazol-1-yl]-1-phenylsulfonamide;
1-[4-(methylsulfonyl)phenyl]-5-[4-(5-thiazolyl)phenyl]-3-trifluoromethyl-1H-pyrazole;
4-[5-[4-(5-chloro-2-thienyl)phenyl]-3-(trifluoromethyl)-1H-pyrazol-1-yl]-1-phenylsulfonamide;
4-[5-[4-(1H-imidazol-1-yl)phenyl]-3-trifluoromethyl-1H-pyrazol-1-yl]-1-phenylsulfonamide;
4-[5-[4-(2,5-dimethylpyrrol-1-yl)phenyl]-3-trifluoromethyl-1H-pyrazol-1-yl]-1-phenylsulfonamide;
4-[5-[4-(2-thienyl)phenyl]-3-(trifluoromethyl)-1H-pyrazol-1-yl]-1-phenylsulfonamide;
4-[5-[4-(2-furyl)phenyl]-3-(trifluoromethyl)-1H-pyrazol-1-yl]-1-phenylsulfonamide;
1-[4-(methylsulfonyl)phenyl]-5-[4-(2-furyl)-3-methylphenyl]-3-trifluoromethyl-1H-pyrazole;
4-[5-[4-(2-furyl)-3-methylphenyl]-3-(trifluoromethyl)-1H-pyrazol-1-yl]-1-phenylsulfonamide;
3-[4-(3-thienyl)phenyl]-4-[4-(methylsulfonyl)phenyl]-2-(5H)-furanone;
3-[4-(2-thienyl)phenyl]-4-[4-(methylsulfonyl)phenyl]-2-(5H)-furanone;
3-[4-(3-furyl)phenyl]-4-[4-(methylsulfonyl)phenyl]-2-(5H)-furanone;
5-[3-fluoro-4-(methylsulfonyl)phenyl]-1-[4-(2-furyl)phenyl]-2-methyl-1H-pyrrole;
5-[3-fluoro-4-(methylsulfonyl)phenyl]-1-[4-(3-furyl)phenyl]-2-methyl-1H-pyrrole;
2,3-dimethyl-1-[4-(3-furyl)phenyl]-5-[4-(methylsulfonyl)phenyl]-1H-pyrrole;
5-[4-(methylsulfonyl)phenyl]-1-[4-(3-furyl)phenyl]-2-methyl-1H-pyrrole;
1-[4-(3-furyl)-3-methylphenyl]-2-methyl-5-[4-(methylsulfonyl)phenyl]-1H-pyrrole;
1-[4-(2-furyl)-3-methylphenyl]-2-methyl-5-[4-(methylsulfonyl)phenyl]-1H-pyrrole;
1-[3-chloro-4-(3-furyl)phenyl]-2-methyl-5-[4-(methylsulfonyl)phenyl]-1H-pyrrole;
1-[3-chloro-4-(2-furyl)phenyl]-2-methyl-5-[4-(methylsulfonyl)phenyl]-1H-pyrrole;
1-(4-biphenyl)-2-methyl-5-[4-(methylsulfonyl)phenyl]-1H-pyrrole;
1-[4-(2-furyl)phenyl]-2-methyl-5-[4-(methylsulfonyl)phenyl]-1H-pyrrole;
2-methyl-5-[4-(methylsulfonyl)phenyl]-1-[4-(2-thienyl)phenyl]-1H-pyrrole;
2-methyl-5-[4-(methylsulfonyl)phenyl]-1-[4-(3-thienyl)phenyl]-1H-pyrrole;
2-methyl-5-[4-(methylsulfonyl)phenyl]-1-[4-(2-pyrrolyl)phenyl]-1H-pyrrole;
2-methyl-5-[4-(methylsulfonyl)phenyl]-1-[[4-(1-tert-butoxycarbonyl)-2-pyrrolyl]phenyl]-1H-pyrrole;
2-methyl-5-[4-(methylsulfonyl)phenyl]-1-[4-(2-thiazolyl)phenyl]-1H-pyrrole;
2-methyl-5-[4-(methylsulfonyl)phenyl]-4-[4-(2-thienyl)phenyl]oxazole;
4-[4-(2-furyl)phenyl]-2-methyl-5-[4-(methylsulfonyl)phenyl]oxazole;
1-[4-(methylsulfonyl)phenyl]-2-[4-(2-thienyl)phenyl]-4-(trifluoromethyl)-1H-imidazole;
2-[4-(2-furyl)phenyl]-1-[4-(methylsulfonyl)phenyl]-4-(trifluoromethyl)-1H-imidazole;
2-[4-(2-furyl)phenyl]-4-methyl-1-(4-sulfamoylphenyl)-1H-pyrrole;
1-[4-(3-furyl)phenyl]-4-methyl-2-[4-(methylsulfonyl)phenyl]-1H-pyrrole;
2-[4-(3-furyl)phenyl]-4-methyl-1-[4-(methylsulfonyl)phenyl]-1H-pyrrole;
2-biphenyl-4-methyl-1-[4-(methylsulfonyl)phenyl]-1H-pyrrole;
1-[4-(2-furyl)phenyl]-4-methyl-2-[4-(methylsulfonyl)phenyl]-1H-pyrrole;
2-[4-(2-furyl)phenyl]-4-methyl-1-[4-(methylsulfonyl)phenyl]-1H-pyrrole;
2-[4-(2-furyl)phenyl]-4-methyl-1-[4-(methylsulfonyl)phenyl]-1H-pyrrole;
1-[3-fluoro-4-(methylsulfonyl)phenyl]-5-[4-(2-furyl)phenyl]-3-(trifluoromethyl)-1H-pyrazole;
1-[4-(fluoromethylsulfonyl)phenyl]]-5-[4-(2-furyl)phenyl]-3-(trifluoromethyl)-1H-pyrazole;
4-[5-[4-(2-furyl)phenyl]-4-cyano-1-[4-(methylsulfonyl)phenyl]-1H-pyrazole;
4-[5-[4-(2-furyl)phenyl]-3-hydroxymethyl-1-[4-(methylsulfonyl)phenyl]-1H-pyrazole;
3-cyanomethyl-4-[5-[4-(2-furyl)phenyl]-1-[4-(methylsulfonyl)phenyl]-1H-pyrazole;
ethyl 5-[4-(2-furyl)phenyl]-1-[4-(methylsulfonyl)phenyl]-1H-pyrazole-3-carboxylate;
5-[4-(1-imidazolyl)phenyl]-1-[4-(methylsulfonyl)phenyl]-3-trifluoromethyl-1H-pyrazol;
5-[4-(2-furyl)phenyl]-1-[4-(methylsulfonyl)phenyl]-1H-pyrazole-3-carboxylic acid;
2-[4-(2-furyl)phenyl]-3-[(4-methylsulfonyl)phenyl]thiophene;
2-[4-(3-furyl)phenyl]-3-[(4-methylsulfonyl)phenyl]thiophene;
4-[5-[3-chloro-4-(2-furyl)phenyl]-3-(trifluoromethyl)-1H-pyrazol-1-yl]-1-phenylsulfonamide;
1-[4-(methylsulfonyl)phenyl]-5-[3-chloro-4-(2-furyl)phenyl]-3-(trifluoromethyl)-1H-pyrazole;
4-[5-[4-(2-furyl)-3-methoxyphenyl]-3-(trifluoromethyl)-1H-pyrazol-1-yl]-1-phenylsulfonamide;
4-[5-[3-fluoro-4-(2-furyl)phenyl]-3-(trifluoromethyl)-1H-pyrazol-1-yl]-1-phenylsulfonamide;
1-[4-(methylsulfonyl)phenyl]-5-[3-fluoro-4-(2-furyl)phenyl]-3-(trifluoromethyl)-1H-pyrazole;
4-[5-[4-(5-oxazolyl)phenyl]-3-(trifluoromethyl)-1H-pyrazol-1-yl]-1-phenylsulfonamide;
1-[4-(methylsulfonyl)phenyl]-5-[4-(5-oxazolyl)phenyl]-3-(trifluoromethyl)-1H-pyrazole;
4-[5-[4-(2-furyl)-2-methylphenyl]-3-(trifluoromethyl)-1H-pyrazol-1-yl]-1-phenylsulfonamide;
1-[4-(methylsulfonyl)phenyl]-5-[4-(2-furyl)-2-methylphenyl]-3-(trifluoromethyl )-1H-pyrazole;
4-[5-[2-fluoro-4-(2-furyl)phenyl]-3-(trifluoromethyl)-1H-pyrazol-1-yl]-1-phenylsulfonamide;
1-[4-(methylsulfonyl)phenyl]-5-[2-fluoro-4-(2-furyl)phenyl]-3-(trifluoromethyl)-1H-pyrazole;

1-[4-(methylsulfonyl)phenyl]-5-[4-(2-furyl)-3-methoxyphenyl]-3-(trifluoromethyl)-1H-pyrazole;

1-[4-(methylsulfonyl)phenyl]-5-[4-(4-thiazolyl)phenyl]-3-(trifluoromethyl)-1H-pyrazole;

1-[3-fluoro-4-(methylsulfonyl)phenyl]-5-[4-(2-furyl)-3-methylphenyl]-3-(trifluoromethyl)-1H-pyrazole;

1-[3-fluoro-4-(methylsulfonyl)phenyl]-5-[4-(5-oxazolyl)phenyl]-3-(trifluoromethyl)-1H-pyrazole;

1-[3-fluoro-4-(methylsulfonyl)phenyl]-5-[4-(3-furyl)phenyl]-3-(trifluoromethyl)-1H-pyrazole;

1-[3-fluoro-4-(methylsulfonyl)phenyl]-5-[4-(2-thienyl)phenyl]-3-(trifluoromethyl)-1H-pyrazole;

1-[3-fluoro-4-(methylsulfonyl)phenyl]-5-[4-(3-thienyl)phenyl]-3-(trifluoromethyl)-1H-pyrazole;

methyl 1-(4-sulfamoylphenyl)-5-[4-(2-thiazolyl)phenyl]-1H-pyrazole-3-carboxylate;

4-[4-cyano-5-[4-(2-thiazolyl)phenyl-1H-pyrazol-1-yl]-1-phenylsulfonamide;

4-[4-chloro-5-[4-(2-thiazolyl)phenyl]-3-trifluoromethyl-1H-pyrazol-1-yl]-1-phenylsulfonamide;

5-[2-fluoro-4-(2-furyl)phenyl]-1-[3-fluoro-4-(methylsulfonyl)phenyl]-3-trifluoromethyl-1H-pyrazole;

1-[3-fluoro-4-(methylsulfonyl)phenyl]-5-[4-(2-furyl)-2-methylphenyl]-3-trifluoromethyl-1H-pyrazole;

1-[3-fluoro-4-(methylsulfonyl)phenyl]-5-[3-chloro-4-(2-furyl)phenyl]-3-(trifluoromethyl)-1H-pyrazole;

4-{4-[1-[3-fluoro-4-(methylsulfonyl)phenyl]-3-(trifluoromethyl)-1H-pyrazol-5-yl]phenyl}-1,3-oxazole;

4-{4-[1-[4-(methylsulfonyl)phenyl]-3-(trifluoromethyl)-1H-pyrazol-5-yl]phenyl}-1,3-oxazole;

2-{4-[1-[3-fluoro-4-(methylsulfonyl)phenyl]-3-(trifluoromethyl)-1H-pyrazol-5-yl]phenyl}-1,3-oxazole;

2-{4-[1-[4-(methylsulfonyl)phenyl]-3-(trifluoromethyl)-1H-pyrazol-5-yl]phenyl}-1,3-oxazole;

4-[5-[4-(1,3-oxazol-2-yl)phenyl]-3-(trifluoromethyl)-1H-pyrazol-1-yl]benzenesulfonamide;

4-{4-[1-[3-fluoro-4-(methylsulfonyl)phenyl]-3-(trifluoromethyl)-1H-pyrazol-5-yl]phenyl}-1,3-thiazole;

4-[5-[4-(1,3-thiazol-4-yl)phenyl]-3-(trifluoromethyl)-1H-pyrazol-1-yl]benzenesulfonamide;

4-{4-[1-[3-methyl-4-(methylsulfonyl)phenyl]-3-(trifluoromethyl)-1H-pyrazol-5-yl]phenyl}-1,3-thiazole;

4-{4-[1-[3-fluoro-4-(methylsulfonyl)phenyl]-3-(trifluoromethyl)-1H-pyrazol-5-yl]phenyl}-2-methyl-1,3-thiazole;

2-fluoro-4-[5-[4-(1,3-thiazol-4-yl)phenyl]-3-(trifluoromethyl)-1H-pyrazol-1-yl]benzenesulfonamide;

4-{4-[1-[3-fluoro-4-(methylsulfonyl)phenyl]-3-(trifluoromethyl)-1H-pyrazol-5-yl]phenyl}-5-methyl-1,3-thiazole;

4-{4-[1-[3-fluoro-4-(methylsulfonyl)phenyl]-3-(trifluoromethyl)-1H-pyrazol-5-yl]-2-fluorophenyl}-1,3-thiazole;

4-{4-[1-[3-fluoro-4-(methylsulfonyl)phenyl]-3-(trifluoromethyl)-1H-pyrazol-5-yl]-2-methylphenyl}-1,3-thiazole;

4-{4-[1-[3-fluoro-4-(methylsulfonyl)phenyl]-3-(trifluoromethyl)-1H-pyrazol-5-yl]-2-methoxyphenyl}-1,3-thiazole;

4-{4-[1-[3-fluoro-4-(methylsulfonyl)phenyl]-3-(trifluoromethyl)-1H-pyrazol-5-yl]-2-methoxyphenyl}-1,3-oxazole;

4-{2-chloro-4-[1-[3-fluoro-4-(methylsulfonyl)phenyl]-3-(trifluoromethyl)-1H-pyrazol-5-yl]phenyl}-1,3-thiazole;

4-{4-[1-[3-fluoro-4-(methylsulfonyl)phenyl]-3-(trifluoromethyl)-1H-pyrazol-5-yl]-2-methylphenyl}-1,3-oxazole;

4-{2-methoxy-4-[1-[4-(methylsulfonyl)phenyl]-3-(trifluoromethyl)-1H-pyrazol-5-yl]phenyl}-1,3-oxazole;

4-{2-methyl-4-[1-[4-(methylsulfonyl)phenyl]-3-(trifluoromethyl)-1H-pyrazol-5-yl]phenyl}-1,3-oxazole;

2-fluoro-4-[5-[3-methyl-4-(1,3-thiazol-4-yl)phenyl]-3-(trifluoromethyl)-1H-pyrazol-1-yl]benzenesulfonamide;

2-fluoro-4-[5-[3-fluoro-4-(1,3-thiazol-4-yl)phenyl]-3-(trifluoromethyl)-1H-pyrazol-1-yl]benzenesulfonamide;

4-{4-[1-[3-hydroxymethyl-4-(methylsulfonyl)phenyl]-3-(trifluoromethyl)-1H-pyrazol-5-yl]phenyl}-1,3-thiazole;

4-[5-[3-methyl-4-(1,3-oxazol-4-yl)phenyl]-3-(trifluoromethyl)-1H-pyrazol-1-yl]benzenesulfonamide;

4-[5-[3-methoxy-4-(1,3-oxazol-4-yl)phenyl]-3-(trifluoromethyl)-1H-pyrazol-1-yl]benzenesulfonamide;

4-[5-[4-(1,3-oxazol-4-yl)phenyl]-3-(trifluoromethyl)-1H-pyrazol-1-yl]benzenesulfonamide;

4-{2-chloro-4-[1-[4-(methylsulfonyl)phenyl]-3-(trifluoromethyl)-1H-pyrazol-5-yl]phenyl}-1,3-thiazole;

4-{2-methoxy-4-[1-[4-(methylsulfonyl)phenyl]-3-(trifluoromethyl)-1H-pyrazol-5-yl]phenyl}-1,3-thiazole;

2-fluoro-4-[5-[4-(1,3-oxazol-4-yl)phenyl]-3-(trifluoromethyl)-1H-pyrazol-1-yl]benzenesulfonamide;

2-fluoro-4-[5-[3-chloro-4-(1,3-thiazol-4-yl)phenyl]-3-(trifluoromethyl)-1H-pyrazol-1-yl]benzenesulfonamide;

2-fluoro-4-[5-[3-methyl-4-(1,3-oxazol-4-yl)phenyl]-3-(trifluoromethyl)-1H-pyrazol-1-yl]benzenesulfonamide;

4-{2-fluoro-4-[1-[4-(methylsulfonyl)phenyl]-3-(trifluoromethyl)-1H-pyrazol-5-yl]phenyl}-1,3-thiazole;

4-{2-methyl-4-[1-[4-(methylsulfonyl)phenyl]-3-(trifluoromethyl)-1H-pyrazol-5-yl]phenyl}-1,3-thiazole;

ethyl 1-[3-Fluoro-4-(methylsulfonyl)phenyl]-5-[4-(2-furyl)phenyl]-1H-pyrazole-3-carboxylate;

1-[3-ethoxy-4-(methylsulfonyl)phenyl]-5-[4-(2-furyl)phenyl]-1H-pyrazole-3-carboxylic acid;

1-[3-fluoro-4-(methylsulfonyl)phenyl]-5-[4-(2-furyl)phenyl]-1H-pyrazole-3-carboxylic acid;

1-[3-fluoro-4-(methylsulfonyl)phenyl]-5-[4-(2-furyl)phenyl]-3-hydroxymethyl-1H-pyrazole;

1-[3-fluoro-4-(methylsulfonyl)phenyl]-5-[4-(2-furyl)phenyl]-3-(4-morpholinecarbonyl)-1H-pyrazole;

N-methyl-1-[3-fluoro-4-(methylsulfonyl)phenyl]-5-[4-(2-furyl)phenyl]-1H-pyrazole-3-carboxamide;

1-[3-fluoro-4-(methylsulfonyl)phenyl]-5-[4-(2-furyl)phenyl]-1H-pyrazole-3-carboxamide;

N,N-dimethyl-1-[3-fluoro-4-(methylsulfonyl)phenyl]-5-[4-(2-furyl)phenyl]-1H-pyrazole-3-carboxamide;

N-methoxy-1-[3-fluoro-4-(methylsulfonyl)phenyl]-5-[4-(2-furyl)phenyl]-1H-pyrazole-3-carboxamide;

5-[4-(2-furyl)phenyl]-1-[4-(methylsulfonyl)-3-(trifluoromethyl)phenyl]-3-trifluoromethyl-1H-pyrazole;

5-[4-(2-furyl)phenyl]-1-[3-methoxy-4-(methylsulfonyl)phenyl]-3-trifluoromethyl-1H-pyrazole;

2-fluoro-4-[5-[4-(2-furyl)phenyl]-3-(trifluoromethyl)-1H-pyrazol-1-yl]benzenesulfonamide;

4-[5-[3-chloro-4-(2-furyl)phenyl]-3-(trifluoromethyl)-1H-pyrazol-1-yl]-2-fluorobenzenesulfonamide;

2-fluoro-4-[5-[4-(2-furyl)-3-methylphenyl]-3-(trifluoromethyl)-1H-pyrazol-1-yl]benzenesulfonamide;

2-chloro-4-[5-[4-(2-furyl)phenyl]-3-(trifluoromethyl)-1H-pyrazol-1-yl]benzenesulfonamide;

3-fluoro-4-[5-[4-(2-furyl)phenyl]-3-(trifluoromethyl)-1H-pyrazol-1-yl]benzenesulfonamide;

[5-[4-(2-furyl)phenyl]1-[4-(methylsulfonyl)-2-methylphenyl]-3-trifluoromethyl-1H-pyrazole;

4-[5-[4-(2-furyl)phenyl]-3-(trifluoromethyl)-1H-pyrazol-1-yl]-2-methylbenzenesulfonamide;

2-chloro-4-[5-[4-(2-furyl)phenyl]-3-(trifluoromethyl)-1H-pyrazol-1-yl]benzenesulfonamide;

4-[5-[4-(2-furyl)phenyl]-3-(trifluoromethyl)-1H-pyrazol-1-yl]-3-methylbenzenesulfonamide;
[5-[4-(2-furyl)phenyl]-1-[4-(methylsulfonyl)-2-methoxylphenyl]-3-trifluoromethyl-1H-pyrazole;
[-5-[4-(2-furyl)phenyl]-1-[4-(methylsulfonyl)-2-(trifluoromethyl)phenyl]-3-trifluoromethyl-1H-pyrazole;
4-[5-[4-(2-furyl)phenyl]-3-(trifluoromethyl)-1H-pyrazol-1-yl]-2-methoxybenzenesulfonamide;
2-chloro-4-[5-[3-methyl-4-(4-thiazolyl)phenyl]-3-(trifluoromethyl)-1H-pyrazol-1-yl]benzenesulfonamide;
3-fluoro-4-[5-[3-methyl-4-(4-thiazolyl)phenyl]-3-(trifluoromethyl)-1H-pyrazol-1yl]benzenesulfonamide;
5-[3-fluoro-4-(methylsulfonyl)phenyl]-2-methyl-1-[4-(4-thiazolyl)phenyl]-1H-pyrrole;
5-[3-fluoro-4-(methylsulfonyl)phenyl]-2-methyl-1-[3-methyl-4-(4-thiazolyl) phenyl]-1H-pyrrole;
1-[3-fluoro-4-(methylsulfonyl)phenyl]-2-[4-(4-thiazolyl)phenyl]-4-trifluoromethyl-1H-imidazole;
2-fluoro-4-[2-[4-(4-thiazolyl)phenyl]-4-(trifluoromethyl)-1H-imidazol-1-yl]benzenesulfonamide;
1-[3-chloro-4-(methylsulfonyl)phenyl]-5-[4-(2-furyl) phenyl]-3-(trifluoromethyl)-1H-pyrazole;
5-[5-[4-(2-furyl)phenyl-3-(trifluoromethyl)-1H-pyrazol-1-yl]-2-(methylsulfonyl) phenyl]methanol;
5-[4-(2-furyl)phenyl]-1-[3-methyl-4-(methylsulfonyl) phenyl]-3-(trifluoromethyl)-1H-pyrazole;
1-[3-chloro-4-(methylsulfonyl)phenyl]-5-4-(4-thiazolyl) phenyl]-3-trifluoromethyl-1H-pyrazole;
5-[4-(2-furyl)phenyl]-1-[3-(methoxymetyl)-4-(methylsulfonyl)phenyl]-3-(trifluoromethyl)-1H-pyrazole;
N-[5-[5-[4-(2-furyl)phenyl]-3-(trifluoromethyl)-1H-pyrazol-1-yl]-2-(methylsulfonyl)benzyl]-N-methylamine hydrochloride;
5-[5-[4-(2-furyl)phenyl]-3-(trifluoromethyl)-1H-pyrazol-1-yl]-2-(methylsulfonyl)phenyl]methanamine hydrochloride;
1-[3-fluoro-4-(methylsulfonyl)phenyl]-5-[4-(2-furyl) phenyl]-1H-pyrazole;
4-cyano-1-[3-fluoro-4-(methylsulfonyl)phenyl]-5-[4-(2-furyl)phenyl]-1H-pyrazole;
N-[1-[3-fluoro-4-(methylsulfonyl)phenyl]-5-[4-(1,3-thiazol-4-yl)phenyl]-1H-pyrazol-4-yl]acetamide;
4-[3-fluoro-4-(methylsulfonyl)phenyl]-3-[4-(1,3-thiazol-4-yl)phenyl]-2(5H)-furanone;
5,5-dimethyl-4-[4-(methylsulfonyl)phenyl]-3-[4-(1,3-thiazol-4-yl)phenyl]-2(5H)-furanone;
2-fluoro-4-[5-oxo-4-[4-(1,3-thiazol-4-yl)phenyl]-2,5-dihydro-3-furanyl]benzenesulfonamide;
4-[3-fluoro-4-(methylsulfonyl)phenyl]-5-methyl-3-[4-(1,3-thiazol-4-yl)phenyl]isoxazole;
5-[3-fluoro-4-(methylsulfonyl)phenyl]-2-methyl-4-[4-(1,3-thiazol-4-yl)phenyl]-1,3-oxazole;
4-[3-fluoro-4-(methylsulfonyl)phenyl]-5-methyl-3-[3-methyl-4-(1,3-thiazol-4-yl) phenyl]isoxazole;
4-{5-methyl-3-[4-(1,3-thiazol-4-yl)phenyl]-4-isoxazolyl}benzenesulfonamide;
2-fluoro-4-{5-methyl-3-[4-(1,3-thiazol-4-yl)phenyl]-4-isoxazolyl}benzenesulfonamide;
5-[3-fluoro-4-(methylsulfonyl)phenyl]-2-methyl-4-[3-methyl-4-(1,3-thiazol-4-yl)phenyl]-1,3-oxazole;
2-fluoro-4-[5-[3-hydroxy-4-(1,3-thiazol-4-yl)phenyl]-3-(trifluoromethyl)-1H-pyrazol-1-yl]benzenesulfonamide;
2-fluoro-4-[5-[3-methoxy-4-(1,3-thiazol-4-yl)phenyl]-3-(trifluoromethyl)-1H-pyrazol-1-yl]benzenesulfonamide;
2-fluoro-4-[5-[4-(1,3-thiazol-4-yl)-3-(trifluoromethyl) phenyl]-3-(trifluoromethyl)-1H-pyrazol-1-yl] benzenesulfonamide;
4-[2-ethyl-4-[1-[3-Fluoro-4-(methylsulfonyl)phenyl]-3-(trifluoromethyl)-1H-pyrazol-5-yl]phenyl]-1,3thiazole;
1-[3-fluoro-4-(methylsulfonyl)phenyl]-2-[3-methyl-4-(4-thiazolyl)phenyl]-4-trifluoromethyl-1H-imidazole;
2-fluoro-4-[4-methyl-2-[4-(4-thiazolyl)phenyl]-1H-imidazol-1-yl]benzenesulfonamide;
5-[3-chloro-5-methyl-4-(4-thiazolyl)phenyl]-1-[3-fluoro-4-(methylsulfonyl) phenyl]-3-trifluoromethyl-1H-pyrazole;
4-chloro-1-[3-fluoro-4-(methylsulfonyl)phenyl]-5-[3-methyl-4-(4-thiazolyl) phenyl]-3-trifluoromethyl-1H-pyrazole;
4-[4-(methylsulfonyl)phenyl]-3-[4-(1,3-thiazol-4-yl) phenyl]-2(5H)-furanone;
4-[5-oxo-4-[4-(1,3-thiazol-4-yl)phenyl]-2,5-dihydro-3-franyl]benzenesulfonamide;
5,5-dimethyl-3-[3-methyl-4-(1,3-thiazol-4-yl)phenyl]-4-[4-(methylsulfonyl) phenyl]-2(5H)-furanone;
2-methyl-4-[4-(methylsulfonyl)phenyl]-5-[4-(1,3-thiazol-4-yl)phenyl]-1,3-thiazole;
1-[4-(methylsulfonyl)phenyl]-5-[2-methyl-4-(4-thiazolyl) phenyl]-3-trifluoromethyl-1H-pyrazole;
1-[3-fluoro-4-(methylsulfonyl)phenyl]-5-[2-methyl-4-(4-thiazolyl)phenyl]-3-trifluoromethyl-1H-pyrazole;
2-fluoro-4-[5-methyl-3-[3-methyl-4-(1,3-thiazol-4-yl) phenyl]-4-isoxazolyl]benzenesulfonamide;
5-methyl-3-[4-(methylsulfonyl)phenyl]-4-[4-(1,3-thiazol-4-yl)phenyl]isoxazole;
4-[3-methyl-5-[4-(1,3-thiazol-4-yl)phenyl]-4-isoxazolyl]benzenesulfonamide;
3-methyl-5-[4-(methylsulfonyl)phenyl]-4-[4-(1,3-thiazol-4-yl)phenyl]isoxazole;
2-fluoro-4-[2-methyl-5-[4-(1,3-thiazol-4-yl)phenyl]-1,3-oxazol-4-yl]benzenesulfonamide;
2-fluoro-4-[2-methyl-5-[4-(1,3-thiazol-4-yl)phenyl]-1,3-oxazol-4-yl]benzenesulfonamide;
3-(Difluoromethyl)-2-fluoro-4-[5-[3-methyl-4-(1,3-thiazol-4-yl)phenyl]-1H-pyrazol-1-yl]benzenesulfonamide;
2-Fluoro-4-[5-[2-fluoro-4-(1,3-thiazol-4-yl)phenyl]-3-(trifluoromethyl)-1H-pyrazol-1-yl]benzenesulfonamide;
2-Fluoro-4-[5-[2-chloro-4-(1,3-thiazol-4-yl)phenyl]-3-(trifluoromethyl)-1H-pyrazol-1-yl]benzenesulfonamide; and
2-Fluoro-4-[5-[3-ethyl-4-(1,3-thiazol-4-yl)phenyl]-3-(trifluoromethyl)-1H-pyrazol-1-yl]benzenesulfonamide.

Most preferred individual compounds are:
2-fluoro-4-[5-[3-methyl-4-(1,3-thiazol-4-yl)phenyl]-3-(trifluoromethyl)-1H-pyrazol-1-yl]benzenesulfonamide;
4-{2-methyl-4-[1-[4-(methylsulfonyl)phenyl]-3-(trifluoromethyl)-1H-pyrazol-5-yl]phenyl}-1,3thiazole;
3-fluoro-4-[5-[3-methyl-4-(4-thiazolyl)phenyl]-3-(trifluoromethyl)-1H-pyrazol-1-yl]benzenesulfonamide;
4-{2-chloro-4-[1-[4-(methylsulfonyl)phenyl]-3-(trifluoromethyl)-1H-pyrazol-5-yl]phenyl}-1,3-thiazole;
2-fluoro-4-[5-[3-methyl-4-(1,3-oxazol-4-yl)phenyl]-3-(trifluoromethyl)-1H-pyrazol-1-yl]benzenesulfonamide;
1-[3-Fluoro-4-(methylsulfonyl)phenyl]-5-[4-(3-furyl) phenyl]-3-(trifluoromethyl)-1H-pyrazole;
4-{4-[1-[3-fluoro-4-(methylsulfonyl)phenyl]-3-(trifluoromethyl)-1H-pyrazol-5-yl]-2methylphenyl}-1,3thiazole;
4-[5-[4-(1,3-oxazol-4-yl)phenyl]-3-(trifluoromethyl)-1H-pyrazol-1-yl]benzenesulfonamide;
4-[5-[3-methyl-4-(1,3-oxazol-4-yl)phenyl]-3-(trifluoromethyl)-1H-pyrazol-1-yl]benzenesulfonamide;
1-[3-Fluoro-4-(methylsulfonyl)phenyl]-5-[4-(2-furyl) phenyl]-3-(trifluoromethyl)-1H-pyrazole;
1-[4-(Methylsulfonyl)phenyl]-5-[3-fluoro-4-(2-furyl) phenyl]-3-(trifluoromethyl)-1H-pyrazole;

1-[3-Fluoro-4-(methylsulfonyl)phenyl]-5-[4-(2-thienyl)
    phenyl]-3-(trifluoromethyl)-1H-pyrazole;
1-[3-Fluoro-4-(methylsulfonyl)phenyl]-5-[4-(3-thienyl)
    phenyl]-3-(trifluoromethyl)-1H-pyrazole;
1-[4-(Methylsulfonyl)phenyl]-5-[4-(2-furyl)-3-
    methoxyphenyl]-3-(trifluoromethyl)-1H-pyrazole;
1-[3-Fluoro-4-(methylsulfonyl)phenyl]-5-[3-chloro-4-(2-
    furyl)phenyl]-3-(trifluoromethyl)-1H-pyrazole;
4-{4-[1-[4-(methylsulfonyl)phenyl]-3-(trifluoromethyl)-
    1H-pyrazol-5-yl]phenyl}-1,3-oxazole;
4-{4-[1-[3-fluoro-4-(methylsulfonyl)phenyl]-3-
    (trifluoromethyl)-1H-pyrazol-5-yl]-2-methoxyphenyl}-1,
    3-thiazole;
4-{2-methyl-4-[1-[4-(methylsulfonyl)phenyl]-3-
    (trifluoromethyl)-1H-pyrazol-5-yl]phenyl}-1,3-oxazole;
2-fluoro-4-[5-oxo-4-[4-(1,3-thiazol-4-yl)phenyl]-2,5-
    dihydro-3-furanyl]benzenesulfonamide; and
1-[3-fluoro-4-(methylsulfonyl)phenyl]-2-[4-(4-thiazolyl)
    phenyl]-4-trifluoromethyl-1H-imidazole.

Also, preferred intermediates of this invention is selected
from
3-fluoro-4-(methylsulfonyl)phenylhydrazine hydrochloride;
3-methoxy-4-(methylsulfonyl)phenylhydrazine hydrochloride;
3-fluoro-4-sulfamoylphenylhydrozine hydrochloride;
2-fluoro-4-sulfamoylphenylhydrazine hydrochloride;
2-methyl-4-(methylsulfonyl)phenylhydrazine hydrochloride;
3-methyl-4-sulfamoylphenylhydrozine hydrochloride;
2-methyl-4-sulfamoylphenylhydrozine hydrochloride.
2-methoxy-4-(methylsulfonyl)phenylhydrazine hydrochloride;
3-methoxy-4-sulfamoylphenylhydrozine hydrochloride;
3-hydroxymethyl-4-(methylsulfonyl)phenylhydrazine
    hydrochloride; and
3-methyl-4-(methylsulfonyl)phenylhydrazine hydrochloride.

General Synthesis

The compounds of general formula (I) can be prepared by
a variety of synthetic routes. The following representative
examples as described hereinafter are illustrative and are not
meant to limit the scope of the invention in anyway. Unless
otherwise stated, A, $R^1$, $R^2$, $R^3$, $R^4$, $R^5$, $R^6$ and $R^7$ are as
defined herein before.
1) Synthesis of Compound (I) by A Ring Formation Compound (I) can be synthesized by a variety of A ring
formation methods.

(I)

Pryazole

When A is a pyrazole ring, the pyrazole (Ia) can be
prepared from an appropriate 1,3-diketone or its equivalents
(2 or 3) and phenylhydrazine (4), as shown in scheme I.

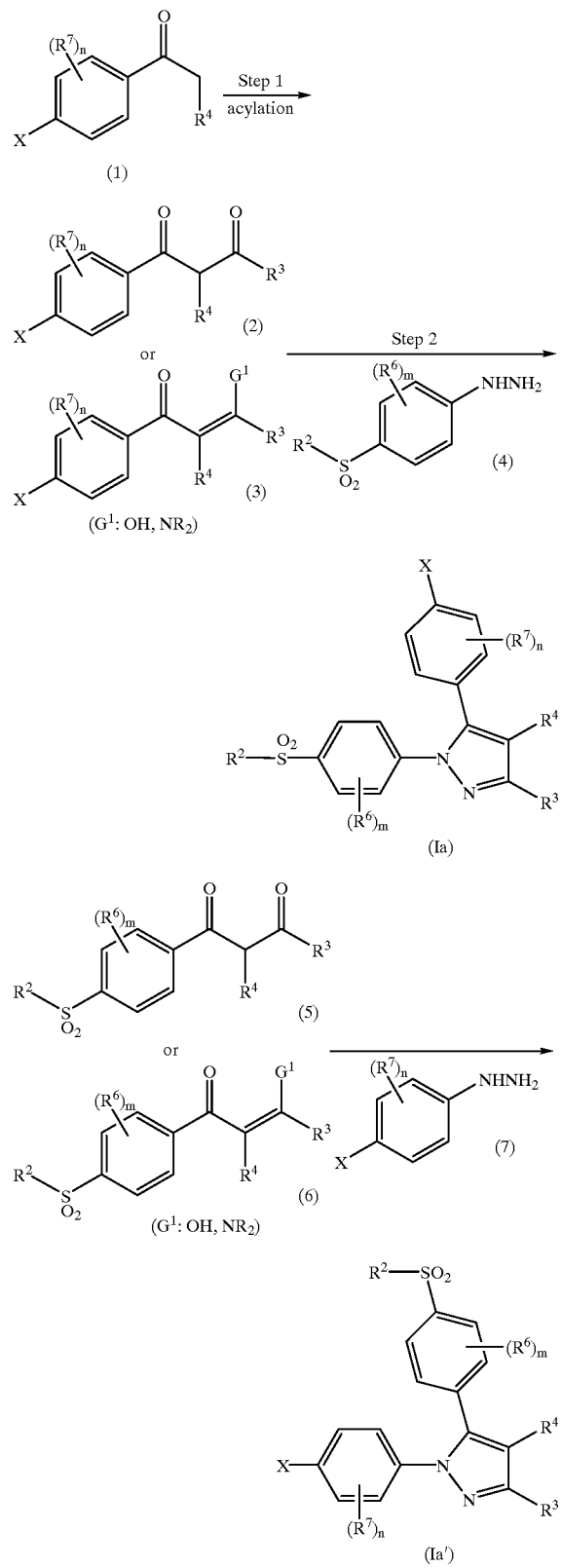

In step 1, ketone (1) is treated with a base (e.g., NaOMe, NaH and Me$_3$Si$_2$NLi preferably NaOMe, wherein Me represents methyl) and an acylating reagent (e.g., ester or ester equivalent such as acylimidazole, dialkylamide and dialkylacetal), in a solvent such as diethylether, tetrahydrofuran, methanol, dichloromethane and methyl tert-butyl ether, to form the 1,3-diketone (2) or 1,3-diketone equivalent (3) (G$^1$ is OH or NR$_2$:R=C$_{1-4}$ alkyl). X in Scheme I is R$^1$, chloro, bromo or OH.

In step 2, the 1,3-diketone (2) or 1,3-diketone equivalent (3) is treated with the salt (such as hydrochloride, hydrobromide, sulfate and oxalate) or the free base of the hydrazine derivative (4) in an anhydrous protic solvent such as ethanol or acetic acid at reflux temperature for from 2 hours to 20 hours to afford the pyrazole compound (Ia).

The starting materials (1) are either commercially available or can be prepared by the method described in *Aust. J. Chem.*, 1977, 30, 229 and Heterocycles, 1990, 31, 1951 and which are incorporated by reference. The regio isomeric pyrazole (Ia') can be also prepared from the corresponding 1,3-diketone (5) or 1,3-diketone equivalent (6) and phenyhydrazine (7), which is well known in the art.

Furanone

Furanone (Ib) can be prepared from aryl bromomethyl ketone (8) and aryl acetic acid (9).

Scheme II

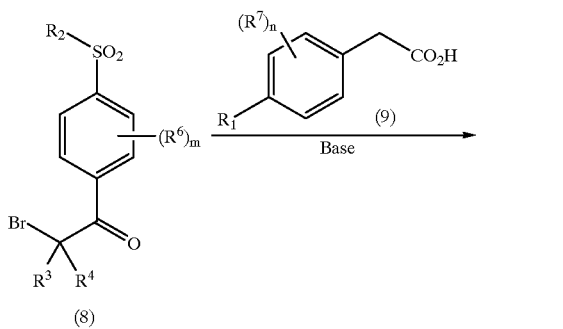

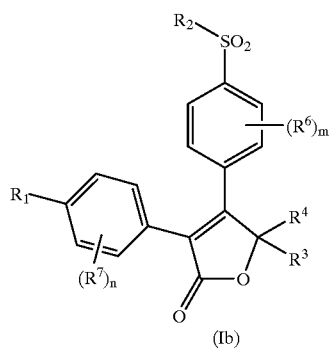

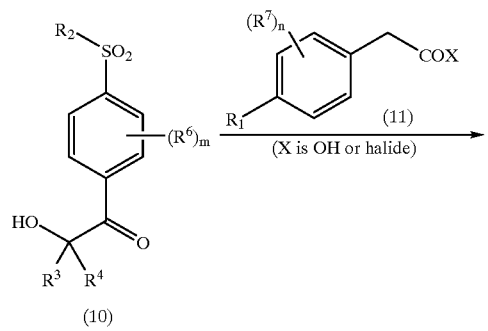

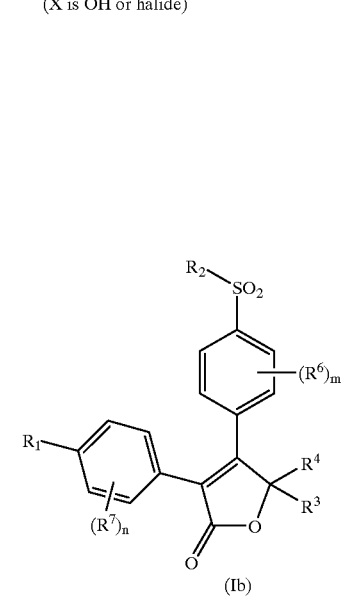

As shown in Scheme II, an appropriately substituted aryl bromomethyl ketone (8) is reacted with an appropriately substituted arylacetic acid (9) in a solvent such as acetonitrile, dimethylsulfoxide, dimethoxyethane and diethylether in the presence of a base such as triethylamine and diisopropylethylamine and then treated with 1,8-diazabicyclo[5.4.0]undec-7-ene (DBU) to afford the furanone (Ib). The α-bromomethylketone (8) can be easily obtained by halogenation of the corresponding acetophenone, which is well known in the art.

Furanone (Ib) can be also prepared by the reaction of α-hydroxy ketone (10) with (11) (X=OH) in the presence of coupling reagent such as 1-cyclohexyl-3-(2-morpholinoethyl)carbodiimide and metho-p-toluenesulfonate, and further treatment with a base such as DBU.

Imidazole

Imidazole (Ic) can be prepared by the reaction of amidine (14) and α-haloketone (15) followed by the dehydration as shown in Scheme III.

Scheme III

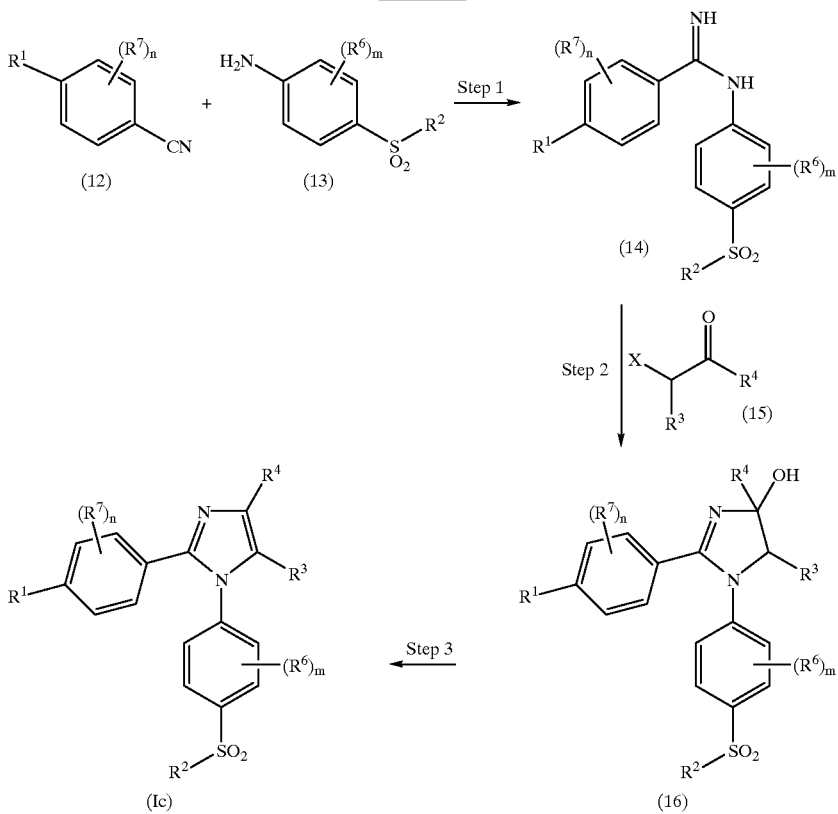

In step 1, the reaction of substituted nitrile (12) with primary phenylamine (13) in the presence of alkylaluminium reagents such as trimethylaluminium, triethylaluminium, diethylaluminium chloride, diethylaluminium chloride in the presence of inert solvents such as toluene, benzene and xylene, gives amidine (14).

In step 2 the reaction of amidine (14) with α-haloketone (15) (where X is bromo or chloro) in the presence of base, such as sodium bicarbonate, potassium carbonate, sodium carbonate and potassium bicarbonate, or hindered tertiary arnines such as N,N'-diisopropylethylamine in the presence of inert solvents such as isopropanol, acetone, and dimethylformamide at a temperature of about 0° C. to about 120° C., for 30 min. to 2 days, preferably at a temperature of about 20° C. to about 100° C., for 30 min. to 8 hours, gives the 4,5-dihydrolmidazole (16).

The obtained 4,5-dihydrolmidazole (16) may be dehydrated in the presence of an acid catalyst such as 4-toluenesulfonic acid, trifluoroacetic acid and mineral acids (such as hydrochloric acid) to form the 1,2-disubstituted Imidazole (Ic) of this invention (step 3). A suitable solvent for this dehydration step are e.g., toluene, xylene or benzene. A compound of (Ic) wherein $R^2$ is amino can be prepared by using a compoud of (Ic) wherein $R^2$ is methyl, for example by the Huang method (*Tetrahedron Lett.*, 1994, 35, 7201.).

In some cases the intermediate (16) may not be readily isolated. The reaction, under the conditions described above, proceeds to give the Imidazole (Ic) directly.

Pyrrole

Pyrrole can be prepared by the Paal-Knorr's method, which is well known in the art (scheme IV).

Scheme IV

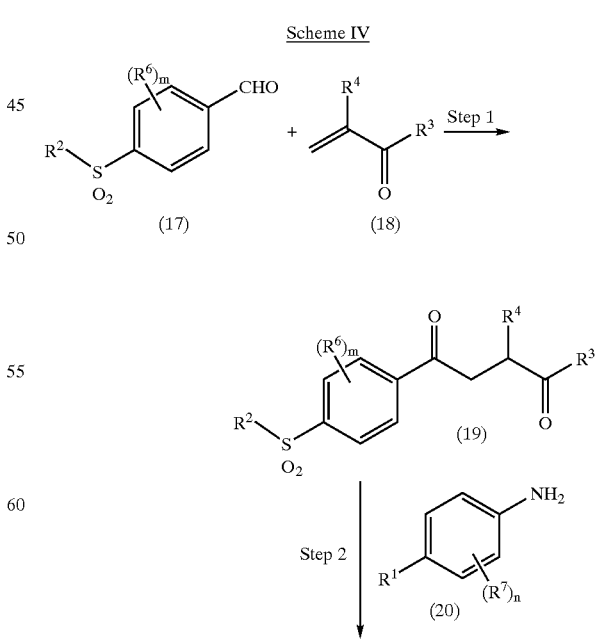

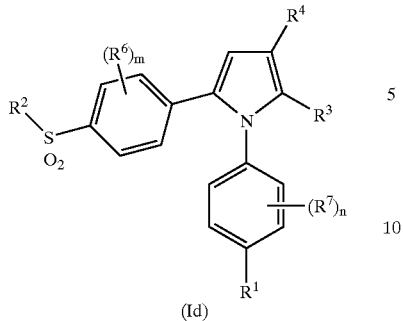

(Id)

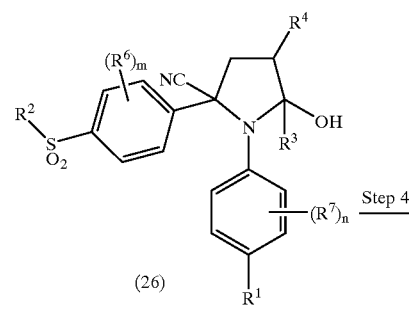

(26)

Step 4

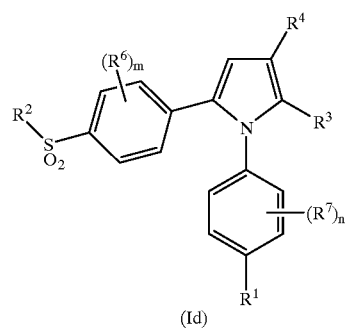

(Id)

The preparation of suitable 1,4-diketone (19) by the Stetter reaction (for a review on Stetter reaction, *Angew. Chem., Int. Ed. Engl.* 1976, 15, 639.) followed by heating with appropriate amines (20) in the Paal-Knorr condensation gives the pyrrole (Id). The Stetter reaction of substituted benzaldehyde (17) with α,β-unsaturated ketone (18) using the thiazolium salt catalyst in the presence of bases such as triethylamine, diisopropylethylamine and pyridine, gives the 1,4-diketone (19). Suitable solvents for this reaction are methanol, ethanol or isopropanol. The reaction may be carried out at temperatures of about 0° C. to about 120° C. for 15 minutes to 2 days, preferably at temperatures of about 20° C. to about 90° C. for 30 minutes to 1 days. The condensation of 1,4-diketone (19) with arylamine (20) in the presence of an acid catalyst such as 4-toluenesulfonic acid gives the pyrrole (Id). Suitable solvents for this condensation step are e.g., toluene, xylene or benzene. A compound of (Id) wherein $R^2$ is amino can be prepared by using a compoud of (Id) wherein $R^2$ is methyl, for example by the Huang method (*Tetrahedron Lett.,* 1994, 35, 7201.).

Alternatively, the pyrrole (Id) can be prepared as shown in Scheme V.

Scheme V

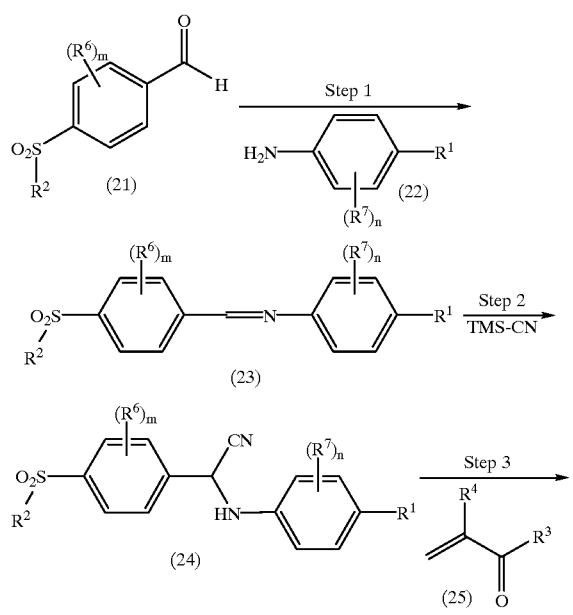

In step 1, an aldimine (23) can be prepared by the dehydration condensation of a benzaldehyde (21) with an aniline (22) in an inert solvent. The reaction is normally and preferably effected in the presence of a solvent. Examples of suitable solvents include aliphatic hydrocarbons such as hexane and heptane; aromatic hydrocarbons such as benzene and toluene; halogenated hydrocarbons such as methylene chloride and chloroform; ether such as diethyl ether, tetrahydrofuran and dioxane; alcohol such as methanol, ethanol and isopropanol. Among these solvents, the alcohol would be preferable. This reaction can be carried out at a temperature of from 5° C. to 200° C., preferably from room temperature to 150° C. for from 10 minutes to 20 hours, more preferably from1hour to 15 hours.

In step 2, an anilinonitrile (24) can be prepared by an addition of hydrogen cyanide to the aldimine (23). prepared as described in step 1. The reaction may be carried out by reacting the aldimine (23) with trimethylsilyl cyanide (TMS-CN) in the presence of a Lewis acid, for example, aluminium chloride, tin chloride and zinc chloride in an inert solvent such as diethyl ether, tetrahydrofuran, dioxane, benzene, and methylene chloride, preferably diethyl ether and tetrahydrofuran. This reaction can be carried out at a temperature of from 5° C. to 200° C., preferably from room temperature to 150° C. for from 10 minutes to 50 hours, more preferably from 1 hour to 20 hours.

In step 3 and 4, the pyrrole (Id) can be prepared by reacting the anilinonitrile (24), prepared as described in step 2, with an α,β-unsaturated aldehyde or ketone (25) to obtain a pyrrolidine compound (26), which can be then dehydrated and dehydrogencyanated.

In step 3, the reaction may be carried out by reacting the anilinonitrile (24) with an α,β-unsaturated aldehyde or ketone (25) in the presence of a base, such as lithium amide, sodium amide, potassium amide, lithium bis(trimethylsilyl) amide, and sodium methoxide, preferably lithium bis(trimethylsilyl)amide in an inert solvent such as diethyl ether, tetrahydrofuran, dioxane, benzene, and methylene chloride, preferably diethyl ether and tetrahydrofuran. This reaction can be carried out at a temperature of from −78° C. to 100° C., preferably from −78° C. to room temperature for from 10 minutes to 30 hours, preferably from 1 hour to 15 hours.

In step 4, the pyrroles (Id) can be prepared by the dehydration and dehydrogencyanation of the pyrrolidine compound (26). This may be achieved by heating the crude product obtained by evaporation of the solvent from the product of step 3, or by heating the crude material obtained by the extraction, at a temperature of from 80° C. to 250° C., in the presence or absence of a solvent after completion of the reaction of step 3. Suitable solvent would be toluene, xylene, diglyme, diphenyl ether, dimethylformamide or the like.

Oxazole

Oxazole (Ie) can be prepared according to the following procedures of Scheme VI.

The oxazole (Ie) can be prepared by heating the α-carbonyloxy ketone (31) in a lower alklcarboxylic acid such as acetic acid, formic acid and propionic acid in the presence of ammonium acetate, ammonium formate and ammonium carbonate. preferably ammonium acetate.

Alternatively, the α-carbonyloxy ketone (31) can be prepared from the corresponding α-hydroxy ketone (32) or α-halo ketone (33) by reacting with an appropriate acid halide or carboxylic acid in the presence of a base such as pyridine and triethylamine in an inert solvent such as methylene chloride and chloroform at a temperature of −10° C. to 100° C. The corresponding α-hydroxy ketone (32) or α-halo ketone (33) can be prepared by oxidation of the

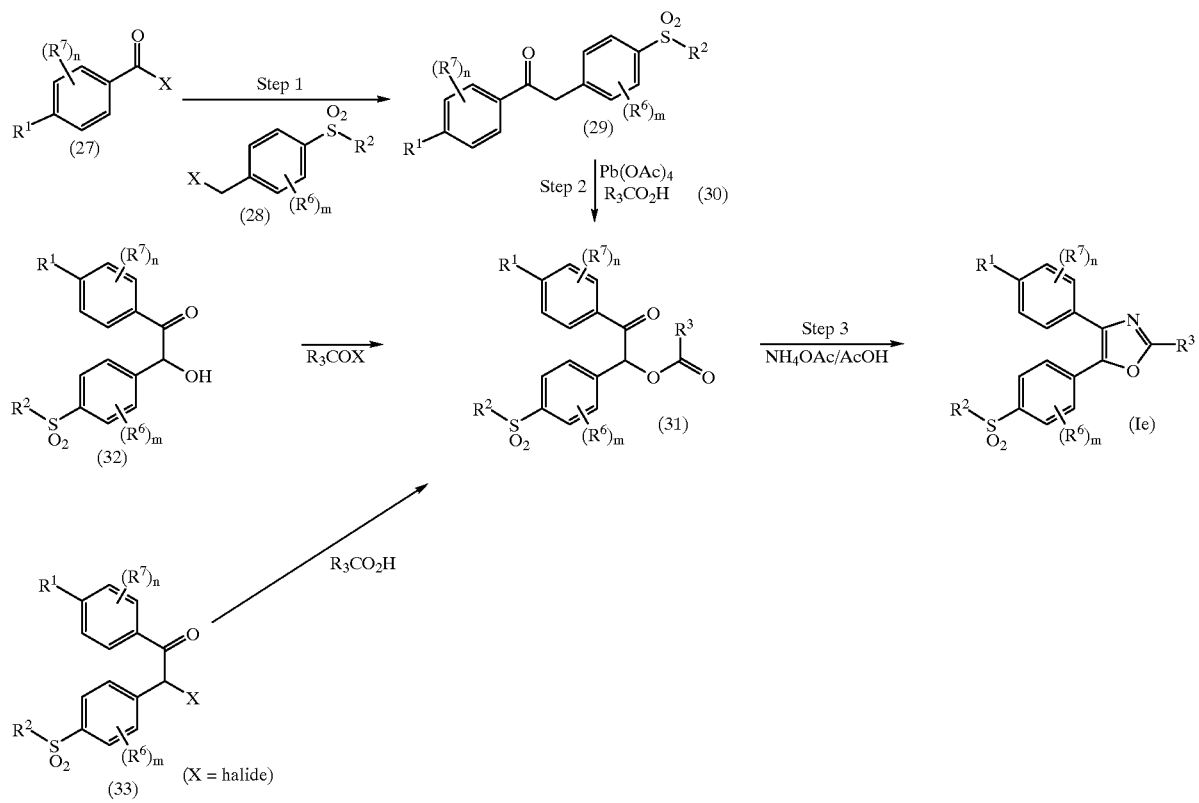

Scheme VI

In step 1, the ketone (29) can be prepared by the reaction of acid halide (27) with 4-sulfonylbenzyl halide (p)referably X=Cl or Br) (28) in the presence of metal such as zinc and magnesium, preferably zinc, in an inert solvent such as 1,2-dimethoxyethane, dioxane, diethyl ether, tetrahydrofuran, methylene chloride, benzene, and toluene at a temperature of from 0° C. to 150° C., preferably from room temperature to 50° C. for from 10 minutes to 30 hours, preferably from 1 hour to 15 hours. Suitable catalyst e.g., tetrakis(triphenylphosphine)palladium can be used in this reaction. In step 2, the α-carbonyloxy ketone (31) can be prepared by the reaction of ketone (29), prepared as described above, with an appropriate carboxylic acid (30) in the presence of lead (IV) acetate and manganese (III) acetate in the presence or absence of a solvent, but when a solvent is used, suitable solvent would be benzene, toluene and xylene. This reaction can be carried out at a temperature of from room temperature to 150° C., preferably from 50° C. to 120° C. for from 10 minutes to 30 hours, more preferably from1hour to 15 hours.

ketone (29) by using iodobenzene diacetate, or by halogenation of the ketone by using bromine, chlorine, and N-bromosuccineimide in the presence of an inert solvent such as 1,2-dimethoxyethane, dioxane, diethyl ether, tetrahydrofuran, benzene and toluene. A compound of (Ie) wherein $R^2$ is amino can be prepared by using a compoud of (Ie) wherein $R^2$ is methyl, for example by the Huang method (*Tetrahedron Lett.*, 1994, 35, 7201.).

The regioisomeric oxazole can be prepared from the corresponding sulfonylbenzoic acid halide and benzyl halide.

Thiophene

Thiophene analogs can be prepared as shown in scheme VII.

Scheme VIII

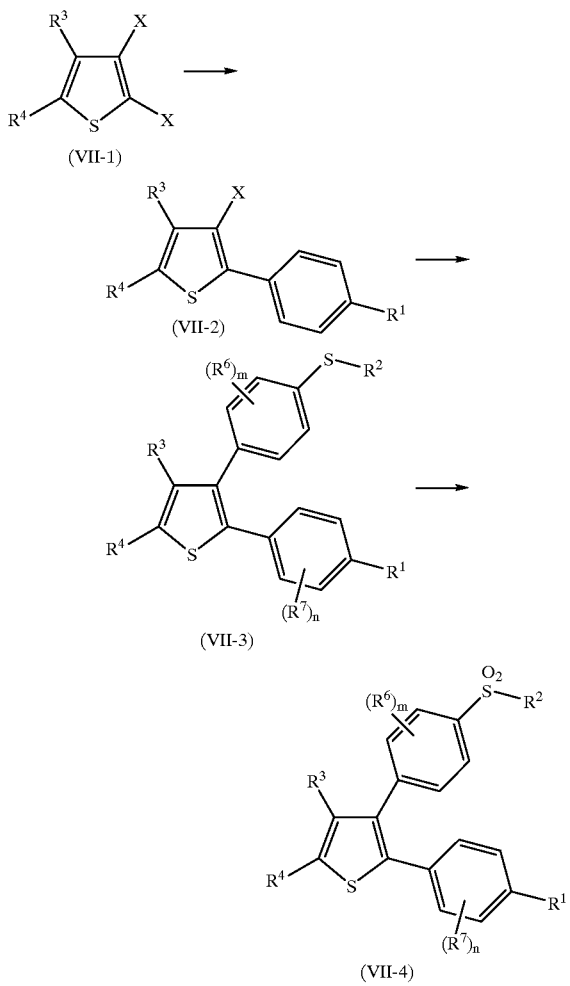

The Suzuki coupling of 2,3-dihalothiophene (VII-1) with 4-(aryl or heteroaryl)phenylboronic acid. followed by the second coupling with 4-($R^2$-thio)phenylboronic acid provides 2-[4-(aryl or heteroaryl)phenyl]-3-[4-(methylthio) phenyl]thiophene. The obtained thiophene (VII-3) may be oxidated by the methods known in the art to give the methylsulfonyl analogs (VII-4).

Alternatively, the other arylmetal reagents such as aryl Grignard reagent, arylzinc reagent, aryltin reagent, or arylsilyl reagent instead of arylboronic acid can be used in this reaction.

The reaction of arylboronic acid with 2,3-dihalothiophene may be carried out in a solvent such as benzene, toluene, dimethoxyethane, dimethylformamide, preferably dimethoxyethane, typically in the presence of a base such as pottasium hydroxide, thallium hydroxide, triethylamine, sodium bicarbonate, or a combination of water and alone solvent preferably water and dimethoxyethane. The catalyst may be selected from those typically employed for the so-called Suzuki reaction (for example, tetrakis (triphenylphosphine)palladium and dichloro bis (triphenylphosphine)palladium). The reaction is carried out at a temperature in the range from 20 to 160° C., usually 60 to 130° C. for 10 minutes to 5 days, usually 30 minutes to 15 hours.

Isoxazoles

When A is an isoxazole ring, the isoxazole derivatives (If), (Ig), and (Ig') can be prepared from appropriate oximes (40) and (47) as shown in scheme VIII and IX.

3,4-Diphenylisoxazoles

Synthesis of 3,4-diphenylisoxazole is shown in scheme VIII.

Scheme VIII

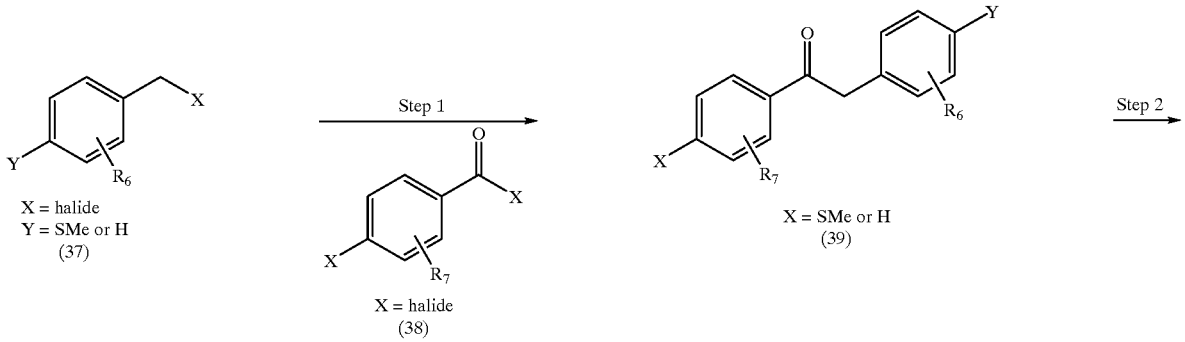

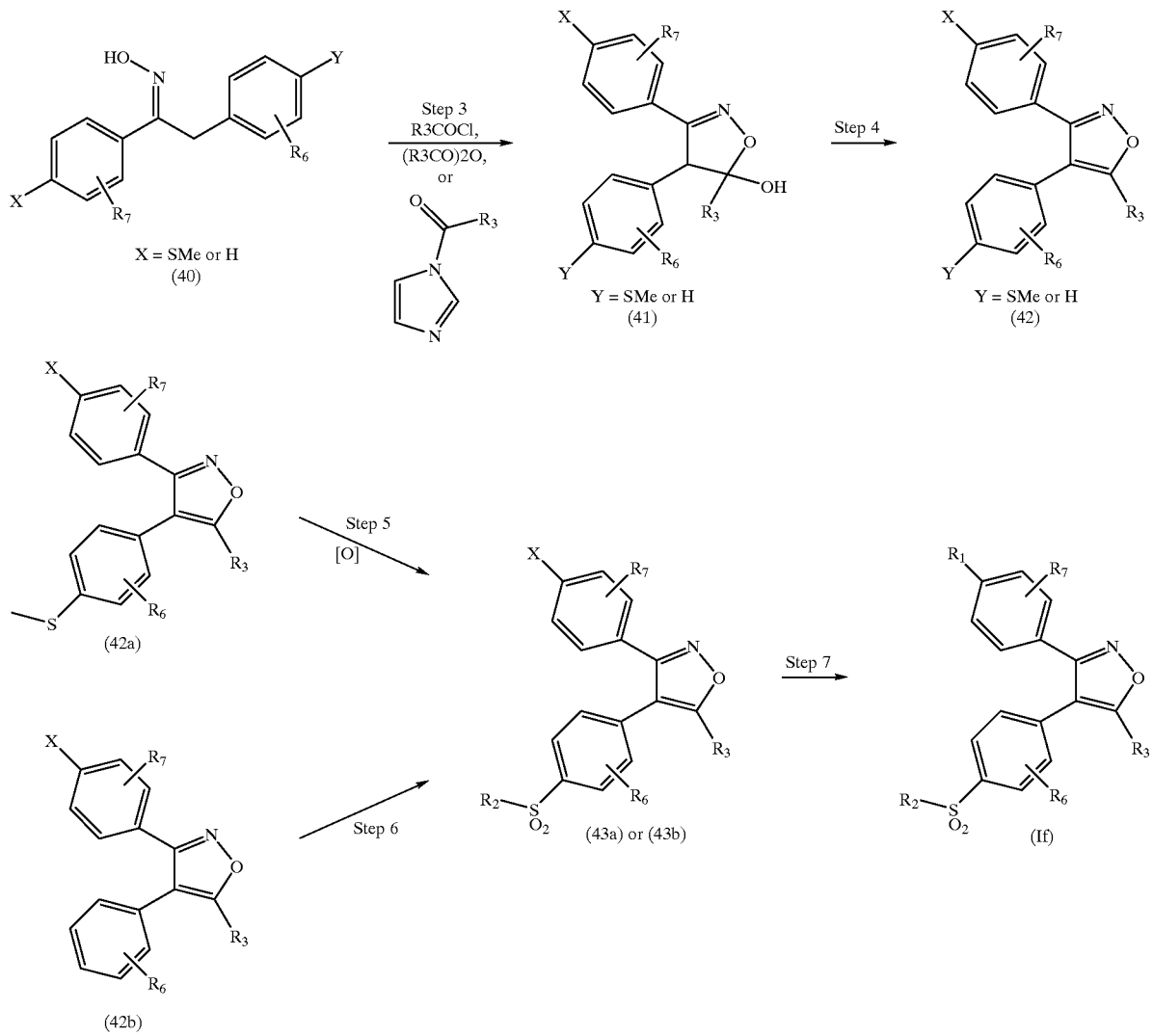

In step 1, the ketone (39) can be prepared from the benzyl halide (37) and the acid halide (38), according to the procedure described in step 1 in oxazole synthesis (Scheme VI).

In step 2, the oxime (40) can be obtained by treatment of the ketone (39) with hydroxylamine hydrochloride in the presence of base such as sodium acetate, in an inert solvent such as water, methanol, ethanol, i-propanol, tetrahydrofuran, 1,4-dioxane, diethyl ether, or a mixture of the above described solvents, preferably a mixture of water and ethanol. This reaction can be carried out at a temperature of from 0° C. to reflux temperature, preferably from 50° C. to reflux temperature for from 15 minutes to 24 hours, preferably from 1 hour to 15 hours.

In step 3, the 4,5-dihydroisoxazole (41) can be prepared via C-acylation of the oxime (40), followed by spontaneous cyclization. This reaction may be carried out by reacting the oxime (40) with an acyl halide, acid anhydride, N-acylimidazole, and carboxamide, in the presence of base such as lithium amide, sodium amide, potassium amide, lithium diisopropylamide, lithium bis(trimethylsilyl)amide, sodium bis(trimethylsilyl)amide, and potassium bis(trimethylsilyl)amide, preferably lithium diisopropylamide, in an inert solvent such as tetrahydrofuran, diethyl ether, 1,2-dimethoxyethane, dioxane, benzene, and methylene chloride, preferably diethyl ether and tetrahydrofuran, at a temperature of from −78° C., to 100° C., preferably −78° C. to room temperature for from 10 minutes to 30 hours, preferably from 30 minutes to 15 hours.

In step 4, the isoxazole (42) can be obtained by dehydration of the dihydroisoxazole (41) using acid. This may be achieved by heating the dihydroisoxazole (41) with acid, such as hydrochloric acid, hydrobromic acid, sulfuric acid, methanesulfonic aicd, p-toluenesulfonic acid, and polyphosphoric acid, in an inert solvent such as methanol, ethanol, 2-propanol, tetrahydrofuran, diethyl ether, 1,4-dioxane, benznen, toluene, xylene, diglyme, dimethylforamide, dimethylsulfoxide or the like, at a temperature of from 40° C. to reflux temperature, preferably 50° C. to 100° C., for from 10 minutes to 30 hours, preferably 30 miutes to 15 hours.

In step 5, the sulfone (43a) can be prepared by oxidation of the sulfide (42a). This reaction may be carried out with an oxidant such as mCPBA, peracetic acid, hydrogen peroxide, and oxone®, in an inert solvent such as chloroform, tetrachlorocarbon, dichloromethane, acetic acid, preferably dichloromethane, at a temperature of from −20° C. to reflux temperature, preferably 0° C. to 50° C., for from 15 minutes to 30 hours, preferably 30 minutes to 15 hours.

In step 6, the sulfonamide (43b) can be prepared by after reacting the isoxazole (42b) with chlorosulfonic acid at a temperature of from −78° C. to 100° C., preferably −78° C. to 70° C., for from 15 minutes to 30 hours, preferably 30 minutes to 15 hours, pouring the reaction mixture into a mixture of ice and concentrated ammonia.

In step 7, the isoxazole (If) can be obtained via the cross coupling reaction of the isoxazole (43), as described hereinafter.

The regioisomeric isoxazole can be prepared from the corresponding 4-methylthiobenzoyl halide and 4-bromobenzyl halide.

5 4,5-Diphenylisoxazoles

Synthesis of 4,5-diphenylisoxazole is shown in scheme IX.

Scheme IX

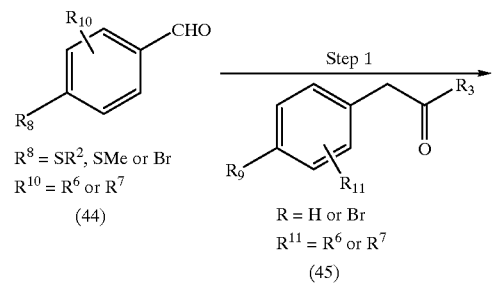

$R^8 = SR^2$, SMe or Br
$R^{10} = R^6$ or $R^7$
(44)

R = H or Br
$R^{11} = R^6$ or $R^7$
(45)

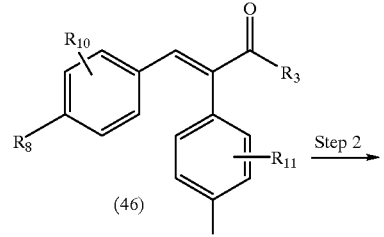

(46)

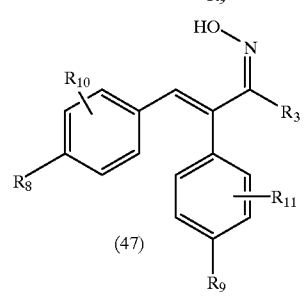

(47)

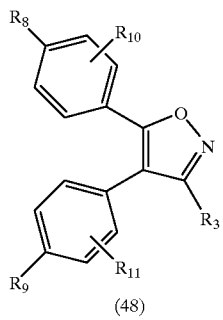

(48)

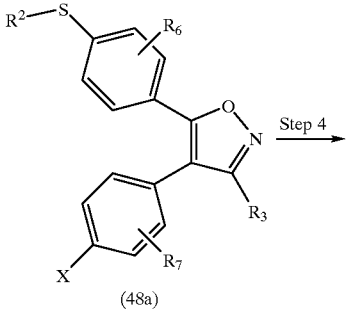

(48a)

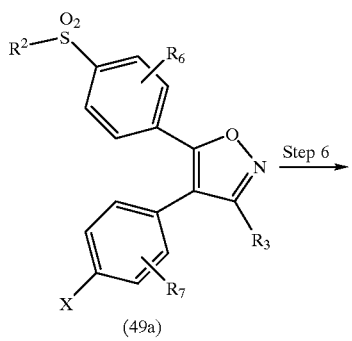

(49a)

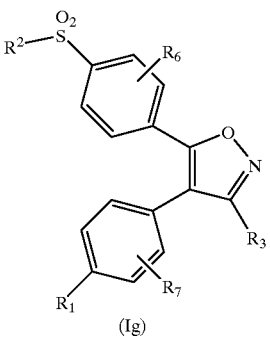

(Ig)

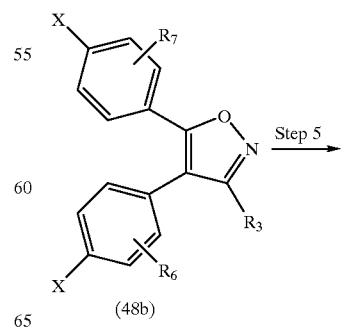

(48b)

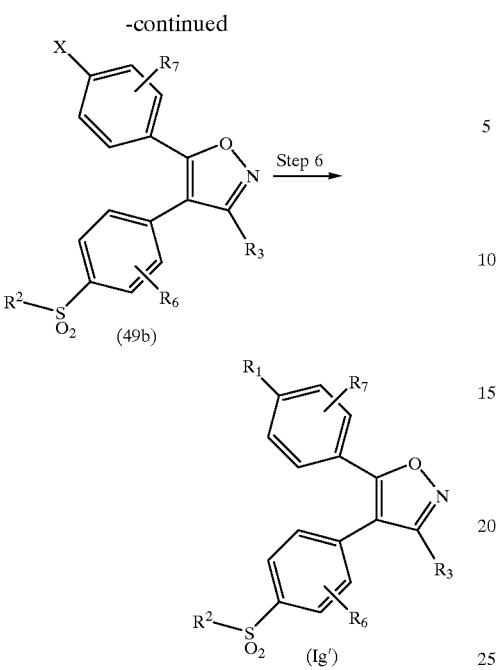

In step 1, the α,β-unsaturated ketone (46) can be prepared by aldol reaction of the benzaldehyde (44) with the ketone (45), followed by β-elimination, in the presence of base, such as potassium carbonate, sodium carbonate, sodium hydride, potassium hydride, lithium amide, sodium amide, potassium amide, litium diisoprppylamide, lithium bis(trimethylsilyl)amide, potassium bis(trimethylsilyl)amide. sodium bis(trimethylsilyl)amide, piperidine, and 1.8-diazabicyclo[5.4.0]undec-7-ene (DBU), preferably piperidine, in an inert solvent such as diethyl ether, tetrahydrofuran, 1,2-dimethoxyethane, 1,4-dioxane, benzene, toluene, xylene, and dimethyl sulfoxide, preferably benzene and toulene. This reaction may be carried out at a temperature of from −78° C. to reflux temperature, preferably room temperature to reflux temperature, for from 15 minutes to 50 hours, preferably 1 hour to 30 hours.

In step 2, the oxime (47) can be obtained from the ketone (46) according to the procedure described in step 2 in 3,4-diphenylisoxazole section.

In step 3, the isoxazole (48) can be prepared by treating the oxime (47) with a mixture of iodine and potassium iodide in the presence of base such as triethylamine, N,N-diisopropylethylamine, DBU, potassium carbonate, sodium carbonate, sodium hydrogen carbonate, potassium hydrogen carbonate, and their aqueous solution, in an appropriate solvent such as diethyl ether, tetrahydrofuran, 1,4-dioxane, 1,2-dimethoxyethane, benzene, toluene, xylene, dimethyl sulfoxide, and N,N-dimethylforamide, preferably tetrahydrofuran. This reaction may be carried out at a temperature of from 0° C. to reflux, preferably room temperature to reflux temperature, for from 15 minutes to 30 hours, preferably 30 minutes to 15 hours.

In step 4, the sulfone (49a) can be obtained from the sulfide (48a), according to the procedure described in step 5 in 3,4-diphenylisoxazole section.

In step 5, the sulfonamide (49b) can be obtained from the isoxazole (48b), according to the procedure described in step 6 in 3,4-diphenylisoxazole section.

In step 6, the isoxazoles (Ig) and (Ig') can be respectively obtained from the isoxazoles (49a) abd (49b) through the cross coupling reaction described hereinafter.

Thiazole

Scheme X

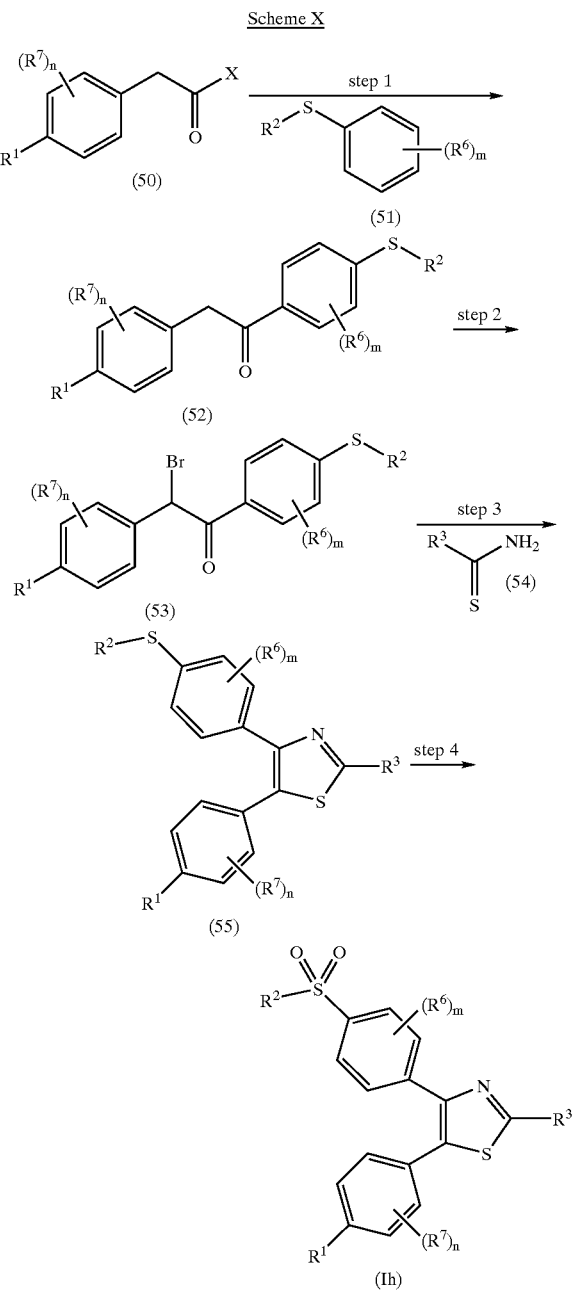

Thiazole can be prepared according to the following procedures of Scheme X. In step 1, the ketone (52) can be prepared by the Friedel Crafts acylation. Acid halide (50) (prferebly X═Cl or Br) is treated with and reacted with $R^2$-thiobenzene (51) and lewis acid such as aluminum chloride, titanium(IV) chloride, and tin(IV) chloride in an inert solvent such as methylene chloride, chloroform, nitrobenzene, dichlorobenzene, chlorobenzene and carbon disulfide, at a temperature of from 0° C. to reflux temperature, preferably from room temperature to 50° C. for from 10 minutes to 30 hours, preferebly from 1 hour to 20 hours. In step 2, the α-bromoketone (53) can be prepared by the reaction of ketone (52) with bromine in an inert solvent such as acetic acid, methylene chloride, chloroform, carbontetrachloride, dioxane, diethyl ether. This reaction can be carried out at a temperature of from room temperature to 150° C., preferably from 0° C. to 100° C. for from 10 minutes to 30 hours, preferably from 1 hour to 5 hours. In step 3, the thiazole ring can be prepared by the reaction of α-bromoketone (53) with the thioamide (54) in an inert solvent such as ethanol, methanol, dioxane, toluene, at a temperature of from 0° C. to reflux temperature, preferably from 50° C. to reflux temperature, for from 10 minutes to 30 hours, preferebly 1 hour to 20 hours. In step 4, Sulfonylbenzene (Ih) can be prepared by the oxidation of sulfide compound (55). This reaction may be carried out with an oxidizing agent such as mCPBA, peracetic acid, hydrogen peroxide and oxone®, preferably mCPBA, in an inert solvent such as tetrachlorocarbon, dichloromethane, chloroform, and acetic acid at a temperature of from −20° C. to reflux temperature, preferably 0° C. to 50° C., for from 10 minutes to 30 hours, preferably from 1 hour to 20 hours.

The compounds of formula (I) wherein A is other than the above-mentioned heterocyclic or carbocyclic, can be prepared according to the known methods.

2) Synthesis of Compound (I) by Cross Coupling Reaction

The compounds of formula (I) can be synthesized by using the method of Kharash, Negishi, Stille, or Suzuki et, al., which are well known in the art. In general, biaryl compounds are synthesized by a number of catalytic cross-coupling reactions from arylhalides or triflates and arylmetal reagents, [for example, Grignard reagent (the so-called Kharasch reaction), arylzinc reagent (the so-called Negishi reaction), aryltin reagent (the so-called still reaction), arylboron reagent (the so-called Suzuki reaction), arylsilyl reagent, etc. (review article showed be cited here; S. P. Stanforth, *Tetrahedron*, 1998, 54, 263–303]. These methods can be applicable to the preparation of compound (1). The compound (I) can be prepared from corresponding aryl halides or triflates (II) and aryl metal reagent (34), as shown in scheme XI.

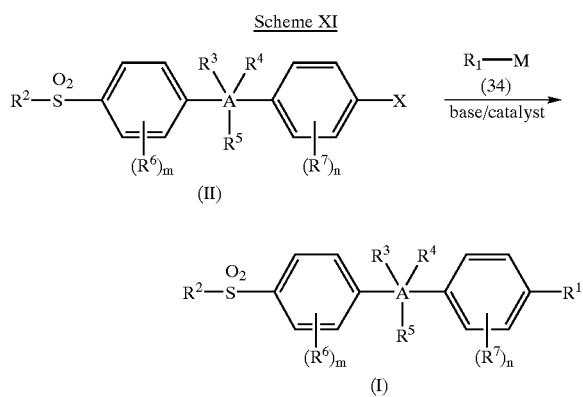

(wherein X is halide or triflate, and M is boronic acid, boronic ester, zinc halide, magnesium halide, or trialkyl tin groups)

The reaction of aryl or heteroarylboronic acid (34) with an arylhalide or triflate (II) may be carried out in a solvent such as benzene, toluene, dimethoxyethane, dimethylformamide, preferably dimethoxyethane, typically in the presence of a base such as pottasium hydroxide, thallium hydroxide, triethylamine, sodium bicarbonate, or a combination of water and alone solvent preferably water and dimethoxyethane. The catalyst may be selected from those typically employed for the so-called Suzuki reaction (for example, tetrakis(triphenylphosphine)palladium and dichloro bis(triphenylphosphine)palladium). The reaction is carried out at a temperature in the range from 20 to 160° C., usually 60 to 130° C. for 10 minutes to 5 days, usually 30 minutes to 15 hours.

The reaction of aryl or heteroarylzinchalide (34) with an arylhalide or triflate (II) may be carried out in a solvent such as tetrahydrofuran, diethylether and dimethoxyethane, preferably tetrahydrofuran. The catalyst may be selected from those typically employed for the so-called Negishi reaction (for example, tetrakis(triphenylphosphine)palladium, tetrakis(triphenylphosphine)nickel, dichlorobis(triphenylphosphine)palladium, dichlorobis(triphenylphosphine)palladium, /n-BuLi, dichlorobis(1,1-bis(diphenylphosphino)ferrocene)palladium and dichlorobis(1,4-bis(diphenylphosphino)butane)palladium,). The reaction is carried out at a temperature in the range from 20 to 160° C., usually 20 to 130° C. for 10 minutes to 5 days, usually 30 minutes to 15 hours.

The reaction of aryl or heteroaryltin reagent (34) with an arylhalide or triflate (II) may be carried out in a solvent such as dimethylformamide, tetrahydrofuran, 1,4-dioxane, benzene, toluene and dimethoxyethane, preferably tetrahydrofuran and 1,4-dioxane, if necessary, a salt such as lithium chloride, anmmonium hydroxide, copper(I) bromide, is used. The catalyst may be selected from those typically employed for the so-called Stille reaction (for example, tetrakis(triphenylphosphine)palladium and dichlorobis(triphenylphosphine)palladium). The reaction is carried out at a temperature in the range from 20 to 160° C. usually 20 to 100° C. for 10 minutes to 5 days, usually 30 minutes to 15 hours.

The reaction of aryl or hetero aryl Grignard reagent (34) with an arylhalide or triflate (II) may be carried out in a solvent such as tetrahydrofuran, 1,4-dioxane, benzene, toluene and dimethoxyethane, preferably tetrahydrofuran, 1,4-dioxane. The catalyst may be selected from those typically employed for the so-called Kharasch reaction (for example, dichlorobis(triphenylphosphine)nickel, dichlorobis(1,4-bis(diphenylphosphino)butane)nickel and dichlorobis(1,2-bis(diphenylphosphino)ethane)nickel,). The reaction is carried out at a temperature in the range from 20 to 160° C., usually 20 to 130° C. for 10 minutes to 5 days, usually 30 minutes to 15 hours.

As apparent to one skilled in the art, the compound (I) can be obtained from a reaction of the compound (III) or (IV), and the compound (36) as shown in scheme XII, Scheme XII

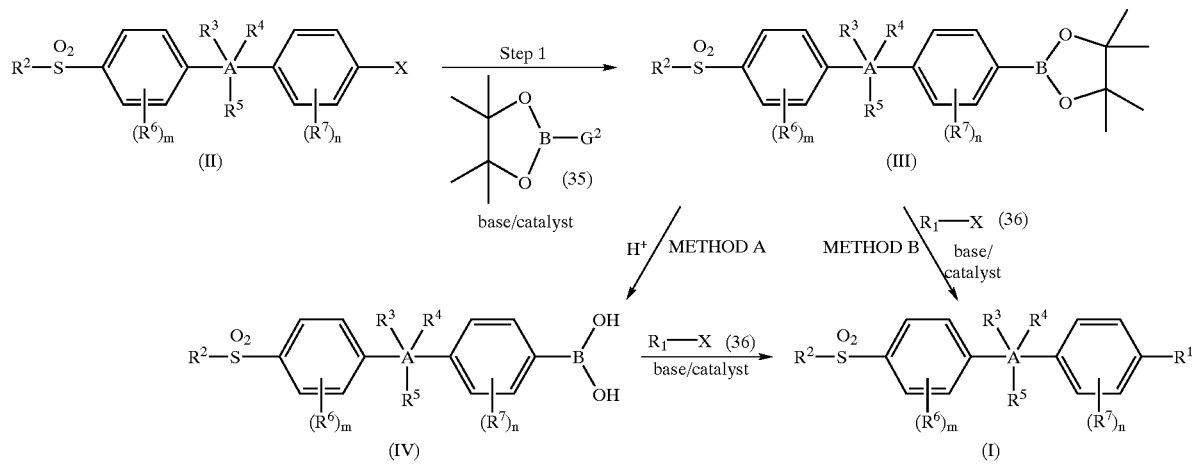

In step 1, the reaction of aryl halide (II) and boron reagent (35) ($G^2$ is H or $B(C_{1-4}alkyl)_2$) in an appropriate solvent such as dimethoxyethane and tetrahydrofuran in the presence of a catalyst such as tetrakis(triphenylphosphine)palladium, dichlorobis(triphenylphosphine)palladium and a base such as potassium acetate, triethylamine, at heating condition (ex. 80° C. to 100° C.) for 2 hours to 20 hours, gives boronic acid ester product (III).

The boronic acid ester (III) can be hydrolyzed by an acid catalyst such as 4-toluenesulfonic acid, trifluoroacetic acid, or mineral acids (sucn as hydrochloric acid) in a solvent such as tetrahydrofuranetoluene, diethylether, benzene, or a combination of water and alone solvent to form the boronic acid (IV).

The biaryl compound (I) can be prepared from boronic acid ester (III) or boronic acid (IV) and arylhalides or triflates (36) in the presence of a catalyst such as tetrakis(triphenylphosphine)palladium, dichlorobis(triphenylphosphine)palladium and a base such as pottasium phosphate, triethylamine, sodium bicarbonate and sodium carbonate, at heating condition (ex., 60° C. to 150° C. ) for 2 hours to 20 hours. Suitable solvents for this coupling reaction are for example benzene, toluene, dimethoxyethane, dimethylformamide, tetrahydrofuran, 1,4-dioxane, or a combination of water and alone solvent, preferably water and dimethoxyethane. The starting material (II), wherein X is halide or triflate can be prepared according to the methods as described in general synthesis 1), as apparent to one skilled in the art.

The starting materials in the aforementioned general syntheses may be obtained by conventional methods known to those skilled in the art. The preparation of such starting materials is described within the accompanying non-limiting examples which are provided for the purpose of illustration only. Alternatively, requisite starting materials may be obtained by analogous procedures, or modifications thereof, to those described hereinafter.

The products which are addressed in the aforementioned general syntheses and illustrated in the experimental examples described herein after may be isolated by standard methods and purification can be achieved by conventional means known to those skilled in the art, such as distillation, crystallization or chromatography techniques.

Certain compounds described herein contain one or more asymmetric centers and are capable of existing in various stereoisomeric forms. The present invention contemplates all such possible stereoisomers as well as their racemic and resolved, enantiomerically pure forms and pharmaceutically acceptable salts thereof.

Certain compounds of the present invention are capable of forming addition salts with inorganic or organic acids. The pharmaceutically acceptable acid salts of the compounds of formula (I) are those which form non-toxic addition salts, such as, but not limited to, the hydrochloride, hydrobromide, sulfate or bisulfate, acetate, benzoate. besylate, citrate, fumarate, glucuronate, hippurate, lactate, tartrate, saccharate, succinate, maleate, methanesulfonate, p-toluenesulfonate, phosphate and pamoate (i.e., 4,4'-methylene-bis-(3-hydroxy-2-naphthoate)) salts. The pharmaceutically acceptable acid salts may be prepared by conventional techniques.

Certain compounds of the present invention are capable of forming pharmaceutically acceptable non-toxic cations. Pharmaceutically acceptable non-toxic cations of compounds of formula (I) may be prepared by conventional techniques by, for example, contacting said compound with a stoichiometric amount of an appropriate alkali or alkaline earth metal (sodium, potassium, calcium and magnesium) hydroxide or alkoxide in water or an appropriate organic solvent such as ethanol, isopropanol, mixtures thereof, or the like.

Also included within the scope of this invention are bioprecursors (also called pro-drugs) of the compounds of the formula (I). A bioprecursor of a compound of the formula (I) is a chemical derivative thereof which is readily converted back into the parent compound of the formula (I) in biological systems. In particular, a bioprecursor of a compound of the formula (I) is converted back to the parent compound of the formula (I) after the bioprecursor has been administered to, and absorbed by, a mammalian subject, e.g., a human subject. When the compounds of the formula (I) of this invention may form solvates such as hydrates, such solvates are included within the scope of this invention.

The compounds of the formula (I) of this invention can be administered via either the oral, parenteral or topical routes to mammals. In general, these compounds are most desirably administered to humans in doses ranging from 0.01 mg to 100 mg per kg of body weight per day, although variations will necessarily occur depending upon the weight, sex and condition of the subject being treated, the disease state being treated and the particular route of administration chosen. However, a dosage level that is in the range of from 0.1 mg to 10 mg per kg of body weight per day, single or divided dosage is most desirably employed in humans for the treatment of abovementioned diseases.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, trochees, hard candies powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene grycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The compounds of formula (I) may also be administered in the form of suppositories for rectal or vaginal administration of the active ingredient. These compositions can be prepared by mixing the active ingredient with a suitable non-irritating excipient which is solid at room temperature (for example, 10° C. to 32° C.) but liquid at the rectal temperature and will melt in the rectum or vagina to release the active ingredient. Such materials are polyethylene glycols, cocoa butter, suppository and wax.

For buccal administration, the composition may take the form of tablets or lozenges formulated in conventional manner.

Combination with Other Drugs

Compounds of Formula I would be useful for, but not limited to, the treatment of inflammation in a subject, and for treatment of other inflammation-associated disorders, such as, as an analgesic in the treatment of pain and headaches, or as an antipyretic for the treatment of fever. For example, combinations of the invention would be useful to treat arthritis, including but not limited to rheumatoid arthritis, spondyloarthopathies, gouty arthritis, osteoarthritis, systemic lupus erythematosus and juvenile arthritis. Such combinations of the invention would be useful in the treatment of asthlna, bronchitis, inmenstrual cramps, tendinitis, bursitis, and skin related conditions such as psoriasis, eczema, burns and dermatitis. Combinations of the invention also would be useful to treat gastrointestinal conditions such as inflammatory bowel disease. Crohn's disease, gastritis, irritable bowel syndrome and ulcerative colitis and for the prevention of colorectal cancer. Combinations of the invention would be useful in creating inflammation in such diseases as vascular diseases, migraine headaches, periarteritis nodosa, thyroiditis, aplastic anemia, Hodgkins disease, sclerodoma, rheumatic fever. type I diabetes, myasthenia gravis, multiple sclerosis, sarcoidosis, nephrotic syndrome. Behcet's syndrome, polymyositis, gingivitis, hypersensitivity, Conjunctivitis, swelling occurring after injury, myocardial ischemia, and the like. The combinations would also be useful for the treatment of certain central nervous system disorders such as Alzheimer's disease and dimentia. The combinations of the invention are useful as anti-inflammatory agents, such as for the treatment of arthritis, with the additional benefit of having significantly less harmful side effects. These compositions would also be useful in the treatment of allergic rhinitis, respiratory distress syndrome, endotoxin shock syndrome, atherosclerosis and central nervous system damage resulting from stroke, ischemia and trauma.

Compounds of formula (I) will be useful as a partial or complete substitute for conventional NSAID's in preparations wherein they are presently co-administered with other agents or ingredients. Thus, the invention encompasses pharmaceutical compositions for treating COX-2 mediated diseases as defined above comprising a non-toxic therapeutically effective amount of the compound of formula (I) and one or more ingredients such as another pain reliever including acetaminophen or phenacetin; a potentiator including caffeine; an $H_2$-antagonist, aluminom or magnesium hydroxide, simethicone, a decongestant including phenylephrine, phenylproanolamine, psuedophedrine, oxyrnetazoline, ephinephrine, naphazoline, xylometazoline, propylhexedrine, or levodesoxyephedrine; an antiitussive including codeine, hydrocodone, caramiphen, carbetapentane, or dextramethorphan; a prostaglandin including misoprostol, enprostil, rioprostil, ornoprotol or rosaprostol; a diuretic; a sedating or non-sedating antihistamine; anticancer agents such as angiostatin and endostatin; anti-Alzheimers such as Doepezil and Tacrine hydrochloride; and TNF alpha inhibitors such as Etanercept.

These cyclooxygenase inhibitors can further be used in combination with a nitric oxide inhibitors disclosed in WO 96/28145.

Also, the invention encompasses pharmaceutical compositions for treating COX-2 mediated diseases as defined above comprising a non-toxic therapeutically effective amount of the compound of formula (I) and one or more anti-ulcer agent and/or prostaglandins, which are disclosed in WO 97/11701.

The useful prostaglandins include misoprostol, plus-minus methyl 11α, 16-dihydroxy-16-methyl-9-oxoprost 13E-en-1-oate; enisoprost and methyl-7-[2B-[6-(1-cyclopenten-1-yl)-4-hydroxy-4-methyl-1E, 5E-hexadienyl]-3α-hydroxy-5-oxo 1 R, 1α-cyclopentyl]-4Z-heptenoate. Prostaglandins within the scope of the invention also include arbaprostil, enprostil, rioprostol, nocloprost, mexiprostil, omoprostol, dimoxaprost, tiprostanide and rosaprostol.

The present compounds may also be used in co-therapies, partially or completely, in place of other conventional antiinflammatories, such as together with steroids, 5-lipoxygenase inhibitors, $LTB_4$ antagonists and LTA4 hydrolase inhibitor's.

An example of $LTB_4$ is disclosed in WO97/29774. Suitable $LTB_4$ inhibitors include, among others, ebselen, Bayer Bay-x-1005, Ciba Geigy compound CGS-25019C, Leo Denmark compound ETH-615, Lilly compound LY-293111, Ono compound ONO-4057, Terumo compound TMK-688, Lilly compounds LY-213024, 264086 and 292728, Ono compound ONO-LB457, Searle compound SC-S3228, calcitrol, Lilly compounds LY-210073, LY223982, LY233469, and LY255283, Ono compound ONO-LB-448, Searle compounds SC-41930, SC-50605 and SC-51146, and SK&F compound SKF-104493. Preferably, the $LTB_4$ inhibitors are selected from ebselen, Bayer Bay-x-1005, Ciba Geigy compound CGS-25019C, Leo Denmark compound ETH-61 S, Lilly compound LY-29311 1, Ono compound ONO-4057 and Terumo compound TMK-688.

An example of 5-LO inhibitors is disclosed in WO97/29776. Suitable 5-LO inhibitors include, among others, masoprocol, tenidap, zileuton, pranlukast, tepoxalin, rilopirox, flezelastine hydrochloride, enazadrem phosphate and bunaprolast.

An example of $LTA_4$ hydrolase inhibitors is disclosed in WO97/29774. Suitable LTA4 hydrolase inhibitors include, among others, Rhone-Poulenc Rorer RP-64966.

The administration of the present invention mav be for either prevention or treatment purposes. The methods and compositions used herein may be used alone or in conjunction with additional therapies known to those skilled in the art in the prevention or treatment of angiogenesis. Alternatively, the methods and compositions described herein may be used as adjunct therapy. By way of example, the cyclooxygenase-2 inhibitor may be administered alone or in conjunction with other antineoplastic agents or other growth inhibiting agents or other drugs or nutrients.

There are large numbers of antineoplastic agents available in commercial use, in clinical evaluation and in pre-clinical development, which could be selected for treatment of angiogenesis by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents. Alternatively, other anti-neoplalstic agents, such as metallomatrix proteases inhibitors (MMP), such as MMP-13 inhibitors including batiastat, marimastat. Agouron Pharmaceuticals AG-3340, and Roche R0-32-3555, or alpha,beta, inhibitors may be used.

A first family of antineoplastic agents which may be used in combination with a selective cyclooxygenase-2 inhibitor consists of antimetabolite-type antineoplastic agents. Suitable antimetabolite antineoplastic agents may be selected from the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku F0-152, isopropyl pyrrolizine, Lilly LY-188011, Lilly LY-264618, methobenzaprim, methotrexate, Wellcome MZPES. norspermnidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT and uricytin.

A second family of antineoplastic agents which may be used in combination with a selective cyclooxygenase-2 inhibitor consists of alkylating-type antineoplastic agents. Suitable alkylating-type antineoplastic agents may be selected from the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153 chlorambucil, cisplatin, cyclophosphamide, American Cyanamid CL-286558. Sanofi CY-233, cyplatate, Degussa D-19-384, Sumimoto DACHP(Myr)2, diphenylspiromustine, diplatinum cytostatic. Erba distamycin derivatives, Chugai DWA-2114R, ITI E09, elmustine, Erbarnont FCE-24517, estramustine phosphate sodium, fotemustine, Unimed G-6-M, Chinoin GYKI-17230, hepsulfam, ifosfamide, iproplatin, Iomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with a selective cyclooxygenase-2 inhibitor consists of antibiotic-type antineoplastic agents. Suitable antibiotic-type antineoplastic agents may be selected from the group consisting of Taiho 4181-A, aclarubicin, actinomycin D, actinoplanone, Erbamont ADR-456, aeroplysinin derivative, Ajinomoto AN-201-II. Ajinomoto AN-3, Nippon Soda anisomycins, anthracycline, azino-mycin-A, bisucaberin, Bristol-Myers BL-6859, Bristol-Myers BMY-25067. Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b. Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-O1, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmvcin, Sumitomo SM-5887, Snow Brand SN-706, Snow Brand SN-07, sorangicin-A, sparsomycin, SS Pharmaceutical SS-21020. SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-2S024 and zorubicin.

A fourth family of antineoplastic agents which may be used in combination with the selective cyclooxygenase-2 inhibitor consists of a miscellaneous family of antineoplastic agents selected from the group consisting of alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston AIO, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-1O, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-1OO, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross H0-221, homoharringtonine, hydroxyurea, BTG ICRF-187, ilmofosine, isoglutamine, isotretinoin. Otsuka JI-36, Ramot K-477, Otsuak K-76COONa, Kureha Chemical K-AM, MECT Corp KI-8110, American Cyanamid L-623, leukoregulin, Ionidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylateddehydroalanines, nafazatrom, Taisho NCU-190, nocodazole derivative, Normosang, NCI NSC-145813, NCI NSC-361456, NCI NSC-604782, NCI NSC-95580, octreotide, Ono ON0-112, oquizanocine, Akzo Org-10172, pancratistatin, pazelliptine, Warner-Lambert PD-111707, Warner-Lambert PD-115934, Warner-Lambert PD-131141, Pierre Fabre PE-1OO1, ICRT peptide D, piroxantrone, polyhaematoporphyrin, polypreic acid, Efamol porphyrin, probimane, procarbazine, proglurnide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, kyowa Hakko UCN-O1, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Examples of radioprotective agents which may be used in the combination chemotherapy of this invention are AD-5, adchnon, amifostine analogues, detox, dimesna, 1-102, MN-159, N-acylated-dehydroalanines, TGF-Genentech, tiprotimod, amifostine, WR-151327, FUT-187, ketoprofen transdermal, naburnetone, superoxide dismutase (Chiron) and superoxide disrrtutase Enzon.

Methods for preparation of the antineoplastic agents described above may be found in the literature. Methods for preparation of doxorubicin, for example, are described in U.S. Pat. Nos. 3,590,028 and 4,012,448. Methods for preparing metallomatrix protease inhibitors are described in EP 780386, WO97/20824. WO96/15096. Methods for preparing SOD mimics are described in EP 524,1O1. Methods for preparing alpha,beta, inhibitors are described in WO97/08174.

In addition, the selective COX-2 inhibitor may be administered in conjunction with other antiinflammatory agents for maximum safety and efficacy, including NSAID's, selective COX-1 inhibitors and inhibitors of the leukotriene pathway, including 5-lipoxygenase inhibitors. Examples of NSAID's include indomethacin, naproxen, ibruprofen, salicylic acid derivatives such as aspirin, diclofenac, ketorolac piroxicam, meloxicam, mefenamic acid, sulindac, tolmetin sodium, zomepirac, fenoprofen, phenylbutazone, oxyphenbutazone, nimesulide, zaltoprofen and letodolac.

Method for Assessing Biological Activities

The activity of the compounds of the formula (I) of the present invention was demonstrated by the following assays.
In Vitro Assays
Human Cell Based COX-1 Assay Human peripheral blood obtained from healthy volunteers was diluted to 1/10 volume with 3.8% sodium citrate solution. The platelet-rich plasma immediately obtained was washed with 0.14 M sodium chloride containing 12 mM Tris-HCl (pH 7.4) and 1.2 mM EDTA. Platelets were then washed with platelet buffer (Hanks buffer (Ca free) containing 0.2% BSA and 20 mM Hepes). Finally, the human washed platelets (HWP) were suspended in platelet buffer at the concentration of $2.85 \times 10^8$ cells/ml and stored at room temperature until use. The HWP suspension (70 $\mu$l aliquots, final $2.0 \times 10^7$ cells/ml) was placed in a 96-well U bottom plate and 10 $\mu$l aliquots of 12.6 mM $CaCl_2$ added. Platelets were incubated with A23187 (final 10 $\mu$M, Sigma) with test compound (0.1–100 $\mu$M) dissolved in DMSO (final concentration; less than 0.01%) at 37° C. for 15 min. The reaction was stopped by addition of EDTA (final 7.7 mM) and TxB2 in the supernatant quantitated by using a radioimmunoassay kit (Amersham) according to the manufacturer's procedure.
Human Cell Based COX-2 Assay
Inhibition of COX-2 Activity after Induction of COX-2 by hIL-1β

The human cell based COX-2 assay was carried out as previously described (Moore et al., *Inflam. Res.*, 45, 54, 1996). Confluent human umbilical vein endothelial cells (HUVECs, Morinaga) in a 96-well U bottom plate were washed with 100 $\mu$l of RPMI1640 containing 2% FCS and incubated with hIL-1β (final concentration 300 U/ml, R & D Systems) at 37° C. for 24 hr. After washing, the activated HUVECs were stimulated with A23187 (final concentration 30 $\mu$M) in Hanks buffer containing 0.2% BSA, 20 mM Hepes and test compound (0.1 nM–100 μM) dissolved in DMSO (final concentration; less than 0.01%) at 37° C. for 15 min. 6-Keto-PGF$_1$α, stable metabolite of PGI$_2$, in the supernatant was quantitated after adequate dilution by using a radioimmunoassay kit (Amersham) according to the manufacturer's procedure.

Inhibition of COX-2 During the Induction Phase

Confluent human umbilical vein endothelial cells (HUVECs, Morinaga) in a 96-well U bottom plate were washed with 100 μl of RPMI1640 containing 2% FCS and test compound (0.1 nM–100 μM) dissolved in DMSO (final concentration; less than 0.01%), and incubated with hIL-1$_β$ (final concentration 300 U/ml, R & D Systems) at 37° C. for 24 hr. After washing, the HUVECs were stimulated with A23187 (final concentration 30 μM) in Hanks buffer containing 0.2% BSA and 20 mM Hepes at 37° C. for 15 min. 6-Keto-PGF$_{1α}$, a stable metabolite of PGI$_2$, in the supernatant was quantitated after adequate dilution by using a radioimmunoassay kit (Amersham) according to the manufacturers procedure.

In Vivo Assays

Carrageenan Induced Foot Edema in Rats

Male Sprague-Dawley rats (5 weeks old, Charles River Japan) were fasted overnight. A line was drawn using a marker above the ankle on the right hind paw and the paw volume (V0) was measured by water displacement using a plethysmometer (Muromachi). Animals were given orally either vehicle (0.1% methyl cellulose or 5% Tween 80) or a test compound (2.5 ml per 100 g body weight). One hour later, the animals were then injected intradermally with λ-carrageenan (0.1 ml of 1% w/v suspension in saline, Zushikagaku) into right hind paw (Winter et al., *Proc. Soc. Exp. Biol. Med.*, 111, 544, 1962; Lombardino et al., *Arzneim. Forsch.*, 25, 1629, 1975) and three hours later, the paw volume (V3) was measured and the increase in volume (V3–V0) calculated. Since maximum inhibition attainable with classical NSAIDs is 60–70%, ED$_{30}$ values were calculated.

Gastric Ulceration in Rats

The gastric ulcerogenicity of test compound was assessed by a modification of the conventional method (Ezer et al., *J Pharm. Pharmacol.*, 28, 655, 1976; Cashin et al., *J Pharm. Pharmacol.*, 29, 330–336, 1977). Male Sprague-Dawley rats (5 weeks old, Charles River Japan), fasted overnight, were given orally either vehicle (0.1% methyl cellulose or 5% Tween 80) or a test compound (1 ml per 100 g body weight). Six hours after, the animals were sacrificed by cervical dislocation. The stomachs were removed and inflated with 1% formalin solution (10 ml). Stomachs were opened by cutting along the greater curvature. From the number of rats that showed at least one gastric ulcer or haemorrhaging erosion (including ecchymosis), the incidence of ulceration was calculated. Animals did not have access to either food or water during the experiment.

Data Analysis

Statistical program packages, SYSTAT (SYSTAT, INC.) and StatView (Abacus Cencepts, Inc.) for Macintosh were used. Differences between test compound treated group and control group were tested for using ANOVA. The IC$_{50}$ (ED$_{30}$) values were calculated from the equation for the log-linear regression line of concentration (dose) versus percent inhibition.

Most compounds prepared in the Working Examples as described herein after were tested by these methods, and showed IC$_{50}$ values of 0.001 μM to 3 μM with respect to inhibition of COX-2.

COX-2 selectivity can be determined by ratio in terms of IC$_{50}$ value of COX-1 inhibition to COX-2 inhibition. In general, it can be said that a compound showing a COX-2/COX-1 inhibition ratio of more than 2 has good COX-2 selectivity.

Some compounds prepared in Examples showed COX-2/COX-1 inhibition ratio of more than 5.

The following examples contain detailed descriptions of the methods of the preparation of compounds of formula (I). These detailed descriptions fall within the scope of the invention and serve to exemplify the above described general synthetic procedures which form part of the invention. These detailed descriptions are presented for illustrative purposes only and are not intended to restrict the scope of the present invention.

EXAMPLES

The invention is illustrated in the following non-limiting examples in which, unless stated otherwise: all operations were carried out at room or ambient temperature, that is, in the range of 18–25° C.; evaporation of solvent was carried out using a rotary evaporator under reduced pressure with a bath of up to 60° C.; reactions were monitored by thin layer chromatography (tlc) and reaction times are given for illustration only; melting points (m.p.) given are uncorrected (polymorphism may result in different melting points); structure and purity of all isolated compounds were assured by at least one of the following techniques: tlc (Merck silica gel 60 F-254 precoated plates), mass spectrometry, nuclear magnetic resonance (NMR) or infrared spectroscopy (IR). IR data were obtained on a FTIR 8200 (SHIMAZU Spectrometer). Yields are given for illustrative purposes only. Flash column chromatography was carried out using Merck silica gel 60 (230–400 mesh ASTM). Low-resolution mass spectral data (EI) were obtained on a Automass 120 (JEOL) mass spectrometer. NMR data was determined at 270 MHz (JEOL JNM-LA 270 spectrometer) using deuterated chloroform (99.8% D), methanol (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br=broad, etc.

The following abbrevation are used:

| | |
|---|---|
| THF | tetrahydrofuran |
| CH$_2$Cl$_2$ | dichloromethane |
| NaHCO$_3$ | sodium bicarbonate |
| HCl | hydrogen chloride |
| MgSO$_4$ | magnesium sulfate |
| Na$_2$SO$_4$ | sodium sulfate |
| DME | dimethoxyethane |
| n-BuLi | n-butyllithium |
| DMF | dimethylformamide |

Example 1

1-[4-(Methylsulfonyl)phenyl]-5-[4-(2-thienyl) phenyl]-3-trifluoromethyl-1H-pyrrazole 1-[4-(Methylsulfonyl)phenyl]-5-(4-bromophenyl)-3-trifluoromethyl-1H-pyrrazole (step 1)

(4-methylsulfonylphenyl)hydrazine hydrochloride (commercially available from Fisher Scientific USA) (0.83 g, 3.7 mmol) was added to a solution of 4,4,4-trifluoro-1-(4-bromophenyl)butane-1,3-dione (1 g, 3.39 mmol), prepared according to the method of *J. Med. Chem.*, 1997, 40, 1347) in EtOH (15 mL). The mixture was heated at reflux temperature for 20 hours and cooled down to room temperature. The reaction mixture was concentrated in vacuo, and the residue was taken up in ethyl acetate, washed with water and brine, dried over sodium sulfate, and concentrated in vacuo. The residue was purified by flash chromatography eluting with hexane/ethyl acetate (1/1) to give the title compound (1.08 g).

$^1$H-NMR (CDCl$_3$) δ: 7.97 (ddd, J=9, 2, 2 Hz, 2H), 7.50–7.57 (m, 4H), 7.11 (ddd, J=9, 2, 2 Hz, 2H), 6.79 (s, 1H), 3.08 (s, 3H).

1-[4-(Methylsulfonyl)phenyl]-5-[4-(2-thienyl)phenyl]-3-trifluoromethyl-1H-pyrrazole. (step 2)

To a stirred solution of 1-[4-(Methylsulfonyl)phenyl]-5-(4-bromophenyl)-3-trifluoromethyl-1H-pyrrazole. (0.27 g, 0.6 mmol) in DME (8 mL) was added 3-thiophenboronic acid (0.09 g, 0.7 mmol), bis(triphenylphosphine)palladium (II)chloride (0.05 g, 0.1 mmol) and saturated NaHCO$_3$ solution (2 mL) at room temperature under nitrogen. The mixture was heated at reflux temperature for 16 hours and cooled down to room temperature. The reaction mixture was purified by flash chromatography eluting with ethyl acetate/hexane (1/1). The resulting solid was recrystallized with dichloroethane-hexane to give title compound (0.171 g, 64% yield).

mp: 191–192° C.

$^1$H-NMR (CDCl$_3$) δ: 7.96 (ddd, J=9, 2, 2 Hz, 2H), 7.63 (ddd, J=9, 2, 2 Hz, 2H), 7.58 (ddd, J=9, 2, 2 Hz, 2H), 7.38 (dd, J=4, 1 Hz, 1H), 7.34 (dd, J=5, 1 Hz, 1H), 7.24 (ddd, J=9, 2, 2 Hz, 2H), 7.11 (dd, J=5, 4 Hz, 1H), 6.82 (s, 1H), 3.70 (s, 3 H). Anal. Calcd. for C$_{21}$H$_{15}$N$_2$O$_2$F$_3$S: C, 56.24; H, 3.37; N, 6.25. Found: C, 55.84; H, 3.49; N, 6.07.

Example 2

1-[4-(Methylsulfonyl)phenyl]-5-[4-(3-thienyl)phenyl]-3-trifluoromethyl-1H-pyrazole The title compound was prepared according to the procedure of Example 1 (Step 2) using 3-thienylboronic acid, instead of 2-thienyboronic acid.

mp: 153.5–155° C.

$^1$H-NMR (CDCl$_3$) δ: 7.96 (ddd, J=9, 2, 2 Hz, 2H), 7.62 (ddd, J=9, 2, 2 Hz, 2H), 7.58 (ddd, J=9, 2, 2 Hz, 2H), 7.53 (dd, J=3, 1 Hz, 1H), 7.45–7.38 (m, 2H), 7.28–7.24 (m, 2H), 6.82 (s, 1H), 3.07 (s, 3H).

Anal. Calcd. for C$_{21}$H$_{15}$N$_2$O$_2$F$_3$S$_2$: C, 56.24; H, 3.37; N, 6.25. Found: C, 56.14; H, 3.40; N, 6.27.

Example 3

1-[4-(Methylsulfonyl)phenyl]-5-[4-(2-furyl)phenyl]-3-trifluoromethyl-1H-pyrazole The title compound was prepared according to the procedure of Example 1(Step 2) using 2-furylboronic acid, instead of 2-thienylboronic acid.

mp: 195.5–196.5° C.

$^1$H-NMR (CDCl$_3$) δ: 7.95 (ddd, J=9, 2, 2 Hz, 2H), 7.68 (ddd, J=9, 2, 2 Hz, 2H), 7.57 (ddd, J=9, 2, 2 Hz, 2H), 7.51 (dd, J=2, 1 Hz, 1H), 7.26–7.22 (m, 2H), 6.81 (s, 1H), 6.74 (dd, J=4, 1 Hz, 1H), 6.51 (dd, J=4, 2 Hz, 1H), 3.07 (s, 3H).

Anal. Calcd. for C$_{21}$H$_{15}$N$_2$O$_3$F$_3$S 1/4 H$_2$O: C, 57.73; H, 3.58; N, 6.41. Found: C, 57.89; H, 3.54; N, 6.30.

Example 4

1-[4-(Methylsulfonyl)phenyl]-5-[4-(benzo[b]furan-2-yl)phenyl]-3-trifluoromethyl-1H-pyrazole The title compound was prepared according to the procedure of Example 1 (Step 2) using 2-benzo[b]furylboronic acid, instead of 2-thienylboronic acid.

mp: 137–138° C.

$^1$H-NMR (CDCl$_3$) δ: 7.98 (ddd, J=9, 2, 2 Hz, 2H), 7.88 (ddd, J=9, 2, 2 Hz, 2H), 7.63–7.51 (m, 4H), 7.36–7.25 (m, 4H), 7.10 (d, J=1 Hz, 1H), 6.85 (s, 1H), 3.08 (s, 3H).

Anal. Calcd. for C$_{25}$H$_{17}$N$_2$O$_3$F$_3$S 1/4 H$_2$O: C, 61.66 H, 3.62; N, 5.75. Found: C, 61.72; H, 3.95; N, 5.42.

Example 5

4-[5-[4-(3-Thienyl)phenyl]-3-(trifluoromethyl)-1H-pyrazol-1-yl]-1-phenylsulfonamide 4-[5-(4-bromophenyl)-3-(trifluoromethyl)-1H-pyrazol-1-yl]-1-phenylsulfonamide (step 1)

4-sulphonamidophenylhydrazine hydrochloride (commercially available from Maybridge Chemical Company ltd.) (7.38 g, 33 mmol) was added to a solution of 4,4,4-trifluoro-1-(4-bromophenyl)butane-1,3-dione (8.85 g, 30 mmol, prepared according to the method of J. Med. Chem., 1997, 40, 1347) in EtOH (120 mL). The mixture was heated at reflux temperature for 20 hours and cooled down to room temperature. The reaction mixture was concentrated in vacuo, and the residue was purified by recrystellized with diisopropyl ether, to give the title compound (9.1 g).

$^1$H-NMR (CDCl$_3$) δ: 7.94 (d, J=8 Hz, 2H). 7.45–7.55 (m, 4H), 7.11 (d, J=8 Hz, 2H), 6.78 (s, 1H), 4.93 (br, 2H).

4-[5-[4-(3-Thienyl)phenyl]-3-(trifluoromethyl)-1H-pyrazol-1-yl]-1-phenylsulfonamide (step 2)

To a stirred solution of 4-[5-(4-bromophenyl)-3-(trifluoromethyl)-1H-pyrazol-1-yl]-1-phenylsulfonamide (0.22 g, 0.50 mmol) in DME (6 mL) was added thiophen-3-boronic acid (0.08 g, 0.6 mmol), bis(triphenylphosphine)palladium(II)chloride (0.05 g, 0.1 mmol) and saturated NaHCO$_3$ solution (2 mL) at room temperature under nitrogen. The mixture was heated at reflux temperature for 16 hours, and cooled down to room temperature. The reaction mixture was purified by flash chromatography eluting with ethyl acetate/hexane (1:5). The resulting solid was recrystallized with CH$_2$Cl$_2$-hexane to give title compound (0.090 g, 40% yield).

mp: 205–207° C.

$^1$H-NMR (DMSO d$_6$) δ: 8.00–7.98 (m, 1H), 7.90 (d, J=8 Hz, 2H), 7.79 (d, J=8 Hz, 2H), 7.67–7.58 (m, 4H), 7.52 (s, 2H), 7.36 (d, J=8 Hz, 2H), 7.29 (s, 1H).

Anal. Calcd. for C$_{20}$H$_{14}$N$_3$O$_2$F$_3$S$_2$: C, 53.44; H, 3.14; N, 9.35. Found: C, 53.13; H, 3.40; N, 9.06

Example 6

4-[5-[4-(3-thienyl)phenyl-4-cyano-1H-pyrazol-1-yl]-1-phenylsulfonamide

The title compound was prepared according to the procedure of Example 5 using 4-[5-[4-Bromophenyl]-4-cyano-1H-pyrazol-1-yl]-1-phenylsulfonamide, instead of 4-[5-(4-bromophenyl)-3-(trifluoromethyl)-1H-pyrazol-1yl]-1phenylsulfonamide.

mp: 201.5–202° C.

$^1$H-NMR (CDCl$_3$) δ: 8.07 (s, 1H), 7.95 (ddd, J=9, 2, 2 Hz, 2H), 7.67 (ddd, J=8, 2, 2 Hz, 2H), 7.55 (dd, J=3, 1 Hz, 1H), 7.49 (ddd, J=9, 2, 2 Hz, 2H), 7.45–7.39 (m, 2H), 7.36 (ddd, J=8, 2, 2 Hz, 2H), 4.87 (br, 2H).

Anal. Calcd. for C$_{20}$H$_{14}$N$_4$O$_2$S$_2$ 1/2 H$_2$O: C, 57.82 H, 3.64; N, 13.48. Found: C, 57.47; H, 3.68; N, 13.13.

Example 7

4-[5-[4-(4-Pyridyl)phenyl]-3-(trifluoromethyl)-1H-pyrazol-1-yl]-1-phenylsulfonamide The title compound was prepared according to the procedure of Example 5 using 4-pyridylboronic acid, instead of 3-thienylboronic acid.

mp: 164–166° C.

¹H-NMR (DMSO d₆) δ: 8.64 (d, J=6 Hz, 2H), 7.91 (d, J=9 Hz, 2H), 7.88 (d, J=8 Hz, 2H), 7.75 (d, J=6 Hz, 2H), 7.61 (d, J=9 Hz, 2H), 7.50 (d, J=6 Hz, 2H), 7.47 (s, 2H), 7.32 (s, 1H).

Anal. Calcd. for $C_{21}H_{15}F_3N_4O_2S$ 1/4 $H_2O$: C, 56.18 H, 3.48; N, 12.48. Found: 56.07; H, 3.56; N, 12.10.

Example 8

4-[5-[4-(3-Pyridyl)phenyl]-3-(trifluoromethyl)-1H-pyrazol-1-yl-1-1-phenylsulfonamide The title compound was prepared according to the procedure of Example 5 using 3-pyridylboronic acid, instead of 3-thienylboronic acid.

mp: 138–140° C.

¹H-NMR (CDCl₃) δ: 8.52 (d, J=5 Hz, 1H), 8.78 (s, 1H), 7.88 (d, J=8 Hz, 2H), 7.55 (d, J=8 Hz, 2H), 7.42 (d, J=9 Hz, 2H), 7.38–7.30 (m, 4H), 6.81 (s, 1H), 6.30 (s, 2H).

Anal. Calcd. for $C_{21}H_{15}F_3N_4O_2S$ 1/10 $H_2O$: C, 56.52 H, 3.43; N, 12.56. Found: C, 56.86; H, 3.83; N, 12.30.

Example 9

4-[5-[4-(5-Methyl-2-thienyl)phenyl]-3-(trifluoromethyl)-1H-pyrazol-1-yl]-1-phenylsulfonamide 5-Methyl-2-thienylboronic acid(step 1)

To a stirred solution of 2-bromo-5-methylthiophene (2.5 g, 14.1 mmol) in THF (30 mL) was added n-BuLi (1.55 M solution in hexane, 10.0 mL, 15.5 mmol) at −78° C. under nitrogen, and the mixture was stirred for 1 hour. Trimethylborate (1.83 g, 17.6 mmol) was added to the mixture, and residue was allowed to warm up to room temperature overnight. The reaction mixture was cooled at 0° C., and 2N HCl (10 mL) was added, and the mixture was stirred for 1 hour. The organic layer was separated and the aqueous layer was extracted with diethylether. The combined organic layer was washed with brine, dried over $MgSO_4$, and concetrated in vacuo. to give the title compound (1.36 g).

¹H-NMR (DMSO d₆) δ: 7.45 (s, 2H), 7.09 (d, J=3 Hz, 1H), 6.88 (d, J=3 Hz, 1H), 1.88 (s, 3H).

4-[5-[4-(5-Methyl-2-thienyl)phenyl]-3-(trifluoromethyl)-1H-pyrazol-1-yl]-1-phenylsulfonamide(step 2)

The title compound was prepared according to the procedure of Example 5 using 5-methyl-2-thienylboronic acid, instead of 3-thienylboronic acid.

mp: 218–220° C.

¹H-NMR (DMSO d₆) δ: 7.90 (d, J=9 Hz, 2H), 7.63 (d, J=7 Hz, 2H), 7.58 (d, J=7 Hz, 2H), 7.52 (s, 2H), 7.40 (d, J=4 Hz, 1H), 7.32 (d, J=9 Hz, 2H), 7.27 (s, 1H), 6.84 (dd, J=4, 1 Hz, 1H), 2.47 (s, 3H).

Anal. Calcd. for $C_{21}H_{16}F_3N_3O_2S_2$: C, 54.42 H, 3.48; N, 9.07. Found: C, 54.43; H, 3.67; N, 8.91.

Example 10

4-[5-[4-(3-Furyl)phenyl]-3-(trifluoromethyl)-1H-pyrazol-1-yl]-1-phenylsulfonamide The title compound was prepared according to the procedure of Example 5 using 3-furylboronic acid (prepared according to the method of *J. Org. Chem.*, 1984, 26. 5241.), instead of 3-thienylboronic acid.

mp: 163–165° C.

¹H-NMR (CDCl₃) δ: 7.93 (d, J=9 Hz, 2H), 7.79–7.74 (m, 1H), 7.54–7.47 (m, 5H), 7.23 (d, J=8 Hz, 1H), 6.79 (m, 1H), 6.72–6.68 (m, 1H), 4.90 (s, 2H).

Anal. Calcd. for $C_{20}H_{14}N_3O_3F_3S$: C, 55.43; H, 3.26; N, 9.70. Found: C, 55.25; H, 3.30; N, 9.64.

Example 11

4-[5-[4-(5-Pyrimidinyl)phenyl]-3-(trifluoromethyl)-1H-pyrazol-1-yl]-1-phenylsulfonamide The title compound was prepared according to the procedure of Example 5 using 5-pyrimidinylboronic acid, instead of 3-thienylboronic acid.

mp: 220–222° C.

¹H-NMR (DMSO d₆) δ: 9.20 (d, J=4 Hz, 2H), 7.91 (d, J=8 Hz, 2H), 7.64–7.49 (m, 9H), 7.35 (s, 1H).

Anal. Calcd. for $C_{20}H_{14}F_3N_5O_2S$ 1/2 $H_2O$: C, 52.86; H, 3.33; N, 15.41. Found: C, 52.91; H, 3.24; N, 15.06.

Example 12

4-[5-[4-(2-Pyrrolyl)phenyl]-3-(trifluoromethyl)-1H-pyrazol-1-yl]-1-phenylsulfonamide The title compound was prepared according to the procedure of Example 5 using (1-tert-butoxycarbonylpyrrol-2yl)boronic acid (prepared according to the method of Synthesis, 613 (1991)), instead of 3-thienylboronic acid.

mp: 263–265° C.

¹H-NMR (DMSO d₆) δ: 11.0 (brs, 1H), 7.89 (d, J=8 Hz 2H), 7.60–7.55 (m, 4H), 7.50 (s, 2H), 7.31 (s, 1H), 7.24–7.21 (m, 3H), 6.80 (s, 1H), 6.48 (s, 1H).

Anal. Calcd. for $C_{20}H_{15}F_3N_4O_2S$ 0.3 $H_2O$: C, 54.87; H, 3.59; N, 12.80. Found: C, 54.63; H, 3.65; N, 12.59.

Example 13

4-[5-[4-(2-Benzothienyl)phenyl]-3-(trifluoromethyl)-1H-pyrazol-1-yl]-1-phenylsulfonamide The title compound was prepared according to the procedure of Example 5 using 2-benzothienyl-boronic acid, instead of 3-thienylboronic acid.

mp: 223–225° C.

¹H-NMR (DMSO d₆) δ: 8.00–7.82 (m, 7H), 7.62 (d, J=9 Hz, 2H), 7.54 (s, 2H), 7.45–7.37 (m, 4H), 7.33 (s, 1H).

Anal. Calcd. for $C_{24}H_{16}F_3N_3O_2S_2$ $H_2O$: C, 57.71; H, 3.23; N, 8.41. Found: C, 57.45; H, 3.36; N, 8.36.

Example 14

4-[5-[4-(5-Acetylthiophene-2-yl)phenyl]-3-(trifluoromethyl)-1H-pyrazol-1-yl]-1-phenylsulfonamide The title compound was prepared according to the procedure of Example 5 using 5-acetyl-2-thienylboronic acid, instead of 3-thienylboronic acid.

mp: 212–214° C.

¹H-NMR (DMSO d₆) δ: 7.95 (d, J=4 Hz, 1H), 7.91 (d, J=8 Hz, 2H), 7.83 (d, J=8 Hz, 2H), 7.73 (d, J=4 Hz, 1H), 7.60 (d, J=8 Hz, 2H), 7.51 (s, 2H), 7.41 (d, J=8 Hz, 2H), 7.31 (s, 1H), 2.25 (s, 3H).

Anal. Calcd. for $C_{22}H_{16}F_3N_3O_3S_2$ 1/10 $H_2O$: C, 53.56; H, 3.31; N, 8.52. Found: C, 53.25; H, 3.40; N, 8.35.

Example 15

4-[5-[4-(3-Pyrrolyl)phenyl]-3-(trifluoromethyl)-1H-pyrazol-1-yl]-1-phenylsulfonamide 4-[5-[4-(1-Triisopropylsilylpyrrol-3-yl)phenyl]-3-(trifluoromethyl)-1H-pyrazol-1-yl]-1-phenylsulfonamide (step 1)

The title compound was prepared according to the procedure of Example 5 using 1-(triisopropylsilyl)pyrrole-3-boronic acid (prepared according to the method of Alejandro Alvarez et, al., *J. Org. Chem.,* 1992, 57, 1653.), instead of 3-thenylboronic acid.

4-[5-[4-(3-Pyrrolyl)phenyl]-3-(trifluoromethyl)-1H-pyrazol-1-yl]-1-phenylsulfonamide(step 2)

To a stirred solution of 4-[5-[4-(1-triisopropylsilylpyrrol-3-yl)phenyl]-3-(trifluoromethyl)-1H -pyrazol-1-yl]-1-phenylsulfonamide (0.50 g, 0.849 mmol) in THF (13 mL) was added tetrabutylammonium fluoride (1.00 M solution in THF, 0.85 mL, 0.85 mmol) at room temperature under nitrogen, and the mixture was stirred for 5 minutes. The solvent was removed in vacuo. The residue was purified by flash chromatography eluting with $CH_2Cl_2$-methanol (20:1). The resulting solid was recrystallized with $CH_2Cl_2$-hexane to give the title compound (0.070 g, 30% overall yield).

mp: 262–264° C.

$^1$H-NMR (DMSO $d_6$) δ: 11.0 (s, 1H), 7.90 (d, J=9 Hz, 2H), 7.57 (d, J=9 Hz, 4H), 7.49 (s, 2H), 7.28 (s, 1H), 7.21 (d, J=9 Hz, 2H), 7.15 (s, 1H), 6.79 (d, J=2 Hz, 1H), 6.47 (d, J=2 Hz, 1H).

Anal. Calcd. for $C_{20}H_{15}F_3N_4O_2S$: C, 55.55; H, 3.50; N, 12.96. Found: C, 55.21; H, 3.68; N, 12.85.

Example 16

4-[5-[4-(3-Methyl-2-thienyl)phenyl]-3-(trifluoromethyl)-1H-pyrazol-1-yl]-1-phenylsulfonamide 3-Methyl-2-thienylboronic acid(step 1)

The title compound was prepared according to the procedure of Example 9 using 2-bromo-3-methylthiophene.

4-[5-[4-(3-Methyl-2-thienyl)phenyl]-3-(trifluoromethyl)-1H-pyrazol-1-yl]-phenylsulfonamide(step 2)

The title compound was prepared according to the procedure of Example 5 using 3-methyl-2-thienylboronic acid, instead of 3-thienylboronic acid.

mp: 164–166° C.

$^1$H-NMR (CDCl$_3$) δ7.95 (d, J=9 Hz, 2H), 7.54 (d, J=9 Hz, 2H), 7.49 (d, J=8 Hz, 2H), 7.27 (d, J=8 Hz, 2H), 7.25 (d, J=5 Hz, 1H), 6.94 (d, J=5 Hz, 1H), 6.81 (s, 1H), 4.91 (s, 2H), 2.35 (s, 3H).

Anal. Calcd. for $C_{21}H_{16}F_3N_3O_2S_2$ $1/2H_2O$: C, 53.38; H, 3.63; N, 8.89. Found: C, 53.42; H, 3.74; N, 8.92.

Example 17

Methyl 1-[4-(sulfamoylphenyl]-5-[4-(3-thienyl)phenyl]1-H-pyrrazole-3-carboxylate Methyl 1-[4-sulfamoylphenyl]-5-(4-bromophenyl)-1H-pyrrazole-3-carboxylate. (step 1)

The subtitle compound was prepared according to the procedure of Example 5 using methyl 4-(4-bromophenyl)-2,4-diketobutyrate (prepared according to the method of *J. Med. Chem.,* 1997, 40, 1347) instead of 4,4,4-trifluoro-1-(4-bromophenyl)butane-1,3-dione in step 1.

$^1$H-NMR (CDCl$_3$) δ: 7.93 (ddd, J=9, 2, 2 Hz, 2H), 7.54–7.53 (m, 4H), 7.10 (ddd, J=8, 2, 2 Hz, 2H), 7.06 (s, 1H), 4.88 (br, 2H), 3.99 (s, 3H).

Methyl 1-[4-(sulfamoylphenyl]-5-[4-(3-thienyl)phenyl]-1H-pyrrazole-3-carboxylate. (step 2)

To a stirred solution of Methyl 1-[4-(sulfamoylphenyl]-5-(4-bromophenyl)-1H-pyrrazole-3-carboxylate. (0.28 g, 0.65 mmol) in DMF (3 mL) was added bis(triphenylphosphine)palladium(II)chloride (0.02 g, 0.03 mmol), 3-thiophenboronic acid (0.09 g, 0.7 mmol) and triethylamine (0.2 g; 1.95mmol) at room temperature under nitrogen. The mixture was heated at 100° C. for 3 hours, and cooled down to room temperature. The reaction mixture was purified by flash chromatography eluting with ethyl acetate/hexane (2/1). The resulting solid was recrystallized with dichloroethanehexane to give title compound (0.15 g, 53% yield).

mp: 138–140° C.

$^1$H-NMR (CDCl$_3$) δ: 7.92 (d, J=9 Hz, 2H), 7.6 (d, J=9 Hz, 2H), 7.5–7.49 (m, 3H), 7.44–7.38 (m, 2H), 7.26–7.23 (2H), 7.08 (s, 1H), 4.90 (s, 2H), 3.99 (s, 3H).

Example 18

4-[3-(Cyanomethyl)-5-[4-(3-thienyl)phenyl]]-1H-pyrazol-1-yl]-1-phenylsulfonamide 4-[3-(Hydroxymethyl)-5-(4-bromophenyll])-1H-pyrazol-1-yl]-1-phenylsulfonamide. (step 1)

To a stirred suspension of lithium alminium hydride (0.278 g, 7.33 mmol) in THF (50 ml) was added asolution of Methyl 1-[4-sulfamoylphenyl]-5-(4-bromophenyl)-1H-pyrrazole-3-carboxylate (4.0 g, 9.17 mmol) (EXAMPLE 17 step 1) in THF (80 ml). Resulting mixture was stirred continured for 1 hour at reflux temperature, and cooled down to room temperature. A suspension of lithium alminium hydride (0.07 g) in THF (1 ml) was added to the reaction mixture and the whole was heated at reflux temperature for 1 hour, then cooled to room temperature. Water (10 ml) was added to the reaction mixture and the resulting mixture was acidified with 20% $H_2SO_4$ solution. The whole was extracted with ethyl acetate and organic layer was washed with water and brine, dried over magesium sulfate, and concentrated in vacuo . The residue was purified by flash chromatography eluting with ethyl acetate/hexane (1/2) to give the title compound (2.9 g).

$^1$H-NMR (CD$_3$OD) δ: 7.90 (ddd, J=9, 2, 2 Hz, 2H), 7.51 (ddd, J=9, 2, 2 Hz, 2H), 7.42 (ddd, J=9, 2, 2 Hz, 2H), 7.17 (ddd, J=9, 2, 2 Hz, 2H), 6.65 (s, 1H), 4.67 (s, 2H).

4-[3-(Chloromethyl)-5-(4-bromophenyll)-1H-pyrazol-1-yl]-1-phenylsulfonamide. (step 2)

To a stirred mixture of 4-[3-(Hydroxymethyl)-5-(4-bromophenyll])-1H-pyrazol-1-yl-1-phenylsulfonamide (1.67 g, 4.1 mmol), p-toluenesulphonic acid (0.78 g, 4.1 mmol), lithium chloride (0.18 g, 4.1 mmol), triethylamine (0.415 g, 4.1 mmol) and THF (60 ml) was heated at reflux temperature for 20 hours, and cooled down to room temperature. The reaction mixture was taken up in ethyl acetate, washed with 1N-HCl solution, sat-NaHCO3 solution and brine, dried over magesium sulfate, and concentrated in vacuo . The residue was purified by flash chromatography eluting with ethyl acetate/hexane (1/1) to give the title compound (0.62 g).

$^1$H-NMR (DMSO $d_6$) δ: 7.85 (d, J=9 Hz, 2H), 7.62 (d, J=8 Hz, 2H), 7.44–7.48 (m, 4H), 7.23 (d, J=8 Hz, 2H), 6.82 (s, 1H), 4.82 (s, 2H).

4-[3-(Cyanomethyl)-5-(4-bromophenyll])-1H-pyrazol-1-yl]-1-phenylsulfonamide. (step 3)

To a stirred solution of sodium cyanide (0.084 g, 1.7 mmol) in DMSO (10 ml) was added asolution of 4-[3-(Chloromethyl)-5-(4-bromophenyll])-1H-pyrazol-1-yl]-1-phenylsulfonamide (0.61 g, 1.43 mmol) in DMSO (10 ml). Resulting mixture was stirred continured for 4 hours at 100° C., and cooled down to room temperature. The reaction mixture was taken up in ethyl acetate, washed with water and brine, dried over magesium sulfate, and concentrated in vacuo. The residue was purified by flash chromatography eluting with ethyl acetate to give the title compound (0.46 g).

$^1$H-NMR (DMSO d6) δ: 7.85 (d, J=9 Hz, 2H), 7.62 (d, J=9 Hz, 2H), 7.44–7.48 (m, 4H), 7.23 (d, J=9 Hz, 2H), 6.74 (s, 1H), 4.15 (s, 2H).

4-[3-(Cyanomethyl)-5-[4-(3-thienyl)phenyl]-1H-pyrazol-1-yl]-1-phenylsulfonamide (step 4)

The title compound was prepared according to the procedure of Example 17 using 4-[3-(Cyanomethyl)-5-(4-bromophenyl])-1H-pyrazol-1-yl]-1-phenylsulfonamide.

mp: 211–212° C.

$^1$H-NMR (CDCl$_3$) δ: 7.95 (ddd, J=9, 2, 2 Hz, 2H), 7.68 (ddd, J=9, 2, 2 Hz, 2H), 7.57 (ddd, J=9, 2, 2 Hz, 2H), 7.51 (dd, J=2, 1 Hz, 1H), 7.26–7.22 (m, 2H), 6.81 (s, 1H), 6.74 (dd, J=4, 1 Hz, 1H), 6.51 (dd, J=4, 2 Hz, 1H), 3.07 (s, 3H).

Anal. Calcd. for C$_{21}$H$_{15}$N$_2$O$_3$F$_3$S 1/4 H$_2$O: C, 57.73; H, 3.58; N, 6.41. Found: C, 57.89; H, 3.54; N, 6.30.

Example 19

4-[3-(Hydroxymethyl)-5-[4-(3-thienyl)phenyl]-1H-pyrazol-1-yl]-1-phenylsulfonamide The title compound was prepared according to the procedure of Example 17 using 4-[5-(4-Bromophenyl])-3-(hydroxymethyl)-1H-pyrazol-1-yl]-1-phenylsulfonamide.

mp: 228–229° C.

$^1$H-NMR (CD$_3$OD) δ: 7.96 (dd, J=3, 2 Hz, 1H), 7.83 (d, J=9 Hz, 2H), 7.77 (d, J=9 Hz, 2H), 7.66 (dd, J=5, 3 Hz, 1H), 7.60 (dd, J=5, 2 Hz, 1H), 7.47–7.44 (m, 4H), 7.29 (d, J=9 Hz, 2H), 6.68 (s, 1H), 5.26 (t, J=6 Hz, 1H), 4.53 (d, J=6 Hz, 2H).

Anal. Calcd. for C$_{20}$H$_{17}$N$_3$O$_3$S$_2$ 1/4 H$_2$O: C, 57.74; H, 4.24; N, 10.10. Found: C, 57.83; H, 4.27; N, 10.01.

Example 20

1-[4-(Methylsulfonyl)phenyl]-5-[4-(3-furyl)phenyl]-3-trifluoromethyl-1H-pyrazole The title compound was prepared according to the procedure of Example 17 using 1-[4-(Methylsulfonyl)phenyl]-5-(4-bromophenyl)-3-trifluoromethyl-1H-pyrazole and furan-3-boronic acid, instead of thiophen-3-boronic acid.

mp: 165–166° C.

$^1$H-NMR (CDCl$_3$) δ: 7.96 (ddd, J=9, 2, 2 Hz, 2H), 7.79 (br, 1H), 7.57 (ddd, J=9, 2, 2 Hz, 2H), 7.52–7.48 (m, 3H), 7.26–7.22 (m, 2H), 6.81 (s, 1H), 6.71 (br, 1H), 3.07 (s, 3H).

Anal. Calcd. for C$_{21}$H$_{15}$N$_2$O$_3$F$_3$S 1/2 H$_2$O: C, 57.14; H, 3.65; N, 6.35. Found: C, 57.48; H, 3.61; N, 6.34.

Example 21

4-[5-[4-(2-Thiazolyl)phenyl]-3-(trifluoromethyl)-1H-pyrazol-1-yl]-1-phenylsulfonamide To a stirred solution of thiazole (1.61 g, 18.9 mmol) in diethylether (20 mL) was added n-BuLi (1.58 M solution in hexane, 12.7 mL, 20.0 mmol) at −78° C. under nitrogen, and the mixture was stirred for 30 minutes. Zinc chloride (1.0 M solution in diethylether, 20 mL, 20 mmol) was added, and the mixture was allowed to warm up to room temperature for 30 minutes. 4-[5-(4-Bromophenyl)-3-(trifluoromethyl)-1H-pyrazol-1-yl]-1-phenylsulfonamide (0.60 g, 1.34 mmol), tetrakis(triphenylphosphine)palladium (0.02 g, 0.173 mmol) was added, and the mixture was heated at reflux temperature for 5 hours, and cooled down to room temperature. The mixture was filtered through celite, and the filtrate was washed with brine, dried over MgSO$_4$, concentrated in vacuo. The residue was purified by flash chromatography eluting with ethyl acetate/hexane (1/2). The resulting solid was recrystallized with CH$_2$Cl$_2$-hexane to give the title compound (0.155 g, 26% yield).

mp: 120–122° C.

$^1$H-NMR (CDCl$_3$) δ: 7.99 (d, J=8 Hz, 2H), 7.93 (d, J=9 Hz, 2H), 7.90 (d, J=3 Hz, 1H), 7.50 (d, J=9 Hz, 2H), 7.40 (d, J=3 Hz, 1H), 7.32 (d,J=8 Hz, 2H), 6.85 (s, 1H), 5.00 (s, 2H).

Anal. Calcd. for C$_{19}$H$_{13}$F$_3$N$_4$O$_2$S$_2$ H$_2$O: C, 48.71; H, 3.23; N, 11.96. Found: C, 48.78; H, 3.00; N, 11.98.

Example 22

1-[4-(Methylsulfonyl)phenyl]-5-[4-(2-thiazolyl)phenyl]-3-trifluoromethyl-1H-pyrazole The title compound was prepared according to the procedure of Example 21 using 1-[4-(Methylsulfonyl)phenyl]-5-(4-bromophenyl)-3-trifluoromethyl-1H-pyrazole.

mp: 206–207° C.

$^1$H-NMR (CDCl$_3$) δ: 8.01–7.94 (m, 4H), 7.91 (d, J=3 Hz, 1H), 7.57 (ddd, J=9, 2, 2 Hz, 2H), 7.41 (d, J=3 Hz, 1H), 7.33 (ddd, J=9, 2, 2 Hz, 2H), 6.86 (s, 1H), 3.08 (s, 3H).

Anal. Calcd. for C$_{20}$H$_{14}$N$_3$O$_2$F$_3$S$_2$: C, 53.44; H, 3.14: N, 9.35. Found: C, 53.20; H, 3.33; N, 9.14.

Example 23

4-[5-[4-(5-Thiazolyl)phenyl]-3-(trifluoromethyl)-1H-pyrazol-1-yl]-1-phenylsulfonamide
2-Trimethylsilyl-5-trimethylstannylthiazole(step 1)

To a stirred solution of n-BuLi (1.61 M solution in hexane, 9.3 mL, 15.0 mmol) in diethylether (60 mL) was added a solution of 2-trimethylsilylthiazole (1.97 g, 12.5 mmol) in diethylether (25 mL) dropwise at −78° C. over 1 hour under nitrogen. The mixture was stirred at −78° C. for 1 hour, and then a solution of 2-trimethyltinchloride (3.00 g, 15.0 mmol) in diethylether (20 mL) was added dropwise over 20 minutes. After an additional 3 hours at −78° C., the reaction mixture was filtered and the filterate was concentrated in vacuo to give 4.17 g of creem colored solid. The compound was used for next reaction without purification.
4-[5-[4-(5-Thiazolyl)phenyl]-3-(trifluoromethyl)-1H-pyrazol-1-yl]-1-phenylsulfonamide(step 2)

To a stirred solution of 4-[5-(4-bromophenyl)-3-(trifluoromethyl)-1H-pyrazol-1-yl]-1-phenylsulfonamide (0.30 g, 0.67 mmol) in benzene (8 mL) was added 2-trimethylsilyl-5-trimethylstannylthiazole (0.26 g, 0.8 mmol), and tetrakis(triphenylphosphine)palladium(0) (0.10 g, 0.087 mmol) at room temperature under nitrogen. The mixture was heated at reflux temperature for 40 hours, and cooled down to room temperature. The reaction mixture was purified by flash chromatography eluting with ethyl acetate/hexane (1/2). The resulting solid was recrystallized with CH$_2$Cl$_2$-hexane to give title compound (0.170 g, 56% yield).

mp: 222–224° C.

$^1$H-NMR (DMSO d$_6$) δ: 9.13 (s, 1H), 8.41 (s, 1H), 7.90 (d, J=8 Hz, 2H), 7.76 (d, J=8 Hz, 2H), 7.60 (d, J=9 Hz, 2H), 7.52 (s, 2H), 7.40 (d, J=8 Hz, 2H), 7.32 (s, 1H).

Anal. Calcd. for C$_{19}$H$_{13}$F$_3$N$_4$O$_2$S$_2$ 1/4 H$_2$O: C, 50.16; H, 2.99; N, 12.31. Found: C, 49.93; H, 3.20; N, 12.26.

Example 24

1-[4-(Methylsulfonyl)phenyl]-5-[4-(5-thiazolyl)phenyl]-3-trifluoromethyl-1H-pyrazole The title compound was prepared according to the procedure of Example 23 (step 2) using 1-[4-(Methylsulfonyl)phenyl]-5-(4-bromophenyl)-3-trifluoromethyl-1H-pyrazole.

mp: 169–170° C.

$^1$H-NMR (CDCl$_3$) δ: 8.81 (s, 1H), 8.14 (s, 1H), 7.98 (d, J=8 Hz, 2H), 7.63–7.56 (m, 4H), 7.29 (d, J=8 Hz, 2H), 6.84 (s, 1H), 3.08 (s, 3H).

Anal. Calcd. for $C_{20}H_{14}N_3O_2F_3S_2$ 1/4 $H_2O$: C, 52.91; H, 3.22; N, 9.26. Found: C, 53.02; H, 3.24; N, 9.30.

Example 25

4-[5-[4-(5-Chloro-2-thienyl)phenyl]-3-(trifluoromethyl)-1H-pyrazol-1-yl]-1-phenylsulfonamide 4-[5-[4-(4,4,5,5-Tetramethyl-[1,3,2]dioxaborolan-2-yl)phenyl]-3-trifluoromethyl-]1H-pyrazol-1-yl]-1-phenylsulfonamide(step 1)

To a stirred solution of 4-[5-(4-bromophenyl)-3-(trifluoromethyl)-1H-pyrazol-1-yl]-1-phenylsulfonamide (2.09 g, 4.69 mmol) in dioxane (28 mL) was added bis(pinacolato)diboron (1.31 g, 5.16 mmol), 1,1'-bis(diphenylphosphino)ferrocene (0.14 g, 0.257 mmol), [1,1'-bis(diphenylphosphino)ferrocene]dichloropalladium (0.21 g, 0.257 mmol) and potassium acetate (1.38 g, 14.1 mmol) at room temperature under nitrogen. The mixture was stirred at 80° C. for 20 hours, and cooled down to room temperature. The reaction mixture was diluted with water and the whole was extracted with ethyl acetate. The organic layer was washed with brine, dried over $MgSO_4$, and concentrated in vacuo. The residue was purified by flash chromatography eluting with ethyl acetate/hexane (1/3) to give the title compound (1.85 g, 80% yield).

$^1$H-NMR (CDCl$_3$) δ: 7.90 (d, J=8 Hz, 2H), 7.79 (d, J=7 Hz, 2H), 7.46 (d, J×8 Hz, 2H), 7.22 (d, J=7 Hz, 2H), 6.80 (s, 1H), 4.95 (s, 2H), 1.35 (s, 12H).

4-[5-[4-(5-Chloro-2-thienyl)phenyl]-3-(trifluoromethyl)-1H-pyrazol-1-yl]-1-phenylsulfonamide(step 2)

To a stirred solution of 4-[5-[4-(4,4,5,5-tetramethyl-[1,3,2]dioxaborolan-2-yl)phenyl]-3-trifluoromethyl-1H-pyrazol-1-phenylsulfonamide (0.10 g, 0.203 mmol) in DME (3 mL) was added 2-bromo-5-chlorothiophen (0.048 g, 0.244 mmol), dichlorobis(triphenylphosphine)palladium (0.1 g, 0.14 mmol) and saturated $NaHCO_3$ solution (1 mL) at room temperature under nitrogen. The mixture was heated at reflux temperature for 20 hours, and cooled down to room temperature. The reaction mixture was purified by flash chromatography eluting with ethyl acetate/hexane (1/4). The resulting solid was recrystallized with $CH_2Cl_2$-hexane to give the title compound (0.045 g, 46% yield).

mp: 181–183° C.

$^1$H-NMR (CDCl$_3$) δ: 7.94 (d, J=9 Hz, 2H), 7.51 (d, J=9 Hz, 4H), 7.23 (d, J=9 Hz, 2H), 7.13 (d, J=4 Hz, 1H), 6.92 (d, J=4 Hz, 1H), 6.80 (s, 1H), 4.92 (s, 2H).

Anal. Calcd. for $C_{20}H_{13}ClF_3N_3O_2S_2$: C, 49.64; H, 2.71; N, 8.68. Found: C, 49.64; H, 3.10; N, 8.48.

Example 26

4-[5-[4-(1H-Imidazol-1-yl)phenyl]-3-trifluoromethyl-1H-pyrazol-1-yl]-1-phenylsulfonamide 4,4,4-Trifluoro-1-[4-(1-Imidazolyl)phenyl]butane-1,3-dione (step 1)

To a THF (5 mL) solution of 1,1,1,3,3,3-hexamethyldisilazane (0.178 g, 1.1 mmol) was added n-butyl lithium (1.6 M solution in hexane, 0.72 mL, 1.2mmol) at 0° C. under nitrogen, and the mixture was stirred for 30 minutes, and cooled to −78° C. 4-(1-Imidazolyl)acetophenone (prepared according to the method of M. A. Khan et, al., *J. Chem. Soc. C.*, 1970, 85., 0.186 g, 1.0 mmol) was added to the mixture, and residue was stirred for 1 hour. Ethyl trifluoroacetate (0.17 g, 1.2 mmol) was added tothe reaction mixture, the residure was warm to room temperature. The reaction mixture was poured into ice water and the whole was extracted with ethyl acetate (30 mL×2). The organic layer was washed with brine, dried over $Na_2SO_4$, and concentrated in vacuo. The resulting solid was washed with small amount of ethyl acetate to give the title compound (0.163 g).

$^1$H-NMR (DMSO d$_6$) δ: 8.34 (s, 1H), 7.94 (d, J=9 Hz, 2H), 7.82 (d, J=2 Hz, 1H), 7.70 (d, J=9 Hz, 2H), 7.13 (s, 1H), 6.02 (s, 1H).

4-[5-[4-(1H-Imidazol-1-yl)phenyl]-3-trifluoromethyl-1H-pyrazol-1-yl]-1-phenylsulfonamide(step 2)

A mixture of 4,4,4-Trifluoro-1-[4-(1-Imidazolyl)phenyl]butane-1,3-dione (0.16 g, 0.57 mmol), 4-sulphonamidophenylhydrazine hydrochloride (commercially available from Maybridge Chem.Co., 0.14 g, 0.62 mmol) and absolute ethanol (20 mL) was heated at reflux temperature for 20 hour. After cooling, ethanol was removed under reduced pressure, then water (100 mL) was added to the mixture. The whole was extracted with ethyl acetate (100 mL), the organic layer was washed with brine, dried over $MgSO_4$, and concentrated in vacuo. The residue was purifed by flash chromatography on silica(NH-silica gel, FUJI SILISIA CHEMICAL LTD. DM2035) eluting with ethyl acetate/$CH_2Cl_2$/methanol (1/1/0.1). The resulting solid was recrystallized with ethyl acetate-diisopropyl ether to give the title compound (0.085 g, 35% yield).

mp: 231–231.5° C.

$^1$H-NMR (DMSO d$_6$) δ: 8.36 (s, 1H), 7.90 (d, J=9 Hz, 2H), 7.83 (br, 1H), 7.76 (d, J=9 Hz, 2H), 7.60 (d, J=9 Hz, 2H), 7.52 (br, 2H), 7.47 (d, J=9 Hz, 2H), 7.32 (s, 1H), 7.12 (s, 1H).

Anal. Calcd. for $C_{19}H_{14}N_5O_2F_3S$ 1/4 $H_2O$: C, 52.11; H, 3.34; N, 15.99. Found: C, 52.04; H, 3.43; N, 15.96.

Example 27

4-[5-[4-(2,5-Dimethylpyrrol-1-yl)phenyl]-3-trifluoromethyl-1H-pyrazol-1-yl]-1-phenylsulfonamide 4,4,4-Trifluoro-1-[4-(2,5-Dimethylpyrrol-1-yl)phenyl]butane-1,3-dione (step 1)

To a THF (20 mL) solution of 1,1,1,3,3,3-hexamethyldisilazane (1.3 g, 8.1 mmol) was added n-butyllithium (1.55 M solution in hexane, 5.2 mL, 8.1 mmol) at 0° C. under nitrogen, and the mixture was stirred for 30 minutes, and cooled to −78° C. 4-(2,5-Dimethylpyrrol-1-yl)acetophenone (commercially available from Lancaster Synthesis, 1.56 g, 7.3 mmol) was added to the mixture, and residue was stirred for 1 hour. N-Trifluoroacetylimidazol (1.44 g, 8.8 mmol) was added to the reaction mixture, the residure was stirred for 3 hour. The reaction mixture was poured into water and the whole was extracted with ethyl acetate (50 mL×2). The organic layer was washed with brine, dried over $MgSO_4$, and concentrated in vacuo. The residue was purified by column chromatography on silica(ethyl acetate/Hexane=1/1) to give the title compound (0.75 g).

$^1$H-NMR (CDCl$_3$) δ7.99 (d, J=9 Hz, 2H), 7.24 (d, J=9 Hz, 2H), 6.45 (s, 1H), 5.19 (s, 2H), 2.04 (s, 3H), 2.0 (s, 3H).

4-[5-[4-(2,5-Dimethylpyrrol-1-yl)phenyl]-3-trifluoromethyl-1H-pyrazol-1-yl]-1-phenylsulfonamide(step 2)

The subtitled compound was prepared according to the procedure of Example 26 (step 2) using 4,4,4-trifluoro-1-[4-(2,5-dimethylpyrrol-1-yl)phenyl]butane-1,3-dione, instead of 4,4,4-trifluoro-1-[4-(1-imidazolyl)phenyl]butane-1,3-dione.

mp: 210–211° C.

$^1$H-NMR (CDCl$_3$) δ: 7.95 (ddd, J=9, 2, 2 Hz, 2H), 7.53 (ddd, J=9, 2, 2 Hz, 2H), 7.34 (ddd, J=9, 2, 2 Hz, 2H), 7.26–7.22 (2H), 6.85 (s, 1H), 5.93 (s, 2H), 4.85 (br, 2H), 2.05 (s, 6H).

Example 28

4-[5-[4-(2-thienyl)phenyl]-3-(trifluoromethyl)-1H-pyrazol-1-yl]-1-phenylsulfonamide

4,4,4-Trifluoro-1-[4-(3-thienyl)phenyl]butane-1,3-dione (step 1)

The subtitled compound was prepared according to the procedure of Example 27 (step 1) using 4-(3-thienyl)acetophenone (prepared according the method of *Heterocycles*, 1990, 31, 1951.) instead of 4-(2,5-dimethylpyrrol-1-yl)acetophenone.

$^1$H-NMR (CDCl$_3$) δ: 7.95–7.90 (m, 2H), 7.8–7.7 (m, 2H), 7.68–7.6 (m, 2H), 7.20–7.15 (m, 1H), 6.32 (1H).

4-[5-[4-(2-thienyl)phenyl]-3-(trifluoromethyl)-1H-pyrazol-1-yl]-1-phenylsulfonamide (step 2)

The title compound was prepared according to the procedure of Example 26 (step 2) using 4,4,4-Trifluoro-1-[4-(3-thienyl)phenyl]butane-1,3-dione, instead of 4,4,4-trifluoro-1-[4-(1-imidazolyl)phenyl]butane-1,3-dione.

mp: 207.5–208° C.

$^1$H-NMR (CDCl$_3$) δ: 7.94 (ddd, J=9, 2, 2 Hz, 2H), 7.62 (ddd, J=9, 2, 2 Hz, 2H), 7.52 (ddd, J=9, 2, 2 Hz, 2H), 7.37 (dd, J=5, 1 Hz, 1H), 7.34 (dd, J=4, 1 Hz, 1H), 7.30–7.22 (m, 2H), 7.11 (dd, J 5, 4 Hz, 1H), 6.81 (s, 1H), 4.87 (br, 2H).

Anal. Calcd. for C$_{20}$H$_{14}$N$_3$O$_2$F$_3$S$_2$: C, 53.44; H, 3.14; N, 9.35. Found: C, 53.71; H, 3.15; N, 9.29.

Example 29

4-[5-[4-(2-Furyl)phenyl]-3-(trifluoromethyl-1 1H-pyrazol-1-yl]-1-phenylsulfonamide

4,4,4-Trifluoro-1-[4-(2-furyl)phenyl]butane-1,3-dione (step 1)

The title compound was prepared according to the procedure of Example 27 (step 1) using 4-(2-furyl)acetophenone (prepared according the method of Heterocycles, 1990, 31, 1951.) instead of 4-(2,5-dimethylpyrrol-1-yl)acetophenone.

$^1$H-NMR (CDCl$_3$) δ: 8.04 (d, J=8 Hz, 2H), 7.79 (d, J=8 Hz, 2H), 7.68 (s, 1H), 6.99 (d, J=3 Hz, 1H), 6.58 (dd, J=3, 2 Hz, 1H) 6.41 (s, 1H).

4-[5-[4-(2-Furyl)phenyl]-3-(trifluoromethyl)-1H-pyrazol-1-yl]-1-phenylsulfonamide (step 2)

The title compound was prepared according to the procedure of Example 26 (step 2) using 4,4,4-Trifluoro-1-[4-(2-furyl)phenyl]butane-1,3-dione, instead of 4,4,4-trifluoro-1-[4-(1-imidazolyl)phenyl]butane-1,3-dione.

mp: 192–193° C.

$^1$H-NMR (CDCl$_3$) δ: 7.92 (ddd, J=9, 2, 2 Hz, 2H), 7.67 (ddd, J=9, 2, 2 Hz, 2H), 7.53–7.48 (m, 3H),7.24 (ddd, J=9, 2, 2 Hz, 2H), 6.80 (s, 1H), 6.73 (dd, J=3, 1 Hz, 1H), 6.51 (dd, J=3,2 Hz, 1H), 4.91 (s, 2H).

Anal. Calcd. for C$_{20}$H$_{14}$N$_3$O$_3$F$_3$S: C, 55.43; H, 3.26; N, 9.70. Found: C, 55.50; H, 3.38; N, 9.52.

Example 30

4-[5-[4-(2-furyl)-3-methylphenyl]-3-(trifluoromethyl)-1H-pyrazol-1-yl]-1]-phenylsulfonamide

Trifluoromethanesulfonic acid 4-acetyl-2methylphenyl ester (step 1)

To a stirred solution of 1-(4-hydroxy-3-methylphenyl)ethanone (3.76 g, 25.0 mmol) in CH$_2$Cl$_2$ (150 mL) was added 2,6-lutidine (3.21 g, 30.0 nmmol), 4-dimethylaminopyridine (0.61 g, 5.0 mmol), trifluoromethanesulfonic anhydride (8.46 g, 30.0 mmol) at −30° C. under nitrogen, and the mixture was stirred for 1 hour, and then allowed to warm up to room temperature for 2 hours. The reaction mixture was diluted with water and the whole was extracted with CH$_2$Cl$_2$. The organic layer was washed with brine, dried over MgSO$_4$, and concentrated in vacuo to give 7.06 g of brown oil. The sub title compound was used for next reaction without purification.

1-[4-(2-Furyl)-3-methylphenyl]ethanone (step 2)

To a stirred solution of trifluoromethanesulfonic acid 4-acetyl-2methylphenyl ester (1.19 g, 4.2 mmol) in 1,4-dioxane (40 mL) was added 2-(tributylstannyl)furan (1.81 g, 5.05 mmols), lithium chloride (0.45 g, 10.5 mmol) and tetrakis(triphenylphosphine)palladium (0.49 g, 0.42 mmol) under nitrogen. The mixture was heated at reflux temperature for 2 hours, and cooled down to room temperature. The reaction mixture was diluted with water and the whole was extracted with diethylether. The organic layer was washed with saturated NaHCO$_3$ aqueous solution, brine, dried over MgSO$_4$, and concentrated in vacuo. The residue was purified by flash chromatography eluting with ethyl acetate/hexane (1/10) to give title compound (0.845 g, quant).

$^1$H-NMR (CDCl$_3$) δ: 7.83–7.82 (m, 3H), 7.56 (d, J=2 Hz, 1H), 6.70 (d, J=4 Hz, 1H), 6.55 (dd, J=4, 2 Hz, 1H), 2.61 (s, 3H), 2.57 (s, 3H).

4,4,4-Trifluoro-1-[4-(2-furyl)-3-methylphenyl]butane-1,3-dione (step 3)

To a stirred soluition of ethyl trifluoroacetate (0.66 g, 4.67 mmol) in t-butylmethylether (15 mL) was added sodium methoxide (28 wt. % solution in methanol; 1.2 mL, 4.98 mmol) over 2 min. A solution of 1-[4-(2-furyl)-3-methylphenyl]ethanone in t-butylmethylether (4 mL) was added dropwise over 5 minutes, and the mixture was stirred for 20 hours. 2N HCl (10 mL) was added, and the whole was extracted with ethyl acetate. The organic layer was washed with brine, dried over MgSO$_4$, and concentrated in vacuo to give 1.12 g of brown oil. The compound was used for next reaction without purification.

4-[5-[4-(2-Furyl)-3-methylphenyl]-3-(trifluoromethyl)-1H-pyrazol-1-yl]-phenylsulfonamide (step 4)

To a stirred soluition of 4,4,4-trifluoro-1-[4-(2-furyl)-3-methylphenyl]butane-1,3-dione (0.53 g, 1.80 mmol) in ethanol (22.5 ml) was added (4-sulfamoylphenyl)hydrazine hydrochloride (0.44 ml, 1.98 mmol), and the mixture was heated at reflux temperature for 16 hours. The mixture was cooled down to room temperature, and concentrated in vacuo. The residue was dissolved in ethyl acetate. washed with brine, dried over MgSO$_4$, and concentrated in vacuo. The residue was purified by flash chromatography eluting with ethyl acetate/hexane (1/3). The resulting solid was recrystallized with dichloromethane-hexane to give the title compound (0.16 g, 20% yield).

$^1$H-NMR (CDCl$_3$) δ: 7.86 (dd, J=9, 2 Hz, 2H), 7.66 (dd, J=8, 2 Hz, 1H), 7.49–7.43 (m, 3H), 7.17 (s, 1H), 6.99 (d, J=8 Hz, 1H), 6.77 (s, 1H), 6.60 (d, J=4 Hz, 1H), 6.50 (dd, J=4,2 Hz, 1H), 5.43 (s, 2H), 2.45 (s, 3H).

Anal. Calcd. for C$_{21}$H$_{16}$N$_3$O$_3$F$_3$S 1/10 H$_2$O: C, 56.15; H, 3.63; N, 9.35. Found: C, 56.29; H, 3.83; N, 8.96.

Example 31

1-[4-(Methylsulfonyl)phenyl]-5-[4-(2-furyl)-3-methylphenyl]-3-(trifluoromethyl)-1H-pyrazole

The title compound was prepared according to the procedure of Example 30 (step 4) using (4-methylsulfonyl)hydrazine hydrochloride instead of (4-sulfamoylphenyl)hydrazine hydrochloride.

mp: 174–176° C.

¹H-NMR (CDCl₃) δ: 7.95 (d, J=9 Hz, 2H), 7.70 (d, J=8 Hz, 1H), 7.58 (d, J×9 Hz, 2H), 7.53 (d, J=2 Hz, 1H), 7.19 (s, 1H), 7.04 (dd, J=8, 2 Hz, 1H), 6.80 (s, 1H), 6.64 (d, J=4 Hz, 1H), 6.53 (dd, J=4,2 Hz, 1H), 3.06 (s, 3H), 2.49 (s, 3H).

Anal. Calcd. for $C_{22}H_{17}N_2O_3F_3S$: C, 59.19; H, 3.84; N, 6.27. Found: C, 58.90; H, 4.17; N, 6.44.

Example 32

3-[4-(3-Thienyl)phenyl]-4-[4-(methylsulfonyl)phenyl]-2-(5H)-furanone 4-(3-Thienyl)phenylacetic acid (step 1)

A mixture of 4-bromophenylacetic acid (1.08 g, 5 mmol), 3-thiopheneboronic acid (0.7 g, 5.5 mmol), NaHCO₃ (1.68 g, 20 mmol), and dichlorobis(triphenylphosphine)palladium (0.35 g, 0.5 mmol) in DME-water (21 mL–7 mL) was heated at reflux temperature for 2 hours under nitrogen. After cooling, the reaction mixture was partitioned between Et₂O (80 mL) and saturated aqueous NaHCO₃ (30 mL). The organic layer was washed with saturated aqueous NaHCO₃ (30 mL) again. The combined aqueous layer was acidified with 2N HCl solution and the whole extracted with CH₂Cl₂ (50 mL×3). The combined organic layer was washed with brine, dried over MgSO₄, and concentrated in vacuo. The residue was purified by flash chromatography (SiO₂) eluting with ethyl acetate/hexane (1/1) to give the subtitle compound (0.56 g, 51% yield).

¹H-NMR (CDCl₃) δ: 7.56 (d, J=8.2 Hz, 2H), 7.44 (dd, J=2.6, 1.8 Hz, 1H), 7.38 (d, J=2.6 Hz, 1H), 7.38 (d, J=1.8 Hz, 1H), 7.32 (d, J=8.2 Hz, 2H), 3.68 (s, 2H).

2-Bromo-1-[4-(methylsulfonyl)phenyl]ethanone

To a stirred solution of 4-(methylthio)acetophenone (5 g, 30 mmol) in CH₂Cl₂ (60 mL) was added m-chloroperbenzoic acid (70% purity, 10.35 g, 60 mmol) in a portionwise at 0° C. After stirring for 2 hours, the mixture was poured into saturated aqueous NaHCO₃ (100 mL). The whole was extracted with CH₂Cl₂ (100 mL×3), the combined organic layer washed with water, brine, dried over MgSO₄, and concentrated in vacuo. The residue was purified by flash chromatography (SiO₂) eluting with ethyl acetate/hexane (1/1) to give 4-(methylsulfonyl)acetophenone (4.86 g, 82% yield).

¹H-NMR (CDCl₃) δ: 8.14 (d, J=8.6 Hz, 2H), 8.05 (d, J=8.6 Hz, 2H), 3.09 (s, 3H), 2.68 (s, 3H).

To a solution of 4-(methylsulfonyl)acetophenone (4.85 g, 24.5 mmol) in CHCl₃ (70 mL) was added aluminum chloride (1 mg) and bromine (1.1 mL) in CHCl₃ (8.5 mL) dropwise. The mixture was stirred overnight, and poured into water. The whole was extracted with ethyl acetate (50 mL×2), the combined organic layer was dried over MgSO₄, and concentrated in vacuo. The resulting residue was recrystallized from ethyl acetate/hexane (1/1) to give the subtitle compound (5.28 g, 78% yield).

¹H-NMR (CDCl₃) δ: 8.21–8.14 (m, 2H), 8.11–8.05 (m, 2H), 4.46 (s, 2H), 3.12 (s, 3H).

3-[4-(3-Thienyl)phenyl]-4-[4-(methylsulfonyl)phenyl]-2-(5H)-furanone (step 2)

To a suspension of 2-bromo-1-[4-(methylsulfonyl)phenyl]ethanone (0.27 g, 1 mmol) and 4-(3-thienyl)phenylacetic acid (0.19 g, 0.9 mmol) in acetonitrile (5 mL) was added Et₃N (0.33 mL) at 0° C. under nitrogen. After stirring for 20 minutes at room temperature, the mixture was chilled in ice bath. DBU (0.29 mL) was added to the mixture, and stirred for 20 minutes at 0° C. To the mixture was added 1N HCl solution (8 mL) and ice-water (10 mL), and the mixture was stirred for 2 minutes. The whole was extracted with CH₂Cl₂ (50 mL×3), the combined organic layer washed with brine, dried over MgSO₄, and concentrated in vacuo. The residue was purified by flash chromatography eluting with ethyl acetate/hexane (1/1) followed by recrystallization from ethyl acetate/hexane to provide the title compound (0.15 g, 39% yield).

mp : 220–222° C.

¹H-NMR (CDCl₃) δ: 7.95 (d, J=8.6 Hz, 2H), 7.63 (d, J=8.4 Hz, 2H), 7.55 (d, J=8.6 Hz, 2H), 7.51 (dd, J=2.6, 1.6 Hz, 1H), 7.44 (d, J=8.4 Hz, 2H), 7.40 (d, J=2.6 Hz, 1H), 7.39 (d, J=1.6 Hz, 1H), 5.20 (s, 2H), 3.08 (s, 3H).

Anal. Calcd. for $C_{21}H_{16}O_4S_2$: C, 63.62; H, 4.07. Found: C, 63.48; H, 4.33.

MS (ESI): 395 (M−1)

Example 33

3-[4-(2-Thienyl)phenyl]-4-[4-(methylsulfonyl)phenyl]-2-(5H)-furanone 4-(2-Thienyl)phenylacetic acid The subtitle compound was prepared according to the procedure of Example 32 using 2-thiopheneboronic acid instead of 3-thiopheneboronic acid in step 1.

¹H-NMR (CDCl₃) δ: 7.56 (d, J=8.2 Hz, 2H), 7.29–7.25 (m, 4H), 7.06 (dd, J=5.1, 3.6 Hz, 1H), 3.64 (s, 2H).

3-[4-(2-Thienyl)phenyl]-4-[4-(methylsulfonyl)phenyl]-2-(5H)-furanone

The title compound was prepared according to the procedure of Example 32 using 4-(2-thienyl)phenylacetic acid instead of 4-(3-thienyl)phenylacetic acid in step 2.

mp: 198–201° C.

¹H-NMR (CDCl₃) δ: 7.95 (d, J=8.6 Hz, 2H), 7.64 (d, J=8.4 Hz, 2H), 7.55 (d, J=8.6 Hz, 2H), 7.43 (d, J=8.4 Hz, 2H), 7.37 (dd, J=3.6, 1.2 Hz, 1H), 7.33 (dd, J=5.1, 1.2 Hz, 1H), 7.10 (dd, J=5.1, 3.6 Hz, 1H), 5.20 (s, 2H), 3.09 (s, 3H).

Anal. Calcd. for $C_{21}H_{16}O_4S_2$ 0.2H₂O: C, 63.04; H, 4.13. Found: C, 63.01; H, 4.31.

MS (ESI): 395 (M−1)

Example 34

3-[4-(3-Furyl)phenyl]-4-[4-(methylsulfonyl)phenyl]-2-(5H)-furanone 4-(3-Furyl)phenylacetic acid The subtitle compound was prepared according to the procedure of Example 32 using 3-furanboronic acid instead of 3-thiopheneboronic acid in step 1.

¹H-NMR (CDCl₃) δ: 7.70 (br.s, 1H), 7.46 (t, J=1.6 Hz, 1H), 7.42 (d, J=8.1 Hz, 2H), 7.27 (d, J=8.1 Hz, 2H), 6.94 (br.s, 1H), 3.63 (s, 2H).

3-[4-(3-Furyl)phenyl]-4-[4-(methylsulfonyl)phenyl-2-(5H)-furanone

The title compound was prepared according-to the procedure of Example 32 using 4-(3-furyl)phenylacetic acid instead of 4-(3-thienyl)phenylacetic acid in step 2.

mp: 188–190° C.

¹H-NMR (CDCl₃) δ: 7.94 (d, J=8.7 Hz, 2H), 7.77 (dd, J=1.5, 1.0 Hz, 1H), 7.58–7.48 (m, 5H), 7.42 (d, J=8.6 Hz, 2H), 6.71 (dd, J=2.0, 1.0 Hz, 1H), 5.19 (s, 2H), 3.08 (s, 3H).

Anal. Calcd. for $C_{21}H_{16}O_5S$ 0.4H₂O: C, 65.07; H, 4.37. Found: C, 65.01; H, 4.58.

MS (ESI): 379 (M−1)

Example 35

5-[3-Fluoro-4-(methylsulfonyl)phenyl]-1-[4-(2-furyl)phenyl]-2-methyl-1H-pyrrole 3-Fluoro-4-(methylthio)benzaldehyde (Step 1)

A mixture of 3,4-difluorobenzaldehyde (4.26 g, 30 mmol) and sodium thiomethoxide (2.1 g, 30 mmol) in DMF (40 mL) was heated at 90° C. for 1 hour. After cooling, 2N aqueous HCl was added to the mixture. The whole was extracted with $Et_2O$ (70 mL×3), the combined organic layer washed with water, brine, dried over $MgSO_4$, and concentrated in vacuo. The residue was purified by flash chromatography on silica gel eluting with ethyl acetate/hexane (1/10) to provide the subtitle compound (3.1 g, 61% yield) as a colorless oil.

$^1$H-NMR (CDCl$_3$) δ: 9.91 (d, J=2.0 Hz, 1H), 7.63 (dd, J=8.0, 1.6 Hz, 1H), 7.50 (dd, J=10, 1.6 Hz, 1H), 7.32 (t, J=7.7 Hz, 1H), 2.54 (s, 3H).

1-[3-Fluoro-4-(methylsulfonyl)phenyl]pentane-1 4-dione (Step 2)

To a stirred solution of 3-fluoro-4-(methylthio) benzaldehyde (3.04 g, 17.9 mmol) in ethanol (12 mL) was added methyl vinyl ketone (1.3 mL, 15.5 mmol), 3-benzyl-5-(2-hydroxyethyl)-4-methylthiazolium chloride (0.84 g, 3.1 mmol), and $Et_3N$ (4.32 mL, 31 mmol) at room temperature. After stirring for 2 hours, volatiles were removed by evaporation. The residue was taken up with ethyl acetate (200 mL), and washed with water (120 mL) dil. aqueous HCl (120 mL). water (120 mL), brine (120 mL), dried over $MgSO_4$, and concentrated in vacuo. The resulting crude residue was purified by flash chromatography on silica gel eluting with ethyl acetate/hexane (1/2) to provide 1-[3-fluoro-4-(methylthio)phenyl]pentane-1,4-dione (2.7 g, 73% yield). To a stirred suspension of 1-[-3-fluoro-4-(methylthio) phenyl]pentane-1,4-dione (2.7 g, 11.25 mmol) in methanol (50 mL) was added Oxone (14.14 g, 23 mmol) in water (50 mL) at room temperature. After stirring for 5 hours, the mixture was diluted with water. The whole was extracted with $CH_2Cl_2$ (50 mL×4), the combined organic layer washed with brine, dried over $MgSO_4$, and evaporated in vacuo to give the subtitle compound (2.8 g, 66% yield).

$^1$H-NMR (CDCl$_3$) δ: 8.09 (dd, J=8.1, 6.6 Hz, 1H), 7.92 (dd, J=8.1, 1.5 Hz, 1H), 7.81 (dd, J=10.4, 1.6 Hz, 1H), 3.25 (d, J=0.6 Hz, 3H), 3.28–3.20 (m, 2H), 3.00–2.91 (m, 2H), 2.26 (s, 3H).

1-(4-Bromophenyl)-2-[3-fluoro-4-(methylsulfonyl)phenyl]-5-methyl-1H-pyrrole (Step 3)

A mixture of 1-[3-fluoro-4-(methylsulfonyl)phenyl] pentane-1,4-dione (2.8 g, 10.3 mmol), 4-bromoaniline (2.12 g, 12.3 mmol), and p-toluenesulfonic acid (150 mg) in toluene (250 mL) was heated at reflux temperature using Dean-Stark apparatus. After cooling down, volatiles were removed by evaporation. The residue was purified by flash chromatography on silica gel eluting with ethyl acetate/hexane (1/5) to give the subtitle compound (4 g, 95% yield).

5-[3-Fluoro-4-(methylsulfonyl)phenyl]1-[4-(2-furyl) phenyl]-2-methyl-1H-pyrrole (Step 4)

To a stirred suspension of 1-(4-bromophenyl)-2-[3-fluoro-4-(methylsulfonyl)phenyl]-5-methyl-1H -pyrrole (0.41 g, 1 mmol), 2-furanboronic acid (0.14 g, 1.26 mmol), $NaHCO_3$ (0.19 g, 2.3 mmol) in DME-water (6 mL–2 mL) was added dichlorobis(triphenylphosphine)palladium (80 mg, 0.115 mmol) at room temperature under nitrogen. The mixture was heated at reflux temperature for 6 hours. After cooling, volatiles were removed by evaporation. The residue was purified by flash chromatography on silica gel eluting with ethyl acetate/hexane (1/2) to give the title compound (0.24 g, 61% yield).

mp: 179–182° C.

$^1$H-NMR (CDCl$_3$) δ: 7.73 (d,J=8.3 Hz, 2H), 7.65 (t,J=8.1 Hz 1H) 7.51 (br. s, 1H), 7.17 (d,J=8.3 Hz, 2H), 6.95 (d,J=8.4 Hz, 1H), 6.89 (d, J=12 Hz, 1H), 6.73 (d, J=3.3 Hz, 1H), 6.55 (d, J=3.3 Hz, 1H), 6.52 (br.s, 1H), 6.14 (d, J=3.6 Hz, 1H), 3.15 (s, 3H), 2.15 (s, 3H).

Anal. Calcd. for $C_{22}H_{18}FNO_3S$: C, 66.82; H, 4.59; N, 3.54. Found: C, 66.73; H, 4.82; N, 3.32.

Example 36

5-[3-Fluoro-4-(methylsulfonyl)phenyl]-1-[4-(3-furyl)phenyl]-2-methyl-1H-pyrrole The title compound was prepared according to the procedure of Example 35 using 3-furanboronic acid instead of 2-furanboronic acid in step 4.

mp: 147–150° C.

$^1$H-NMR (CDCl$_3$) δ: 7.79 (s, 1H), 7.66 (t, J=8.0 Hz, 1H), 7.55 (d, J=8.2 Hz, 2H), 7.52 (t, J=1.5 Hz, 1H), 7.17 (d, J=8.2 Hz, 2H), 6.95 (dd, J=8.4, 1.5 Hz, 1H), 6.88 (dd, J=11.9, 1.5 Hz, 1H), 6.73 (br. s, 1H), 6.55 (d, J=3.6 Hz, 1H), 6.14 (d, J=3.6 Hz, 1H), 3.16 (s, 3H), 2.16 (s, 3H).

Anal. Calcd. for $C_{22}H_{18}FNO_3S$: C, 66.82; H, 4.59; N, 3.54. Found: C, 66.83; H, 4.80; N, 3.26.

Example 37

2,3-Dimethyl-1-[4-(3-furyl)phenyl]-5-[4-(methylsulfonyl)phenyl]-1H-pyrrole

1-[4-(methylsulfonyl)phenyl]-3-methylpentane-1,4-dione

To a stirred solution of 4-(methylsulfonyl)benzaldehyde (1.84 g, 10 mmol) in ethanol (8 mL) was added 3-methyl-3-buten-2-one (0.8 g, 9.5 mmol), 3-benzyl-5-(2-hydroxyethyl)-4-methylthiazolium chloride (0.51 g, 1.9 mmol), and $Et_3N$ (2.65 mL, 19 mmol) at room temperature. After stirring for 3 hours, volatiles were removed by evaporation. The residue was purified by flash chromatography on silica gel eluting with ethyl acetate/hexane (1/2) to provide the subtitle compound (0.11 g).

$^1$H-NMR (CDCl$_3$) δ: 8.13 (d, J=8.2 Hz, 2H), 8.03 (d, J=8.2 Hz, 2H), 3.57 (dd, J=18.0, 9.1 Hz, 1H), 3.34–3.21 (m, 1H), 3.08 (s, 3H), 2.90 (dd, J=18.0, 4.1 Hz, 1H), 2.31 (s, 3H), 1.25 (d, J=7.4 Hz, 3H).

1-(4-Bromophenyl)-2,3-dimethyl-5-[4-(methylsulfonyl) phenyl]-1H-pyrrole

A mixture of 1-[4-(methylsulfonyl)phenyl]-3-methylpentane-1,4-dione (110 mg, 0.41 mmol), 4-bromoaniline (71 mg, 0.41 mmol), and p-toluenesulfonic acid (10 mg) in toluene (3 mL) was heated at reflux temperature using Dean-Stark apparatus. After cooling down, volatiles were removed by evaporation. The residue was purified by flash chromatography on silica gel eluting with ethyl acetate/hexane (1/3) to give the subtitle compound (110 mg, 67% yield).

$^1$H-NMR (CDCl$_3$) δ: 7.68 (d, J=8.4 Hz, 2H), 7.53 (d, J=8.4 Hz, 2H), 7.14 (d, J=8.4 Hz, 2H), 7.02 (d, J=8.4 Hz, 2H), 6.40 (s, 1H), 3.02 (s, 3H), 2.30 (s, 3H), 2.04 (s, 3H).

2,3-Dimethyl-1-[4-(3-furyl)phenyl]-5-[4-(methylsulfonyl) phenyl]-1H-pyrrole

The title compound was prepared according to the procedure of Example 35 using 1-(4-bromophenyl)-2,3-dimethyl-5-[4-(methylsulfonyl)phenyl]-1H-pyrrole instead of 1-(4-bromophenyl)-2-[3-fluoro-4-(methylsulfonyl) phenyl]-5-methyl-1H-pyrrole and 3-furanboronic acid instead of 2-furanboronic acid in step 4.

mp: 215–219° C.

$^1$H-NMR (CDCl$_3$) δ: 7.78 (t, J=1.5 Hz, 1H), 7.65 (d, J=8.6 Hz, 2H), 7.55–7.49 (m, 3H), 7.19 (d, J=8.6 Hz, 2H), 7.14 (d,

J=8.6 Hz, 2H), 6.72 (dd, J=1.5, 0.8 Hz, 1H), 6.42 (s, 1H), 3.00 (s, 3H), 2.13 (s, 3H), 2.08 (s, 3H).

Anal. Calcd. for $C_{23}H_{21}NO_3S$ $0.5H_2O$: C, 68.98; H, 5.54; N, 3.50. Found: C, 69.89; H, 5.48; N, 3.15.

Example 38

5-[4-(Methylsulfonyl)phenyl]-1-4-(3-furyl)phenyl]-2-methyl-1H-pyrrole 1-(4-Bromophenyl)-2-methyl-5-[4-(methylsulfonyl) phenyl]-1H-pyrrole (Step 1)

A mixture of 1-[4-(methylsulfonyl)phenyl]pentane-1,4-dione (3 g, 11.8 mmol), 4-bromoaniline (2.03 g, 11.8 mmol), and p-toluenesulfonic acid (150 mg) in toluene (250 mL) was heated at reflux temperature using Dean-Stark apparatus. After cooling down, volatiles were removed by evaporation. The residue was purified by flash chromatography on silica gel eluting with ethyl acetate/hexane (1/3) to give the subtitle compound (2.5 g, 54% yield).

$^1$H-NMR (CDCl$_3$) δ: 7.70 (d, J=8.4 Hz, 2H), 7.54 (d, J=8.4 Hz, 2H), 7.17 (d, J=8.4 Hz, 2H), 7.04 (d, J=8.4 Hz, 2H), 6.50 (d, J=3.5 Hz, 1H), 6.14 (d, J=3.5 Hz, 1H), 3.02 (s, 3H), 2.14 (s, 3H).

5-[4-(Methylsulfonyl)phenyl]-1-4-(3-furyl)phenyl]-2-methyl-1H-pyrrole (Step 2)

The title compound was prepared according to the procedure of Example 35 using1-(4-bromophenyl)-2-methyl-5-[4-(methylsulfonyl)phenyl]-1H-pyrrole instead of 1-(4-bromophenyl)-2-[3-fluoro-4-(methylsulfonyl)phenyl]-5-methyl-1H-pyrrole and 3-furanboronic acid instead of 2-furanboronic acid in step 4.

mp: 200–202° C.

$^1$H-NMR (CDCl$_3$) δ: 7.78 (s, 1H), 7.66 (d, J=8.4 Hz, 2H), 7.52 (m, 3H), 7.22 (d, J=8.4 Hz, 2H), 7.15 (d, J=8.4 Hz, 2H), 6.72 (br.s, 1H), 6.52 (d, J=3.6 Hz, 1H), 6.14 (d, J=3.6 Hz, 1H), 2.99 (s, 3H), 2.17 (s, 3H).

Anal. Calcd. for $C_{22}H_{19}NO_3S$ $0.2H_2O$: C, 69.34; H, 5.13; N, 3.68. Found: C, 69.45; H, 5.19; N, 3.44.

Example 39

1-[4-(3-Furyl)-3-methylphenyl]-2-methyl-5-[4-(methylsulfonyl)phenyl]-1H-pyrrole 1-(4-Bromo-3-methylphenyl)-2-methyl-5-[4-(methylsulfonyl)phenyl]-1H-pyrrole The subtitle compound was prepared according to the procedure of Example 38 using 4-bromo-3-methylaniline instead of 4-bromoaniline in step 1.

$^1$H-NMR (CDCl$_3$) δ: 7.70 (d, J=8.4 Hz, 2H), 7.55 (d, J=8.4 Hz, 1H), 7.20 (d, J=8.4 Hz, 2H), 7.04 (d, J=2.5 Hz, 1H), 6.85 (dd, J=8.4, 2.5 Hz, 1H), 6.50 (d, J=3.6 Hz, 1H), 6.12 (d, J=3.6 Hz, 1H), 3.02 (s, 3H), 2.39 (s, 3H), 2.13 (s, 3H).

1-[4-(3-Furyl)-3-methylphenyl]-2-methyl-5-[4-(methylsulfonyl)phenyl-1H-pyrrole

The title compound was prepared according to the procedure of Example 35 using 1-(4-bromo-3-methylphenyl)-2-methyl-5-[4-(methylsulfonyl)phenyl]-1H-pyrrole instead of 1-(4-bromophenyl)-2-[3-fluoro-4-(methylsulfonyl) phenyl]-5-methyl-1H-pyrrole and 3-furanboronic acid instead of 2-furanboronic acid in step 4.

mp: 69–75° C.

$^1$H-NMR (CDCl$_3$) δ: 7.68 (d, J=8.4 Hz, 2H), 7.59 (br.s, 1H), 7.52 (t, J=1.6 Hz, 1H), 7.36 (d, J=8.1Hz, 1H), 7.23 (d, J=8.4 Hz, 2H), 7.06–6.97 (m, 2H), 6.63 (br.s, 1H), 6.52 (d, J=3.6 Hz, 1H), 6.13 (d, J=3.6 Hz, 1H), 3.00 (s, 3H), 2.38 (s, 3H), 2.16 (s, 3H).

Anal. Calcd. for $C_{23}H_{21}NO_3S$ $0.2H_2O$: C, 69.92; H, 5.46; N, 3.55. Found: C, 69.92; H, 5.52; N, 3.30.

Example 40

1-4-(2-Furyl)-3-methylphenyl]-2-methyl-5-]4-(methylsulfonyl)phenyl]1H-pyrrole

1-[4-(2-Furyl)-3-methylphenyl]-2-methyl-5-[4-(methylsulfonyl)phenyl]-1H-pyrrole

The title compound was prepared according to the procedure of Example 35 using 1-(4-bromo-3-methylphenyl)-2-methyl-5-[4-(methylsulfonyl)phenyl]-1H-pyrrole instead of 1-(4-bromophenyl)-2-[3-fluoro-4-(methylsulfonyl) phenyl]-5-methyl-1H-pyrrole in step 4.

mp: 160–162° C.

$^1$H-NMR (CDCl$_3$) δ: 7.75 (d, J=8.9 Hz, 1H), 7.68 (d, J=8.4 Hz, 2H), 7.54 (d, J=1.8 Hz, 1H), 7.23 (d, J=8.4 Hz, 2H), 7.07–7.02 (m, 2H), 6.62 (d, J=3.3 Hz, 1H), 6.60–6.50 (m, 2H), 6.13 (d, J=3.6 Hz, 1H), 3.00 (s, 3H), 2.49 (s, 3H), 2.16 (s, 3H).

Anal. Calcd. for $C_{23}H_{21}NO_3S$ $0.35H_2O$: C, 69.45; H, 5.50; N, 3.52. Found: C, 69.43; H, 5.44; N, 3.43.

Example 41

1-[3-Chloro-4-(3-furyl)phenyl]-2-methyl-5-[4-(methylsulfonyl)phenyl]-1H-pyrrole 1-(4-Bromo-3-chlorophenyl)-2-methyl-5-[4-(methylsulfonyl)phenyl]-1H-pyrrole The subtitle compound was prepared according to the procedure of Example 38 using 4-bromo-3-chloroaniline instead of 4-bromoaniline in step 1.

$^1$H-NMR (CDCl$_3$) δ: 7.73 (d, J=8.4 Hz, 2H), 7.64 (d, J=8.4 Hz, 1H), 7.30 (d, J=2.3 Hz, 1H), 7.20 (d, J=8.4 Hz, 2H), 6.91 (dd, J=8.4, 2.5 Hz, 1H), 6.49 (d, J=3.6 Hz, 1H), 6.13 (d, J=3.6 Hz, 1H), 3.03 (s, 3H), 2.15 (s, 3H).

1-[3-Chloro-4-(3-furyl)phenyl]-2-methyl-5-[4-(methylsulfonyl)phenyl]-1H-pyrrole

The title compound was prepared according to the procedure of Example 35 using 1-(4-bromo-3-chlorophenyl)-2-methyl-5-[4-(methylsulfonyl)phenyl]-1H-pyrrole instead of 1-(4-bromophenyl)-2-[3-fluoro-4-(methylsulfonyl) phenyl]-5-methyl-1H-pyrrole and 3-furanboronic acid instead of 2-furanboronic acid in step 4.

mp: 165–168° C.

$^1$H-NMR (CDCl$_3$) δ: 7.93 (br.s, 1H), 7.72 (d, J=8.4 Hz, 2H), 7.53 (t, J=1.5 Hz, 1H), 7.46 (d, J=8.4 Hz, 1H), 7.31 (d, J=2.2 Hz, 1H), 7.23 (d, J=8.2 Hz, 2H), 7.05 (dd, J=8.2, 2.2 Hz, 1H), 6.77 (br.s, 1H), 6.51 (d, J=3.8 Hz, 1H), 6.15 (d, J=3.8 Hz, 1H), 3.02 (s, 3H), 2.19 (s, 3H).

Anal. Calcd. for $C_{22}H_{18}ClNO_3S$: C, 64.15; H, 4.40; N, 3.40. Found: C, 63.79; H, 4.54; N, 3.13.

Example 42

1-]3-Chloro-4-(2-furyl)phenyl]-2-methyl-5-[4-(methylsulfonyl)phenyl]-1H-pyrrole

The title compound was prepared according to the procedure of Example 35 using1-(4-bromo-3-chlorophenyl)-2-methyl-5-[4-(methylsulfonyl)phenyl]-1H-pyrrole instead of 1-(4-bromophenyl)-2-[3-fluoro-4-(methylsulfonyl)phenyl]-5-methyl-1H-pyrrole in step 4.

mp: 127–131° C.

$^1$H-NMR (CDCl$_3$) δ: 7.92 (d, J=8.4 Hz, 1H), 7.72 (d, J=8.4 Hz, 2H), 7.55 (d, J=1.8 Hz, 1H), 7.30–7.20 (m, 4H), 7.10 (dd, J=8.9, 2.1 Hz, 1H), 6.59–6.54 (m, 1H), 6.50 (d, J=3.5 Hz, 1H), 6.14 (d,J=3.6 Hz, 1H), 3.01 (s, 3H), 2.18 (s, 3H).

Anal. Calcd. for $C_{22}H_{18}ClNO_3S$: C, 64.15; H, 4.40; N, 3.40. Found: C, 63.86; H, 4.56; N, 3.23.

Example 43

1-(4-Biphenyl)-2-methyl-5-[4-(methylsulfonyl)phenyl]-1H-pyrrole

The title compound was prepared according to the procedure of Example 36 using 4-aminobiphenyl instead of 4-bromoaniline in step 1.

mp: 150–152° C.

$^1$H-NMR (CDCl$_3$) δ: 7.70–7.62 (m, 6H), 7.50–7.35 (m, 3H), 7.26–7.21 (m, 4H), 6.53 (d, J=3.6 Hz, 1H), 6.15 (d, J=3.6 Hz, 1H), 3.00 (s, 3H), 2.19 (s, 3H).

Anal. Calcd. for $C_{24}H_{21}NO_2S$: 0.4 $H_2O$: C, 73.03; H, 5.57; N, 3.55. Found: C, 73.20; H, 5.50; N, 3.49.

Example 44

1-[4-(2-Furyl)phenyl]-2-methyl-5-[4-(methylsulfonyl)phenyl]-1H-pyrrole 4-(2-Furyl)aniline (step 1)

To a suspension of 2-(4-nitrophenyl)furan (0.378 g, 2 mmol, prepared according to the method of *Heterocycles*, 1990, 31, 1951) in ethanol (20 mL) was heated to 70° C. and added stannous chloride dihydrate (2.26 g, 10 mmol) and the mixture was stirred for 2 hours. The reaction mixture was cooled to room temperature and poured into water (50 mL), the whole was extracted with ethyl acetate (30 mL×2). The organic layer was dried over $Na_2SO_4$, filtered through celite and concentrated to give the crude subtitle compound (0.35 g).

MS (EI): m/z 159 (M$^+$)

1-[4-(2-Furyl)phenyl]-2-methyl-5-[4-(methylsulfonyl)phenyl]-1H-pyrrole. (step 2)

A mixture of 1-[4-(methylsulfonyl)phenyl]pentene-1 4-dione (0.305 g, 1.2 mmol prepared according to the method of *J. Med. Chem.*, 1997, 40, 1619), 4-(2-furyl)aniline (0.35 g, 2 mmol), and p-toluenesulfonic acid monohydrate (0.015 g) in toluene (40 mL) was heated at reflux temperature for 16 hours using Dean-Stark apparatus. After cooling, volatiles were removed by evaporation. The residue was purified by flash chromatography eluting with hexane/ethyl acetate (4/1). The resulting solid was recrystallized from $CH_2Cl_2$/hexane to give the title compound (0.11 g, 24.3% yield).

mp: 145–147° C.

$^1$H-NMR (CDCl$_3$) δ:7.73–7.66 (m, 4H), 7.50 (d, J=1 Hz, 1H), 7.24–7.15 (m, 4H), 6.71 (d, J=3 Hz, 1H), 6.53–6.50 (m, 2H), 6.14 (dd, J=1, 3 Hz, 1H), 3.00 (s, 3H), 2.17 (s, 3H).

Anal. Calcd. for $C_{22}H_{19}NO_3S$: C, 70.00; H, 5.07; N, 3.71. Found: C, 69.88; H, 5.18; N, 3.32.

MS (EI): m/z 377 (M$^+$)

Example 45

2-Methyl-5-[4-(methylsulfonyl)phenyl]-1-[4-(2-thienyl)phenyl-1H-pyrrole 4-(2-Thienyl)aniline (step 1)

The subtitle compound was prepared according to the procedure of Example 44 (step 1) using 2-(4-nitrophenyl)thiophene (prepared according to the method of *Heterocycles*, 1990, 31, 1951).

MS (EI): m/z 175 (M$^+$)

2-Methyl-5-[4-(methylsulfonyl)phenyl]1-[4-(2-thienyl)phenyl]-1H-pyrrole (step 2)

The title compound was prepared according to the procedure of Example 44 (step 2) using 4-(2-thienyl)aniline.

mp: 185–186° C.

$^1$H-NMR (CDCl$_3$) δ:7.71–7.63 (m, 4H), 7.38–7.32 (m, 2H), 7.25–7.10 (m, 5H), 6.52 (d, J=4 Hz, 1H), 6.15 (dd, J=4, 1 Hz, 1H). 3.00 (s, 3H), 2.18 (s, 3H).

Anal. Calcd. for $C_{22}H_{19}NO_2S2.0$. $1H_2O$: C, 66.84; H, 4.90; N, 3.54. Found: C, 66.56; H, 4.97; N, 3.65.

MS (EI): m/z 393 (M$^+$)

Example 46

2-Methyl-5-[4-(methylsulfonyl)phenyl]-1-[4-(3-thienyl)phenyl]-1H-pyrrole

2-Methyl-5-[4-(methylsulfonyl)phenyl]-1-[4-(3-thienyl)phenyl]-1H-pyrrole

To a stirred solution of 2-methyl 5-[4-(methylsulfonyl)phenyl]-1-(4-bromophenyl)-1H-pyrrole (0.2 g, 0.51 mmol) in DME (6 ML) was added thiophene-3-boronic acid (0.079 g, 0.61 mmol), bis(triphenylphosphine)palladium(II) chloride (0.04 g, 0.06 mmol) and saturated $NaHCO_3$ solution (2 mL) at room temperature under nitrogen. The mixture was heated at reflux temperature for 6 hours, and cooled down to room temperature. The reaction mixture was filtered through celite, the filtrate was poured into water and the whole was extracted with ethyl acetate (10 mL×3). The organic layer was washed with brine, dried over $Na_2SO_4$, and concentrated in vacuo. The residue was purified by flash chromatography eluting with hexane/ethyl acetate (4/1). The resulting solid was recrystallized from ethyl acetate/hexane to give the title compound (0.15 g, 75.0% yield).

mp: 187–188° C.

$^1$H-NMR (CDCl$_3$) δ:7.69–7.63 (m, 4H), 7.53–7.51 (m, 1H), 7.43 (d, J=1 Hz, 1H), 7.42 (s, 1H), 7.23 (d, J=9 Hz, 2H), 7.18 (d, J=8 Hz, 2H), 6.53 (d, J=3 Hz, 1H), 6.15 (dd, J=4, 1 Hz, 1H), 3.00 (s, 3H), 2.18 (s, 3H).

Anal. Calcd. for $C_{22}H_{19}NO_2S_2$ 0.2 $1H_2O$: C, 66.54; H, 4.92; N, 3.53. Found: C, 66.61; H, 5.01; N, 3.23.

MS (EI): m/z 393 (M$^+$)

Example 47

2-Methyl-5-[4-(methylsulfonyl)phenyl]-1-[4-(2-pyrrolyl)phenyl]-1H-pyrrole

The title compound was prepared according to the procedure of Example 46 using (1-tert-butoxycarbonyl)pyrrole-2-boronic acid, instead of thiophene-3-boronic acid.

mp: 225–227° C.

$^1$H-NMR (CDCl$_3$) δ:8.36 (brs, 1H), 7.66 (d, J=9 Hz, 2H), 7.57 (d, J=9 Hz, 2H), 7.24 (d, J=9 Hz, 2H), 7.16–7.14 (m, 1H), 7.12 (d, J=8 Hz, 2H), 6.87 (dd, J=5, 3 Hz, 1H), 6.58–6.56 (m, 1H), 6.52 (d, J=3 Hz, 1H), 6.13 (d, J=4 Hz, 1H), 2.99 (s, 3H), 2.17 (s, 3H).

Anal. Calcd. for $C_{22}H_{20}N_2O_2S$,1.2$H_2O$: C, 66.38; H, 5.67; N, 7.04. Found: C, 66.60; H, 5.33; N, 6.73.

MS (EI): m/z 376 (M$^+$)

Example 48

2-Methyl-5-[4-(methylsulfonyl)phenyl]-1-1 [4-(1-tert-Butoxycarbonyl)-2-pyrrolyl]phenyl]-1H-pyrrole The title compound was prepared according to the procedure of Example 46 using (1-tert-butoxycarbonyl)pyrrole-2-boronic acid, instead of thiophene-3-boronic acid.

mp: 169–170° C.

$^1$H-NMR (CDCl$_3$) δ: 7.68 (d, J=9 Hz, 2H), 7.41–7.37 (m, 3H), 7.24 (d, J=9 Hz, 2H), 7.14 (d, J=9 Hz, 2H), 6.52 (d, J=4 Hz, 1H), 6.27–6.24 (m, 2H), 6.15 (d, J=3 Hz, 1H), 3.00 (s, 3H), 2.18 (s, 3H), 1.56 (s, 9H).

Anal. Calcd. for $C_{27}H_{28}N_2O_4S$: C, 68.04; H, 5.92; N, 5.88. Found: C, 68.01; H, 6.10; N, 5.82.

MS (EI): m/z 476 (M$^+$)

Example 49

2-Methyl-5-[4-(methylsulfonyl)phenyl]-1-[4-(2-thiazolyl)phenyl]-1H-pyrrole

2-Methyl-5-[4-(methylsulfonyl)phenyl]-1-[4-(2-thiazolyl)phenyl]-1H-pyrrole

To a stirred solution of thiazole (0.072 g, 0.85 mmol) in anhydrous ether (2 mL) was added n-BuLi (0.58 mL, 1.61 M solution in hexane, 0.94 mmol) at −78° C. under nitrogen, the mixture was stirred for 30 minutes at −78° C., and then zinc chloride (2.55 mL, 1.0 M solution in ether, 2.55 mmol) was added at −78° C., the mixture was stirred for 30 minutes at −78° C. The reaction mixture was warmed to 0° C., and added the solution of 2-methyl 5-[4-(methylsulfonyl)phenyl]-1-(4-bromophenyl)-1H-pyrrole (0.3 g, 0.77 mmol) in THF (5 mL), tetrakis(triphenylphosphine)palladium (0) (0.088 g, 0.08 mmol). The reaction mixture was heated at reflux temperature for 19 hours, and cooled down to room temperature. The reaction mixture was filtered through celite, the filtrate was poured into water and the whole was extracted with ethyl acetate (20 mL×3). The organic layer was washed with brine, dried over $Na_2SO_4$, and concentrated in vacuo. The residue was purified by flash chromatography eluting with hexane/ethyl acetate (2/1). The resulting solid was recrystallized from $CH_2Cl_2$/hexane to give the title compound (0.040 g, 13.2% yield).

mp: 190–191° C.

$^1$H-NMR (CDCl$_3$) δ: 8.03 (d, J=9 Hz, 2H), 7.90 (d, J=3 Hz, 1H), 7.69 (d, J=9 Hz, 2H), 7.39 (d, J=3 Hz, 1H), 7.25–7.21 (m, 4H), 6.53 (d, J=4 Hz, 1H), 6.16 (dd, J=4, 1 Hz, 1H), 3.00 (s, 3H), 2.19 (s, 3H).

Anal. Calcd. for $C_{21}H_{18}N_2 O_2S_2$ 0.6$H_2O$: C, 62.23; H, 4.77; N, 6.91. Found: C, 62.01; H, 4.70; N, 6.78.

MS (EI): m/z 395 (M$^+$+1)

Example 50

2-Methyl-5-[4-(methylsulfonyl)phenyl]-4-[4-(2-thienyl)phenyl]oxazole

2-Methyl-5-[4-(methylsulfonyl)phenyl]4-[4-(2-thienyl)phenyl]oxazole

To a stirred solution of 2-methyl-5-[4-(methylsulfonyl)phenyl]-4-(4-bromophenyl)-oxazole (0.314 g, 0.8 mmol) in DME (10 mL) was added thiophene-2-boronic acid (0.123 g,0.96 mmol), bis(triphenylphosphine)palladium(II)chloride (0.064 g, 0.09 mmol) and saturated $NaHCO_3$ solution (3.2 mL) at room temperature under nitrogen. The mixture was heated at reflux temperature for 4.5 hours, and cooled down to room temperature. The reaction mixture was filtered through celite, the filtrate was poured into water and the whole was extracted with ethyl acetate (10 mL×3). The organic layer was washed with brine, dried over $Na_2SO_4$, and concentrated in vacuo. The residue was purified by flash chromatography eluting with hexane/ethyl acetate (3/2). The resulting solid was recrystallized from ethyl acetate/hexane to give the title compound (0.225 g, 71.2% yield).

mp: 183–185° C.

$^1$H-NMR (CDCl$_3$) δ: 7.92 (d, J=9 Hz, 2H), 7.81 (d, J=9 Hz, 2H), 7.68–7.61 (m, 4H), 7.38 (dd,J=4, 1 Hz 1H), 7.32 (dd,J=5, 1Hz, 1H), 7.11 (dd, J=4, 5 Hz, 1H), 3.09 (s, 3H), 2.60 (s, 3H).

Anal. Calcd. for $C_{21}H_{17}NO_3S_2$, 0.2$H_2O$: C, 63.20 H, 4.39; N, 3.51. Found: C, 63.22 H, 4.36; N, 3.21.

MS (EI): m/z 395 (M$^+$)

Example 51

4-[4-(2-Furyl)phenyl]-2-methyl-5-[4-(methylsulfonyl)phenyl]oxazole

The title compound was prepared according to the procedure of Example 50 using furan-2-boronic acid, instead of thiophene-2-boronic acid.

mp: 143–144° C.

$^1$H-NMR (CDCl$_3$) δ:7.91 (d, J=9 Hz, 2H), 7.80 (d, J=9 Hz, 2H), 7.72 (d, J=9 Hz, 2H), 7.63 (d, J=9 Hz, 2H), 7.50 (dd, J=2, 0.7 Hz, 1H), 6.72 (dd, J=3, 0.7 Hz, 1H), 6.50 (dd, J=3,2 Hz, 1H), 3.08 (s, 3H), 2.59 (s, 3H).

Anal. Calcd. for $C_{21}H_{17}NO_4S$ 0.2$H_2O$: C, 65.85 ;H, 4.58 ;N, 3.66. Found: C, 65.76; H, 4.61 ;N, 3.53.

MS (EI): m/z 379 (M$^+$)

Example 52

1-[4-(Methylsulfonyl)phenyl]-2-[4-(2-thienyl)phenyl]-4-(trifluoromethyl)-1H-imidazole N-[4-(Methylsulfonyl)phenyl]-4-(2-thienyl)benzenecarboximidamide. (step 1)

To a suspension of 4-(methylsulfonyl)aniline (0.428 g, 2.5 mmol) in toluene (15 mL) at 0° C. was added over 5 minutes trimethylaluminum (3.83 mL, 0.98 M solution in hexane, 3.75 mmol). The reaction mixture was warmed to room temperature and stirred for 3.5 hours. A solution of 2-(4-cyanophenyl)thiophene (0.926 g, 5 mmol, prepared according to the method of *Heterocycles*, 1990, 31, 1951) in toluene (10 mL) was added over 5 minutes and the reaction mixture heated to 70° C. After 18.5 hours, the reaction mixture was cooled to room temperature and poured over a slurry of silicagel in chloroform-methanol (2:1, 150 mL). After filtration, the residue was washed with a mixture of $CH_2Cl_2$—methanol (2:1, 75 mL). The combined filtrates were concentrated in vacuo ,and the resulting yellowish solid was washed with hexane-ether (2:1, 100 mL) to give the subtitle compound (0.711 g).

MS (EI): m/z 356 (M$^+$)

4-Hydroxy-1-[4-(methylsulfonyl)phenyl]-2-[4-(2-thienyl)phenyl]-4-(trifluoromethyl)-4,5dihydro-1H-imidazole (step 2)

To a mixture of N-[4-(methylsulfonyl)phenyl]-4-(2-thienyl)benzenecarboximidamide (0.7 g, 1.96 mmol) and sodium bicarbonate (0.33 g, 3.93 mmol) in 2-propanol (30 mL) was added 3-bromo-1,1,1-trifluoroacetone (0.449 g, 2.35 mmol). After the reaction mixture was heated to 80° C. for 21 hours, the solvent was removed. The residue was redissolved in $CH_2Cl_2$ (50 mL) and washed with water (30 mL×2). The organic fractions were combined, dried over $Na_2SO_4$, filtered, and concentrated in vacuo. The crude mixture was purified by flash chromatography eluting with hexane/ethyl acetate (2/1) to give the subtitle compound (0.351 g, 30.1% yield, via 2 steps).

$^1$H-NMR (DMSO d$_6$) δ:7.80–7.74 (m, 4H), 7.64 (d, J=4 Hz, 2H), 7.53 (d, J=9 Hz, 2H), 7.43 (s, 1H), 7.19–7.16 (m, 1H), 7.11 (d, J=9 Hz, 2H), 4.51 (d, J=12 Hz, 1H), 3.97 (d, J=12 Hz, 1H), 3.17 (s, 3H).

MS (EI): m/z 466(M$^+$)

1-[4-(Methylsulfonyl)phenyl]-2-[4-(2-thieyl)phenyl]-4-(trifluoromethyl)-1H-imidazole (step 3)

A mixture of 4-hydroxy-1-[4-(methylsulfonyl)phenyl]-2-[4-(2-thienyl)phenyl]-4-(trifluoromethyl)-4,5-dihydro-1H-imidazole (0.345 g, 0.74 mmol) and p-toluenesulfonic acid monohydrate (0.035 g) in toluene (40 mL) was heated to reflux for 7 hours. The reaction mixture was cooled and the solvent removed under reduced pressure. The crude residue was redissolved in CH$_2$Cl$_2$ (50 mL) and the whole washed with water, aqueous NaHCO$_3$ (30 mL), and brine. After dried over Na$_2$SO$_4$, and concentration in vacuo. The crude mixture was purified by flash chromatography eluting with hexane/ethyl acetate (2/1). The resulting solid was recrystallized from ethyl acetate-hexane to give the title compound (0.212 g, 63.9% yield).

mp: 95–97° C.

$^1$H-NMR (CDCl$_3$) δ: 8.05 (d, J=9 Hz, 2H), 7.56 (d, J=9 Hz, 2H), 7.54–7.53(m, 1H), 7.48 (d, J=9 Hz, 2H), 7.38 (d, J=9 Hz, 2H), 7.36–7.31 (m, 2H), 7.09 (dd, J=5, 4 Hz, 1H), 3.13 (s, 3H).

Anal. Calcd. for. C$_{21}$H$_{15}$F$_3$N$_2$O$_2$S$_2$: C, 56.24; H, 3.37; N, 6.25. Found: C, 56.15; H, 3.73; N, 6.00.

MS (EI): m/z 448 (M$^+$)

Example 53

2-[4-(2-Furyl)phenyl]-1-[4-(methylsulfonyl)phenyl]-4-(trifluoromethyl)-1H-imidazole N-[4-(Methylsulfonyl)phenyl]-4-(2-furyl)benzenecarboximidamide (step 1)

The subtitle compound was prepared according to the procedure of Example 52 (step 1) using 2-(4-cyanophenyl)furan (prepared according to the method of *Heterocycles*, 1990, 31, 1951).

MS (EI): m/z 339 (M$^+$–1)

4-Hydroxy-1-[4-(methylsulfonyl)phenyl]-2-[4-(2-furyl)phenyl]-4-(trifluoromethyl)-4,5-dihydro-1H-imidazole (step 2)

The subtitle compound was prepared according to the procedure of Example 52 (step 2) using N-[4-(Methylsulfonyl)phenyl]4-(2-furyl)benzenecarboximidamide.

MS (EI): m/z 450 (M$^+$)

2-[4(2-Furyl)phenyl]-1-[4-(methylsulfonyl)phenyl]-4-(trifluoromethyl)-1H-imidazole (step 3)

The title compound was prepared according to the procedure of Example 52 (step 3) using 4-hydroxy-1-[4-(methylsulfonyl)phenyl]-2-[4-(2-furyl)phenyl]-4-(trifluoromethyl)-4,5-dihydro-1H-imidazole.

mp: 82–84° C.

$^1$H-NMR (CDCl$_3$) δ: 8.04 (d, J=9 Hz, 2H), 7.61 (d, J=8 Hz, 2H), 7.53–7.45 (m, 4H), 7.38 (d, J=8 Hz, 2H), 6.71 (d, J=3 Hz, 1H), 6.49 (m, 1H), 3.12 (s, 3H).

Anal. Calcd. for. C$_{21}$H$_{15}$F$_3$N$_2$O$_3$S, 0.5 H$_2$O: C, 57.14; H, 3.65; N, 6.35. Found: C, 57.23; H, 3.89; N, 6.13.

MS (EI): m/z 432 (M$^+$)

Example 54

2-[4-(2-Furyl)phenyl]-4-methyl-1-(4-sulfamoylphenyl)-1H-pyrrole

4-Sulfamoyl-N-[4-(2-furyl)benzylidene]aniline (step 1)

A mixture of 2-(4-formylphenyl)furan (0.335 g, 1.95 mmol, prepared according to the method of *Heterocycles*, 1990, 31, 1951), sulfanilamide (0.336 g, 1.95 mmol) in ethanol (8 mL) was heated at reflux temperature for 2.5 hour. After cooling to room temperature, the crystals which collected by filtration and washed with ethanol to give the subtitle compound (0.378 g).

$^1$H-NMR (DMSO-d$_6$) δ: 8.65 (s, 1H), 8.01 (d, J=8 Hz, 2H), 7.89–7.84 (m, 5H), 7.42–7.34 (m, 4H), 7.15 (d, J=3 Hz, 1H), 6.67 (dd, J=3, 2 Hz, 1H).

α-4-Sulfamoylanilino-α-[4-(2-furyl)phenyl]acetnitrile (step 2)

To a suspension of 4-sulfamoyl-N-[4-(2-furyl)benzylidene]aniline (0.37 g, 1.13 mmol) in anhydrous THF (5 mL) at 0° C. was added trimethylsilyl cyanide (0.135 g, 1.36 mmol),zinc chloride (1.36 mL, 1.0 M solution in ether, 1.36 mmol). The temperature of the reaction mixture was then allowed to return to room temperature, and the mixture was stirred overnight. The reaction mixture was poured into water and the whole was extracted with ethyl acetate (20 mL×2). The organic layer was washed with brine, dried over Na$_2$SO$_4$, and concentrated to give the subtitle compound (0.288 g).

$^1$H-NMR (DMSO-d$_6$) δ: 7.84–7.78 (m, 3H), 7.65–7.60 (m, 4H), 7.39 (d, J=9 Hz, 1H), 7.04–7.01 (m, 3H), 6.91 (d, J=9 Hz, 2H), 6.62 (dd, J=3, 2 Hz, 1H), 6.16 (d, J=9 Hz, 1H).

MS (EI): m/z 353 (M$^+$)

2-[4-(2-Furyl)phenyl]-4-methyl-1-(4-sulfamoylphenyl)-1H-pyrrole (step 3)

To a suspension of α-4-sulfamoylanilino-α-[4-(2-furyl)phenyl]acetnitrile (0.28 g, 0.79 mmol) in anhydrous THF (3 mL) at -70° C. was added methacrolein (0.061 g, 0.87 mmol), and then dropwise lithium bis(trimethylsilyl)amide (0.83 mL, 1.0 M solution in hexane, 0.83 mmol). The reaction mixture was stirred at –60° C. to –65° C. for 1 hour, and then the temperature of the reaction mixture was allowed to return to room temperature, and the mixture was stirred for a further 2 hours. The reaction mixture was added a saturated aqueous solution of NH$_4$Cl (10 mL) and the whole was extracted with ethyl acetate (10 mL×2). The organic layer was washed with water, dried over Na$_2$SO$_4$, and concentrated in vacuo. The residue was redissolved in toluene (5 mL) and heated at reflux temperature for 1 hour. The reaction mixture was concentrated in vacuo. The residue was purified by thin-layer chromatography eluting with hexane/ethyl acetate (2/1). The resulting solid was recrystallized from CH$_2$Cl$_2$-hexane to give the title compound (0.012 g, 5.6% yield).

mp: 153–155° C.

$^1$H-NMR (CDCl$_3$) δ: 7.85 (d, J=9 Hz, 2H), 7.54 (d, J=8 Hz, 2H), 7.45 (s, 1H), 7.26 (d, J=9 Hz, 2H), 7.12 (d, J=8 Hz, 2H), 6.76 (s, 1H), 6.62 (d, J=3 Hz, 1H), 6.46 (dd, J=3, 2 Hz, 1H), 6.34 (d, J=2 Hz, 1H), 4.84 (brs, 2H), 2.19 (s, 3H).

MS (EI): m/z 378 (M$^+$)

Example 55

1-[4-(3-Furyl)phenyl]-4-methyl-2-[4-(methylsulfonyl)phenyl]-1H-pyrrole

1-[4-(3-Furyl)phenyl]-4-methyl-2-[4-(methylsulfonyl)phenyl]-1H-pyrrole

To a stirred solution of 1-(4-bromophenyl)-4-methyl-2-[4-(methylsulfonyl)phenyl]-1H-pyrrole (0.08 g, 0.2 mmol) in DME (2.5 mL)was added furan-3-boronic acid (0.027 g, 0.24 mmol), bis(triphenylphosphine)palladium(II)chloride (0.016 g, 0.02 mmol) and saturated NaHCO$_3$ solution (0.8 mL) at room temperature under nitrogen. The mixture was heated at reflux temperature for 4 hours, and cooled down to room temperature. The reaction mixture was filtered through celite, the filtrate was poured into water and the whole was extracted with ethyl acetate (10 mL×3). The organic layer was washed with brine, dried over Na$_2$SO$_4$, and concentrated in vacuo. The residue was purified by thin-layer chromatography eluting with hexane/ethyl acetate (3/1). The resulting solid was recrystallized from CH$_2$Cl$_2$-hexane to give the title compound (0.01 g, 13.3% yield).

mp:154–156° C.

$^1$H-NMR (CDCl$_3$) δ: 7.76–7.73 (m, 3H), 7.50–7.49 (m, 1H), 7.46 (d, J=8 Hz, 2H), 7.29 (d, J=9 Hz, 2H), 7.13 (d, J=9 Hz, 2H), 6.80 (s, 1H), 6.70 (s, 1H), 6.43 (d, J=1 Hz, 1H), 3.03 (s, 3H), 2.19 (s, 3H).

Anal. Calcd. for $C_{22}H_{19}NO_3S$: C, 70.00; H, 5.07; N, 3.71. Found: C, 69.72; H, 5.39; N, 3.51.

MS (EI): m/z 377 (M$^+$)

Example 56

2-[4-(3-Furyl)phenyl]-4-methyl-1-[4-(methylsulfonyl)phenyl]-1H-pyrrole

The title compound was prepared according to the procedure of Example 55 using 2-(4-bromophenyl)-4-methyl-1-[4-(methylsulfonnyl)phenyl]-1H-pyrrole.

mp:193–195° C.

$^1$H-NMR (CDCl$_3$) δ: 7.87 (d, J=9 Hz, 2H), 7.72 (s, 1H), 7.47 (s, 1H), 7.37 (d, J=8 Hz, 2H), 7.31 (d, J=9 Hz, 2H), 7.11 (d, J=8 Hz, 2H), 6.77 (m, 1H), 6.68 (m, 1H), 6.35 (m, 1H), 3.08 (s, 3H), 2.19 (s, 3H).

Anal. Calcd. for $C_{22}H_{19}NO_3S$, 1.0$H_2O$: C, 66.82; H, 5.35; N, 3.54. Found: C, 66.65; H, 5.18; N, 3.60.

MS (EI): m/z 377 (M$^+$)

Example 57

2-Biphenyl-4-methyl-1-[4-(methylsulfonyl)phenyl]-1H-pyrrole

The title compound was prepared according to the procedure of Example 55 using 2-(4-bromophenyl)-4-methyl-1-[4-(methylsulfonyl)phenyl]-1H-pyrrole, and phenylboronic acid, instead of furan-3-boronic acid.

$^1$H-NMR (CDCl$_3$) δ: 7.88 (d, J=9 Hz, 2H), 7.58 (d, J=8 Hz, 2H), 7.49 (d, J=8 Hz, 2H), 7.46–7.40 (m, 2H), 7.36–7.31 (m, 3H), 7.17 (d, J=8 Hz, 2H), 6.78 (s, 1H), 6.37 (d, J=2 Hz, 1H), 3.07 (s, 3H), 2.20 (s, 3H).

MS (EI): m/z 387 (M$^+$)

Example 58

1-[4-(2-Furyl)phenyl]-4-methyl-2-[4-(methylsulfonyl)phenyl]-1H-pyrrole

1-[4-(2-Furyl)phenyl]-4-methyl-2-[4-(methylsulfonyl)phenyl]-1H-pyrrole

To a stirred solution of 1-(4-bromophenyl)-4-methyl-2-[4-(methylsulfonyl)phenyl]-1H-pyrrole (0.1 g, 0.26 mmol) in dioxane (5 mL) was added 2-(tributylstannyl)furan (0.118 g, 0.33 mmol), LiCl (0.027 g, 0.64 mmol), tetrakis(triphenylphosphine)palladium(0) (0.03 g, 0.026 mmol) at room temperature under nitrogen. The mixture was heated at reflux temperature for 0.5 hours. After cooling, volatiles were removed by evaporation. The residue was purified by flash chromatography eluting with hexane/ethyl acetate (4/1). The resulting solid was recrystallized from $CH_2Cl_2$/hexane to give the title compound (0.026 g, 26.5% yield).

mp:133–135° C.

$^1$H-NMR (CDCl$_3$) δ: 7.74 (d, J=9 Hz, 2H), 7.64 (d, J=9 Hz, 2H), 7.48 (dd, J=2, 1 Hz, 1H), 7.29 (d, J=9 Hz, 2H), 7.14 (d, J=9 Hz, 2H), 6.80 (m, 1H) 6.67 (d, J=3 Hz, 1H), 6.49 (dd, J=3, 2 Hz, 1H), 6.43 (d, J=2 Hz, 1H), 3.03 (s, 3H), 2.19 (s, 3H).

Anal. Calcd. for $C_{22}H_{19}NO_3S$, 0.8$H_2O$: C, 67.43: H, 5.30; N, 3.57. Found: C, 67.21, H, 5.39; N, 3.96.

MS (EI): m/z 377 (M$^+$)

Example 59

2-[4-(2-Furyl)phenyl]-4-methyl-1-[4-(methylsulfonyl)phenyl]-1H-pyrrole

The title compound was prepared according to the procedure of Example 58 using 2-(4-bromophenyl)-4-methyl-1-[4-(methylsulfonyl)phenyl]-1H-pyrrole.

mp: 193–194° C.

$^1$H-NMR (CDCl$_3$) δ: 7.87 (d, J=9 Hz, 2H), 7.55 (d, J=9 Hz, 2H), 7.45 (d, J=2 Hz, 1H), 7.31 (d, J=9 Hz, 2H), 7.11 (d, J=9 Hz, 2H), 6.77 (s, 1H), 6.63 (d, J=3 Hz, 1H), 6.45 (dd, J=3, 2 Hz, 1H), 6.35 (d, J=2 Hz, 1H), 3.07 (s, 3H), 2.19 (s, 3H).

Anal. Calcd. for $C_{22}H_{19}NO_3S$ 1.2 $H_2O$: C, 66.21; H, 5.40; N, 3.51. Found: C, 66.08; H, 5.01; N, 3.89.

MS (EI): m/z 377 (M$^+$)

Example 60

1-[3-Fluoro-4-(methylsulfonyl)phenyl]-5-[4-(2-furyl)phenyl]-3-(trifluoromethyl)-1H-pyrazole 4,4,4-Trifluoro-1-[4-(2-furyl)phenyl]butane-1,3-dione (step 1)

To a stirred solution of 4,4,4-trifluoro-1-(4-bromophenyl)butane-1,3-dione (1 g, 3.39 mmol, prepared according to the method of *J. Med. Chem.*, 1997, 40, 1347) in DME (40 mL) was added furan-2-boronic acid (0.455 g, 4.07 mmol), bis(triphenylphosphine) palladium(II)chloride (0.271 g, 0.386 mmol) and saturated NaHCO$_3$ solution (12 mL) at room temperature under nitrogen. The mixture was heated at reflux temperature for 5 hours, and cooled down to room temperature. The reaction mixture was filtered through celite, the filtrate was poured into water and the whole was extracted with ethyl acetate (30 mL×3). The organic layer was washed with brine, dried over sodium sulfate, and concentrated in vacuo. The residue was purified by flash chromatography eluting with hexane/ethyl acetate (3/1) to give the subtitle compound (0.586 g, 61.2% yield).

MS (EI): m/z 282 (M$^+$)

1-[3-Fluoro-4-(methylsulfonyl)phenyl]-5-[4-(2-furyl)phenyl]-3-(trifluoromethyl)-1H-pyrazole (step 2)

3-fluoro-4-(methylsulfonyl)phenyl]hydrazine hydrochloride (0.188 g, 0.78 mmol) was added to a solution of 4,4,4-Trifluoro-1-[4-(2-furyl)phenyl]butane-1,3-dione (0.2 g, 0.71 mmol) in EtOH (15 mL). The mixture was heated at reflux temperature for 17 hours and cooled down to room temperature. The reaction mixture was concentrated in vacuo, and the residue was taken up in ethyl acetate, washed with water and brine, dried over sodium sulfate, and concentrated in vacuo. The residue was purified by flash chromatography eluting with hexane/ethyl acetate (3/1). The resulting solid was recrystallized from ethyl acetate/hexane to give the title compound (0.185 g, 58.0% yield).

mp:129–130° C.

$^1$H-NMR (CDCl$_3$) δ: 7.92 (dd, J=9, 8 Hz, 1H), 7.71 (d, J=9 Hz, 2H), 7.52 (dd, J=2, 1 Hz, 1H), 7.42 (dd, J=2, 10 Hz, 1H), 7.27 (d, J=8 Hz, 2H), 7.23 (d, J=2 Hz, 1H), 6.81 (s, 1H), 6.76 (d, J=3 Hz, 1H), 6.52 (dd, J=3, 2 Hz, 1H), 3.23 (s, 3H).

Anal. Calcd. for $C_{21}H_{14}F_4N_2O_3S$, 0.1 hexane: C, 56.34; H, 3.31; N, 6.14. Found: C, 56.34; H, 3.55; N, 5.79.

MS (EI): m/z 450 (M$^+$)

3-Fluoro-4-(methylsulfonyl)phenylhydrazine hydrochloride was prepared as follows 3-Fluoro-4-(methylsulfonyl)nitrobenzene A mixture of 3,4-difluoronitrobenzene (10 g, 62.9 mmol) and sodium methanesulfinate (8.3 g, 69.1 mmol) in DMSO (60 mL) was heated at 130° C. for 8 hours. After cooling down to room temperature, the mixture was poured into ice-water. The whole was extracted with ethyl acetate (200 mL×2), the combined organic layer washed with water (80 mL), brine (80 mL), dried over MgSO$_4$, and concentrated in vacuo. The residue was crystallized from hexane and triturated withhexane to give the subtitle compound (10.2 g, 74% yield).

$^1$H-NMR (CDCl$_3$) δ: 8.25–8.10 (m, 3H), 3.29 (s, 3H).
MS (EI): 219 (M$^+$).

3-Fluoro-4-(methylsulfonyl)aniline

A mixture of 3-fluoro-4-(methylsulfonyl)nitrobenzene (8 g, 36.5 mmol), iron powder (22 g, 394 mmol), and acetic acid (0.3 mL) in water (200 mL) was heated at 95° C. for 3 hours. After cooling, insolubles were filtered off by Celite. The filtrate was extracted with ethyl acetate (200 mL×2), the combined organic layer washed with water, brine, dried over MgSO$_4$, and concentrated in vacuo. Chromatographic purification of the residue eluting with ethyl acetate/hexane (1/1) provided the subtitle compound (6.2 g, 90% yield).

$^1$H-NMR (CDCl$_3$) δ: 7.65 (t, J=8.2 Hz, 1H), 6.46 (dd, J=8.6, 2.3 Hz, 1H), 6.40 (dd, J=12, 2.3 Hz, 1H), 4.37 (br.s, 2H), 3.15 (s, 3H).

3-Fluoro-4-(methylsulfonyl)phenylhydrazine hydrochloride

To a stirred suspension of 3-fluoro-4-(methylsulfonyl) aniline (8.1 g, 42.9 mmol) in 20% aqueous HCl (27 mL) was added dropwise a solution of sodium nitrite (3 g, 43.5 mmol) in water (20 mL) at 0° C. After stirring for 1 hour, the resulting suspension was added to a solution of sodium sulfite (13.5 g, 110 mmol) in water (60 mL) and 20% aqueous NaOH (3 mL) at 0–5° C. Then the mixture was heated at 60–70° C. for 2 hours, and conc. HCl (3.5 mL) was added. The resulting mixture was heated for further 5 hours at 60° C. After cooling down to room temperature, the mixture was made basic by Na$_2$CO$_3$. The whole was extracted with THF (150 mL×3), the combined organic layer washed with brine (100 mL), dried over MgSO$_4$, and concentarted in vacuo. The resulting solid was recrystallized from EtOH to give 3-fluoro-4-(methylsulfonyl) phenylhydrazine (5 g, 57% yield).

$^1$H-NMR (CDCl$_3$) δ: 7.64 (t, J=8.7 Hz, 1H), 6.67 (dd, J=12.9, 2.2 Hz, 1H), 6.56 (dd, J=8.7, 2.2 Hz, 1H), 5.85 (br.s, 1H), 3.72 (br.s, 2H), 3.15 (s, 3H).

The solid (5 g) was dissolved in 10% methanolic HCl (30 mL), and volatiles were removed by evaporation. The residue was recrystallized from MeOH to give the title compound (4.66 g).

$^1$H-NMR (DMSO-d$_6$) δ: 10.65 (br.s), 9.42 (br.s, 1H), 7.70 (t, J=8.2 Hz, 1H), 7.10–6.86 (m, 2H), 3.24 (s, 3H).

Example 61

1-[4-(Fluoromethylsulfonyl)phenyl]]-5-[4-(2-furyl)phenyl]-3-(trifluoromethyl)-1H-pyrazole

[4-(Fluoromethylsulfonyl)phenyl]hydrazine hydrochloride. (step 1)

A mixture of 4-chlorophenyl fluoromethyl sulfone (1.97 g, 9.44 mmol. prepared according to the method of *Ukrainskill Khimicheskill Zhurnal*, 1972, 38. 1034) and hydrazine anhydrous (1.84 g, 57.5 mmol) in DMF (30 mL) was heated to 120° C. for 16 hours, and cooled down to room temperature. The reaction mixture was poured into water (150 mL) and the whole was extracted with ethyl acetate/hexane/ether (2/1/1, 60 mL×3). The organic layer was washed with brine, dried over sodium sulfate, and concentrated in vacuo. The resulting solid (1.56 g, 7.64 mmol) was added HCl-MeOH reagent 10 (10 mL) at room temperature and stirred for 10 minutes. The mixture was concentrated in vacuo to give the subtitle compound (0.91 g, 49.4% yield).

MS (EI): m/z 204 (M$^+$)

1-[4-(Fluoromethylsulfonyl)phenyl]]-5-[4-(2-furyl)phenyl]-3-(trifluoromethyl)-1H-pyrazole (step 2)

[4-(fluoromethylsulfonyl)phenyl]hydrazine hydrochloride (0.481 g, 2 mmol) was added to a solution of 4,4,4-Trifluoro-1-[4-(2-furyl)phenyl]butane-1,3-dione (0.564 g, 2 mmol) in EtOH (15 mL). The mixture was heated at reflux temperature for 4.5 hours and cooled down to room temperature. The reaction mixture was concentrated in vacuo, and the residue was taken up in ethyl acetate, washed with water and brine, dried over sodium sulfate, and concentrated in vacuo. The residue was purified by flash chromatography eluting with hexane/ethyl acetate (3/1). The resulting solid was recrystallized from methylene chloride/hexane to give the title compound (0.14 g, 15.5% yield).

mp:149–152° C.

$^1$H-NMR (CDCl$_3$) δ: 7.97 (d, J=9 Hz, 2H), 7.69 (d, J=9 Hz, 2H), 7.61 (d, J=9 Hz, 2H), 7.51 (d, J=1 Hz, 1H), 7.25 (d, J=9 Hz, 2H), 6.82 (s, 1H), 6.74 (d, J=3 Hz, 1H), 6.51 (dd, J=3, 2 Hz, 1H), 5.14 (d, J=47 Hz, 2H).

Anal. Calcd. for. C$_{21}$H$_{14}$F$_4$N$_2$O$_3$S, 1H$_2$O, 0.1 hexane: C, 54.20; H, 3.61; N, 5.91. Found: C, 54.24; H, 3.32; N, 5.55.

MS (EI): m/z 450 (M$^+$)

Example 62

4-[5-[4-(2-Furyl)phenyl]-4-cyano-1-[4-(methylsulfonyl)phenyl]-1H-pyrazole

4-[5-[4-Bromophenyl]-4-cyano-1-[4-(methylsulfonyl) phenyl]-1H-pyrazole (step 1)

The subtitle compound was prepared according to the procedure of Example 1 using 2-(4-Bromobenzoyl)-3-(dimethylamino)acrylonitrile (prepared according to the method of patent No. # DE 2330913) instead of 4,4,4-trifluoro-1-(4-bromophenyl)butane-1,3-dione in step 1

$^1$H-NMR (CDCl3) δ: 8.07 (s, 1H), 7.98 (ddd, J=9, 2, 2 Hz, 2H), 7.61 (ddd, J=9, 2, 2 Hz, 2H), 7.50 (ddd, J=9, 2, 2 Hz, 2H), 7.21 (ddd, J=9, 2, 2 Hz, 2H), 3.09 (s, 3H).

4-[5-[4-(2-Furyl)phenyl]-4-cyano-1-[4-(methylsulfonyl) phenyl-1H-pyrazole (step 2)

The title compound was prepared according to the procedure of Example 1 using 2-furanboronic acid instead of thiophen-3-boronic acid and 4-[5-[4-Bromophenyl]-4-cyano-1-[4-(methylsulfonyl)phenyl]-1H-pyrazole instead of 1-[4-(Methylsulfonyl)phenyl]-5-(4-bromophenyl)-3-trifluoromethyl-1H-pyrazole in step 2.

mp: 229–230° C.

$^1$H-NMR (CDCl3) δ: 8.07 (s, 1H), 7.96 (d, J=8 Hz, 2H), 7.74 (d, J=8 Hz, 2H), 7.55–7.51 (m, 3H), 7.34 (d, J=8 Hz, 2H) 6.77 (d, J=3 Hz, 1H), 6.53–6.50 (m, 1H), 3.73 (s, 3H).

Anal. Calcd. for: C$_{21}$H$_{15}$N$_3$O$_3$S 1/3H$_2$O: C, 63.79 H, 3.99; N, 10.63. Found: C, 63.77; H, 4.04; N, 10.55.

Example 63

4-[5-[4-(2-Furyl)phenyl]-3-hydroxymethyl-1-[4-(methylsulfonyl)phenyl]-1H-pyrazole Ethyl 5-(4-Bromophenyl)-1-[4-(methylsulphonyl)phenyl]-1H-pyrazole-3-carboxylate (step 1)

The subtitle compound was prepared according to the procedure of Example 1 using Ethyl 4-(4-bromophenyl)-2,4-diketobutyrate (prepared according to the method of *J. Med. Chem.*, 1997, 40, 1347) instead of 4,4,4-trifluoro-1-(4-bromophenyl)butane-1,3-dione in step 1.

$^1$H-NMR (CDCl$_3$) δ: 7.936 (ddd, J=9, 2, 2 Hz, 2H), 7.58–7.49 (m, 4H), 7.10 (ddd, J=9, 2, 2 Hz, 2H), 7.06 (s, 1H), 4.66 (q, J=7 Hz 2H), 3.07 (s, 3H), 1.43 (t, J=7 Hz 3H).

4-[5-(4-Bromophenyl)-3-hydroxymethyl-1-[4-(methylsulfonyl)phenyl]-1H-pyrazole (step 2)

The subtitle compound was prepared according to the procedure of Example 18 using Ethyl 5-(4-Bromophenyl 1-[4-(methylsulphonyl)phenyl]-1H-pyrrazole-3-carboxylate instead of Methyl 5-(4-Bromophenyl)-1-[4-sulfamoylphenyl]-1H-pyrrazole-3-carboxylate in step 1.

$^1$H-NMR (CDCl$_3$) δ: 7.92 (d, J=8 Hz, 2H), 7.52–7.46 (m, 4H), 7.11 (d, J=8 Hz, 2H), 6.56 (s, 1H), 4.80 (br, 2H), 3.07 (s, 3H), 2.10 (br, 1H).

4-[5-[4-(2-Furyl)phenyl]-3-hydroxymethyl-1-[4-(methylsulfonyl)phenyl]-1H-pyrazole (step 3)

The title compound was prepared according to the procedure of Example 1 using 2-furanboronic acid instead of 2-thiophenboronic acid acid and 4-[5-[4-Bromophenyl]-3-hydroxymethy-1-[4-(methylsulfonyl)phenyl]-1H-pyrazole instead of 1-[4-(Methylsulfonyl)phenyl]-5-(4-bromophenyl)-3-trifluoromethyl-1H-pyrazole in step 2.

mp: 175.5–176° C.

$^1$H-NMR (CDCl3) δ: 7.90 (ddd, J=9, 2, 2 Hz, 2H), 7.66 (ddd, J=9, 2, 2 Hz, 2H), 7.53 (ddd, J=9, 2, 2 Hz, 2H), 7.50 (dd, J=2, 1 Hz, 1H), 7.26–7.23 (2H), 6.71 (dd, J=3, 1 Hz, 1H), 6.58 (s, 1H), 6.50 (dd, J=3, 2 Hz, 1H), 4.81 (d, J=6 Hz, 2H), 3.06 (s, 3H) 2.09 (t, J=6Hz, 1H).

Anal. Calcd. for: $C_{21}H_{18}N_2O_4S_1$: C, 63.95 H, 4.60; N, 7.10. Found: C, 63.67; H, 4.65; N, 7.12.

Example 64

3-Cyanomethyl-4-[5-[4-(2-furyl)phenyl]-1-[4-(methylsulfonyl)phenyl]-1H-pyrazole

4-[5-[4-Bromophenyl]-3-cyanomethyl-1-[4-(methylsulfonyl)phenyl]-1H-pyrazole (step 1)

The subtitle compound was prepared according to the procedure of Example 18 using 4-[5-[4-Bromophenyl]-3-hydroxymethyl-[4-(methylsulfonyl)phenyl]-1H-pyrazole (prepared according to the procedure of EXAMPLE 63, step 2) instead of 4-[3-(Hydroxymethyl)-5-(4-bromophenyll)-1H-pyrazol-1-yl]-1-phenylsulfonamide in step 2 and step 3.

$^1$H-NMR (CDCl$_3$) δ: 7.94 (ddd, J=9, 2, 2 Hz, 2H), 7.52 (ddd, J=9, 2, 2 Hz, 2H), 7.48 (ddd, J=9, 2, 2 Hz, 2H), 7.11 (ddd, J=9, 2,2 Hz, 2H), 6.59 (s, 1H), 3.86 (s, 2H), 3.07 (s, 3H).

3-Cyanomethyl-4-[5-[4-(2-furyl)phenyl]-1-[4-(methylsulfonyl)phenyl]-1H-pyrazole (step 2)

The title compound was prepared according to the procedure of Example 1 using 2-furanboronic acid instead of 2-thiophenboronic acid and 4-[5-[4-Bromophenyl]-3-cyanomethyl-1-[4-(methylsulfonyl)phenyl]-1H-pyrazole instead of 1-[4-(Methylsulfonyl)phenyl]-5-(4-bromophenyl)-3-trifluoromethyl-1H-pyrazole.

mp: 193–193.5° C.

$^1$H-NMR (CDCl3) δ: 7.90 (ddd, J=9, 2, 2 Hz, 2H), 7.67 (ddd, J=9, 2, 2 Hz, 2H), 7.53–7.50 (m, 3H), 7.24 (ddd, J=9, 2, 2 Hz, 2H), 6.73 (d, J=3 Hz, 1H), 6.62 (s, 2H), 6.50 (dd, J=3, 2 Hz, 1H), 3.87 (s, 2H), 3.07 (s, 3H).

Anal. Calcd. for: $C_{22}H_{17}N_3O_3S$ 1/4H$_2$O: C, 64.77 H, 4.32; N, 10.30. Found: C, 64.90; H, 4.40; N,10.53.

Example 65

Ethyl 5-[4-(2-furyl)phenyl]-1-[4-(methylsulfonyl)phenyl]-1H-pyrazole-3-carboxylate The title compound was prepared according to the procedure of Example 1 using 2-furanboronic acid instead of 2-thiophenboronic acid and Ethyl 5-(4-bromophenyl)-1-[4-(methylsulfonyl)phenyl]-1H-pyrazole-3-carboxylate prepared according to the procedure of EXAMPLE 63, step 1) instead of 1-[4-(Methylsulfonyl)phenyl]-5-(4-bromophenyl)-3-trifluoromethyl-1H-pyrazole.

mp: 180.9–181.1° C.

$^1$H-NMR (CDCl$_3$) δ: 7.94 (ddd, J=9, 2, 2 Hz, 2H), 7.67 (ddd, J=9, 2, 2 Hz, 2H), 7.60 (ddd, J=9, 2, 2 Hz, 2H), 7.50 (d, J=2 Hz, 1H), 7.24 (ddd, J=9, 2, 2 Hz, 2H), 7.08 (s, 1H), 6.73 (d, J=3 Hz, 1H), 6.50 (dd, J=3, 2 Hz, 1H), 4.77 (q, J=7 Hz, 2H), 3.06 (s, 3H), 1.44 (t, J=7 Hz, 3 H).

Anal. Calcd. for: $C_{23}H_{20}N_2O_5S$ 1/2H$_2$O: C, 62.01 H, 4.75; N, 6.29. Found: C, 62.37; H, 4.70; N, 6.38.

Example 66

5-[4-(1-Imidazolyl)phenyl]-1-[4-(methylsulfonyl)phenyl]-3-trifluoromethyl-1H-pyrazol To a suspension of sodium hydride (0.04 g: 1 mmol) (60% mineral oil dispersion; washed with dry hexane (3 mL)) in DMF(2 mL) was added imidazol (0.068 g) at room temperature and the mixture was stirred 30 minutes. Then, 4-[5-[4-Bromophenyl]-3-trifluoromethyl-1-[4-(methylsulfonyl)phenyl]-1H-pyrazole (0.445 g) and copper powder (0.0063 g) were added and the whole was heated at 150° C. for 3 hours. After cooling, water (30 mL) was added to the reaction mixture and the whole was extracted with CH$_2$Cl$_2$ (30 mL×2), the extract was washed with water and brine, dried over MgSO$_4$,and concentrated in vacuo. The residue was purified by flash chromatography eluting with ethyl acetate/methanol (1/0.03). The resulting solid was recrystallized with dichloroethane-diisopropyl ether to give the title compound (0.07 g).

mp: 183–184° C.

$^1$H-NMR (CDCl$_3$) δ7.99 (d, J=9 Hz, 2H), 7.93 (br, 1H), 7.57 (d, J=9 Hz, 2H), 7.45 (d, J=9 Hz, 2H), 7.37 (d,J=9 Hz, 2H), 7.34 (br, 1H), 7.26 (1H), 6.85 (s, 1H), 3.08 (s, 3H).

Anal. Calcd. for $C_{20}H_{15}N_4O_2F_3S$: C, 55.55; H, 3.50; N, 12.96 Found: C, 55.34; H, 3.83; N, 12.89.

Example 67

5-[4-(2-Furyl)phenyl]-1-[4-(methylsulfonyl)phenyl]-1H -pyrazole-3-carboxylic acid To a stirred solution of Ethyl 5-[4-(2-furyl)phenyl]-1-[4-(methylsulfonyl)phenyl]-1H-pyrazole-3-carboxylate (prepared according to the procedure of Example 63, step 1) (0.1 g) in ethanol (5 ML)-THF (3 mL) was added 2N-Sodium hydroxied solution in water (1 mL) and the mixture was heated at reflux temperature for 1.5 hours. After cooling, 2N-HCl solution (2 mL) and water (20 mL) were addedto the mixture. The whole was extracted with CH$_2$Cl$_2$ (50 mL×2), the organic layer was washed with brine, dried over MgSO$_4$,and concentrated in vacuo. The resultig solid was recrystallized with isopropanol-water to give the title compound (0.08 g).

mp: >280° C.

$^1$H-NMR (DMSO-d$_6$) δ: 7.94 (d, J=9 Hz, 2H), 7.77 (d, J=2 Hz, 1H), 7.71 (d, J=9 Hz, 2H), 7.55 (d, J=9 Hz, 2H), 7.30 (d, J=9 Hz, 2H), 7.01 (d, J=3 Hz, 1H), 6.74 (s, 1H), 6.61 (dd, J=3, 2 Hz, 1H), 3.26 (s, 3H).

Example 68

2-[4-(2-Furyl)phenyl]-3-[(4-methylsulfonyl)phenyl]thiophene

3-Bromo-[2-(4-methoxy)phenyl]thiophene

To a sirred suspension of 2,3-dibromothiophene (7.96 g, 0.033 mmol), 4-methoxybenzeneboronic acid (5 g, 0.033 mmol), and NaHCO$_3$ (5 g, 0.06 mmol) in DME-water (120 mL–40 mL) was added dichlorobis(triphenylphosphine) palladium (2.4 g, 3.3 mmol) at room temperature under N$_2$. The resulting mixture was heated at reflux temperature for 3 hours. After cooling, volatiles were removed by evaporation. The residue was purified by flash chromatography eluting with hexane to give the subtitle compound (4.03 g, 45% yield).

$^1$H-NMR (CDCl$_3$) δ: 7.56 (d, J=8.8 Hz, 2H), 7.22 (d, J=5.5 Hz, 1H), 7.02 (d, J=5.5 Hz, 1H), 6.95 (d, J=8.8 Hz, 2H), 3.84 (s, 3H).

2-[(4-Methoxy)phenyl]-3-[(4-methylthio)phenyl]thiophene

To a stirred suspension of 3-bromo-[2-(4-methoxy)phenyl]thiophene (4.03 g, 0.015 mmol), 4-(methylthio)benzeneboronic acid (2.77 g. 0.016 mmol), and $NaHCO_3$ (3.78 g, 0.045 mmol) in DME-water (90 mL–30 mL) was added dichlorobis(triphenylphosphine)palladium (1.05 g, 1.5 mmol) at room temperature under $N_2$. The resulting mixture was heated at reflux temperature for 3 hours. After cooling, volatiles were removed by evaporation. The residue was purified by flash chromatography eluting with hexane to give the subtitle compound (3.4 g, 73% yield).

$^1$H-NMR (CDCl$_3$) δ: 7.28–7.10 (m, 8H), 6.80 (d, J=8.9 Hz, 2H), 3.80 (s, 3H), 2.48 (s, 3H).

2-[(4-Methoxy)phenyl]-3-[(4-methylsulfonyl)phenyl]thiophene

To a stirred solution of 2-[(4-methoxy)phenyl]-3-[(4-methylthio)phenyl]thiophene (3.4 g, 11 mmol) in $CH_2Cl_2$ (50 mL) was added mCPBA (70% purity, 5.18 g, 30 mmol) at 5–10° C. After stirring for 1 hour at room temperature, the mixture was poured into saturated $NaHCO_3$ and partitioned. The organic layer was washed with brine, dried over $MgSO_4$, and concentrated in vacuo. The residue was purified by flash chromatography eluting with ethyl acetate/hexane (1/2) to give the subtitle compound (2.67 g, 71% yield).

$^1$H-NMR (CDCl$_3$) δ: 7.83 (d, J=8.6 Hz, 2H), 7.46 (d, J=8.6 Hz, 2H), 7.33 (d, J=5.3 Hz, 1H), 7.19 (d, J=8.9 Hz, 2H), 7.15 (d, J=5.3 Hz, 1H), 6.83 (d, J=8.9 Hz, 2H), 3.82 (s, 3H), 3.07 (s, 3H).

2-[(4-Hydroxy)phenyl]-3-[(4-methylsulfonyl)phenyl]thiophene

A mixture of 2-[(4-methoxy)phenyl]-3-[(4-methylsulfonyl)phenyl]thiophene (2.0 g, 5 mol) and 48% hydrogen bromide (29 mL) was heated at 140° C. for 15 hours. After cooling, the mixture was poured into water. The whole was extracted with ethyl acetate (70 mL×3), the combined organic layer washed with brine, dried over $MgSO_4$, and evaporated in vacuo. Chromatographic purification eluting with ethyl acetate/hexane (1/2) provided the subtitle compound (1.58 g, 82% yield).

$^1$H-NMR (CDCl$_3$) δ: 7.82 (d, J=8.7 Hz, 2H), 7.46 (d, J=8.7 Hz, 2H), 7.33 (d, J=5.3 Hz, 1H), 7.17–7.10 (m, 3H), 6.76 (d, J=8.7 Hz, 2H), 3.08 (s, 3H).

3-[(4-Methylsulfonyl)phenyl]-2-[(4-trifluoromethylsulfonyloxy)phenyl]-thiophene

To a stirred solution of 2-[(4-hydroxy)phenyl]-3-[(4-methylsulfonyl)phenyl]thiophene (1.58 g, 4.79 mmol), triethylamine (1.45 g, 14.4 mmol) in $CH_2Cl_2$ (100 mL) was added triflic anhydride (1.69 g 5.98 mmol) at −78° C. under $N_2$. After stirring for 5 minutes at same temperature, the mixture was allowed to warm to room temperature. The mixture was poured into water, and the whole was extracted with $CH_2Cl_2$ (50 mL×2). The combined organic layer was washed with brine, dried over $MgSO_4$, and evaporated in vacuo. Chromatographic purification eluting with ethyl acetate/hexane (1/2) provided the subtitle compound (1.93 g, 87% yield).

$^1$H-NMR (CDCl$_3$) δ: 7.87 (d, J=8.4 Hz, 2H), 7.46–7.41 (m, 3H), 7.34 (d, J=8.9 Hz, 2H), 7.21 (d, J=8.9 Hz, 2H), 7.18 (d, J=5.3 Hz, 1H), 3.08 (s, 3H).

2-[4-(2-Furyl)phenyl]-3-[(4-methylsulfonyl)phenyl]thiophene

The title compound was prepared according to the procedure of Example 35 using 3-[(4-methylsulfonyl)phenyl]-2-[(4-trifluoromethylsulfonyloxy)phenyl]-thiophene instead of 1-(4-bromophenyl)-2-[3-fluoro-4-(methylsulfonyl)phenyl]-5-methyl-1H-pyrrole in step 4.1 mp: 220–223° C.

$^1$H-NMR (CDCl$_3$) δ: 7.84 (d, J=8.6 Hz, 2H), 7.60 (d, J=8.7 Hz, 2H), 7.51–7.46 (m, 3H), 7.38 (d, J=5.3 Hz, 1H), 7.28 (d, J=8.7 Hz, 2H), 7.17 (d, J=5.3 Hz, 1H), 6.67 (d, J=3.5 Hz, 1H), 6.48 (dd, J=3.5, 1.8 Hz, 1H), 3.07 (s, 3H).

Anal. Calcd. for $C_{21}H_{16}O_3S_2$ 0.3$H_2O$: C, 65.36; H, 4.34. Found: C, 65.44; H, 4.37.

Example 69

2-[4-(3-Furyl)phenyl]-3-[(4-methylsulfonyl)phenyl]thiophene

The title compound was prepared according to the procedure of Example 35 using 3-[(4-methylsulfonyl)phenyl]-2-[(4-trifluoromethylsulfonyloxy)phenyl]-thiophene instead of 1-(4-bromophenyl)-2-[3-fluoro-4-(methylsulfonyl)phenyl]-5-methyl-1H-pyrrole and 3-furanboronic acid instead of 2-furanboronic acid in step 4.

mp: 235–237° C.

$^1$H-NMR (CDCl$_3$) δ: 7.85 (d, J=8.6 Hz, 2H), 7.75 (br.s, 1H), 7.52–7.47 (m, 3H), 7.42 (d, J=8.6 Hz, 2H), 7.38 (d, J=5.3 Hz, 1H), 7.27 (d, J=8.6 Hz, 2H), 7.17 (d, J=5.3 Hz, 1H), 6.70 (dd, J=2.0, 1.0 Hz, 1H), 3.07 (s, 3H).

Anal. Calcd. for $C_{21}H_{16}O_3S_2$ 0.1$H_2O$: C, 65.98; H, 4.27. Found: C, 65.80; H, 4.35.

Example 70

4-[5-[3-Chloro-4-(2-furyl)phenyl]-3-(trifluoromethyl)-1H-pyrazol-1-yl]-1-phenylsulfonamide 1-(4-Hydroxy-3-chlorophenyl)ethanone(step 1)

To a stirred solution of 2-chlorophenol (10.0 g, 77.8 mmol) in carbon disulfide (20 ml) was added aluminum chloride (21.8 g, 163.4 mmol) at 0° C. under nitrogen. Acetyl chloride (6.72 g, 85.6 mmol) was added, and the mixture was heated at reflux temperature for 6 hours. The mixture was cooled down to room temperature, and poured into ice-water. The whole was extracted with diethylether. The organic layer was washed with brine, dried over $MgSO_4$, and concentrated in vacuo. The residue was recrystallized with diethylether-hexane to give the title compound (6.39 g, 48% yield).

$^1$H-NMR (CDCl$_3$) δ: 7.99 (d, J=2 Hz, 1H), 7.82 (dd, J=9, 2 Hz, 1H), 7.08 (d, J=9 Hz, 1H), 6.17 (s, 1H), 2.56 (s, 3H).

4-[5-[3-Chloro-4-(2-furyl)phenyl-3-(trifluoromethyl)-1H-pyrazol-1-yl]-1-phenylsulfonamide(step 2)

The title compound was prepared according to the procedure of Example 30 using 1-(4-hydroxy-3-chlorophenyl)ethanone instead of 1-(4-hydroxy-3-methylphenyl)ethanone.

mp: 150–152° C.

$^1$H-NMR (CDCl$_3$) δ: 7.95 (d, J=9 Hz, 2H), 7.86 (d, J=8 Hz, 1H), 7.54–7.50 (m, 3H), 7.42 (d, J=2 Hz, 1H), 7.24 (d, J=4 Hz, 1H), 7.08 (dd, J=8, 2 Hz, 1H), 6.83 (s, 1H), 6.56 (dd, J=4, 2 Hz, 1H), 4.98 (s, 2H).

Anal. Calcd. for $C_{20}H_{13}ClF_3N_3O_3S$: C, 51.35; H, 2.80; N, 8.98. Found: C, 51.03; H 3.05; N, 8.75.

Example 71

1-[4-(Methylsulfonyl)phenyl]-5-[3-chloro-4-(2-furyl)phenyl]-3-(trifluoromethyl)-1H-pyrazole The title compound was prepared according to the procedure of Example 70 using (4-methylsulfonyl)hydrazine hydrochloride instead of (4-sulfamoylphenyl)hydrazine hydrochloride.

mp: 143–145° C.

$^1$H-NMR (CDCl$_3$) δ: 7.99 (d, J=9 Hz, 2H), 7.88 (d, J=8 Hz, 1H), 7.59 (d, J=9 Hz, 2H), 7.55 (d, J=2 Hz, 1H), 7.41 (d, J=2 Hz, 1H), 7.25 (d, J=4 Hz, 1H), 7.09 (dd, J=8, 2 Hz, 1H), 6.84 (s, 1H), 6.56 (dd, J=4, 2 Hz, 1H), 3.08 (s, 3H).

Anal. Calcd. for $C_{21}H_{14}ClF_3N_2O_3S$ 1/4 Hexane: C, 55.33; H, 3.61; N, 5.74. Found: C, 55.57; H, 3.58; N, 5.55.

Example 72

4-[5-[4-(2-Furyl)-3-methoxyphenyl]-3-(trifluoromethyl)-1H-pyrazol-1-yl]-1-phenylsulfonamide

The title compound was prepared according to the procedure of Example 30 using 1-(4-hydroxy-3-methoxyphenyl)ethanone instead of 1-(4-hydroxy-3-methylphenyl)ethanone.

mp: 161–163° C.

$^1$H-NMR (CDCl$_3$) δ: 7.91 (d, J=9 Hz, 2H), 7.83 (d, J=8 Hz, 1H), 7.53–7.47 (m, 3H), 7.00 (d, J=3 Hz, 1H), 6.87–6.78 (m, 3H), 6.50 (dd, J=4,2 Hz, 1H), 4.98 (s, 2H), 3.79 (s, 3H).

Anal. Calcd. for C$_{21}$H$_{16}$F$_3$N$_3$O$_4$S 1/5 H$_2$O: C, 54.01; H, 3.54; N, 9.00. Found: C, 53.80; H, 3.68; N, 8.94.

Example 73

4-[5-[3-Fluoro-4-(2-furyl)phenyl]-3-(trifluoromethyl)-1H-pyrazol-1-yl]-1-phenylsulfonamide

The title compound was prepared according to the procedure of Example 70 using 2-fluorophenol instead of 2-chlorophenol.

mp: 166–168° C.

$^1$H-NMR (CDCl$_3$) δ: 7.95 (d, J=9 Hz, 2H), 7.86–7.80 (m, 1H), 7.53–7.50 (m, 3H), 7.04 (d, J=11 Hz, 2H), 6.94–6.91 (m, 1H), 6.82 (s, 1H), 6.55 (dd, J=4, 2 Hz, 1H), 4.92 (s, 2H).

Anal. Calcd. for C$_{20}$H$_{13}$F$_4$N$_3$O$_3$S 1/10 H$_2$O: C, 53.01; H, 2.94; N, 9.27. Found: C, 52.62; H, 2.92; N, 9.12.

Example 74

1-[4-(Methylsulfonyl)phenyl]-5-[3-fluoro-4-(2-furyl)phenyl]-3-(trifluoromethyl)-1H-pyrazole

The title compound was prepared according to the procedure of Example 73 using (4-methylsulfonyl)hydrazine hydrochloride instead of (4-sulfamoylphenyl)hydrazine hydrochloride.

mp: 183–185° C.

$^1$H-NMR (CDCl$_3$) δ: 7.98 (d, J=9 Hz, 2H), 7.87–7.81 (m, 1H), 7.58 (d, J=9 Hz, 2H), 7.54 (d, J=2 Hz, 1H), 7.07–7.05 (m, 1H), 7.02 (s, 1H), 6.94–6.91 (m, 1H), 6.83 (s, 1H), 6.55 (dd, J=4, 2 Hz, 1H), 3.08 (s, 3H).

Anal. Calcd. for C$_{21}$H$_{14}$F$_4$N$_2$O$_3$S: C, 56.00; H, 3.13; N, 6.22. Found: C, 55.81; H, 3.23; N, 6.11.

Example 75

4-[5-[4-(5-Oxazolyl)phenyl]-3-(trifluoromethyl)-1H-pyrazol-1-yl]-1-phenylsulfonamide

2-(4-Formylphenyl)-2-methyl-1,3-dioxolane(step 1)

To a stirred solution of 2-(4-bromophenyl)-2-methyl-1,3-dioxolane (2.0 g, 8.23 mmol) in THF (7 ml) was added n-BuLi (1.61 M solution in hexane, 5.47 ml, 8.8 mmol) at −78° C. under nitrogen, and the mixture was stirred for 2 hour, then allowed to warm up to 0° C. for 30 min. A solution of 1-formylpiperidine (930 mg, 8.23 mmol) in THF (5 ml) was added, and the mixture was stirred for 2 hours. The mixture was made neutral by addition of 1N HCl solution, and the whole was extracted with diethylether. The organic layer was washed with saturated NaHCO$_3$ aqueous solution, brine, dried over MgSO$_4$, and concentrated in vacuo. The compound was used for next reaction without purification.

$^1$H-NMR (CDCl$_3$) δ: 10.02 (s, 1H), 7.87 (d, J=8 Hz, 2H), 7.66 (d, J=8 Hz, 2H), 4.11–3.75 (m, 4H), 1.66 (s, 3H).

2-[4-(5-Oxazolyl)phenyl]-2-methyl-1,3-dioxolane(step 2)

To a stirred solution of 2-(4-formylphenyl)-2-methyl-1,3-dioxolane (1.58 g, 8.23 mmol) in methanol (10 ml) was added tosylmethyl isocyanide (2.0 g, 10.3 mmol), potassium carbonate (1.42 g, 10.3 mmol), and the mixture was heated at reflux temperature for 2 hours. The reaction mixture was diluted with water and the whole was extracted with CH$_2$Cl$_2$. The organic layer was washed with brine, dried over MgSO$_4$, and concentrated in vacuo. The residue was purified by flash chromatography eluting with ethyl acetate-hexane (1:4) to give the title compound (711 mg, 37% yield).

$^1$H-NMR (CDCl$_3$) δ7.92 (s, 1H), 7.64 (d, J=8 Hz 2H), 7.55 (d, J=8 Hz, 2H), 7.36 (s, 1H), 4.09–3.77 (m, 4H), 1.67 (s, 31H).

1-[4-(5-Oxazolyl)phenyl]ethanone(step 3)

To a stirred solution of 2-[4-(5-oxazolyl)phenyl]-2-methyl-1,3-dioxolane (711 mg, 3.08 mmol) in acetone (18 ml) and water (2.8 ml) was added pyridinium p-toluenesulfonate (116 mg, 0.46 mmol), and the mixture was heated at reflux temperature for 8 hours. The mixture was cooled down to room temperature, and concentrated in vacuo. The residue was dissolved in diethylether and washed with saturated NaHCO$_3$ aqueous solution, brine, dried over MgSO$_4$, and concentrated in vacuo. The compound was used for next reaction without purification.

$^1$H-NMR (CDCl$_3$) δ8.03 (d, J=9 Hz, 2H), 7.98 (s, 1H), 7.75 (d, J=9 Hz, 2H), 7.49 (s, 1H), 2.63 (s, 3H).

4-[5-[4-(5-Oxazolyl)phenyl]-3-(trifluoromethyl)-1H-pyrazol-1-yl]-phenylsulfonamide (step 4)

The title compound was prepared according to the procedure of Example 30 using 1-[4-(5-oxazolyl)phenyl]ethanone instead of 1-[4-(2-furyl)-3-methylphenyl]ethanone.

mp: 128–130° C.

$^1$H-NMR (DMSO-d$_6$) δ: 8.48 (s, 1H), 7.89 (d, J=8 Hz, 2H), 7.77 (d, J=8 Hz, 2H), 7.79 (s, 1H), 7.59 (d, J=8 Hz, 2H), 7.51 (s, 2H), 7.43 (d, J=8 Hz, 2H), 7.32 (s, 1H).

Anal. Calcd. for C$_{19}$H$_{13}$F$_3$N$_4$O$_3$S 0.56 Dichloromethane: C, 48.75; H, 2.95; N, 11.62. Found: C, 47.35; H, 3.28; N, 10.66.

Example 76

1-[4-(Methylsulfonyl)phenyl]-[4-(5-oxazolyl)phenyl]-3-(trifluoromethyl)-1H-pyrazole

The title compound was prepared according to the procedure of Example 75 using (4-methylsulfonyl)hydrazine hydrochloride instead of (4-sulfamoylphenyl)hydrazine hydrochloride.

mp: 178–180° C.

$^1$H-NMR (CDCl$_3$) δ: 7.98 (s, 1H), 7.97 (d, J=8 Hz, 2H), 7.70 (d, J=8 Hz, 2H), 7.58 (d, J=8 Hz, 2H), 7.44 (s, 1H), 7.33 (d, J=8 Hz, 2H), 6.87 (s, 1H), 3.09 (s, 3H).

Anal. Calcd. for C$_{20}$H$_{14}$F$_3$N$_3$O$_3$S 1/5 H$_2$O: C, 54.97: H, 3.32; N, 9.62. Found: C, 54.64; H, 3.48; N, 9.61.

Example 77

4-[5-[4-(2-Furyl)-2-methylphenyl]-3-(trifluoromethyl)-1H-pyrazol-1-yl]-1-phenylsulfonamide

Trifluoromethanesulfonic acid 4-acetyl-3-methylphenyl ester(step 1)

To a stirred solution of 1-(4-hydroxy-2-methylphenyl)ethanone (0.939 g, 6.25 mmol) in dichloromethane (37.5 ml) was added lutidine (0.804 g, 7.5 mmol), 4-dimethylaminopyridine (0.153 g, 1.25 mmol), trifluoromethanesulfonic anhydride (2.11 g, 7.5 mmol) at −30° C. under nitrogen, and the mixture was stirred for 1 hour, and then allowed to warm up to room temperature for 2 hours. The reaction mixture was diluted with water and the whole was extracted with dichloromethane. The organic layer was washed with brine, dried over $MgSO_4$, and concentrated in vacuo to give 1.76 g of brown oil. The compound was used for next reaction without purification.

1-[4-(2-Furyl)-2-methylphenyl]ethanone(step 2)

To a stirred solution of trifluoromethanesulfonic acid 4-acetyl-3-methylphenyl ester (1.76 g, 6.25 mmol) in dioxane (60 ml) was added 2-(tributylstannyl)furan (2.68 g, 7.5 mmol), lithium chloride (0.66 g, 15.6 mmol) and tetrakis (triphenylphosphine)palladium(0) (0.722 g, 0.62 mmol) under nitrogen. The mixture was heated at reflux temperature for 2 hours, and cooled down to room temperature. The reaction mixture was diluted with water and the whole was extracted with diethylether. The organic layer was washed with saturated potassium fluoride aqueous solution, brine, dried over $MgSO_4$, and concentrated in vacuo. The residue was purified by flash chromatography eluting with ethyl acetate-hexane (1:10) to give title compound (1.15 g, 92%).

$^1$H-NMR ($CDCl_3$) δ: 7.75 (d, J=9 Hz, 1H), 7.57–7.51 (m, 3H), 6.76 (d, J=4 Hz, 1H), 6.50 (dd, J=4, 2 Hz, 1H), 2.59 (s, 3H), 2.58 (s, 3H).

4,4,4-Trifluoro-1-[4-(2-furyl)-2-methylphenyl]butane-1,3-dione(step 3)

To a stirred solution of ethyl trifluoroacetate (0.90 g, 6.31 mmol) in t-butylmethylether (3 ml) was added sodium methoxide (28 wt. % solution in methanol, 1.5 ml, 6.23 mmol) over 2 min. A solution of 1-[4-(2-furyl)-2-methylphenyl]ethanone (1.15 g, 5.74 mmol) in t-butylmethylether (4 ml) was added dropwise over 5 min, and the mixture was stirred for 20 hours. 2N HCl (10 ml) was added, and the whole was extracted with ethyl acetate. The organic layer was washed with brine, dried over $MgSO_4$, and concentrated in vacuo to give 1.78 g of brown oil. The compound was used for next reaction without purification.

4-[5-[4-(2-Furyl)-2-methylphenyl]-3-(trifluoromethyl)-1H-pyrazol-1-yl]-1-phenylsulfonamide(step 4)

To a stirred solution of 4,4,4-trifluoro-1-[4-(2-furyl)-2-methylphenyl]butane-1,3-dione (0.796 g, 2.69 mmol) in ethanol (31 ml) was added (4-sulfamoylphenyl)hydrazine hydrochloride (0.66 g, 2.96 mmol), and the mixture was heated at reflux temperature for 16 hours. The mixture was cooled down to room temperature, and concentrated in vacuo. The residue was dissolved in ethyl acetate, washed with brine, dried over $MgSO_4$, and concentrated in vacuo. The residue was purified by flash chromatography eluting with ethyl acetate-hexane (1:3). The resulting solid was recrystallized with diisopropylether-hexane to give the title compound (0.26 g, 22% yield).

mp: 135–137° C.

$^1$H-NMR ($CDCl_3$) δ7.83 (d, J=9 Hz, 2H), 7.55–7.42 (m, 5H), 7.21 (d, J=9 Hz, 1H), 6.73–6.71 (m, 2H), 6.50 (dd, J=4,2 Hz, 1H), 4.91 (s, 2H), 2.04 (s, 3H).

Anal. Calcd. for $C_{21}H_{16}F_3N_3O_3S$: C, 56.37; H, 3.60; N, 9.39. Found: C, 56.13; H, 3.64; N, 9.23.

Example 78

1-[4-(Methylsulfonyl)phenyl]-5-[4-(2-furyl)-2-metbylphenyl]-3-(trifluoromethyl)-1H-pyrazole The title compound was prepared according to the procedure of Example 77 (step 4) using (4-methylsulfonyl) hydrazine hydrochloride instead of (4-sulfamoylphenyl) hydrazine hydrochloride.

mp: 175–177° C.

$^1$H-NMR ($CDCl_3$) δ: 7.88 (d, J=9 Hz, 2H), 7.57-7.49 (m, 5H), 7.22 (d, J=9 Hz, 1H), 6.74–6.73 (m, 2H), 6.51 (dd, J=4, 2 Hz, 1H), 3.03 (s, 3H), 2.05 (s, 3H).

Anal. Calcd. for $C_{22}H_{17}F_3N_2O_3S$: C, 59.19; H, 3.84; N, 6.27. Found: C, 59.04; H, 3.78; N, 6.18.

Example 79

4-[5-[2-Fluoro-4-(2-furyl)phenyl]-3-(trifluoromethyl)-1H-pyrazol-1-yl]-1-phenylsulfonamide 1-(2-Fluoro-4-hydroxyphenyl)ethanone(step 1)

To a stirred suspension of aluminum chloride (41.6 g, 312 mmol) in 1,2-dichloroethane (100 ml) was added 3-fluorophenol (30.95 g, 276 mmol) dropwise at 0° C. Acetyl chloride (24.0 g, 306 mmol) was added dropwise, and the mixture was heated at reflux temperature for 6 hours. The mixture was cooled down to room temperature, and poured into ice. The whole was extracted with diethylether. The organic layer was washed with brine, dried over $MgSO_4$, and concentrated in vacuo, The residue was recrystallized with hexane to give the title compound (3.57 g, 8% yield).

$^1$H-NMR ($CDCl_3$) δ: 7.88–7.82 (m, 1H), 6.74 (dd, J=9, 2 Hz, 1H), 6.64 (dd, J=13, 2 Hz, 1H), 2.62 (d,J=5 Hz, 3H).

4-[5-[2-Fluoro-4-(2-furyl)phenyl]-3-(trifluoromethyl)-1H-pyrazol-1-yl]-1-phenylsulfonamide(step 2)

The title compound was prepared according to the procedure of Example 77 (step 4) using 1-(2-fluoro-4-hydroxyphenyl)ethanone instead of 1-(4-hydroxy-2-methylphenyl)ethanone.

mp: 203–205° C.

$^1$H-NMR ($CDCl_3$) δ: 7.92 (d, J=9 Hz, 2H), 7.52–7.47 (m, 4H), 7.38 (dd, J=11,2 Hz, 1H), 7.28–7.22 (m, 1H), 6.86 (s, 1H), 6.76 (d, J=4 Hz, 1H), 6.52 (dd, J=4, 2 Hz, 1H), 4.89 (s, 2H).

Anal. Calcd. for $C_{20}H_{13}F_4N_3O_3S$: C, 53.22; H, 2.90; N, 9.31. Found: C, 53.05; H, 3.03; N, 9.39.

Example 80

1-[4-(Methylsulfonyl)phenyl]-5-[2-fluoro-4-(2-furyl)phenyl]-3-(trifluoromethyl)-1H-pyrazole The title compound was prepared according to the procedure of Example 79 (step 4) using (4-methylsulfonyl) hydrazine hydrochloride instead of (4-sulfamoylphenyl) hydrazine hydrochloride.

mp: 223–225° C.

$^1$H-NMR (DMSO-$d_6$) δ: 8.01 (d, J=9 Hz, 2H), 7.83 (d, J=1 Hz, 1H), 7.67–7.64 (m 3H), 7.60–7.52 (m, 2H), 7.35 (s, 1H), 7.18 (d, J=4 Hz, 1H), 6.66 (dd, J=3, 2 Hz, 1H), 3.33 (s, 3H).

Anal. Calcd. for $C_{21}H_{14}F_4N_2O_3S$: C, 56.00; H, 3.13: N, 6.22. Found: C, 55.67; H, 3.37; N, 6.16.

Example 81

1-[4-(Methylsulfonyl)phenyl]-5-[4-(2-furyl)-3-methoxyphenyl]-3-(trifluoromethyl)-1H -pyrazole The title compound was prepared according to the procedure of Example 72 using (4-methylsulfonyl)hydrazine hydrochloride instead of (4-sulfamoylphenyl)hydrazine hydrochloride.

mp: 138–140° C.

$^1$H-NMR (CDCl$_3$) δ: 7.96 (d, J=9 Hz, 2H), 7.84 (d, J=8 Hz, 1H), 7.59 (d, J=9 Hz, 2H), 7.49–7.48 (m, 1H), 7.01 (d, J=4 Hz, 1H), 6.86 (dd, J=8, 2 Hz, 1H), 6.83 (s, 1H), 6.79 (d, J=2 Hz, 1H), 6.51 (dd, J=4,2 Hz, 1H), 3.80 (s, 3H), 3.06 (s, 3H).

Anal. Calcd. for C$_{22}$H$_{17}$F$_3$N$_2$O$_4$S: C, 57.14; H, 3.71: N, 6.06. Found: C, 56.75; H, 4.04; N, 5.85.

Example 82

1-[4-(Methylsulfonyl)phenyl]-5-[4-(4-thiazolyl) phenyl]-3-(trifluoromethyl)-1H-pyrazole 1-(4-Acetylphenyl)-2-bromo-1-ethanone(step 1)

To a stirred solution of 1,4-diacetylbenzene (5.3 g, 32.7 mmol), aluminum chloride (0.05 g, 0.38 mmol) in diethylether (50 ml) was added bromine (5.3 g, 32.7 mmol) dropwise over 20 minutes. The mixture was stirred for 30 minutes, and diluted with water. The whole was concentrated to remove diethylether, and the aqueous suspension was filtered to give 7.0 g of white solid. The compound was used for next reaction without purification.

$^1$H-NMR (CDCl$_3$) δ: 8.09–8.05 (m, 4H), 4.47 (s, 2H), 2.65 (s, 3H).

1-[4-(4-Thiazolyl)phenyl]ethanone(step 2)

To a stirred suspension of phosphorus pentasulfide (24.5 g, 110 mmol) in dioxane (250 ml) was added formamide (28.4 g, 630 mmol), and the mixture was heated at reflux temperature for 2 hours. The reaction mixture was cooled down to room temperature, and the solution was decanted away from solids. To a stirred solution of 1-(4-acetylphenyl)-2-bromo-1-ethanone (2.0 g, 8.3 mmol) in dioxane (80 ml) was added the thioformamide solution, and the mixture was heated at reflex temperature for 13 hours. The reaction mixture was cooled down to room temperature, and made basic by addition of 0.5M NaOH aqueous solution. The whole was extracted with diethylether. The organic layer was washed with brine, dried over MgSO$_4$, and concentrated in vacuo. The residue was purified by flash chromatography eluting with ethyl acetate-hexane 1:4) to give the title compound (610 mg, 36% yield).

$^1$H-NMR (CDCl$_3$) δ: 8.91 (d, J=2 Hz, 1H), 8.04–8.02 (m, 4H), 7.69 (d, J=2 Hz, 1H), 2.64 (s, 3H).

4,4,4-Trifluoro-1-[4-(4-thiazolyl)phenyl]butane-1,3-dione (step 3)

To a stirred solution of ethyl trifluoroacetate (0.47 g, 3.3 mmol) in t-butylmethylether (3 ml) was added sodium methoxide (28 wt. % solution in methanol, 0.78 ml, 3.26 mmol) over 2 min. A solution of 1-[4-(4-thiazolyl)phenyl]ethanone (0.61 g, 3.0 mmol) in t-butylmethylether (4 ml) was added dropwise over 5 min, and the mixture was stirred for 20 hours. 2N HCl (10 ml) was added, and the whole was extracted with ethyl acetate. The organic layer was washed with brine, dried over MgSO$_4$, and concentrated in vacuo to give 0.54 g of brown oil. The compound was used for next reaction without purification.

1-[4-(Methylsulfonyl)phenyl]-5-[4-(4-thiazolyl)phenyl]-3-(trifluoromethyl)-1H-pyrazole(step 4)

The title compound was prepared according to the procedure of Example 77 using (4-methylsulfonyl)hydrazine hydrochloride instead of (4-sulfamoylphenyl)hydrazine hydrochloride.

mp: 168–170° C.

$^1$H-NMR (CDCl$_3$) δ: 8.90 (d, J=2 Hz, 1H), 7.97 (d, J=8 Hz, 2H), 7.95 (d, J×9 Hz, 2H), 7.63 (d, J=2 Hz, 1H), 7.58 (d, J=8 Hz, 2H), 7.32 (d, J=8 Hz, 2H), 6.84 (s, 1H), 3.07 (s, 3H).

Anal. Calcd. for C$_{20}$H$_{14}$F$_3$N$_3$O$_2$S$_2$ 1/10 H$_2$O: C, 53.23; H, 3.17; N, 9.31. Found: C, 52.96: H, 3.17; N, 9.13.

Example 83

1-[3-Fluoro-4-(methylsulfonyl)phenyl]-5-[4-(2-furyl)-3-methylphenyl]-3-(trifluoromethyl)-1H-pyrazole The title compound was prepared according to the procedure of Example 60 using 4,4,4-trifluoro-1-[4-(2-furyl)-3-methylphenyl]butane-1,3-dione instead of 4,4,4-trifluoro-1-[4-(2-furyl)phenyl]butane-1,3-dione.

mp: 123–125° C.

$^1$H-NMR (CDCl$_3$) δ: 7.94–7.88 (m, 1H), 7.75 (d, J=8 Hz, 1H), 7.55 (d, J=2 Hz, 1H), 7.44 (dd, J=10, 2 Hz, 1H), 7.23–7.21 (m, 2H), 7.07 (d, J=8 Hz, 1H), 6.79 (s, 1H), 6.66 (d, J=4 Hz, 1H), 6.54 (dd, J=3, 2 Hz, 1H), 3.23 (s, 3H), 2.52 (s, 3H).

Anal. Calcd. for C$_{22}$H$_{16}$F$_4$N$_2$O$_3$S: C, 56.9; H, 3.47; N, 6.03. Found: C, 56.82; H, 3.61; N, 6.03.

Example 84

1-[3-Fluoro-4-(methylsulfonyl)phenyl]-5-[4-(5-oxazolyl)phenyl]-3-(trifluoromethyl)-1H-pyrazole The title compound was prepared according to the procedure of Example 60 using 4,4,4-trifluoro-1-[4-(5-oxazolyl)phenyl]butane-1,3-dione instead of 4,4,4-trifluoro-1-[4-(2-furyl)phenyl]butane-1,3-dione.

mp: 170–172° C.

$^1$H-NMR (CDCl$_3$) δ: 7.97 (s, 1H), 7.96–7.90 (m, 1H), 7.72 (d, J=9 Hz, 2H), 7.46 (s, 1H), 7.42 (dd, J=10, 2 Hz, 1H), 7.33 (d, J=9 Hz, 2H), 7.25–7.21 (m, 1H), 6.83 (s, 1H), 3.24 (s, 3H).

Anal. Calcd. for C$_{20}$H$_{13}$F$_4$N$_3$O$_3$S: C, 53.22; H, 2.90; N, 9.31. Found: C, 53.02; H, 3.16; N, 9.02.

Example 85

1-[3-Fluoro-4-(methylsulfonyl)phenyl]-5-[4-(3-furyl)phenyl]-3-(trifluoromethyl)-1H-pyrazole 5-(4-Bromophenyl)-1-[3-fluoro-4-(methylsulfonyl)phenyl]-3-(trifluoromethyl)-1H-pyrazole (step 1)

[3-fluoro-4-(methylsulfonyl)phenyl]hydrazine hydrochloride (0.354 g, 1.47 mmol) was added to a solution of 4,4,4-Trifluoro-1-(4-bromophenyl)butane-1,3-dione (0.395 g, 1.34 mmol) in EtOH (20 mL). The mixture was heated at reflux temperature for 17 hours and cooled down to room temperature. The reaction mixture was concentrated in vacuo, and the residue was taken up in ethyl acetate, washed with water and brine, dried over sodium sulfate, and concentrated in vacuo. The residue was purified by flash chromatography eluting with hexane/ethyl acetate (3/1). The resulting solid was recrystallized from ethyl acetate/hexane to give the subtitle compound (0.537 g, 86.6% yield).

mp: 64–65° C.

$^1$H-NMR (CDCl$_3$) δ: 7.94 (dd, J=9, 8 Hz, 1H), 7.58 (d, J=9 Hz, 2H), 7.39 (dd, J=10, 2 Hz, 1H), 7.21–7.18 (m, 1H), 7.14 (d, J=9 Hz, 2H), 6.79 (s, 1H), 3.24 (s, 3H).

Anal. Calcd. for C$_{17}$H$_{11}$BrF$_4$N$_2$O$_2$S: C, 44.08; H, 2.39; N, 6.05. Found: C, 44.05; H, 2.78; N, 5.88.

MS (EI): m/z 462 (M$^+$), 464(M+2)

1-[3-Fluoro-4-(methylsulfonyl)phenyl]-5-[4-(3-furyl) phenyl]-3-(trifluoromethyl)-1H-pyrazole (step 2)

To a stirred solution of 5-(4-bromophenyl)-1-[3-fluoro-4-(methylsulfonyl)phenyl]-3-(trifluoromethyl)-1H-pyrazole (0.15 g, 0.324 mmol) in DME (3.9 mL) was added furan-3-boronic acid (0.044 g, 0.389 mmol), bis(triphenylphosphine)palladium(II)chloride (0.025 g, 0.04 mmol) and saturated NaHCO$_3$ solution (1.3 mL) at room temperature under nitrogen. The mixture was heated at reflux temperature for 4 hours, and cooled down to room temperature. The reaction mixture was filtered through celite, the filtrate was poured into water and the whole was extracted with ethyl acetate (20 mL×3). The organic layer was washed with brine, dried over sodium sulfate, and concentrated in vacuo. The residue was purified by flash chromatography eluting with hexane/ethyl acetate (3/1) to give the title compound (0.066 g, 45.2% yield).

mp: 74–76° C.

$^1$H-NMR (CDCl$_3$) δ: 7.93 (dd, J=9, 8 Hz, 1H), 7.80 (s, 1H), 7.55–7.51 (m, 3H), 7.42 (dd, J=2, 10 Hz, 1H), 7.28–7.24 (m, 3H), 6.80 (s, 1H), 6.72 (dd, J=2, 1 Hz, 1H), 3.24 (s, 3H).

Anal. Calcd. for C$_{21}$H$_{14}$F$_4$N$_2$O$_3$S, 0.3H$_2$O: C, 55.34; H, 3.23; N, 6.15. Found: C, 55.39; H, 3.58; N, 6.18.

MS (EI): m/z 450 (M$^+$)

Example 86

1-[3-Fluoro-4-(methylsulfonyl)phenyl]-5-[4-(2-thienyl)phenyl]-3-(trifluoromethyl)-1H-pyrazole The title compound was prepared according to the procedure of Example 85 (step 2) using thiophene-2-boronic acid, instead of furan-3-boronic acid.

mp: 75–76° C.

$^1$H-NMR (CDCl$_3$) δ: 7.94 (dd, J=9, 8 Hz, 1H), 7.66 (d, J=9 Hz, 2H), 7.45–7.35 (m, 3H), 7.28–7.24 (m, 3H), 7.12 (dd, J=5, 4 Hz, 1H), 6.81 (s, 1H), 3.24 (s, 3H).

Anal. Calcd. for C$_{21}$H$_{14}$F$_4$N$_2$O$_2$S$_2$, 0.05 Hexane: C, 54.25; H, 3.11; N, 5.97. Found: C, 53.95; H, 3.48; N, 5.63.

MS (EI): m/z 466 (M$^+$)

Example 87

1-[3-Fluoro-4-(methylsulfonyl)phenyl]-5-[4-(3-thienyl)phenyl]-3-(trifluoromethyl)-1H-pyrazole The title compound was prepared according to the procedure of Example 1 (step 2) using thiophene-3-boronic acid, instead of furan-3-boronic acid.

mp: 72–74° C.

$^1$H-NMR (CDCl$_3$) δ: 7.93 (t, J=8 Hz, 1H), 7.65 (d, J=8 Hz, 2H), 7.58–7.52 (m, 1H), 7.45–7.40 (m, 3H), 7.29 (d, J=8 Hz, 2H), 7.27–7.23 (m, 1H), 6.81 (s, 1H), 3.23 (s, 3H).

Anal. Calcd. for C$_{21}$H$_{14}$F$_4$N$_2$O$_2$S$_2$, 0.05 Hexane: C, 54.25; H, 3.11; N, 5.97. Found: C, 53.96; H, 3.46; N, 5.61.

MS (EI): m/z 466 (M$^+$)

Example 88

Methyl 1-(4-sulfamoylphenyl)-5-[4-(2-thiazolyl)phenyl]-1H-pyrazole-3-carboxylate The title compound was prepared according to the procedure of Example 21 using methyl 1-(4-sulfamoylphenyl)-5-(4-bromophenyl)-1H-pyrazole-3-carboxylate, instead of 4-[5-(4-bromophenyl)-3-(trifluoromethyl)-1H-pyrazol-1-yl]-1-phenylsulfonamide.

mp: 204–206° C.

$^1$H-NMR (CDCl$_3$) δ: 7.97 (dt, J=9, 2 Hz, 2H), 7.92 (dt, J=9, 2 Hz, 2H), 7.90 (d, J=3 Hz, 1H), 7.52 (dt, J=9, 2 Hz, 2H), 7.39 (d, J=3 Hz, 1H), 7.30 (ddd, J=9, 2, 2 Hz, 2H), 7.12 (s, 1H), 4.93 (br, 2H), 3.99 (s, 3H).

Anal. Calcd. for C$_{20}$H$_{16}$N$_4$O$_4$S$_2$ 1/2H$_2$O: C, 53.44; H, 3.81; N, 12.46. Found: C, 53.43; H, 4.00; N, 12.30.

Example 89

4-[4-Cyano-5-[4-(2-thiazolyl)phenyl]-1H-pyrazol-1-yl]-1-phenylsulfonamide

The title compound was prepared according to the procedure of Example 21 using 4-[4-cyano-5-(4-bromophenyl)-1H-pyrazol-1-yl]-1-phenylsulfonamide, instead of 4-[5-(4-bromophenyl)-3-(trifluoromethyl)-1H-pyrazol-1-yl]-1-phenylsulfonamide.

mp: 216–217° C.

$^1$H-NMR (DMSO-d$_6$) δ: 8.53 (s, 1H), 8.08 (d, J=9 Hz, 2H), 7.99 (d, J=3 Hz, 1H), 7.89–7.86 (m, 3H), 7.58–7.51 (m, 4H), 7.49 (br, 2H).

Anal. Calcd. for C$_{19}$H$_{13}$N$_5$O$_2$S$_2$: C, 56.01; H, 3.22; N, 17.19. Found: C, 55.76; H, 3.46; N, 16.88.

Example 90

4-[4-Chloro-5-[4-(2-thiazolyl)phenyl]-3-trifluoromethyl-1H-pyrazol-1-yl]-1-phenylsulfonamide 4-[4-Chloro-5-(4-bromophenyl)-3-trifluoromethyl-1H-pyrazol-1-yl]-1-phenylsulfonamide (step 1)

To a stirred solution of 4-[5-(4-bromophenyl)-3-trifluoromethyl-1H-pyrazol-1-yl]-1-phenylsulfonamide (0.8 g) in CH$_2$Cl$_2$ (6 mL) was added sulfuryl chloride (3 mL) at room temperature. The mixture was stirred for 8 hours. The reaction mixture was poured into water and the whole was vigorously stirred 10 minutes. The resulting mixture was extracted with CH$_2$Cl$_2$ (20 mL). The organic layer was washed with saturated NaHCO$_3$ solution and brine, dried over sodium sulfate, and concentrated in vacuo. The resulting solid was recrystallized with CH$_2$Cl$_2$-diisopropyl ether to give the title compound (0.47 g).

$^1$H-NMR (CDCl$_3$) δ: 7.93 (d, J=9 Hz, 2H), 7.59 (d, J=9 Hz, 1H), 7.41 (d, J=9 Hz, 2H), 7.16 (d, J=9 Hz, 2H), 4.87 (br, 2H).

4-[4-Chloro-5-[4-(2-thiazolyl)phenyl]-3-trifluoromethyl-1H-pyrazol-1-yl]-1-phenylsulfonamide (step 2)

The title compound was prepared according to the procedure of Example 21 using 4-[4-Chloro-5-(4-bromophenyl)-3-trifluoromethyl-1H-pyrazol-1-yl]-1-phenylsulfonamide, instead of 4-[5-(4-bromophenyl)-3-(trifluoromethyl)-1H-pyrazol-1-yl]-1-phenylsulfonamide.

mp: 233–236° C. (decomposition)

$^1$H-NMR (CDCl$_3$) δ: 8.05 (d, J=9 Hz, 2H), 7.93–7.90 (m, 3H), 7.47–7.36 (m, 5H), 4.84 (br, 2H).

Anal. Calcd. for C$_{19}$H$_{12}$N$_4$O$_2$S$_2$ClF$_3$ 1/3H$_2$O: C, 46.49; H, 2.60; N, 11.41. Found: C, 46.86; H, 2.85; N, 11.03.

Example 91

5-[2-Fluoro-4-(2-furyl)phenyl]-1-[3-fluoro-4-(methylsulfonyl)phenyl]-3-trifluoromethyl-1H-pyrazole The title compound was prepared according to the procedure of Example 79 (step 2) using 3-fluoro-4-(methylsulfonyl)phenyl hydrazine hydrochloride instead of (4-sulfamoylphenyl)hydrazine hydrochloride.

mp: 156–160° C.

$^1$H-NMR (DMSO-d$_6$) δ: 7.94 (t, J=8.1 Hz, 1H), 7.84 (br.s, 1H), 7.73–7.53 (m, 4H), 7.44 (d, J=8.4 Hz, 1H), 7.38 (s, 1H), 7.19 (d, J=3.5 Hz, 1H), 668–6.65 (s, 1H), 3.33 (s, 3H).

Example 92

1-[3-Fluoro-4-(methylsulfonyl)phenyl]-5-[4-(2-furyl)-2-methylphenyl]-3-trifluoromethyl-1H-pyrazole The title compound was prepared according to the procedure of Example 77 (step 4) using 3-fluoro-4-

(methylsulfonyl)phenyl hydrazine hydrochloride instead of (4-sulfamoylphenyl)hydrazine hydrochloride.

mp: 77–79° C.

$^1$H-NMR (DMSO-d$_6$) δ: 7.84 (t, J=8.2 Hz, 1H), 7.60 (s, 1H), 7.58–7.50 (m, 2H), 7.41–7.34 (m, 1H), 7.25–7.15 (m, 2H), 6.73 (s, 1H), 6.78–6.70 (m, 1H), 6.52 (dd, J=3.5 Hz, 1.8 Hz, 1H), 3.20 (s, 3H), 2.07 (s, 3H).

Example 93

1-[3-Fluoro-4-(methylsulfonyl)phenyl]-5-[3-chloro-4-(2-furyl)phenyl-3-(trifluoromethyl)-1H-pyrazole The title compound was prepared according to the procedure of Example 60 using 4,4,4-trifluoro-1-[3-chloro-4-(2-furyl)phenyl]butane-1,3-dione instead of 4,4,4-trifluoro-1-[4-(2-furyl)phenyl]butane-1,3dione.

mp: amorphous.

$^1$H-NMR (CDCl$_3$) δ: 7.98–7.92 (m, 1H), 7.92 (d, J=8 Hz, 1H), 7.56 (d, J=2 Hz, 1H), 7.47–7.41 (m, 2H), 7.28–7.23 (m, 2H), 7.12 (d, J=8 Hz, 1H), 6.84 (s, 1H), 6.57 (dd, J=4,2 Hz, 1H), 3.24 (s, 3H).

Anal. Calcd. for C$_{21}$H$_{13}$ClF$_4$N$_2$O$_3$S: C, 52.02; H, 2.70; N, 5.78. Found: C, 52.12; H, 2.79; N, 5.63.

Example 94

4-{4-[1-[3-Fluoro-4-(methylsulfonyl)phenyl]-3-(trifluoromethyl)-1H-pyrazol-5-yl]phenyl}-1,3-oxazole 4-(4-Bromophenyl)-1,3-oxazole (step 1)

To a stirred solution of 2,4'-dibromoacetophenone (9.66 g, 34.8 mmol) in formic acid (42 ml) was added ammonium formate (7.58 g, 120.6 mmol), and the mixture was heated at reflux temperature for 3 hours. The reaction mixture was cooled down to room temperature, and made basic by addition of 50% NaOH aqueous solution. The whole was extracted with CH$_2$H$_2$. The organic layer was washed with brine, dried over MgSO$_4$, and concentrated in vacuo. The residue was purified by flash chromatography eluting with ethyl acetate-hexane (1:5) to give title compound (2.0 g, 26% yield).

$^1$H-NMR (CDCl$_3$) δ: 7.95–7.93 (m, 2H), 7.62 (d, J=9 Hz, 2H), 7.53 (d, J=9 Hz, 2H).

1-[4-(1,3-Oxazol-4-yl)phenyl]-1-ethanone (step 2)

To a stirred solution of 4-(4-bromophenyl)-1,3-oxazole (469 mg, 2.09 mmol) in dioxane (20 ml) was added tributyl (1-ethoxyvinyl)tin (906 mg, 2.51 mmol), tetrakis (triphenylphosphine)palladium (240 mg, 0.207 mmol), lithium chloride (221 mg, 5.23 mmol), and the mixture was heated at reflux temperature for 8 hours. The reaction mixture was cooled down to room temperature, and diluted with ethyl acetate. The whole was washed with saturated potassium fluoride aqueous solution, and the precipitate was removed by filteration through celite. The resulting solution was extracted with ethyl acetate. The organic layer was washed with brine, dried over MgSO$_4$, and concentrated in vacuo. To the residue was added THF (10 ml), 2N HCl aqueous solution (10 ml), and the mixture was heated at reflux temperature for 8 hours. The reaction mixture was cooled down to room temperature, made neutral by addition of NaHCO$_3$, and extracted with ethyl acetate. The organic layer was washed with brine, dried over MgSO$_4$, and concentrated in vacuo. The residue was purified by flash chromatography eluting with ethyl acetate-hexane (1:5) to give title compound (256 mg, 65% yield).

$^1$H-NMR (CDCl$_3$) δ: 8.06 (d, J=1 Hz, 1H), 8.01 (d, J=9 Hz, 2H), 7.98 (d, J=1 Hz, 1H) 7.85 (d, J=9 Hz, 2H), 2.62 (s. 3H).

4,4,4-Trifluoro-1-[4-(1,3-oxazol-4-yl)phenyl]-1,3-butanedione (step 3)

To a stirred solution of 1-[4-(1,3-oxazol-4-yl)phenyl]-1-ethanone (256 mg, 1.37 mmol), ethyl trifluoroacetate (214 mg, 1.51 mmol) in t-butylmethylether (22 ml) was added sodium methoxide (28 wt. % solution in methanol; 0.4 ml, 1.67 mmol) over 5 minutes, and the mixture was stirred for 20 hours. The mixture was made neutral by addition of 2N HCl, and the whole was extracted with ethyl acetate. The organic layer was washed with brine, dried over MgSO$_4$, and concentrated in vacuo. The residue was used for next reaction without further purification. (433 mg, 99% yield).

4-{4-[1-[3-Fluoro-4-(methylsulfonyl)phenyl]-3-(trifluoromethyl)-1H-pyrazol-5-yl]phenyl}-1,3-oxazole (step 4)

The title compound was prepared according to the procedure of Example 60 using 4,4,4-trifluoro-1-[4-(1,3-oxazol-4-yl)phenyl]-1,3-butanedione instead of 4,4,4-trifluoro-1-[4-(2-furyl)phenyl]-1,3butanedione.

mp: 164–166° C.

$^1$H-NMR (CDCl$_3$) δ: 8.01 (d, J=15 Hz, 2H), 7.95–7.89 (m, 1H), 7.82 (d, J=8 Hz, 2H), 7.41 (dd, J=10, 2 Hz, 1H), 7.32 (d, J=9 Hz, 2H), 7.23–7.21 (m, 1H), 6.83 (s, 1H), 3.24 (s, 3H).

Anal. Calcd. for C$_{20}$H$_{13}$F$_4$N$_3$O$_3$S: C, 53.22; H, 2.90. N, 9.31. Found: C, 53.17; H, 2.99; N, 9.35.

Example 95

4-{4-[1-[4-(Methylsulfonyl)phenyl]-3-(trifluoromethyl)-1H-pyrazol-5-yl]phenyl}-1,3-oxazole The title compound was prepared according to the procedure of Example 94 using (4-methylsulfonylphenyl)hydrazine hydrochloride instead of (2-fluoro-4-methylsulfonylphenyl)hydrazine hydrochloride.

mp: 175–177° C.

$^1$H-NMR (CDCl$_3$) δ: 8.01 (d, J=1 Hz, 1H), 7.97–7.94 (m, 3H), 7.78 (d, J=9 Hz, 2H), 7.57 (d, J=9 Hz, 2H), 7.30 (d, J=9 Hz, 2H), 6.83 (s, 1H), 3.07 (s, 3H).

Anal. Calcd. for C$_{20}$H$_{14}$F$_3$N$_3$O$_3$S: C, 55.43; H, 3.26; N, 9.70. Found: C, 55.11; H, 3.47; N, 9.41.

Example 96

2-{4-[1-[3-Fluoro-4-(methylsulfonyl)phenyl]-3-(trifluoromethyl)-1H-pyrazol-5-yl]phenyl}-1,3-oxazole 4-Bromo-N-(2,2-diethoxyethyl)benzamide (step 1)

To a stirred solution of aminoacetaldehyde diethyl acetal (6.66 g, 50.0 mmol) in CH$_2$Cl$_2$ (100 ml) was added triethylamine (5.06 g, 50.0 mmol), 4-bromobenzoyl chloride (10.97 g, 50.0 mmol), and the mixture was stirred for 6 hours. The reaction mixture was concentrated in vacuo. The residue was dissolved in ethyl acetate. The solution was washed with 0.5N HCl aqueous solution, water, saturated NaHCO$_3$ aqueous solution, brine, dried over MgSO$_4$, and concentrated in vacuo. The residue was recystallized with ethyl acetate-hexane to give title compound (10.45 g, 66% yield).

$^1$H-NMR (CDCl$_3$) δ: 7.65 (d, J=9 Hz, 2H), 7.58 (d, J=9 Hz, 2H), 6.35 (s, 1H), 4.61 (t, J=5 Hz, 1H), 3.81–3.69 (m, 2H), 3.64–3.53 (m, 4H), 1.24 (t, J=7 Hz, 6H).

2-(4-Bromophenyl)-1,3-oxazole (step 2)

4-Bromo-N-(2,2-diethoxyethyl)benzamide was dissolved in concentrated sulfuric acid at 0° C. To phosphorus pentoxide (5.2 g, 18.3 mmol) was added the sulfuric acid solution, and the mixture was heated at 180° C. for 30 minutes. The reaction mixture was cooled down to room temperature, and poured into ice. The whole was made basic by addition of NaHCO$_3$ and ammonia aqueous solution. The whole was extracted with ethyl acetate. The organic layer was washed with brine, dried over MgSO$_4$, and concentrated in vacuo to give title compound (1.23 g, 70% yield).

$^1$H-NMR (DMSO-d$_6$) δ: 8.26 (s, 1H), 7.93 (d, J 9 Hz, 2H), 7.75 (d, J 9 Hz, 2H), 7.42 (s, 1H).

1-[4-(1,3-Oxazol-2-yl)phenyl]-1-ethanone (step 3)

The title compound was prepared according to the procedure of Example 94 (step 2) using 2-(4-bromophenyl)-1,3-oxazole instead of 4-(4-bromophenyl)-1,3-oxazole.

$^1$H-NMR (CDCl$_3$) δ: 8.15 (d, J=9 Hz, 2H), 8.05 (d, J=9 Hz, 2H), 7.77 (d, J=1 Hz, 1H), 7.30 (d, J=1 Hz, 1H), 2.65 (s, 3H).

4,4,4-Trifluoro-1-[4-(1,3-oxazol-2-yl)phenyl]-1,3-butanedione (step 4)

The title compound was prepared according to the procedure of Example 94 (step 3) using 1-[4-(1,3-oxazol-2-yl)phenyl]-1-ethanone instead of 1-[4-(1,3-oxazol-4-yl)phenyl]-1ethanone. The compound was used for next reaction without purification.

2-{4-[1-[3-Fluoro-4-(methylsulfonyl)phenyl]-3-(trifluoromethyl)-1H-pyrazol-5-yl]phenyl}-1,3oxazole (step 5)

The title compound was prepared according to the procedure of Example 60 using 4,4,4-trifluoro-1-[4-(1,3-oxazol-2-yl)phenyl]-1,3-butanedione instead of 4,4,4-trifluoro-1-[4-(2-furyl)phenyl]-1,3-butanedione.

mp: 140–142° C.

$^1$H-NMR (CDCl$_3$) δ: 8.11 (d, J=8 Hz, 2H), 7.93 (dd, J=8, 8 Hz, 1H), 7.77 (d, J=1 Hz, 1H), 7.43 (d, J=2 Hz, 1H), 7.38 (d, J=9 Hz, 2H), 7.29 (d, J=1 Hz, 1H), 7.23 (dd, J=9, 2 Hz, 1H), 6.86 (s, 1H), 3.24 (s 3H).

Anal. Calcd. for C$_{20}$H$_{13}$F$_4$N$_3$O$_3$S: C, 53.22; H, 2.90; N, 9.31. Found: C, 53.02; H, 3.01; N, 9.27.

Example 97

2-{4-[1-[4-(Methylsulfonyl)phenyl]-3-(trifluoromethyl)-1H-pyrazol-5-yl]phenyl}-1,3-oxazole The title compound was prepared according to the procedure of Example 96 using (4-methylsulfonylphenyl)hydrazine hydrochloride instead of (2-fluoro-4-methylsulfonylphenyl)hydrazine hydrochloride.

mp: 190–192° C.

$^1$H-NMR (CDCl$_3$) δ: 8.07 (d, J=8 Hz, 2H), 7.96 (d, J=9 Hz, 2H), 7.76 (s, 1H), 7.56 (d, J=9 Hz, 2H), 7.35 (d, J=9 Hz, 2H), 7.28–7.26 (m, 1H), 6.83 (s, 1H), 3.07 (s, 3H).

Anal. Calcd. for C$_{20}$H$_{14}$F$_3$N$_3$O$_3$S 1/10 Diisopropyl ether+1/2 H$_2$O: C, 54.66; H, 3.65; N, 9.28. Found: C, 54.52; H, 3.58; N, 8.98.

Example 98

4-[5-[4-(1,3-Oxazol-2-yl)phenyl]-3-(trifluoromethyl)-1H-pyrazol-1-yl]benzenesulfonamide The title compound was prepared according to the procedure of Example 96 using (4-sulfamoylphenyl)hydrazine hydrochloride instead of (2-fluoro-4-methylsulfonylphenyl)hydrazine hydrochloride.

mp: 215–217° C.

$^1$H-NMR (DMSO-d$_6$) δ: 8.26 (s, 1H), 8.01 (d, J=8 Hz, 2H), 7.90 (d, J=8 Hz, 2H), 7.59 (d, J=9 Hz, 2H), 7.51–7.48 (m, 4H), 7.42 (s, 1H), 7.36 (s. 1H).

Anal. Calcd. for C$_{19}$H$_{13}$F$_3$N$_4$O$_3$S 1.5 H$_2$O: C, 49.46; H, 3.50; N, 12.14. Found: C, 49.65; H, 3.44; N, 11.76.

Example 99

4-{4-[1-[3-Fluoro-4-(methylsulfonyl)phenyl]-3-(trifluoromethyl)-1H-pyrazol-5-yl]phenyl}-1,3-thiazole 4-(4-Bromophenyl)-1,3-thiazole (step 1)

To a stirred solution of phosphorus pentasulfide (24.5 g, 55 mmol) in dioxane (250 ml) was added formamide (28.4 g, 630 mmol), and the mixture was heated at reflux temperature for 2 hours. The reaction mixture was cooled down to room temperature, and the solution was decanted away from solids. To a stirred solution of 2,4'-dibromoacetophenone (15 g, 54 mmol) in dioxane (100 ml) was added the thioformamide solution, and the mixture was heated at reflux temperature for 6 hours. The reaction mixture was cooled down to room temperature, and made basic by addition of 2N NaOH aqueous solution. The whole was extracted with diethyl ether. The organic layer was washed with brine, dried over MgSO$_4$, and concentrated in vacuo. The residue was purified by flash chromatography eluting with CH$_2$Cl$_2$ to give title compound (12.3 g, 95% yield).

$^1$H-NMR (CDCl$_3$) δ: 8.87 (d, J=2 Hz, 1H), 7.80 (d, J=8 Hz, 2H), 7.56 (d, J=8 Hz, 2H), 7.53 (d, J=2 Hz, 1H).

1-[4-(1,3-Thiazol-4-yl)phenyl]-1-ethanone (step 2)

The title compound was prepared according to the procedure of Example 94 (step 2) using 4-(4-bromophenyl)-1,3-thiazole instead of 4-(4-bromophenyl)-1,3-oxazole.

$^1$H-NMR (CDCl$_3$) δ: 8.92–8.90 (m, 1H), 8.04–8.02 (m, 4H), 7.69 (d, J=2 Hz, 1H), 2.64 (s, 3H).

4,4,4-Trifluoro-1-[4-(1,3-thiazol-4-yl)phenyl]-1,3-butanedione (step 3)

The title compound was prepared according to the procedure of Example 94 (step 3) using 1-[4-(1,3-thiazol-4-yl)phenyl]-1-ethanone instead of 1-[4-(1,3-oxazo-4-yl)phenyl[-1-ethanol. The compound was used for next reaction without purification.

4-{4-[1-[3-Fluoro-4-(methylsulfonyl)phenyl]-3-(trifluoromethyl)-1H-2pyrazol-5-yl]phenyl}-1,3-thiazole (step 4)

The title compound was prepared according to the procedure of Example 60 using 4,4,4-trifluoro-1-[4-(1,3-thiazol-4-yl)phenyl]-1,3-butanedione instead of 4,4,4-trifluoro-1-[4-(2-furyl)phenyl]-1,3-butanedione.

mp: 125–127° C.

$^1$H-NMR (CDCl$_3$) δ: 8.92 (d, J=2 Hz, 1H), 8.01 (d, J=8 Hz, 2H), 7.95–7.89 (m, 1H), 7.65 (d, J=2 Hz, 1H), 7.42 (dd, J=10, 2 Hz, 1H), 7.33 (d, J=8 Hz, 2H), 7.27–7.22 (m, 1H), 6.84 (s, 1H), 3.23 (s, 3H).

Anal. Calcd. for C$_{20}$H$_{13}$F$_4$N$_3$O$_2$S$_2$ 1/4 Hexane: C, 52.81; H, 3.40; N, 8.59. Found: C, 52.98; H, 3.06; N, 8.91.

Example 100

4-[5-[4-(1,3-Thiazol-4-yl)phenyl]-3-(trifluoromethyl)-1H-pyrazol-1-yl]benzenesulfonamide The title compound was prepared according to the procedure of Example 99 using (4-sulfamoylphenyl)hydrazine hydrochloride instead of (2-fluoro-4-methylsulfonylphenyl)hydrazine hydrochloride.

mp: 188–190° C.

$^1$H-NMR (DMSO-d$_6$) δ: 9.21 (d, J=2 Hz, 1H), 8.28 (d, J=2 Hz, 1H), 8.04 (d, J=8 Hz, 2H), 7.90 (d, J=9 Hz, 2H), 7.60 (d, J=9 Hz, 2H), 7.52 (s, 2H), 7.41 (d, J=8 Hz, 2H), 7.31 (s, 1H).

Anal. Calcd. for $C_{19}H_{13}F_3N_4O_2S_2$ 1/2 Diisopropyl ether+ 1/2 $H_2O$: C, 51.76; H, 4.15; N, 10.97. Found: C, 51.92; H, 3.38; N, 10.83.

Example 101

4-{4-[1-[3-Methyl-4-(methylsulfonyl)phenyl]-3-(trifluoromethyl)-1H-pyrazol-5-yl]phenyl}-1,3-thiazole The title compound was prepared according to the procedure of Example 99 using (2-methyl-4-methylsulfonylphenyl)hydrazine hydrochloride instead of (2-fluoro-4-methylsulfonylphenyl)hydrazine hydrochloride.

mp: 147–149° C.

$^1$H-NMR (CDCl$_3$) δ: 8.90 (d, J=2 Hz, 1H), 8.00–7.94 (m, 3H), 7.62 (d, J=2 Hz, 1H), 7.53 (d, J=2 Hz, 1H), 7.31 (d, J=9 Hz, 2H), 7.21 (dd, J=9, 2 Hz, 1H), 6.83 (s, 1H), 3.09 (s, 3H), 2.70 (s, 3H).

Anal. Calcd. for $C_{21}H_{16}F_3N_3O_2S_2$: C, 54,42; H, 3.48; N, 9.07. Found: C, 54.38; H, 3.66; N, 8.98.

Example 102

4-{4-[1-[3-Fluoro-4-(methylsulfonyl)phenyl]-3-(trifluoromethyl)-1H-pyrazol-5-yl]phenyl}-2-methyl-1,3-thiazole 4-(4-Bromophenyl)-2-methyl-1,3-thiazole (step 1)

To a stirred solution of 2,4-dibromoacetophenone (5 g, 18 mmol) in dioxane (180 ml) was added thioacetamide (6.76 g, 90 mmol), and the mixture was heated at reflux temperature for 8 hours. The reaction mixture was cooled down to room temperature, and made basic by addition of 2N NaOH aqueous solution. The whole was extracted with diethyl ether. The organic layer was washed with brine, dried over MgSO$_4$, and concentrated in vacuo. The residue was purified by flash chromatography eluting with ethyl acetate-hexane (1:5) to give title compound (4.73 g, 99% yield).

$^1$H-NMR (CDCl$_3$) δ: 7.74 (d, J=8 Hz, 2H), 7.52 (d, J=8 Hz, 2H), 7.30 (s, 3H), 2.76 (s, 3H). 1-[4-(2-Methyl-1,3-thiazol-4-yl)phenyl]-1-ethanone (step 2)

The title compound was prepared according to the procedure of Example 94 (step 2) using 4-(4-bromophenyl)-2-methyl-1,3-thiazole instead of 4-(4-bromophenyl)-1,3-oxazole.

$^1$H-NMR (CDCl$_3$) δ: 8.03–7.95 (m, 4H), 7.46 (s, 1H), 2.79 (s, 3H), 2.63 (s, 3H).

4,4,4-Trifluoro-1-[4-(2-methyl-1,3-thiazol-4-yl)phenyl]-1,3-butanedione (step 3)

The title compound was prepared according to the procedure of Example 94 (step 3) using 1-[4-(2-methyl-1,3-thiazol-4-yl)phenyl]-1-ethanone instead of 1-[4-(1,3-oxazol-4yl)phenyl]-1-ethanone. The compound was used for next reaction without purification.

4-{4-[1-[3-Fluoro-4-(methylsulfonyl)phenyl]-3-(trifluoromethyl)-1H-pyrazol-5-yl]phenyl}-2-methyl-1,3-thiazole (step 4)

The title compound was prepared according to the procedure of Example 60 using 4,4,4-trifluoro-1-[4-(2-methyl-1,3-thiazol-4-yl)phenyl]-1,3-butanedione instead of 4,4,4-trifluoro-1-[4-(2-furyl)phenyl]-1,3-butanedione.

mp: 139–141° C.

$^1$H-NMR (CDCl$_3$) δ: 7.95–7.88 (m, 3H), 7.43–7.39 (m, 2H), 7.32–7.23 (m, 3H), 6.82 (s, 1H), 3.23 (s, 3H), 2.79 (s, 3H).

Anal. Calcd. for $C_{21}H_{15}F_4N_3O_2S_2$: C, 52.39; H, 3.14; N, 8.73. Found: C, 51.99; H, 3.33; N, 8.63.

Example 103

2-Fluoro-4-[5-[4-(1,3-thiazol-4-yl)phenyl]-3-(trifluoromethyl)-1H-pyrazol-1-yl]benzenesulfonamide The title compound was prepared according to the procedure of Example 99 using (2-fluoro-4-sulfamoylphenyl)hydrazine hydrochloride instead of (2-fluoro-4-methylsulfonylphenyl)hydrazine hydrochloride.

mp: 168–170° C.

$^1$H-NMR (CDCl$_3$) δ: 8.88–8.87 (m, 1H), 7.94 (dd, J=9, 2 Hz, 2H), 7.82–7.75 (m, 1H), 7.63–7.62 (m, 1H), 7.35–7.29 (m, 3H), 7.13 (d, J=9 Hz, 1H), 6.81 (s, 1H), 5.75 (s, 2H).

Anal. Calcd. for $C_{19}H_{12}F_4N_4O_2S_2$: C, 48.72; H, 2.58; N, 11.96. Found: C, 48.59; H, 2.85; N, 11.75.

Example 104

4-{4-[1-[3-Fluoro-4-(methylsulfonyl)phenyl]-3-(trifluoromethyl)-1H-pyrazol-5-yl]phenyl}-5-methyl-1,3-thiazole 4-(4-Bromophenyl)-5-methyl-1,3-thiazole (step 1)

The title compound was prepared according to the procedure of Example 99 (step 1) using 2,4'-dibromopropiophenone instead of 2,4'-dibromoacetophenone.

$^1$H-NMR (CDCl$_3$) δ: 8.65 (s,1H), 7.60–7.53 (m, 4H), 2.59 (s, 3H).

1-[4-(5-Methyl-1,3-thiazol-4-yl)phenyl]-1-ethanone (step 2)

The title compound was prepared according to the procedure of Example 94 (step 2) using 4-(4-bromophenyl)-5-methyl-1,3-thiazole instead of 4-(4-bromophenyl)-1,3-oxazole $^1$H-NMR (CDCl$_3$) δ: 8.68 (s, 1H), 8.05 (d, J=9 Hz, 2H), 7.80 (d, J=9 Hz, 2H), 2.65 (s, 3H), 2.64 (s, 3H).

4,4,4-Trifluoro-1-[4-(5-methyl-1,3-thiazol-4-yl)phenyl]-1,3-butanedione (step 3)

The title compound was prepared according to the procedure of Example 94 (step 3) using 1-[4-(5-methyl-1,3-thiazol-4-yl)phenyl]-1-ethanone instead of 1-[4-(1,3-oxazol-4-yl)phenyl]-1-ethanone. The compound was used for next reaction without purification.

4-{4-[1-[3-Fluoro-4-(methylsulfonyl)phenyl]-3-(trifluoromethyl)-1H-pyrazol-5-yl]phenyl}-5-methyl-1,3-thiazole (step 4)

The title compound was prepared according to the procedure of Example 60 using 4,4,4-trifluoro-1-[4-(5-methyl-1,3-thiazol-4-yl)phenyl]-1,3-butanedione instead of 4,4,4-trifluoro-1-[4-(2-furyl)phenyl]-1,3-butanedione.

mp: 170–172° C.

$^1$H-NMR (CDCl$_3$) δ: 8.67 (s, 1H), 7.94–7.88 (m, 1H), 7.77 (d, J=8 Hz, 2H), 7.44 (dd, J=10, 2 Hz, 1H), 7.37 (d, J=8 Hz, 2H), 7.27 (dd, J=9, 2 Hz, 1H), 6.85 (s, 1H), 3.23 (s, 3H), 2.65 (s, 3H).

Anal. Calcd. for $C_{21}H_{15}F_4N_3O_2S_2$ 1/5 Hexane+1/5 $H_2O$: C, 53.08; H, 3.65; N, 8.36. Found: C, 52.77; H, 3.48; N, 7.99.

Example 105

4-{4-[1-[3-Fluoro-4-(methylsulfonyl)phenyl]-3-(trifluoromethyl)-1H-pyrazol-5-yl]-2-fluorophenyl}-1,3-thiazole 1-(2-Fluoro-4-hydroxyphenyl)-1-ethanone (step 1)

To a stirred suspension of aluminum chloride (42 g, 312 mmol) in 1,2-dichloroethane (100 ml) was added 3-fluorophenol (31 g, 276 mmol) dropwise at 0° C. After addition, acetyl chloride (24 g, 306 mmol) was added dropwise and then the mixture was heated at reflux temperature for 16 hours. The mixture was cooled down to room temperature, and poured into ice. The whole was extracted with diethylether. The organic layer was washed with brine, dried over MgSO$_4$, and concentrated in vacuo. The residue was recystallized with hexane to give title compound (3.57 g, 8% yield).

¹H-NMR (CDCl₃) δ: 7.88–7.82 (m, 1H), 6.74 (dd, J=9, 2 Hz, 1H), 6.64 (dd, J=13, 2 Hz, 1H), 2.62 (d, J=5 Hz, 3H).
2-Bromo-1-(2-fluoro-4-hydroxyphenyl)-1-ethanone (step 2)

To a stirred solution of 1-(2-fluoro-4-hydroxyphenyl)-1-ethanone (2.56 g, 16.6 mmol) in dioxane (4 ml) was added a solution of bromine (2.70 g, 16.9 mmol) in dioxane (15 ml) dropwise, and the mixture was stirred for 3 hours. The volatile was evaporated in vacuo, and the residue was used for next reaction without purification. (2.4 g, 62% yield).

¹H-NMR (CDCl₃) δ: 7.95–7.89 (m, 1H), 6.73 (dd, J=9, 2 Hz, 1H), 6.63 (dd, J=13, 3 Hz, 1H), 5.96 (s, 1H), 4,48 (d, J=3 Hz, 2H).
3-Fluoro-4-(1,3-thiazol-4-yl)phenol (step 3)

To a stirred solution of phosphorus pentasulfide (4.0 g, 9.0 mmol) in dioxane (40 ml) was added formamide (4.8 g, 106 mmol), and the mixture was heated at reflux temperature for 2 hours. The reaction mixture was cooled down to room temperature, and the solution was decanted away from solids. To a stirred solution of 2-bromo-1-(2-fluoro-4-hydroxyphenyl)-1-ethanone (1.2 g, 5.15 mmol) in dioxane (14 ml) was added the thioformamide solution, and the mixture was heated at reflux temperature for 6 hours. The reaction mixture was cooled down to room temperature, and made basic by addition of 2N NaOH aqueous solution. The whole was extracted with ethyl acetate. The organic layer was washed with brine, dried over MgSO₄, and concentrated in vacuo. The residue was purified by flash chromatography eluting with ethyl acetate-hexane (1:4) to give title compound (864 mg, 86% yield).

¹H-NMR (DMSO-d₆) δ: 10.03 (s,1H), 9.04 (d, J=2 Hz, 1H), 7.89–7.83 (m, 1H), 7.67–7.64 (m, 1H), 6.64–6.53 (m, 2H).
3-Fluoro-4-(1,3-thiazol-4-yl)phenyl trifluoromethanesulfonate (step 4)

To a stirred solution of 3-fluoro-4-(1,3-thiazol-4-yl) phenol (864 mg, 4.43 mmol) in CH₂Cl₂ (27 ml) was added 2,6-lutidine (570 mg, 5.32 mmol), 4-dimethylaminopyridine (108 mg, 0.89 mmol), trifluoromethanesulfonic anhydride (1.5 g, 5.32 mmol) at −30° C., and the mixture was stirred for 1 hour, and then allowed to warm up to room temperature for 2 hours. The reaction mixture was diluted with water and the whole was extracted with CH₂Cl₂. The organic layer was washed with brine, dried over MgSO₄, and concentrated in vacuo, and the residue was used for next reaction without further purification. (1.45 g, 99% yield).
1-[3-Fluoro-4-(1,3-thiazol-4-yl)phenyl]-1-ethanone (step 5)

To a stirred solution of 3-fluoro-4-(1,3-thiazol-4-yl) phenyl trifluoromethanesulfonate (1.45 g, 4.43 mmol) in dioxane (42 ml) was added tributyl(1-ethoxyvinyl)tin (1.92 g, 5.32 mmol), tetrakis(triphenylphosphine)palladium (512 mg, 0.44 mmol), lithium chloride (466 mg, 11.0 mmol), and the mixture was heated at reflux temperature for 16 hours. The reaction mixture was cooled down to room temperature, and diluted with ethyl acetate. The whole was washed with saturated potassium fluoride aqueous solution, and the precipitate was removed by filteration through celite. The resulting solution was extracted with ethyl acetate. The organic layer was concentrated in vacuo. To the residue was added THF (20 ml), 2N HCl aqueous solution (20 ml), and the mixture was heated at reflux temperature for 8 hours. The reaction mixture was cooled down to room temperature, made neutral by addition of NaHCO₃, and extracted with ethyl acetate. The organic layer was washed with brine, dried over MgSO₄, and concentrated in vacuo. The residue was purified by flash chromatography eluting with ethyl acetate-hexane (1:5) to give title compound (666 mg, 68% yield).

¹H-NMR (CDCl₃) δ: 8.90–8.89 (m, 1H), 8.41–8.35 (m, 1H), 7.99–7.97 (m, 1H), 7.83 (dd, J=8, 2 Hz, 1H), 7.75 (dd, J=12, 2 Hz, 1H), 2.63 (s, 3H).
4,4,4-Trifluoro-1-[3-fluoro-4-(1,3-thiazol-4-yl)phenyl]-1,3-butanedione (step 6)

To a stirred solution of 1-[3-fluoro-4-(1,3-thiazol-4-yl) phenyl]-1-ethanone (666 mg, 3.01 mmol), ethyl trifluoroacetate (470 mg, 3.31 mmol) in t-butylmethylether (40 ml) was added sodium methoxide (28 wt. % solution in methanol; 0.8 ml, 3.6 mmol) over 5 minutes, and the mixture was stirred for 20 hours. The mixture was made neutral by addition of 2N HCl aqueous solution, and the whole was extracted with ethyl acetate. The organic layer was washed with brine, dried over MgSO₄, and concentrated in vacuo. The residue was used for next reaction without purification. (1.06 g, 99% yield).
4-{4-[1-[3-Fluoro-4-(methylsulfonyl)phenyl]-3-(trifluoromethyl)-1H-pyrazol-5-yl]-2-fluorophenyl}-1,3-thiazole (step 7)

The title compound was prepared according to the procedure of Example 60 using 4,4,4-trifluoro-1-[3-fluoro-4-(1,3-thiazol-4-yl)phenyl]-1,3-butanedione instead of 4,4,4-trifluoro-1-[4-(2-furyl)phenyl]-1,3-butanedione.

mp: 156–158° C.

¹H-NMR (CDCl₃) δ: 8.90 (d, J=2 Hz, 1H), 8.37–8.31 (m, 1H), 7.97–7.91 (m, 2H), 7.43 (dd, J=10, 2 Hz, 1H), 7.26 (dd, J=9, 2 Hz, 1H), 7.17–7.10 (m, 2H), 6.86 (s, 1H), 3.24 (s, 3H).

Anal. Calcd for $C_{20}H_{12}F_5N_3O_2S_2$: C, 49.48; H, 2.49; N, 8.66. Found: C, 49.58; H, 2.63; N, 8.49.

Example 106

4-{4-[1-[3-Fluoro-4-(methylsulfonyl)phenyl]-3-(trifluoromethyl)-1H-pyrazol-5-yl]-2-methylphenyl}-1,3-thiazole 2-Bromo-1-(4-hydroxy-2-methylphenyl)-1-ethanone (step 1)

The title compound was prepared according to the procedure of Example 105 (step 2) using 1-(4-hydroxy-2-methylphenyl)-1-ethanone instead of 1-(2-fluoro-4-hydroxyphenyl)-1-ethanone.

¹H-NMR (CDCl₃) δ: 7.71 (d, J=9 Hz, 1H), 6.76–6.71 (m, 2H), 5.71 (s, 1H), 4.40 (s, 2H), 2.55 (s, 3H).
3-Methyl-4-(1,3-thiazol-4-yl)phenol (step 2)

The title compound was prepared according to the procedure of Example 105 (step 3) using 2-bromo-1-(4-hydroxy-2-methylphenyl)-1-ethanone instead of 2-bromo-1-(2-fluoro-4-hydroxyphenyl)-1-ethanone.

¹H-NMR (DMSO-d₆) δ: 9.46 (s, 1H), 9.10 (d, J=2 Hz, 1H), 7.59 (d, J=2 Hz, 1H), 7.39 (d, J=8 Hz, 1H), 6.67–6.61 (m, 2H), 2.30 (s, 3H).
3-Methyl-4-(1,3-thiazol-4-yl)phenyl trifluoromethanesulfonate (step 3)

The title compound was prepared according to the procedure of Example 105 (step 4) using 3-methyl-4-(1,3-thiazol-4-yl)phenol instead of 3-fluoro-4-(1,3-thiazol-4-yl) phenol. The compound was used for next reaction without purification.
1-[3-Methyl-4-(1,3-thiazol-4-yl)phenyl]-1-ethanone (step 4)

The title compound was prepared according to the procedure of Example 105 (step 5) using 3-methyl-4-(1,3-thiazol-4-yl)phenyl trifluoromethanesulfonate instead of 3-fluoro-4-(1,3-thiazol-4-yl)phenyl trifluoromethanesulfonate.

¹H-NMR (CDCl₃) δ: 8.92 (d, J=2 Hz, 1H), 7.89–7.84 (m, 2H), 7.74 (d, J=8 Hz, 1H), 7.44 (d, J=2 Hz, 1H), 2.64 (s, 3H), 2.53 (s, 3H).

4,4,4-Trifluoro-1-[3-methyl-4-(1,3-thiazol-4-yl)phenyl]-1,3-butanedione (step 5)

The title compound was prepared according to the procedure of Example 105 (step 6) using 1-[3-methyl-4-(1,3-thiazol-4-yl)phenyl]-1-ethanone instead of 1-[3-fluoro-4-(1,3-thiazol-4-yl)phenyl]-1-ethanone.

$^1$H-NMR (CDCl$_3$) δ: 8.93 (d, J=2 Hz, 1H), 7.88–7.78 (m, 3H), 7.49 (d, J=2 Hz, 1H), 6.61 (s, 1H), 2.56 (s, 3H).

4-{4-[1-[3-Fluoro-4-(methylsulfonyl)phenyl]-3-(trifluoromethyl)-1H-pyrazol-5-yl]-2-methylphenyl}-1,3-thiazole (step 6)

The title compound was prepared according to the procedure of Example 60 using 4,4,4-trifluoro-1-[3-methyl-4-(1,3-thiazol-4-yl)phenyl]-1,3-butanedione instead of 4,4,4-trifluoro-1-[4-(2-furyl)phenyl]-1,3-butanedione.

mp: 112–114° C.

$^1$H-NMR (CDCl$_3$) δ: 8.92 (d, J=2 Hz, 1H), 7.95–7.90 (m, 1H), 7.65 (d, J=8 Hz, 1H), 7.49–7.44 (m, 2H), 7.28–7.24 (m, 2H), 7.09 (dd, J=8, 2 Hz, 1H), 6.81 (s, 1H), 3.24 (s, 3H), 2.48 (s, 3H).

Anal. Calcd. for C$_{21}$H$_{15}$F$_4$N$_3$O$_2$S$_2$: C, 52.39; H, 3.14; N, 8.73. Found: C, 52.65; H, 3.47; N, 8.42.

Example 107

4-{4-[1-[3-Fluoro-4-(methylsulfonyl)phenyl]-3-(trifluoromethyl)-1H-pyrazol-5-yl]-2-methoxyphenyl}-1,3-thiazole 3-Bromophenyl acetate (step 1)

To a stirred solution of 3-bromophenol (25 g, 145 mmol) in acetic anhydride (14 ml) was added a few drop of sulfuric acid, and the mixture was stirred for 2 hours. The mixture was poured into a solution of NaHCO$_3$ (1.3 g, 15.5 mmol) in water (160 ml). The whole was extracted with diethylether. The organic layer was washed with saturated NaHCO$_3$ aqueous solution, brine, dried over MgSO$_4$, and concentrated in vacuo. The residue was used for next reaction without purification. (31 g, 99% yield).

$^1$H-NMR (CDCl$_3$) δ: 7.39–7.35 (m, 1H), 7.29–7.22 (m, 2H), 7.07–7.02 (m, 1H), 2.30 (s, 3H).

1-(4-Bromo-2-hydroxyphenyl)-1-ethanone (step 2)

A mixture of 3-bromophenyl acetate (31 g, 145 mmol), aluminum chloride (34 g, 256 mmol) was heated at 160° C. for 2 hours. The mixture was cooled down to room temperature, and poured into ice. The whole was extracted with CH$_2$Cl$_2$. The organic layer was washed with brine, dried over MgSO$_4$, and concentrated in vacuo. The residue was used for next reaction without further purification. (31 g, 99% yield).

$^1$H-NMR (CDCl$_3$) δ: 12.34 (s, 1H), 7.58 (d, J=9 Hz, 1H), 7.18 (d, J=2 Hz, 1H), 7.04 (dd, J=9, 2 Hz, 1H), 2.61 (s,3H).

1-(4-Bromo-2-methoxyphenyl)-1-ethanone (step 3)

To a stirred solution of 1-(4-bromo-2-hydroxyphenyl)-1-ethanone (28.8 g, 134 mmol), potassium carbonate (48.6 g, 352 mmol) in DMF (63 ml) was added methyl iodide (25 g, 176 mmol), and the mixture was stirred for 20 hours. The mixture was poured into water. The whole was extracted with diethylether. The organic layer was washed with brine, dried over MgSO$_4$, and concentrated in vacuo. The residue was used for next reaction without purification. (31.5 g, 99% yield).

$^1$H-NMR (CDCl$_3$) δ: 7.62 (d, J=8 Hz, 1H), 7.17–7.12 (m, 2H), 3.92 (s, 3H), 2.59 (s, 3H).

2-Bromo-1-(4-bromo-2-methoxyphenyl)-1-ethanone (step 4)

To a stirred solution of 1-(4-bromo-2-methoxyphenyl)-1-ethanone (31.5 g, 138 mmol) in dioxane (32 ml) was added a solution of bromine (21.8 g, 136 mmol) in dioxane (123 ml), and the mixture was stirred for 3 hours. Then the volatile was evaporated in vacuo. The residue was recystallized with hexane-dichloromethane to give title compound (32.1 g, 76% yield).

$^1$H-NMR (CDCl$_3$) δ: 7.70 (d, J=8 Hz, 1H), 7.19 (dd, J=8, 2 Hz, 1H), 7.15 (d, J=2 Hz, 1H), 4.55 (s,2H), 3.96 (s, 3H).

4-(4-Bromo-2-methoxyphenyl)-1,3-thiazole (step 5)

The title compound was prepared according to the procedure of Example 99 (step 1) using 2-bromo-1-(4-bromo-2-methoxyphenyl)-1-ethanone instead of 2,4'-dibromoacetophenone.

$^1$H-NMR (CDCl$_3$) δ: 8.83 (d, J=2 Hz, 1H), 8.15 (d, J=8 Hz, 1H), 7.97 (d, J=2 Hz, 1H), 7.21 (dd, J=8, 2 Hz, 1H), 7.14 (d, J=2 Hz, 1H), 3.96 (s, 3H).

1-[3-Methoxy-4-(1,3-thiazol-4-yl)phenyl]-1-ethanone (step 6)

The title compound was prepared according to the procedure of Example 94 (step 2) using 4-(4-bromo-2-methoxyphenyl)-1,3-thiazole instead of 4-(4-bromophenyl)-1,3-oxazol.

$^1$H-NMR (CDCl$_3$) δ: 8.87 (d, J=2 Hz, 1H), 8.41 (d, J=9 Hz, 1H), 8.17 (d, J=2 Hz, 1H), 7.67–7.64 (m, 2H), 4.04 (s, 3H), 2.65 (s, 3H).

4,4,4-Trifluoro-1-[3-methoxy-4-(1,3-thiazol-4-yl)phenyl]-1,3-butanedione (step 7)

The title compound was prepared according to the procedure of Example 94 (step 3) using 1-[2-methoxy-4-(1,3-thiazol-4-yl)phenyl]-1-ethanone instead of 1-[4-(1,3-oxazol-4-yl)phenyl]-1-ethanone. The compound was used for next reaction without purification.

4-{4-[1-[3-Fluoro-4-(methylsulfonyl)phenyl]-3-(trifluoromethyl)-1H-pyrazol-5-yl]-2-methoxyphenyl}-1,3-thiazole (step 8)

The title compound was prepared according to the procedure of Example 60 using 4,4,4-trifluoro-1-[3-methoxy-4-(1,3-thiazol-4-yl)phenyl]-1,3-butanedione instead of 4,4,4-trifluoro-1-[4-(2-furl)phenyl]-1,3-butanedione.

mp: 155–157° C.

$^1$H-NMR (CDCl$_3$) δ: 8.86 (d, J=2 Hz, 1H), 8.34 (d, J=8 Hz, 1H), 8.09 (d, J=2 Hz, 1H), 7.92 (dd, J=8, 7 Hz, 1H), 7.45 (dd, J=10, 2 Hz, 1H), 7.30–7.26 (m, 1H), 6.94 (dd, J=8, 2 Hz, 1H), 6.90–6.85 (m, 2H), 3.88 (s, 3H), 3.23 (s, 3H).

Anal. Calcd. for C$_{21}$H$_{15}$F$_4$N$_3$O$_3$S$_2$: C, 50.70; H, 3.04; N, 8.45. Found: C, 50.59; H, 3.18; N, 8.17.

Example 108

4-{4-[1-[3-Fluoro-4-(methylsulfonyl)phenyl]-3-(trifluoromethyl)-1H-pyrazol-5-yl]-2-methoxyphenyl}-1,3oxazole 4-(4-Bromo-2-methoxyphenyl)-1,3-oxazole (step 1)

The title compound was prepared according to the procedure of Example 94 (step 1) using 2-bromo-1-(4-bromo-2-methoxyphenyl)-1-ethanone instead of 2,4'-dibromoacetophenone.

$^1$H-NMR (CDCl$_3$) δ: 8.16 (d, J=1 Hz, 1H), 8.00 (d, J=8 Hz, 1H), 7.91 (d, J=1 Hz, 1H), 7.21 (dd, J=8, 2 Hz, 1H), 7.10 (d, J=2 Hz, 1H), 3.96 (s, 3H).

4,4,4-Trifluoro-1-[3-methoxy-4-(1,3-oxazol-4-yl)phenyl]-1,3-butanedione (step 2)

The title compound was prepared according to the procedure of Example 94 (step 2,3) using 4-(4-bromo-2-methoxyphenyl)-1,3-oxazole instead of 4-(4-bromophenyl)-1,3-oxazole. The compound was used for next reaction without purification.

4-{4-[1-[3-Fluoro-4-(methylsulfonyl)phenyl]-3-(trifluoromethyl)-1H-pyrazol-5-yl]-2-methoxyphenyl}-1,3-oxazole (step 3)

The title compound was prepared according to the procedure of Example 60 using 4,4,4-trifluoro-1-[3-methoxy-4-(1,3-oxazol-4-yl)phenyl]-1,3-butanedione instead of 4,4,4-trifluoro-1-[4-(2-furl)phenyl]-1,3-butanedione.

mp: 148–150° C.

$^1$H-NMR (CDCl$_3$) δ: 8.24 (d, J=1 Hz, 1H), 8.18 (d, J=8 Hz, 1H), 7.95 (d, J=1 Hz, 1H), 7.92–7.89 (m, 1H), 7.43 (dd, J=10.2 Hz, 1H), 7.26 (dd, J=8, 2 Hz, 1H), 6.94 (dd, J=8, 2 Hz, 1H), 6.85–6.83 (m, 2H), 3.89 (s, 3H), 3.23 (s, 3H).

Anal. Calcd. for C$_{21}$H$_{15}$F$_4$N$_3$O$_4$S: C, 52.39; H, 3.14: N, 8.73. Found: C, 52.33; H, 3.39; N, 8.46.

Example 109

4-{2-Chloro-4-[1-[3-fluoro-4-(methylsulfonyl)phenyl]-3-(trifluoromethyl)-1H-pyrazol-5-yl]phenyl}-1,3-thiazole 1-(4-Bromo-2-chlorophenyl)-1-ethanone (step 1)

To a stirred solution of methylmagnesium iodide (0.82 M solution in diethylether; 113 ml, 92.4 mmol) was added a solution of 4-bromo-2-chlorobenzonitrile (10 g, 46.2 mmol) in diethylether (92 ml) dropwise, and the mixture was heated at reflux temperature for 16 hours. The mixture was cooled down to room temperature, added concentrated hydrochloric acid (50 ml), and the mixture was stirred for 5 hours. The whole was extracted with diethylether. The organic layer was washed with brine, dried over MgSO$_4$, and concentrated in vacuo. The residue was purified by flash chromatography eluting with ethyl acetate-hexane (1:10) to give title compound (7.77 g, 72% yield).

$^1$H-NMR (CDCl$_3$) δ: 7.61 (dd, J=7, 1 Hz, 1H), 7.47–7.46 (m, 2H), 2.64 (s, 3H).

2-Bromo-1-(4-bromo-2-chlorophenyl)-1-ethanone (step 2)

To a stirred solution of 1-(4-bromo-2-chlorophenyl)-1-ethanone (11.58 g, 50 mmol) in dioxane (12 ml) was added a solution of bromine (8.12 g, 51 mmol) in dioxane (46 ml), and the mixture was stirred for 3 hours. Then the volatile was evaporated in vacuo. The residue was used for next reaction without purification. (15.6 g, 99% yield).

$^1$H-NMR (CDCl$_3$) δ: 7.65 (d, J=2 Hz, 1H), 7.54–7.45 (m, 2H), 4.48 (s, 2H).

4-(4-Bromo-2-chlorophenyl)-1,3-thiazole (step 3)

The title compound was prepared according to the procedure of Example 99 (step 1) using 2-bromo-1-(4-bromo-2-chlorophenyl)-1-ethanone instead of 2,4'-dibromoacetophenone.

$^1$H-NMR (CDCl$_3$) δ: 8.87 (d, J=2 Hz, 1H), 7.92 (d, J=2 Hz, 1H), 7.88 (d, J=8 Hz, 1H), 7.65 (d, J=2 Hz, 1H), 7.49 (dd, J=8, 2 Hz, 1H).

1-[3-Chloro-4-(1,3-thiazol-4-yl)phenyl]-1-ethanone (step 4)

The title compound was prepared according to the procedure of Example 94 (step 2) using 4-(4-bromo-2-chlorophenyl)-1,3-thiazole instead of 4-(4-bromophenyl)-1,3-oxazole.

$^1$H-NMR (CDCl$_3$) δ: 8.91 (d, J=2 Hz, 1H), 8.16 (d, J=8 Hz, 1H), 8.09–8.07 (m, 2H), 7.91 (dd, J=8, 2 Hz, 1H), 2.64 (s, 3H).

4,4,4-Trifluoro-1-[3-chloro-4-(1,3-thiazol-4-yl)phenyl]-1,3-butanedione (step 5)

The title compound was prepared according to the procedure of Example 94 (step 3) using 1-[2-chloro-4-(1,3-thiazol-4-yl)phenyl]-1-ethanone instead of 1-[4-(1,3-oxazol-4-yl)phenyl]-1ethanone. The compound was used for next reaction without purification.

4-{2-Chloro-4-[1-[3-fluoro-4-(methylsulfonyl)phenyl]-3-(trifluoromethyl)-1H-pyrazol-5-yl]phenyl}-1,3-thiazole (step 6)

The title compound was prepared according to the procedure of Example 60 using 4,4,4-trifluoro-1-[3-chloro-4-(1,3-oxazol-4-yl)phenyl]-1,3-butanedione instead of 4,4,4-trifluoro-1-[4-(2-furl)phenyl]-1,3-butanedione.

mp: 108–110° C.

$^1$H-NMR (CDCl$_3$) δ: 8.91 (d, J=2 Hz, 1H), 8.08 (d, J=8 Hz, 1H), 8.05 (d, J=2 Hz, 1H), 7.99–7.93 (m, 1H), 7.49 (d, J=2 Hz, 1H), 7.46 (dd, J=10, 2 Hz, 1H), 7.28–7.24 (m, 1H), 7.18 (dd, J=8, 2 Hz, 1H), 6.86 (s, 1H), 3.24 (s, 3H).

Anal. Calcd. for C$_{20}$H$_{12}$ClF$_4$N$_3$O$_2$S$_2$ 1/10 Hexane: C, 48.46; H, 2.65; N, 8.23. Found: C, 48.28; H, 2.83; N, 8.10.

Example 110

4-{4-[1-[3-Fluoro-4-(methylsulfonyl)phenyl]-3-(trifluoromethyl)-1H-pyrazol-5-yl]-2-methylphenyl}-1,3-oxazole 3-Methyl-4-(1,3-oxazol-4-yl)phenol (step 1)

A mixture of 2-bromo-1-(4-hydroxy-2-methylphenyl)-1-ethanone (18 g, 78 mmol), ammonium fornate (17 g, 273 mmol) in formic acid (100 ml) was heated at reflux temperature for 3 hours. The mixture was cooled down to room temperature and made basic by addition of 50% NaOH aqueous solution at 0° C. The whole was extracted with CH$_2$Cl$_2$. The organic layer was washed with brine, dried over MgSO$_4$, and concentrated in vacuo. The residue was purified by flash chromatography eluting with ethyl acetate-hexane (1:5) to give title compound (1.8 g, 13% yield).

$^1$H-NMR (DMSO-d$_6$) δ: 9.42 (s, 1H), 8.31 (s, 1H), 8.09 (s, 1H), 7.53 (d, J=9 Hz, 1H), 6.62–6.58 (m, 2H).

3-Methyl-4-(1,3-oxazol-4-yl)phenyl trifluoromethanesulfonate (step 2)

The title compound was prepared according to the procedure of Example 105 (step 4) using 3-methyl-4-(1,3-oxazol-4-yl)phenol instead of 3-fluoro-4-(1,3-thiazol-4-yl)phenol.

4,4,4-Trifluoro-1-[3-methyl-4-(1,3-oxazol-4-yl)phenyl]-1,3-butanedione (step 3)

The title compound was prepared according to the procedure of Example 105 (step 5,6) using 3-methyl-4-(1,3-oxazol-4-yl)phenyl trifluoromethanesulfonate instead of 3-fluoro-4-(1,3-thiazol-4-yl)phenyl trifluoromethanesulfonate. The compound was used for next reaction without purification.

4-{4-[1-[3-Fluoro-4-(methylsulfonyl)phenyl]-3-(trifluoromethyl)-1H-pyrazol-5-yl]-2-methylphenyl}-1,3-oxzaole (step 4)

The title compound was prepared according to the procedure of Example 60 using 4,4,4-trifluoro-1-[3-methyl-4-(1,3-oxazol-4-yl)phenyl]-1,3-butanedione instead of 4,4,4-trifluoro-1-[4-(2-furl)phenyl]-1,3-butanedione.

mp: 141–143° C.

$^1$H-NMR (CDCl$_3$) δ: 7.99 (d, J=1 Hz, 1H), 7.94–7.88 (m, 3H), 7.44 (dd, J=10, 2 Hz, 1H), 7.26–7.22 (m, 2H), 7.12 (dd, J=8, 2 Hz, 1H), 6.80 (s, 1H), 3.23 (s, 3H), 2.48 (s, 3H).

Anal. Calcd. for C$_{21}$H$_{15}$F$_4$N$_3$O$_3$S: C, 54.19; H, 3.25; N, 9.03. Found: C, 54.01; H, 3.21; N, 8.80.

Example 111

4-{2-Methoxy-4-[1-[4-(methylsulfonyl)phenyl]-3-(trifluoromethyl)-1H-pyrazol-5-yl]phenyl}-1,3-oxazole The title compound was prepared according to the procedure of Example 108 using (4-methylsulfonylphenyl)hydrazine hydrochloride instead of (2-fluoro-4-methylsulfonylphenyl)hydrazine hydrochloride.

mp: 171–173° C.

$^1$H-NMR (CDCl$_3$) δ: 8.22 (d, J=1 Hz, 1H), 8.14 (d, J=8 Hz, 1H), 7.97–7.94 (m, 3H), 7.59 (d, J=8 Hz, 2H), 6.94 (dd,

J 8, 2 Hz, 1H), 6.85 (s, 1H), 6.80 (d, J=2 Hz, 1H), 3.82 (s, 3H), 3.07 (s, 3H).

Anal. Calcd. for $C_{21}H_{16}F_3N_3O_4S$: C, 54,43; H, 3.48; N, 9.07. Found: C, 54.35; H, 3.50; N, 8.96.

Example 112

4-{2-Methyl-4-[1-[4-(methylsulfonyl)phenyl]-3-(trifluoromethyl)-1H-pyrazol-5-yl]phenyl}-1,3-oxazole The title compound was prepared according to the procedure of Example 110 using (4-methylsulfonylphenyl)hydrazine hydrochloride instead of (2-fluoro-4-methylsulfonylphenyl)hydrazine hydrochloride.

mp: 148–150° C.

$^1$H-NMR (CDCl$_3$) δ: 7.99–7.85 (m, 5H), 7.57 (d, J=8 Hz, 2H), 7.21 (s, 1H), 7.09 (d, J=8 Hz, 1H), 6.81 (s, 1H), 3.06 (s, 3H), 2.45 (s, 3H).

Anal. Calcd. for $C_{21}H_{16}F_3N_3O_3S$: C, 56.37; H, 3.60; N, 9.39. Found: C, 56.46; H, 3.80; N, 9.17.

Example 113

2-Fluoro-4-[5-[3-methyl-4-(1,3-thiazol-4-yl)phenyl]-3-(trifluoromethyl)-1H-pyrazol-1-yl]benzenesulfonamide The title compound was prepared according to the procedure of Example 106 using (2-fluoro-4-sulfamoylphenyl)hydrazine hydrochloride instead of (2-fluoro-4-methylsulfonylphenyl)hydrazine hydrochloride.

mp: 125–127° C.

$^1$H-NMR (CDCl$_3$) δ: 8.91 (d, J=2 Hz, 1H), 7.89–7.83 (m, 1H), 7.64 (d, J=8 Hz, 1H), 7.43 (d, J=2 Hz, 1H), 7.39 (d, J=2 Hz, 1H), 7.26 (s, 1H), 7.19 (dd, J=8, 2 Hz, 1H), 7.07 (dd, J=8, 2 Hz, 1H), 6.80 (s, 1H), 5.26 (s, 2H), 2.47 (s,3H).

Anal. Calcd. for $C_{20}H_{14}F_4N_4O_2S_2$ 1/2 H$_2$O: C, 48.88; H, 3.08; N, 11.40. Found: C, 48.61; H, 3.06; N, 11.26.

Example 114

2-Fluoro-4-[5-[3-fluoro-4-(1,3-thiazol-4-yl)phenyl]-3-(trifluoromethyl)-1H-pyrazol-1-yl]benzenesulfonamide The title compound was prepared according to the procedure of Example 105 using (2-fluoro-4-sulfamoylphenyl)hydrazine hydrochloride instead of (2-fluoro-4-methylsulfonylphenyl)hydrazine hydrochloride.

mp: 196–198° C.

$^1$H-NMR (DMSO-d$_6$) δ: 9.14 (d, J=2 Hz, 1H), 8.09–8.03 (m, 2H), 7.80–7.71 (m, 3H), 7.51 (dd, J=11, 2 Hz, 1H), 7.33 (dd, J=12, 2 Hz, 1H), 7.28 (s, 1H), 7.27 (dd, J=8, 2 Hz, 1H), 7.13 (dd, J=8, 2 Hz, 1H).

Anal. Calcd. for $C_{19}H_{11}F_5N_4O_2S_2$: C, 46.91; H, 2.28; N, 11.52. Found: C, 46.91; H, 2.32; N, 11.33.

Example 115

4-{4-[1-[3-Hydroxymethyl-4-(methylsulfonyl)phenyl]-3-(trifluoromethyl)-1H-pyrazol-5-yl]phenyl}-1,3thiazole The title compound was prepared according to the procedure of Example 99 using (2-hydroxymethyl-4-methylsulfonylphenyl)hydrazine hydrochloride instead of (2-fluoro-4-methylsulfonylphenyl)hydrazine hydrochloride.

mp: 203–205° C.

$^1$H-NMR (CDCl$_3$) δ: 8.90 (d, J=2 Hz, 1H), 8.00–7.95 (m, 3H), 7.79 (d, J=2 Hz, 1H), 7.62 (d, J=2 Hz, 1H), 7.37–7.31 (m, 3H), 6.84 (s, 1H), 4.95 (s, 2H), 3.17 (s, 3H).

Anal. Calcd. for $C_{21}H_{16}F_3N_3O_2S_2$ 1/20 H$_2$O: C, 52.50; H, 3.38; N, 8.75. Found: C, 52.88; H, 3.77; N, 8.47.

Example 116

4-[5-[3-Methyl-4-(1,3-oxazol-4-yl)phenyl]-3-(trifluoromethyl)-1H-pyrazol-1-yl]benzenesulfonamide The title compound was prepared according to the procedure of Example 110 using (4-sulfamoylphenyl)hydrazine hydrochloride instead of (2-fluoro-4-methylsulfonylphenyl)hydrazine hydrochloride.

mp: 112–114° C.

$^1$H-NMR (CDCl$_3$) δ: 7.98 (d, J=1 Hz, 1H) 7.92 (d, J=9 Hz 2H), 7.88 (d, J=1 Hz, 1H), 7.85 (d, J=8 Hz, 1H), 7.51 (d, J=9 Hz, 2H), 7.22 (s, 1H), 7.08 (d, J=8 Hz, 1H), 6.80 (s, 1H), 4.95 (s, 2H), 2.45 (s, 3H).

Anal. Calcd. for $C_{20}H_{15}F_3N_4O_3S$ 1/2 H$_2$O: C, 52.52; H, 3.53; N, 12.25. Found: C, 52.20; H, 3.72; N, 11.99.

Example 117

4-[5-[3-Methoxy-4-(1,3-oxazol-4-yl)phenyl]-3-(trifluoromethyl)-1H-pyrazol-1-yl]benzenesulfonamide The title compound was prepared according to the procedure of Example 108 using (4-sulfamoylphenyl)hydrazine hydrochloride instead of (2-fluoro-4-methylsulfonylphenyl)hydrazine hydrochloride.

mp: 143–145° C.

$^1$H-NMR (CDCl$_3$) δ: 8.22 (s, 1H), 8.12 (d, J=8 Hz, 1H), 7.93–7.90 (m, 3H), 7.52 (d, J=9 Hz, 2H), 6.91 (d, J=8 Hz, 1H), 6.84 (s, 1H), 6.80 (s, 1H), 5.01 (s, 2H), 3.82 (s, 3H).

Anal. Calcd. for $C_{20}H_{15}F_3N_4O_4S$ 1/10 Hexane: C, 52.31; H, 3.49; N, 11.84. Found: C, 52.28; H, 3.80; N, 11.51.

Example 118

4-[5-[4-(1,3-Oxazol-4-yl)phenyl]-3-(trifluoromethyl)-1H-pyrazol-1-yl]benzenesulfonamide The title compound was prepared according to the procedure of Example 94 using (4-sulfamoylphenyl)hydrazine hydrochloride instead of (2-fluoro-4-methylsulfonylphenyl)hydrazine hydrochloride.

mp: 170–172° C.

$^1$H-NMR (CDCl$_3$) δ: 7.98 (d, J=11 Hz, 2H), 7.90 (d, J=9 Hz, 2H), 7.75 (d, J=8 Hz, 2H), 7.48 (d, J=9 Hz, 2H), 7.28 (d, J=8 Hz, 2H), 6.82 (s, 1H), 5.15 (s, 2H).

Anal. Calcd. for $C_{19}H_{13}F_3N_4O_3S$ 1/5 Hexane: C, 52.10; H, 3.08; N, 12.79. Found: C, 51.88; H, 3.27; N, 12.48.

Example 119

4-{2-Chloro-4-[1-[4-(methylsulfonyl)phenyl]-3-(trifluoromethyl)-1H-pyrazol-5-yl]phenyl}-1,3-thiazole The title compound was prepared according to the procedure of Example 109 using (4-methylsulfonylphenyl)hydrazine hydrochloride instead of (2-fluoro-4-methylsulfonylphenyl)hydrazine hydrochloride.

mp: 128–130° C.

¹H-NMR (CDCl₃) δ: 8.90 (d, J=2 Hz, 1H), 8.05–7.98 (m, 4H), 7.59 (d, J=9 Hz, 2H), 7.46 (d, J=2 Hz, 1H), 7.15 (dd, J=8,2 Hz, 1H), 6.87 (s, 1H), 3.08 (s, 3H).

Anal. Calcd. for $C_{20}H_{13}ClF_3N_3O_2S_2$: C, 49.64; H, 2.71: N, 8.68. Found: C, 49.70; H, 2.92; N, 8.54.

Example 120

4-{2-Methoxy-4-[1-[4-(methylsulfonyl)phenyl]-3-(trifluoromethyl)-1H-pyrazol-5-yl]phenyl}-1,3-thiazole The title compound was prepared according to the procedure of Example 107 using (4-methylsulfonylphenyl)hydrazine hydrochloride instead of (2-fluoro-4-methylsulfonylphenyl)hydrazine hydrochloride.

mp: 164–166° C.

¹H-NMR (CDCl₃) δ: 8.85 (d, J=2 Hz, 1H), 8.31 (d, J=8 Hz, 1H), 8.06 (d, J=2 Hz, 1H), 7.96 (d, J=9 Hz, 2H), 7.60 (d, J=9 Hz, 2H), 6.94 (dd, J=8, 2 Hz, 1H), 6.86–6.83 (m, 2H), 3.82 (s, 3H), 3.06 (s, 3H).

Anal. Calcd. for $C_{21}H_{16}F_3N_3O_3S_2$: C, 52.60; H, 3.36; N, 8.76. Found: C, 52.61; H, 3.52; N, 8.72.

Example 121

2-Fluoro-4-[5-[4-(1,3-oxazol-4-yl)phenyl]-3-(trinfluoromethyl)-1H-pyrazol-1-yl]benzenesulfonamide The title compound was prepared according to the procedure of Example 94 using (2-fluoro-4-sulfamoylphenyl)hydrazine hydrochloride instead of (2-fluoro-4-methylsulfonylphenyl)hydrazine hydrochloride.

mp: Not Detected.

¹H-NMR (CDCl₃) δ: 8.00 (d, J=13 Hz, 2H), 7.90–7.84 (m, 2H), 7.81 (d, J=8 Hz, 1H), 7.37 (dd, J=11, 2 Hz, 2H), 7.31 (d, J=8 Hz, 1H), 7.19 (d, J=9 Hz, 1H), 6.82 (s, 1H), 5.12 (s, 2H).

Anal. Calcd. for $C_{19}H_{12}F_4N_4O_3S$ 1/10 Hexane+1/2 $H_2O$: C, 50.09; H, 3.09; N, 11.92. Found: C, 50.39; H, 3.17; N, 11.59.

Example 122

2-Fluoro-4-[5-[3-chloro-4-(1,3-thiazol-4-yl)phenyl]-3-(trifluoromethyl)-1H-pyrazol-1-yl]benzenesulfonamide The title compound was prepared according to the procedure of Example 109 using (2-fluoro-4-sulfamoylphenyl)hydrazine hydrochloride instead of (2-fluoro-4-methylsulfonylphenyl)hydrazine hydrochloride.

mp: 173–175° C.

¹H-NMR (DMSO-d₆) δ: 9.24 (d, J=2 Hz, 1H), 8.27 (d, J=2 Hz, 1H), 7.95–7.85 (m, 4H), 7.71 (d, J=2 Hz, 1H), 7.65 (dd, J=11, 2 Hz, 1H), 7.44 (s, 1H), 7.41 (dd, J=8, 2 Hz, 1H), 7.31 (dd,J=8, 2 Hz, 1H).

Anal. Calcd. for $C_{19}H_{11}ClF_4N_4O_2S_2$: C, 45.38; H, 2.20; N, 11.14. Found: C, 45.28; H, 2.38; N, 11.00.

Example 123

2-Fluoro-4-[5-[3-methyl-4-(1,3-oxazol-4-yl)phenyl]-3-(trifluoromethyl)-1H-pyrazol-1-yl]benzenesulfonamide The title compound was prepared according to the procedure of Example 110 using (2-fluoro-4-sulfamoylphenyl) hydrazine hydrochloride instead of (2-fluoro-4-methylsulfonylphenyl)hydrazine hydrochloride.

mp: Not Detected.

¹H-NMR (CDCl₃) δ: 8.00 (s, 1H), 7.91–7.83 (m, 3H), 7.40 (dd, J=11, 2 Hz, 1H), 7.26–7.24 (m, 1H), 7.18 (d, J=9 Hz, 1H), 7.11 (d, J=9 Hz, 1H), 6.80 (s, 1H), 5.13 (s, 2H), 2.48 (s, 3H).

Anal. Calcd. for $C_{20}H_{14}F_4N_4O_3S$ 1/2 $H_2O$: C, 50.53; H, 3.18; N, 11.78. Found: C, 50.72; H, 3.36; N, 11.48.

Example 124

4-{2-Fluoro-4-[1-[4-(methylsulfonyl)phenyl]-3-(trifluoromethyl)-1H-pyrazol-5-yl]phenyl}-1,3-thiazole The title compound was prepared according to the procedure of Example 105 using (4-methylsulfonylphenyl)hydrazine hydrochloride instead of (2-fluoro-4-methylsulfonylphenyl)hydrazine hydrochloride.

mp: 176–178° C.

¹H-NMR (CDCl₃) δ: 8.90 (d, J=2 Hz, 1H), 8.33–8.27 (m, 1H), 7.98 (d, J=9 Hz, 2H), 7.92–7.91 (m, 1H), 7.59 (d, J=9 Hz, 2H), 7.14–7.06 (m, 2H), 6.86 (s, 1H), 3.08 (s, 3H).

Anal. Calcd. for $C_{20}H_{13}F_4N_3O_2S_2$: C, 51.39; H, 2.80; N, 8.99. Found: C, 51.45; H, 2.95; N, 8.81.

Example 125

4-{2-Methyl-4-[1-[4-(methylsulfonyl)phenyl]-3-(trifluoromethyl)-1H-pyrazol-5-yl]phenyl}-1,3-thiazole The title compound was prepared according to the procedure of Example 106 using (4-methylsulfonylphenyl)hydrazine hydrochloride instead of (2-fluoro-4-methylsulfonylphenyl)hydrazine hydrochloride.

mp: 140–142° C.

¹H-NMR (CDCl₃) δ: 8.91 (d, J=2 Hz, 1H), 7.96 (d, J=9 Hz, 2H), 7.64–7.57 (m, 3H), 7.42 (d, J=2 Hz, 1H), 7.24 (d, J=1Hz, 1H), 7.07 (dd, J=8, 2 Hz, 1H), 6.82 (s, 1H), 3.07 (s, 3H), 2.45 (s, 3H).

Anal. Calcd. for $C_{21}H_{16}F_3N_3O_2S_2$: C, 54,42; H, 3.48; N, 9.07. Found: C, 54.52; H, 3.66; N, 8.95.

Example 126

Ethyl 1-[3-Fluoro-4-(methylsulfonyl)phenyl]-5-[4-(2-furyl)phenyl]-1H-pyrazole-3-carboxylate Ethyl 5-(4-bromophenyl)-1-[3-fluoro-4-(methylsulfonyl)phenyl]-1H-pyrazole-3-carboxylate (step 1)

The subtitle compound was prepared according to the procedure of Example 85 using methyl 4-(4-bromophenyl)-2,4-diketobutyrate (prepared according to the method of *J. Med. Chem.*, 1997, 40, 1347) instead of 4,4,4-trifluoro-1-(4-bromophenyl)butane-1,3-dione in step 1.

¹H-NMR (CDCl₃) δ: 7.92 (dd, J=8, 9 Hz, 1H), 7.56 (d, J=8 Hz, 2H), 7.43 (dd, J=2, 10 Hz, 1H), 7.21 (d, J=8 Hz, 1H), 7.13 (d, J=8 Hz, 2H), 7.04 (s, 1H), 4.46 (q, J=7 Hz, 2H), 3.24 (s, 3H), 1.43 (t, J=7 Hz, 3H).

Ethyl 1-[3-Fluoro-4-(methylsulfonyl)phenyl]-5-[4-(2-furyl)phenyl]-1H-pyrazole-3-carboxylate (step 2)

The title compound was prepared according to the procedure of Example 85 using ethyl 5-(4-bromophenyl)-1-[3-fluoro-4-(methylsulfonyl)phenyl]-1H-pyrazole-3-carboxylate instead of 5-(4-bromophenyl)-1-[3-fluoro-4-(methylsulfonyl)phenyl]-3-(trifluoromethyl)-1H-pyrazole and 2-furanboronic acid instead of 3-furanboronic acid in step 2.

mp: 172.0° C.

$^1$H-NMR (CDCl$_3$) δ: 7.90 (dd, J=8, 9 Hz, 1H), 7.70 (d, J=9 Hz, 2H), 7.51 (d, J=1 Hz, 1H), 7.46 (dd, J=2, 11 Hz, 1H), 7.28–7.24 (m, 3H), 7.07 (s, 1H), 6.74 (d, J=3 Hz, 1H), 6.51 (dd, J=2, 4 Hz, 1H), 4,47 (q, J=7 Hz, 2H), 3.23 (s, 3H), 1.44 (t, J=7 Hz, 3H).

Anal. Calcd. for. C$_{23}$H$_{19}$FN$_2$O$_5$S: C, 60.78; H, 4.21; N, 6.16. Found: C, 60.39; H, 4.38; N, 6.04.

MS (EI): m/z 454 (M$^+$)

Example 127

1-[3-Ethoxy-4-(methylsulfonyl)phenyl]-5-[4-(2-furyl)phenyl]-1H-pyrazole-3-carboxylic Acid To a stirred solution of ethyl 1-[3-fluoro-4-(methylsulfonyl)phenyl]-5-[4-(2-furyl)phenyl]-1H-pyrazole-3-carboxylate (0.57 g, 1.25 mmol) in ethanol (15 mL) was added 2N-NaOH solution in water (1.6 mL, 3.14 mmol), and the mixture was heated at reflux temperature for 30 minutes. After cooling, 2N-HCl solution (4 mL) and water (30 mL) were added to the mixture. The whole was extracted with ethyl acetate (20 mL×3), the organic layer was washed with brine, dried over MgSO$_4$, and concentrated in vacuo. The resulting solid was washed with methylene chloride to give the title compound (0.413 g, 73.0%, yield).

mp: 256.0–257.0° C.

$^1$H-NMR (DMSO-d$_6$) δ: 7.73–7.60 (m, 4H), 7.25 (d, J=7 Hz, 2H), 7.16 (s, 1H), 7.03 (d, J=2 Hz, 1H), 6.96 (s, 1H), 6.92 (d, J=4 Hz, 1H), 6.50 (t, J=2 Hz, 1H), 3.99 (q, J=7 Hz, 2H), 3.17 (s, 3H), 1.15 (t, J=7 Hz, 3H).

Anal. Calcd. for. C$_{23}$H$_{20}$N$_2$O$_6$S, 0.3H$_2$O: C, 60.33; H, 4.53; N, 6.12. Found: C, 60.07; H, 4.59; N, 5.94.

MS (EI): m/z 452 (M$^+$)

Example 128

1-[3-Fluoro-4-(methylsulfonyl)phenyl]-5-[4-(2-furyl)phenyl]-1H-pyrazole-3-carboxylic Acid The title compound was prepared according to the procedure of Example 127 using THF instead of ethanol.

mp:171.5–173.0° C.

$^1$H-NMR (CDCl$_3$) δ: 7.92 (dd, J=8, 8 Hz, 1H), 7.71 (d, J=8 Hz, 2H), 7.51 (d, J=2 Hz, 1H),7.46 (dd, J=2, 10 Hz, 1H), 7.29–7.25 (m, 3H), 7.12 (s, 1H), 6.75 (d, J=3 Hz, 1H), 6.51 (dd, J=2, 4 Hz, 1H), 3.24 (s, 3H).

Anal. Calcd. for. C$_{21}$H$_{15}$FN$_2$O$_5$S, 0.05 Hexane, 0.6H$_2$O: C, 57.85; H, 3.82; N, 6.36. Found: C, 57.92; H, 4.08; N, 5.97.

MS (EI): n/z 426 (M$^+$)

Example 129

1-[3-Fluoro-4-(methylsulfonyl)phenyl]-5-[4-(2-furyl)phenyl]-3-hydroxymethyl-1H-pyrazole To a solution of 1-[3-fluoro-4-(methylsulfonyl)phenyl]-5-[4-(2-furyl)phenyl]-1H-pyrazole-3-carboxylic acid (0.1 g, 0.235 mmol) in THF (2 mL) at 0° C. was added dropwise 1M borane-THF complex (0.7 mL). The mixture was stirred at room temperature for 3 hours. The solution was added water (1 mL) and ethyl acetate (20 mL), and the mixture was washed with 1N HCl, saturated NaHCO$_3$, and brine, dried over MgSO$_4$, filtered, and concentrated in vacuo. The crude mixture was purified by flash chromatography eluting with hexane/ethyl acetate (1/1) to give the title compound (0.051 g, 52.6% yield).

$^1$H-NMR (CDCl$_3$) δ: 7.86 (dd, J=8, 8 Hz, 1H), 7.69 (d, J=8 Hz, 2H), 7.51 (d, J=2 Hz, 1H), 7.36 (dd, J=2, 10 Hz, 1H), 7.27 (d, J=8 Hz, 2H), 7.20 (d, J=9 Hz, 1H), 6.73 (d, J=4 Hz, 1H), 6.57 (s, 1H), 6.51 (dd, J=2, 3, Hz, 1H), 4.81 (s, 2H), 3.22 (s, 3H)

Anal. Calcd. for. C$_{21}$H$_{17}$FN$_2$O$_4$S, 0.1H$_2$O: C, 60.89; H, 4.19; N, 6.76. Found: C, 60.69; H, 4.56; N, 6.52.

MS (EI): m/z412 (M$^+$)

Example 130

1-[3-Fluoro-4-(methylsulfonyl)phenyl]-5-[4-(2-furyl)phenyl]-3-(4-morpholinecarbonyl)-1H-pyrazole A solution of 1-[3-fluoro-4-(methylsulfonyl)phenyl]-5-[4-(2-furyl)phenyl]-1H-pyrazole-3-carboxylic acid (0.2 g, 0.469 mmol), 1-ethyl-3-(3-dimethylaminopropyl) carbodiimide hydrochloride (WSC, 0.108 g, 0.563 mmol), and morpholine (0.04 mL, 0.492 mmol) in methylene chloride (10 mL) was stirred at room temperature for 3.5 hours. The mixture was diluted with methylene chloride (20 mL) and washed with saturated NaHCO$_3$, water, and brine, dried over MgSO$_4$, filtered, and concentrated in vacuo. The crude mixture was purified by flash chromatography eluting with methylene chloride/methanol (30/1). The resulting solid was recrystallized from methylene chloride-hexane to give the title compound to give the title compound (0.1 g, 43.1% yield).

mp: 221.0–222.0° C.

$^1$H-NMR (CDCl$_3$) δ: 7.90 (dd, J=8, 8 Hz, 1H), 7.71 (d, J=8 Hz, 2H), 7.51 (d, J=2 Hz, 1H),7.35 (dd, J=2, 11 Hz, 1H), 7.29–7.26 (m, 2H), 7.22 (d, J=8 Hz, 1H), 6.97 (s, 1H), 6.75 (d, J=3 Hz, 1H), 6.51 (dd, J=2, 4 Hz, 1H), 4.14 (brs, 2H), 3.83–3.76 (m, 6H), 3.24 (s, 3H).

Anal. Calcd. for. C$_{25}$H$_{22}$FN$_3$O$_5$S, 0.05H$_2$O: C, 60.49; H, 4,49; N, 8.46. Found: C, 60.19; H, 4.63; N, 8.28.

MS (EI): m/z 495 (M$^+$)

Example 131

N-Methyl-1-[3-fluoro-4-(methylsulfonyl)phenyl]-5-[4-(2-furyl)phenyl]-1H-pyrazole-3-carboxamide The title compound was prepared according to the procedure of Example 130 using 2M-methylamine in THF solution instead of morpholine.

mp:196.0–198.0° C.

$^1$H-NMR (CDCl$_3$) δ: 7.91 (dd, J=8, 8 Hz, 1H), 7.70 (d, J=8 Hz, 2H), 7.51 (d, J=2 Hz, 1H), 7.37 (dd, J=2, 10 Hz, 1H), 7.27 (d, J=8 Hz, 2H), 7.22 (d, J=2 Hz, 1H), 7.08 (s, 1H), 6.97–6.90 (brm, 1H), 6.74 (d, J=4 Hz, 1H), 6.51 (dd, J=2, 4 Hz, 1H), 3.24 (s, 3H), 3.04 (d, J=5 Hz, 3H).

Anal. Calcd. for. C$_{22}$H$_{18}$FN$_3$O$_4$S: C, 60.13; H, 4.13; N, 9.56. Found: C, 60.02; H, 4.50; N, 9.21.

MS (EI): m/z 439 (M$^+$)

Example 132

1-[3-Fluoro-4-(methylsulfonyl)phenyl]-5-[4-(2-furyl)phenyl]-1H-pyrazole-3-carboxamide The title compound was prepared according to the procedure of Example 130 using 0.5M-ammonia in 1,4-dioxane solution instead of morpholine.

mp: 239.0–240.0° C.

$^1$H-NMR (CDCl$_3$) δ: 7.92 (dd, J=8, 8 Hz, 1H), 7.71 (d, J=8 Hz, 2H), 7.51 (d, J=2 Hz, 1H), 7.24 (dd, J=2, 10 Hz, 1H), 7.27 (d, J=8 Hz, 2H), 7.24–7.23 (m, 1H), 7.10 (s, 1H), 6.83 (brs, 1H), 6.75 (d, J=3 Hz, 1H), 6.51 (dd, J=2, 3 Hz, 1H), 5.54 (brs, 1H), 3.25(s, 3H)

Anal. Calcd. for. $C_{21}H_{16}FN_3O_4S$, $0.2H_2O$: C, 58.79; H, 3.85; N, 9.79. Found: C, 58.42; H, 4.01; N, 9.41.

MS (EI): m/z 425 (M$^+$)

Example 133

N,N-Dimethyl-1-[3-fluoro-4-(methylsulfonyl) phenyl]-5-[4-(2-furyl)phenyl]-1H-pyrazole-3-carboxamide The title compound was prepared according to the procedure of Example 130 using dimethylamine hydrochloride and triethylamine instead of morpholine.

mp:167.0–168.0° C.

$^1$H-NMR (CDCl$_3$) δ: 7.89 (dd, J=8, 8 Hz, 1H), 7.70 (d, J=9 Hz, 2H), 7.51 (d, H=1 Hz, 1H), 7.37 (dd, J=2, 11 Hz, 1H), 7.30–7.26 (m, 2H), 7.25–7.20 (m, 1H), 6.95 (s, 1H), 6.74 (d, J=3 Hz, 1H), 6.51 (dd, J=2, 3 Hz, 1H), 3.43 (s, 3H), 3.23(s, 3H), 3.13 (s, 3H).

Anal. Calcd. for. $C_{23}H_{20}FN_3O_4S$: C, 60.92; H, 4,45; N, 9.27. Found: C, 60.64; H, 4.66; N, 9.06.

MS (EI): m/z 453 (M$^+$)

Example 134

N-Methoxy-1-[3-fluoro-4-(methylsulfonyl)phenyl]-5-[4-(2-furyl)phenyl]-1H-pyrazole-3-carboxamide The title compound was prepared according to the procedure of Example 130 using methoxylamine hydrochloride and triethylamine instead of morpholine.

mp:126.0–128.0° C.

$^1$H-NMR (CDCl$_3$) δ: 9.38 (s, 1H), 7.92 (dd, J=8, 8 Hz, 1H), 7.70 (d, J=8 Hz, 2H), 7.51 (d, J=2 Hz, 1H), 7.36 (dd, J=2, 10 Hz, 1H), 7.27–7.21 (m, 3H), 7.12 (s, 1H), 6.75 (d, J=4 Hz, 1H), 6.51 (dd, J=2, 4 Hz, 1H), 3.93 (s, 3H), 3.25(s, 3H).

Anal. Calcd. for. $C_{22}H_{18}FN_3O_5S$, $0.7H_2O$ , 0.1 Hexane: C, 56.77; H, 4.34; N, 8.87. Found: C, 57.00; H, 4,41; N, 8.50.

MS (EI): m/z 455 (M$^+$)

Example 135

5-[4-(2-Furyl)phenyl]-1-[4-(methylsulfonyl)-3-(trifluoromethyl)phenyl]-3-trifluoromethyl-1H-pyrazole 4-(Methylsulfonyl)-3-(trifluoromethyl)nitrobenzene (step 1)

A mixture of 2-fluoro-5-nitrobenzotrifluoride (2.09 g, 10 mmol) and sodium methanesulfinate (1.32 g, 11 mmol) in DMSO (20 mL) was heated at 130° C. for 17.5 hours. After cooling down to room temperature, the mixture was poured into ice-water. The whole was extracted with ethyl acetate (30 mL×2), the combined organic layer washed with water, brine, dried over MgSO$_4$, and concentrated in vacuo. The residue was crystallized from hexane to give the subtitle compound (1.56 g, 57.8%, yield).

$^1$H-NMR (CDCl$_3$) δ: 8.75 (m, 1H), 8.61–8.58 (m, 2H), 3.26 (s, 3H).

4-(Methylsulfonyl)-3-(trifluoromethyl)aniline (step 2)

A mixture of 4-(methylsulfonyl)-3-(trifluoromethyl) nitrobenzene (1.55 g, 5.76 mmol), iron powder (1.61 g, 28.8 mmol), and ammonium chloride (0.031 g, 0.58 mmol) in ethanol (30 mL), and water (8 mL) was heated at reflux temperature for 1 hour. After cooling, insolubles were filtered off by Celite, and volatiles were removed by evaporation. The residue was redissolved in ethyl acetate (50 mL) and the whole washed with water and brine. After dried over MgSO$_4$ and concentration in vacuo. The residue was washed with hexane to give the subtitle compound (1.05 g, 76.2%, yield).

$^1$H-NMR (CDCl$_3$) δ: 8.01 (d, J=9 Hz, 1H),7.05 (d, J=3 Hz, 1H), 6.82 (dd, J=3, 9 Hz, 1H), 4,47 (brs, 2H), 3.13 (s, 3H).

4-(Methylsulfonyl)-3-(trifluoromethyl)phenylhydrazine hydrochloride (step 3)

To a stirred suspension of 4-(methylsulfonyl)-3-(trifluoromethyl)aniline (1.04 g, 4.35 mmol) in conc. HCl (10 mL) was added dropwise a solution of sodium nitrate (0.315 g, 4.57 mmol) in water (10 mL) at −20° C. After stirring for 30 minutes, the resulting suspension was added Tin(II) chloride dihydrate (4.92 g, 21.8 mmol) in conc.HCl (10 mL) at −10° C. After stirring for 1 hour at −5° C., the mixture was stirred further 1 hour at room temperature. The reaction mixture was made alkaline with aqueous NaOH at 0–5° C. The mixture was filtered through Celite, the filterate was extracted with THF (30 mL×3), the combined organic layer washed with brine, dried over MgSO$_4$ and concentration in vacuo to give the subtitle compound (1 g).

$^1$H-NMR (CDCl$_3$) δ: 8.06 (d, J=9 Hz, 1H), 7.04–6.97 (m, 2H), 5.95 (brs, 1H), 3.77 (brs, 2H), 3.13 (s, 3H).

The solid (1 g) was dissolved in 10% methanolic HCl (3 mL), and volatiles were removed by evaporation. The residue was recrystallized from methylene chloride-ether to give the subtitle compound (0.869 g, 68.8% yield, via 2 steps). 5-[4-(2-Furyl)phenyl]-1-[4-(methylsulfonyl)-3-(trifluoromethyl)phenyl]-3-trifluoromethyl-1H-pyrazole (step 4)

The title compound was prepared according to the procedure of Example 60 using 4-(methylsulfonyl)-3-(trifluoromethyl)phenylhydrazine hydrochloride instead of 3-fluoro-4-(methylsulfonyl)phenylhydrazine hydrochloride in step 2.

mp: 159–160° C.

$^1$H-NMR (CDCl$_3$) δ: 8.26 (d, J=9 Hz, 1H), 8.05 (d, J=2 Hz, 1H), 7.72 (d, J×8 Hz, 2H), 7.63 (dd, J=2, 9 Hz, 1H), 7.52 (d, J=2 Hz, 1H), 7.26 (d, J=8 Hz, 2H), 6.83 (s, 1H), 6.76 (d, J=4 Hz, 1H), 6.52 (dd, J=2, 4 Hz, 1H), 3.20 (s, 3H).

Anal. Calcd. for. $C_{22}H_{14}F_6N_2O_3S$: C, 52.80; H, 2.82; N, 5.60. Found: C, 53.09; H, 3.06; N, 5.46.

MS (EI): m/z 500 (M$^+$)

Example 136

5-[4-(2-Furyl)phenyl]-1-[3-methoxy-4-(methylsulfonyl)phenyl]-3-trifluoromethyl-1H-pyrazole 3-Methoxy-4-(methylsulfonyl)nitrobenzene (step 1)

The subtitle compound was prepared according to the procedure of Example 135 using 2-chloro-5-nitroanisole instead of 2-fluoro-5-nitrobenzotrifluoride in step 1.

$^1$H-NMR (CDCl$_3$) δ: 8.19 (d, J=8 Hz, 1H), 7.96 (dd, J=2, 9 Hz, 1H), 7.91 (d, J=2 Hz, 1H), 4.13 (s, 3H), 3.26 (s, 3H).

3-Methoxy-4-(methylsulfonyl)aniline (step 2)

The subtitle compound was prepared according to the procedure of Example 135 using 3-methoxy-4-(methylsulfonyl)nitrobenzene instead of 4-(methylsulfonyl)-3-(trifluoromethyl)nitrobenzene in step 2.

$^1$H-NMR (CDCl$_3$) δ: 7.69 (d, J=8 Hz, 1H), 6.21–6.21 (m, 2H), 4.21 (brs, 2H), 3.91 (s, 3H), 3.15 (s, 3H).

3-Methoxy-4-(methylsulfonyl)phenylhydrazine hydrochloride (step 3)

The subtitle compound was prepared according to the procedure of Example 135 using 3-methoxy-4-(methylsulfonyl)aniline instead of 4-(methylsulfonyl)-3-(trifluoromethyl)aniline in step 3.

5-[4-(2-Furyl)phenyl]-1-[3-methoxy-4-(methylsulfonyl) phenyl]-3-trifluoromethyl-1H-pyrazole (step 4)

The title compound was prepared according to the procedure of Example 60 using 3-methoxy-4-(methylsulfonyl)phenylhydrazine hydrochloride instead of 3-fluoro-4-(methylsulfonyl)phenylhydrazine hydrochloride in step 2.

mp: 138.9° C.

$^1$H-NMR (CDCl$_3$) δ: 7.92 (d, J=9 Hz, 1H), 7.69 (d, J=8 Hz, 2H), 7.51 (s, 1H), 7.28–7.26 (m, 2H), 7.17 (s, 1H), 6.97 (d, J=8 Hz, 1H), 6.81 (s, 1H), 6.73 (s, 1H), 6.51 (s, 1H), 3.90 (s, 3H), 3.21 (s, 3H).

Anal. Calcd. for. C$_{22}$H$_{17}$F$_3$N$_2$O$_4$S: C, 57.14; H, 3.71; N, 6.06. Found: C, 57.10; H, 3.88; N, 6.09.

MS (EI): m/z 462 (M$^+$)

Example 137

2-Fluoro-4-[5-[4-(2-furyl)phenyl]-3-(trifluoromethyl)-1H-pyrazol-1-yl] benzenesulfonamide 4-Acetamido-2-fluorobenzenesulfonamide (step 1)

To a stirred chlorosulfonic acid (33 mL, 0.5 mol) was added dropwise 3-fluoroacetanilide (15.3 g, 0.1 mol) at 0° C. The mixture was heated at 70° C. for 6 hours and cooled down to room temperature. The mixture was diluted with methylene chloride (50 mL) and poured into ice-water. The whole was extracted with methylene chloride (30 mL×2). The combined organic layer was added 25% ammonium hydroxide (20 mL) at 0° C., and the mixture was stirred for 1 hour at room temperature. The suspension was filtered to give the subtitle compound (11.17 g, 48.1% yield, via 2 steps).

$^1$H-NMR (DMSO-d$_6$) δ: 10.47 (s, 1H), 7.77–7.68 (m, 2H), 7.54 (brs, 2H), 7.38 (dd, J=2, 9 Hz, 1H), 2.10 (s, 3H).

4-Amino-2-fluorobenzenesulfonamide (step 2)

A mixture of 4-acetamido-2-fluorobenzenesulfonamide (11.15 g, 48 mmol) and sodium hydroxide (11.5 g, 480 mmol) in water (80 mL) was heated at reflux temperature for 3 hours. The mixture was made neutral by addition of 2N-HCl solution, and resulting suspension was filtered to give the subtitle compound (5.8 g, 63.5% yield).

$^1$H-NMR (DMSO-d$_6$) δ: 7.41–7.34 (m, 1H), 7.14 (brs, 2H), 6.39 (brs, 1H), 6.36–6.33 (m, 1H), 6.11 (brs, 2H).

3-Fluoro-4-sulfamoylphenylhydrozine hydrochloride (step 3)

The subtitle compound was prepared according to the procedure of Example 135 using 4-amino-2-fluorobenzenesulfonamide instead of 4-(methylsulfonyl)-3-(trifluoromethyl)aniline in step 3.

$^1$H-NMR (DMSO-d$_6$) δ: 7.71 (brs, 1H), 7.42 (t, J=9 Hz, 1H), 7.15 (brs, 2H), 6.61–6.49 (brs, 2H), 4.26 (brs, 2H).

2-Fluoro-4-[5-[4-(2-furyl)phenyl]-3-(trifluoromethyl)-1H-pyrazol-1-yl]benzenesulfonamide (step 4)

The title compound was prepared according to the procedure of Example 60 using 3-fluoro-4-sulfamoylphenylhydrazine hydrochloride instead of 3-fluoro-4-(methylsulfonyl)phenylhydrazine hydrochloride in step 2.

mp: 151.0° C.

$^1$H-NMR (CDCl$_3$) δ: 7.86 (dd, J=8, 8 Hz, 1H), 7.71 (d, J=9 Hz, 2H), 7.51 (dd, J=1 Hz, 1H), 7.38 (dd, J=2, 11 Hz, 1H), 7.26 (d, J=9 Hz, 2H), 7.21–7.16 (m, 1H), 6.80 (s, 1H), 6.75 (d, J=4 Hz, 1H), 6.51 (dd, J=2, 4 Hz, 1H), 5.12 (brs, 2H).

Anal. Calcd. for. C$_{20}$H$_{13}$F$_4$N$_3$O$_3$S: C, 53.22; H, 2.90; N, 9.31. Found: C, 53.38; H, 3.18; N, 8.93.

MS (EI): m/z 451 (M$^+$)

Example 138

4-[5-[3-Chloro-4-(2-furyl)phenyl]-3-(trifluoromethyl)-1H-pyrazol-1-yl]-2-fluorobenzenesulfonamide The title compound was prepared according to the procedure of Example 60 using 3-fluoro-4-sulfamoylphenylhydrazine hydrochloride instead of 3-fluoro-4-(methylsulfonyl)phenylhydrazine hydrochloride and 4,4,4-trifluoro-1-[3-chloro-4-(2-furyl)phenyl]butane-1,3-dione instead of 4,4,4-trifluoro-1-[4-(2-furyl)phenyl]butane-1,3-dione in step 2.

mp: 171.8° C.

$^1$H-NMR (CDCl$_3$) δ: 7.92–7.86 (m, 2H), 7.55 (dd, J=1, 2 Hz, 1H), 7.45–7.38 (m, 2H), 7.27–7.26 (m, 1H), 7.18 (dd, J=2, 8 Hz, 1H), 7.10 (dd, J=2, 8 Hz, 1H), 6.83 (s, 1H), 6.57 (dd, J=2, 4 Hz, 1H), 5.13 (brs, 2H).

Anal. Calcd. for. C$_{20}$H$_{12}$ClF$_4$N$_3$O$_3$S, 0.1 Hexane: C, 49.84; H, 2.67; N, 8.55. Found: C, 49.95; H, 2.78; N, 8.30.

MS (EI): m/z 485 (M$^+$)

Example 139

2-Fluoro-4-[5-[4-(2-furyl)-3-methylphenyl]-3-(trifluoromethyl)-1H-pyrazol-1-yl] benzenesulfonamide The title compound was prepared according to the procedure of Example 60 using 3-fluoro-4-sulfamoylphenylhydrazine hydrochloride instead of 3-fluoro-4-(methylsulfonyl)phenylhydrazine hydrochloride and 4,4,4-trifluoro-1-[4-(2-furyl)-3-methylphenyl]butane-1,3-dione instead of 4,4,4-trifluoro-1-[4-(2-furyl)phenyl]butane-1,3-dione in step 2.

mp: 78–80° C.

$^1$H-NMR (CDCl$_3$) δ: 7.85 (dd, J=8, 8 Hz, 1H), 7.73 (d, J=8 Hz, 1H), 7.54 (d, J=2, 1H), 7.40 (dd, J=2, 11 Hz, 1H), 7.19 (d, J=9 Hz, 2H), 7.05 (d, J=8 Hz, 1H), 6.79 (s, 1H), 6.65 (d, J=4 Hz, 1H), 6.54 (dd, J=2, 4 Hz, 1H), 5.14 (brs, 2H), 2.51 (s, 3H).

Anal. Calcd. for. C$_{21}$H$_{15}$F$_4$N$_3$O$_3$S: C, 54.19; H, 3.25; N, 9.03. Found: C, 54.24; H, 3.56; N, 8.87.

MS (EI): m/z 465 (M$^-$)

Example 140

3-Chloro-4-[5-[4-(2-furyl)phenyl]-3-(trifluoromethyl)-1H-pyrazol-1-yl] benzenesulfonamide 3-Chloro-4-fluorobenzenesulfonamide (step 1)

To a solution of 3-chloro-4-fluorobenzenesulfonyl chloride (2.29 g, 10 mmol) in methylene chloride (30 mL) was added 25% ammonium hydroxide (10 mL) at room temperature and the mixture was stirred for 1 hour. The solvent was removed in vacuo. The residue was redissolved in ethyl acetate (50 mL) and the whole washed with water and brine. After dried over MgSO$_4$ and concentration in vacuo. The resulting solid was recrystallized from ether-hexane to give the title compound (1.429 g, 68.2% yield).

$^1$H-NMR (DMSO-d$_6$) δ: 8.00 (dd, J=2, 7 Hz, 1H), 7.83 (ddd, J=2, 7, 9 Hz, 1H), 7.65 (t, J=9 Hz, 1H), 7.54 (brs, 2H).

2-Chloro-4-sulfamoylphenylhydrazine hydrochloride (step 2)

The title compound was prepared according to the procedure of Example 61 using 3-chloro-4-fluorobenzenesulfonamide instead of 4-chlorophenyl fluoromethyl sulfone in step 1.

$^1$H-NMR (CDCl$_3$) δ: 7.59 (s, 1H), 7.27–7.21 (m, 3H), 7.09 (brs, 2H), 4.33 (brs, 2H).

3-Chloro-4-[5-[4-(2-furyl)phenyl]-3-(trifluoromethyl)-1H-pyrazol-1-yl]benzenesulfonamide (step 3)

The title compound was prepared according to the procedure of Example 60 using 2-chloro-4-sulfamoylphenylhydrazine hydrochloride instead of 3-fluoro-4-(methylsulfonyl)phenylhydrazine hydrochloride in step 2.

mp: 190.3° C.

$^1$H-NMR (CDCl$_3$) δ: 8.01 (d, J=2 Hz, 1H), 7.91 (dd, J=2, 8 Hz, 1H), 7.66–7.59 (m, 3H), 7.47 (d, J=2 Hz, 1H), 7.18 (d, J=9 Hz, 2H), 6.84 (s, 1H), 6.69 (d, J=4 Hz, 1H), 6.47 (dd, J=2, 4 Hz, 1H), 5.07 (brs, 2H).

Anal. Calcd. for. C$_{20}$H$_{13}$ClF$_3$N$_3$O$_3$S, 0.05 Hexane: C, 51.54; H, 2.89; N, 8.93. Found: C, 51.19; H, 3.20; N, 8.57.

MS (EI): m/z 467 (M)

Example 141

3-Fluoro-4-[5-[4-(2-furyl)phenyl]-3-(trifluoromethyl)-1H-pyrazol-1-yl]benzenesulfonamide 3,4-Difluorobenzenesulfonamide (step 1)

The subtitle compound was prepared according to the procedure of Example 137 using 1,2-difluorobenzene instead of 3-fluoroacetanilide in step 1.

$^1$H-NMR (CDCl$_3$) δ: 7.80–7.71 (m, 2H), 7.39–7.27 (m, 1H), 5.06 (brs, 2H).

2-Fluoro-4-sulfamoylphenylhydrazine hydrochloride (step 2)

The title compound was prepared according to the procedure of Example 61 using 3,4-difluorobenzenesulfonamide instead of 4-chlorophenyl fluoromethyl sulfone in step 1.

3-Fluoro-4-[5-[4-(2-furyl)phenyl]-3-(trifluoromethyl)-1H-pyrazol-1-yl]benzenesulfonamide (step 3)

The title compound was prepared according to the procedure of Example 60 using 2-fluoro-4-sulfamoylphenylhydrazine hydrochloride instead of 3-fluoro-4-(methylsulfonyl)phenylhydrazine hydrochloride in step 2.

mp: 174.4° C.

$^1$H-NMR (CDCl$_3$) δ: 7.84 (m, 1H), 7.77–7.68 (m, 2H), 7.63 (dd, J=2, 9 Hz, 2H), 7.49 (d, J=2 Hz, 1H), 7.21 (d, J=9 Hz, 2H), 6.83 (s, 1H), 6.71 (d, J=3 Hz, 1H), 6.49 (dd, J=2, 3 Hz, 1H), 4.94 (brs, 2H).

Anal. Calcd. for. C$_{20}$H$_{13}$F$_4$N$_3$O$_3$S, 0.3H$_2$O: C, 52.59; H, 3.00; N, 9.20. Found: C, 52.85; H, 3.14; N, 8.83.

MS (EI): m/z 451 (M$^+$)

Example 142

[5-[4-(2-Furyl)phenyl]-1-[4-(methylsulfonyl)-2-methylphenyl]-3-trifluoromethyl-1H-pyrazole 2-Methyl-4-(methylsulfonyl)nitrobenzene (step 1)

The subtitle compound was prepared according to the procedure of Example 135 using 5-fluoro-2-nitrotoluene instead of 2-fluoro-5-nitrobenzotrifluoride in step 1.

$^1$H-NMR (CDCl$_3$) δ: 8.09 (d, J=8 Hz, 1H), 7.98–7.92 (m, 2H), 3.12 (s, 3H).

2-Methyl-4-(methylsulfonyl)aniline (step 2)

The subtitle compound was prepared according to the procedure of Example 135 using 2-methyl-4-(methylsulfonyl)nitrobenzene instead of 4-(methylsulfonyl)-3-(trifluoromethyl)nitrobenzene in step 2.

$^1$H-NMR (CDCl$_3$) δ: 7.59 (s, 1H), 7.56 (d, J=2 Hz, 1H), 6.71 (dd, J=1, 7 Hz, 1H), 4.17 (brs, 2H), 3.00 (s, 3H), 2.20 (s, 3H).

2-Methyl-4-(methylsulfonyl)phenylhydrazine hydrochloride (step 3)

The subtitle compound was prepared according to the procedure of Example 135 using 2-methyl-4-(methylsulfonyl)aniline instead of 4-(methylsulfonyl)-3-(trifluoromethyl)aniline in step 3.

[5-[4-(2-Furyl)phenyl]-1-[4-(methylsulfonyl)-2-methylphenyl]-3-trifluoromethyl-1H-pyrazole (step 4)

The title compound was prepared according to the procedure of Example 60 using 2-methyl-4-(methylsulfonyl)phenylhydrazine hydrochloride instead of 3-fluoro-4-(methylsulfonyl)phenylhydrazine hydrochloride in step 2.

mp: 205.0° C.

$^1$H-NMR (CDCl$_3$) δ: 7.89–7.83 (m, 2H), 7.60 (d, J=9 Hz, 2H), 7.50–7.47 (m, 2H), 7.14 (d, J=9 Hz, 2H), 6.86 (s, 1H), 6.69 (d, J=3 Hz, 1H), 6.48 (dd, J=2, 4 Hz, 1H), 3.07 (s, 3H), 2.12 (s, 3H).

Anal. Calcd. for. C$_{22}$H$_{17}$F$_3$N$_2$O$_3$S: C, 59.19; H, 3.84; N, 6.27. Found: C, 59.32; H, 4.13; N, 6.17.

MS (EI): m/z 446 (M$^+$)

Example 143

[4-[5-[4-(2-Furyl)phenyl]-3-(trifluoromethyl)-1H-pyrazol-1-yl]-2-methylbenzenesulfonamide 4-Acetamido-2-methylbenzenesulfonamide (step 1)

The subtitle compound was prepared according to the procedure of Example 137 using m-acetotoluidide instead of 3-fluoroacetanilide in step 1.

$^1$H-NMR (DMSO-d$_6$) δ: 10.2 (s, 1H), 7.78 (s, 1H), 7.74 (s, 1H), 7.56 (m, 1H), 7.53 (s, 2H), 2.54 (s, 3H), 2.06 (s, 3H).

4-Amino-2-methylbenzenesulfonamide (step 2)

The subtitle compound was prepared according to the procedure of Example 137 using 4-acetamido-2-methylbenzenesulfonamide instead of 4-acetamido-2-fluorobenzenesulfonamide in step 2.

$^1$H-NMR (DMSO-d$_6$) δ: 7.48 (d, J=8 Hz, 1H), 6.88 (brs, 2H), 6.42 (s, 1H), 6.38 (dd, J=2, 8 Hz, 1H), 5.68 (brs, 2H), 2.42 (s, 3H).

3-Methyl-4-sulfamoylphenylhydrozine hydrochloride (step 3)

The subtitle compound was prepared according to the procedure of Example 135 using 4-amino-2-methylbenzenesulfonamide instead of 4-(methylsulfonyl)-3-(trifluoromethyl)aniline in step 3.

$^1$H-NMR (DMSO-d$_6$) δ: 7.55 (d, J=9 Hz, 1H), 7.29 (brs, 1H), 6.90 (brs, 2H), 6.62 (s, 1H), 6.59 (dd, J=3, 9 Hz, 1H), 4.10 (brs, 2H), 2.46 (s, 3H).

4-[5-[4-(2-Furyl)phenyl]-3-(trifluoromethyl)-1H-pyrazol-1-yl]-2-methylbenzenesulfonamide (step 4)

The title compound was prepared according to the procedure of Example 60 using 3-methyl-4-sulfamoylphenylhydrazine hydrochloride instead of 3-fluoro-4-(methylsulfonyl)phenylhydrazine hydrochloride in step 2.

mp: 137.4° C.

$^1$H-NMR (CDCl$_3$) δ: 7.95 (d, J=9 Hz, 1H), 7.67 (d, J=8 Hz, 2H). 7.50 (d, J=2 Hz, 1H), 7.48 (d, J=2 Hz, 1H), 7.24 (d, J=8 Hz, 2H), 7.14 (dd, J=2, 9 Hz, 1H), 6.79 (s, 1H), 6.73 (d, J=4 Hz, 1H), 6.50 (dd, J=2, 3 Hz, 1H), 4.91 (brs, 2H). 2.67 (s, 3H).

Anal. Calcd. for. $C_{21}H_{16}F_3N_3O_3S$: C, 56.37; H, 3.60; N, 9.39. Found: C, 56.60; H, 3.85; N, 9.04.

MS (EI): m/z 447 (M⁺)

Example 144

2-Chloro-4-[5-[4-(2-furyl)phenyl]-3-(trifluoromethyl)-1H-pyrazol-1-yl] benzenesulfonamide 4-Acetamido-2-chlorobenzenesulfonamide (step 1)

The subtitle compound was prepared according to the procedure of Example 137 using m-chloroacetanilide instead of 3-fluoroacetanilide in step 1.

$^1$H-NMR (DMSO-$d_6$) δ: 10.4 (s, 1H), 7.94 (d, J=2 Hz, 1H), 7.90 (d, J=9 Hz, 1H), 7.56 (dd, J=2, 9 Hz, 1H) 7.36 (brs, 2H), 2.10 (s, 3H).

4-Amino-2-chlorobenzenesulfonamide (step 2)

The subtitle compound was prepared according to the procedure of Example 137 using 4-acetamido-2-chlorobenzenesulfonamide instead of 4-acetamido-2-fluorobenzenesulfonamide in step 2.

$^1$H-NMR (DMSO-$d_6$) δ: 7.58 (d, J=9 Hz, 1H), 7.09 (brs, 2H), 6.67 (d, J=2 Hz, 1H), 6.50 (dd, J=2, 9 Hz, 1H), 6.07 (brs, 2H).

3-Chloro-4-sulfamoylphenylhydrozine hydrochloride (step 3)

The subtitle compound was prepared according to the procedure of Example 135 using 4-amino-2-chlorolbenzenesulfonamide instead of 4-(methylsulfonyl)-3-(trifluoromethyl)aniline in step 3.

$^1$H-NMR (DMSO-$d_6$) δ: 7.67 (brs, 1H), 7.58 (d, J=9 Hz, 1H), 7.11 (brs, 2H), 6.87 (d, J=2 Hz, 1H), 6.66 (dd, J=2, 9 Hz, 1H), 4.27 (brs, 2H)).

2-Chloro-4-[5-[4-(2-furyl)phenyl]-3-(trifluoromethyl)-1H-pyrazol-1-yl]benzenesulfonamide (step 4)

The title compound was prepared according to the procedure of Example 60 using 3-chloro-4-sulfamoylphenylhydrazine hydrochloride instead of 3-fluoro-4-(methylsulfonyl)phenylhydrazine hydrochloride in step 2.

mp: 192.6° C.

$^1$H-NMR (CDCl₃) δ: 8.03 (d, J=9 Hz, 1H), 7.73–7.68 (m, 3H), 7.51 (s, 1H), 7.28–7.23 (m, 3H), 6.80 (s, 1H), 6.75 (d, J=3 Hz, 1H), 6.51 (dd, J=2, 4 Hz, 1H), 5.19 (brs, 2H).

Anal. Calcd. for. $C_{20}H_{13}ClF_3N_3O_3S$, 0.1H₂O: C, 51.15; H, 2.83; N, 8.95. Found: C, 51.26; H, 3.12; N, 8.55.

MS (EI): mn/z 467 (M⁺)

Example 145

4-[5-[4-(2-Furyl)phenyl]-3-(trifluoromethyl)-1H-pyrazol-1-yl]-3-methylbenzenesulfonamide 4-Acetamido-3-methylbenzenesulfonamide (step 1)

The subtitle compound was prepared according to the procedure of Example 137 using o-acetotoluidide instead of 3-fluoroacetanilide in step 1.

$^1$H-NMR (DMSO-$d_6$) δ: 9.47 (s, 1H), 7.94 (brs, 1H), 7.72–7.36 (m, 4H), 2.26 (s, 3H), 2.09 (s, 3H).

4-Amino-3-methylbenzenesulfonamide (step 2)

The subtitle compound was prepared according to the procedure of Example 137 using 4-acetamido-3-methylbenzenesulfonamide instead of 4-acetamido-2-fluorobenzenesulfonamide in step 2.

2-Methyl-4-sulfamoylphenylhydrozine hydrochloride (step 3)

The subtitle compound was prepared according to the procedure of Example 135 using 4-amino-3-methylbenzenesulfonamide instead of 4-(methylsulfonyl)-3-(trifluoromethyl)aniline in step 3.

4-[5-[4-(2-Furyl)phenyl]-3-(trifluoromethyl)-1H-pyrazol-1-yl-3-methylbenzenesulfonamide (step 4)

The title compound was prepared according to the procedure of Example 60 using 2-methyl-4-sulfamoylphenylhydrazine hydrochloride instead of 3-fluoro-4-(methylsulfonyl)phenylhydrazine hydrochloride in step 2.

mp: 87–89° C.

$^1$H-NMR (CDCl₃) δ: 7.86–7.80 (m, 2H), 7.59 (d, J=8 Hz, 2H), 7.47 (s, 1H), 7.43 (d, J=8 Hz, 1H), 7.15 (d, J=8 Hz, 2H), 6.85 (s, 1H), 6.68 (d, J=3 Hz, 1H), 6.48 (m, 1H), 4.95 (brs, 2H), 2.08 (s, 3H).

Anal. Calcd. for. $C_{21}H_{16}F_3N_3O_3S$, 0.1H₂O: C, 56.15; H, 3.63; N, 9.35. Found: C, 56.02; H, 3.91; N, 8.97.

MS (EI): m/z 447 (M⁺)

Example 146

[5-[4-(2-Furyl)phenyl]-1-[4-(methylsulfonyl)-2-methoxylphenyl]-3-trifluoromethyl-1H-pyrazole 2-Methoxy4-(methylsulfonyl)nitrobenzene (step 1)

The subtitle compound was prepared according to the procedure of Example 135 using 5-chloro-2-nitroanisole instead of 2-fluoro-5-nitrobenzotrifluoride in step 1.

$^1$H-NMR (CDCl₃) δ: 7.80 (d, J=8 Hz, 1H), 7.67 (d, J=1 Hz, 1), 7.62 (dd, J=2, 8 Hz, 1H), 4.06 (s, 3H), 3.11 (s, 3H).

2-Methoxy-4-(methylsulfonyl)aniline (step 2)

The subtitle compound was prepared according to the procedure of Example 135 using 2-methoxy-4-(methylsulfonyl)nitrobenzene instead of 4-(methylsulfonyl)-3-(trifluoromethyl)nitrobenzene in step 2.

$^1$H-NMR (CDCl₃) δ: 7.38 (dd, J=2, 8 Hz, 1H), 7.27 (s, 1H), 6.74 (d, J=8 Hz, 1H), 4.36 (brs, 2H), 3.92 (s, 3H), 3.02 (s, 3H).

2-Methoxy-4-(methylsulfonyl)phenylhydrazine hydrochloride (step 3)

The subtitle compound was prepared according to the procedure of Example 135 using 2-methoxy-4-(methylsulfonyl)aniline instead of 4-(Methylsulfonyl)-3-(trifluoromethyl)aniline in step 3.

$^1$H-NMR (CDCl₃) δ: 7.51 (dd, J=2, 8 Hz, 1H), 7.23 (d. J=2 Hz, 1H), 7.10 (d, J=8 Hz, 1H), 6.07 (brs, 1H), 3.90 (s, 3H), 3.63 (brs, 2H), 3.02 (s, 3H).

[5-[4-(2-Furyl)phenyl]-1-[4-(methylsulfonyl)-2-methoxylphenyl]-3-trifluoromethyl-1H-pyrazole (step 4)

The title compound was prepared according to the procedure of Example 60 using 2-methoxy-4-(methylsulfonyl)phenylhydrazine hydrochloride instead of 3-fluoro-4-(methylsulfonyl)phenylhydrazine hydrochloride in step 2.

mp: 200.2° C.

$^1$H-NMR (CDCl₃) δ: 7.76 (d, J=8 Hz, 1H), 7.67 (dd, J=2, 8 Hz, 1H), 7.60 (d, J=9 Hz, 2H), 7.48 (dd, J=1, 2 Hz, 1H), 7.42 (d, J=2 Hz, 1H), 7.19 (d, J=9 Hz, 2H), 6.80 (s, 1H), 6.69 (d, J=4 Hz, 1H), 6.48 (dd, J=2, 4 Hz, 1H), 3.52 (s, 3H), 3.08 (s, 3H).

Anal. Calcd. for. $C_{22}H_{17}F_3N_2O_4S$: C, 57.14; H, 3.71; N, 6.06. Found: C, 57.06; H, 3.68; N, 5.96.

MS (EI): m/z 462 (M⁺)

Example 147

[5-[4-(2-Furyl)phenyl]-1-[4-(methylsulfonyl)-2-(trifluoromethyl)phenyl]-3-trifluoromethyl-1H-pyrzole 4-(Methylsulfonyl)-2-(trifluoromethyl)nitrobenzene (step 1)

The subtitle compound was prepared according to the procedure of Example 135 using 5-fluoro-2- nitrobenzotrifluoride instead of 2-fluoro-5-nitrobenzotrifluoride in step 1.

$^1$H-NMR (CDCl$_3$) δ: 8.41 (s, 1H), 8.34 (d, J=8 Hz, 1H), 8.06 (d, J=8 Hz, 1H), 3.16 (s, 3H).

4-(Methylsulfonyl)-2-(trifluoromethyl)aniline (step 2)

The subtitle compound was prepared according to the procedure of Example 135 using 4-(methylsulfonyl)-2-(trifluoromethyl)nitrobenzene instead of 4-(methylsulfonyl)-3-(trifluoromethyl) nitrobenzene in step 2.

$^1$H-NMR (CDCl$_3$) δ: 8.01 (s, 1H), 7.82 (dd, J=2, 9 Hz, 1H), 6.83 (d, J=9 Hz, 1H), 4.76 (brs, 2H), 3.03 (s, 3H).

4-(Methylsulfonyl)-2-(trifluoromethyl)phenylhydrazine hydrochloride (step 3)

The subtitle compound was prepared according to the procedure of Example 135 using 4-(methylsulfonyl)-2-(trifluoromethyl)aniline instead of 4-(Methylsulfonyl)-3-(trifluoromethyl)aniline in step 3.

[5-[4-(2-Furyl)phenyl]-1-[4-(methylsulfonyl)-2-(trifluoromethyl)phenyl]-3-trifluoromethyl-1H-pyrazole (step 4)

The title compound was prepared according to the procedure of Example 60 using 4-(methylsulfonyl)-2-(trifluoromethyl)phenylhydrazine hydrochloride instead of 3-fluoro-4-(methylsulfonyl)phenylhydrazine hydrochloride in step 2.

$^1$H-NMR (CDCl$_3$) δ: 8.40 (s, 1H), 8.16 (d, J=8 Hz, 1H), 7.61 (d, J=9 Hz, 2H), 7.53 (d, J=8 Hz, 1H), 7.48 (s, 1H), 7.15 (d, J=8 Hz 2H), 6.86 (s, 1H), 6.71–6.68 (s, 1H), 3.12 (s, 3H).

Anal. Calcd. for. C$_{22}$H$_{14}$F$_6$N$_2$O$_3$S, 0.05 Hexane, 0.4H$_2$O: C, 52.23; H, 3.02; N, 5.49. Found: C, 52.37; H, 2.94; N, 5.09.

MS (EI): m/z 500 (M$^+$)

Example 148

4-[5-[4-(2-Furyl)phenyl]-3-(trifluoromethyl-1H-pyrazol-1-yl]-2-methoxybenzenesulfonamide 3-Methoxyacetanilide (step 1)

To a stirred solution of m-anisidine (12.3 g, 0.1 mol) in THF (80 mL) was added acetic anhydride (11.3 mL, 0.12 mol) at 0° C. The mixture was stirred at room temperature for 30 minutes. The reaction mixture was washed with water (50 mL), brine (30 mL), dried over MgSO$_4$, and concentrated in vacuo. The resulting solid was recrystallized from methylene chloride-hexane to give the subtitle compound (15.9 g, 96.4% yield).

$^1$H-NMR (CDCl$_3$) δ: 7.43 (brs, 1H), 7.27–7.26 (m, 1H), 7.20 (dd, J=8, 8 Hz, 1H), 6.97 (d, J=8 Hz, 1H), 6.65 (dd, J=2, 8 Hz, 1H), 3.79 (s, 3H), 2.16 (s, 3H).

4-Acetamido-2-methoxybenzenesulfonamide (step 2)

The subtitle compound was prepared according to the procedure of Example 137 using 3-methoxyacetanilide instead of 3-fluoroacetanilide in step 1.

4-Amino-2-methoxybenzenesulfonamide (step 3)

The subtitle compound was prepared according to the procedure of Example 137 using 4-acetamido-2-methylbenzenesulfonamide instead of 4-acetamido-2-fluorobenzenesulfonamide in step 2.

$^1$H-NMR (DMSO-d$_6$) δ: 7.34 (d, J=8 Hz, 1H), 6.57 (brs, 2H), 6.25 (d, J=2 Hz, 1H), 6.12 (dd, J=2, 8 Hz, 1H), 5.81 (brs, 2H), 3.77 (s, 3H).

3-Methoxy-4-sulfamoylphenylhydrozine hydrochloride (step 4)

The subtitle compound was prepared according to the procedure of Example 135 using 4-amino-2-methoxybenzenesulfonamide instead of 4-(methylsulfonyl)-3-(trifluoromethyl)aniline in step 3.

4-[5-[4-(2-Furyl)phenyl]-3-(trifluoromethyl)-1H-pyrazol-1-yl]-2-methoxybenzenesulfonamide (step 5)

The title compound was prepared according to the procedure of Example 60 using 3-methoxy-4-sulfamoylphenylhydrazine hydrochloride instead of 3-fluoro-4-(methylsulfonyl)phenylhydrazine hydrochloride in step 2.

mp: 206.7° C.

$^1$H-NMR (CDCl$_3$) δ: 7.85 (d, J=8 Hz, 1H), 7.69 (dd, J=2, 8 Hz, 2H), 7.51 (d, J=2 Hz, 1H), 7.26 (d, J=8 Hz, 2H), 7.16 (d, J=2 Hz, 1H), 6.94 (dd, J=2, 8 Hz, 1H), 6.80 (s, 1H), 6.73 (d, J=4 Hz, 1H), 6.51 (dd, J=2, 4 Hz, 1H), 5.05 (brs, 2H), 3.91 (s, 3H).

Anal. Calcd. for. C$_{21}$H$_{16}$F$_3$N$_3$O$_4$S, 0.1H$_2$O: C, 54.22; H, 3.51; N, 9.03. Found: C, 54.41; H, 3.73; N, 8.63.

MS (EI): m/z 463 (M$^+$)

Example 149

2-Chloro-4-[5-[3-methyl-4-(4-thiazolyl)phenyl]-3-(trifluoromethyl)-1H-pyrazol-1-yl]benzenesulfonamide The title compound was prepared according to the procedure of Example 60 using 3-chloro-4-sulfamoylphenylhydrazine hydrochloride instead of 3-fluoro-4-(methylsulfonyl)phenylhydrazine hydrochloride and 4,4,4-trifluoro-1-[3-methyl-4-(4-thiazolyl)phenyl]butane-1,3-dione instead of 4,4,4-trifluoro-1-[4-(2-furyl)phenyl]butane-1,3-dione in step 2.

mp: 113.0–115.0° C.

$^1$H-NMR (CDCl$_3$) δ: 8.92 (d, J=2 Hz, 1H), 8.03 (d, J=9 Hz, 1H), 7.79 (d, J=2 Hz, 1H), 7.64 (d, J=8 Hz, 1H), 7.43 (d, J=2 Hz, 1H), 7.27–7.22 (m, 2H), 7.07 (d, J=8 Hz, 1H), 6.81 (s, 1H), 5.20 (brs, 2H), 2.47 (s, 3H).

Anal. Calcd. for. C$_{20}$H$_{14}$ClF$_3$N$_4$O$_2$S$_2$, 0.4 Hexane: C, 49.68; H, 3.47; N, 10.73. Found: C, 49.96; H, 3.84; N, 10.36.

MS (EI): m/z 498 (M$^+$)

Example 150

3-Fluoro-4-[5-[3-methyl-4-(4-thiazolyl)phenyl]-3-trifluoromethyl)-1H-pyrazol-1-yl]benzenesulfonamide The title compound was prepared according to the procedure of Example 60 using 2-fluoro-4-sulfamoylphenylhydrazine hydrochloride instead of 3-fluoro-4-(methylsulfonyl)phenylhydrazine hydrochloride and 4,4,4-trifluoro-1-[3-methyl-4-(4-thiazolyl)phenyl]butane-1,3-dione instead of 4,4,4-trifluoro-1-[4-(2-furyl)phenyl]butane-1,3-dione in step 2.

$^1$H-NMR (CDCl$_3$) δ: 8.87 (d, J=2 Hz, 1H), 7.81–7.60 (m, 3H), 7.53 (d, J=8 Hz, 1H), 7.38 (d, J=2 Hz, 1H), 7.22–7.21 (brs, 1H), 7.00 (d, J=8 Hz, 1H), 6.83 (s, 1H), 5.39 (brs, 2H), 2.40 (s, 3H).

Anal. Calcd. for. C$_{20}$H$_{14}$F$_4$N$_4$O$_2$S$_2$, 0.3H$_2$O: C, 49.24; H, 3.02; N, 11.48. Found: C, 49.51; H, 3.35; N, 11.12.

MS (EI): m/z 482 (M$^+$)

Example 151

5-[3-Fluoro-4-(methylsulfonyl)phenyl]-2-methyl-1-[4-(4-thiazolyl)phenyl]-1H-pyrrole To a stirred solution of 1-(4-bromophenyl)-2-[3-fluoro-4-(methylsulfonyl)phenyl]-5-methyl-1H-pyrrole (0.318 g, 0.78 mmol, Example 35, step 3) in 1,4-dioxane (12 mL) was added 4-(tributylstannyl)thiazole (0.35 g, 0.94 mmol), lithiun chloride (0.083 g, 1.95 mmol), and tetrakis(triphenylphosphine)palladium(0) (0.090 g, 0.078 mmol) at room temperature under nitrogen. The mixture was heated at reflux temperature for 3.5 hours. After cooling, volatiles were removed by evaporation. The residue was redissolved in ethyl acetate (30 mL) and the whole washed with water and brine. After dried over $MgSO_4$ and concentration in vacuo. The crude mixture was purified by flash chromatography eluting with hexane/ethyl acetate (3/1). The resulting solid was recrystallized from ethyl acetate-hexane to give the title compound (0.221 g, 68.8% yield).

mp: 215.0° C.

$^1$H-NMR (CDCl$_3$) δ: 8.91 (d, J=2 Hz, 1H), 8.02 (d, J=9 Hz, 2H), 7.65 (dd, J=7, 8 Hz, 1H), 7.63 (d, J=2 Hz, 1H), 7.24 (d, J=9 Hz, 2H), 6.99–6.88 (m, 2H), 6.56 (d, J=4 Hz, 1H), 6.16 (d, J=4 Hz, 1H), 3.15 (s, 3H), 2.17 (s, 3H).

Anal. Calcd. for. $C_{21}H_{17}FN_2O_2S_2$, 0.5$H_2O$: C, 59.84; H, 4.30; N, 6.65. Found: C, 59.57; H, 4.37; N, 6.36.

MS (EI): m/z 412 (M$^+$)

Example 152

5-[3-Fluoro-4-(methylsulfonyl)phenyl]-2-methyl-1-[3-methyl-4-(4-thiazolyl)phenyl]-1H-pyrrole The title compound was prepared according to the procedure of Example 151 using 5-[3-fluoro-4-(methylsulfonyl)phenyl]-2-methyl-1-[3-methyl-4-(4-thiazolyl)phenyl]1H-pyrrole instead of 1-(4-Bromophenyl)-2-[3-fluoro-4-(methylsulfonyl)phenyl]-5-methyl-1H-pyrrole (Example 39).

mp: 179.0–181.0° C.

$^1$H-NMR (CDCl$_3$) δ: 8.92 (d, J=2 Hz, 1H), 7.72–7.63 (m, 2H), 7.45 (d, J=2 Hz, 1H), 7.10–7.05 (m, 2H), 6.99–6.92 (m, 2H), 6.55 (d, J=4 Hz, 1H), 6.14 (d, J=4 Hz, 1H), 3.17 (s, 3H), 2.47 (s, 3H), 2.16 (s, 3H).

Anal. Calcd. for. $C_{22}H_{19}FN_2O_2S_2$, 0.3$H_2O$: C, 61.18; H, 4.57; N, 6.49. Found: C, 60.98; H, 4.55; N, 6.21.

MS (EI): m/z 426 (M$^+$)

Example 153

1-[3-Fluoro-4-(methylsulfonyl)phenyl]-2-[4-(4-thiazolyl)phenyl]-4-trifluoromethyl-1H-imidazole N-[3-Fluoro-4-(methylsulfonyl)phenyl]-4-(bromophenyl)benzenecarboximidamide (step 1)

To a suspension of 3-fluoro-4-(methylsulfonyl)aniline (6.24 g, 33 mmol) in toluene (100 mL) at 0° C. was added over 5 minutes trimethylaluminum (50.5 mL, 0.98 M solution in hexane, 49.5 mmol). The reaction mixture was warmed to room temperature and stirred for 3.5 hours. A solution of 4-bromobenzonitrile (12 g, 65.9 mmol) in toluene (60 mL) was added over 15 minutes and the reaction mixture heated to 70° C. After 20 hours, the reaction mixture was cooled to room temperature and poured over a slurry of silicagel in chloroform-methanol (2:1, 750 mL). After filtration, the residue was washed with a mixture of methylene chloride-methanol (2:1, 375 mL). The combined filtrates were concentrated in vacuo, and the resulting yellowish solid was washed with hexane-ether (2:1, 300 mL) to give the subtitle compound (12.78 g).

MS (EI): m/z 370 (M$^+$)

2-(4-Bromophenyl)-1-[3-fluoro-4-(methylsulfonyl)phenyl]-4-hydroxy4-trifluoromethyl-4,5-dihydro-1H-imidazole (step 2)

To a mixture of N-[3-fluoro-4-(methylsulfonyl)phenyl]-4-(bromophenyl)benzenecarboximidamide (12.77 g, 33 mmol) and sodium bicarbonate (5.54 g, 66 mmol) in 2-propanol (250 mL) was added 3-bromo-1,1,1-trifluoroacetone (7.56 g, 39.6 mmol). After the reaction mixture was heated to 80° C. for 17.5 hours, the solvent was removed. The residue was redissolved in ethyl acetate (200 mL) and washed with water (100 mL×2). The organic fractions were combined, dried over $MgSO_4$, filtered, and concentrated in vacuo. The crude mixture was purified by flash chromatography eluting with hexane/ethyl acetate (4/1) to give the subtitle compound (3.05 g, 19.2% yield, via 2 steps).

$^1$H-NMR (DMSO-d$_6$) δ: 7.58 (d, J=8 Hz, 2H), 7.53 (dd, J=8, 9 Hz, 1H), 7.35 (d, J=8 Hz, 2H), 6.98 (dd, J=2, 12 Hz, 1H), 6.60 (dd, J=2, 9 Hz, 1H), 4.41 (d, J=12 Hz, 1H), 3.88 (d, J=12 Hz, 1H), 3.15 (s, 3H).

MS (EI): m/z 481 (M$^+$)

2-(4-Bromophenyl)-1-[3-fluoro-4-(methylsulfonyl)phenyl]-4-trifluoromethyl-1H-imidazole (step 3)

A mixture of 2-(4-bromophenyl)-1-[3-fluoro-4-(methylsulfonyl)phenyl]-4-hydroxy-4-trifluoromethyl-4,5-dihydro-1H-imidazole (3.05 g, 6.33 mmol) and p-toluenesulfonic acid monohydrate (0.300 g) in toluene (250 mL) was heated to reflux for 21 hours. The reaction mixture was cooled and the solvent removed under reduced pressure. The crude residue was redissolved in methylene chloride (150 mL) and the whole washed with water, aqueous NaHCO$_3$ (50 mL), and brine. After dried over $MgSO_4$, and concentrated in vacuo. The crude mixture was purified by flash chromatography eluting with hexane/ethyl acetate (3/1) to give the subtitle compound (1.517 g, 51.8% yield).

$^1$H-NMR (CDCl$_3$) δ: 8.07 (dd, J=8,8 Hz, 1H), 7.51 (d, J=8 Hz, 2H), 7.52 (s, 1H), 7.27 (d, J=8 Hz, 2H), 7.26–7.16 (m, 2H), 3.29 (s, 3H).

MS (EI): m/z 462 (M$^+$)

1-[3-Fluoro-4-(methylsulfonyl)phenyl]-2-[4-(4-thiazolyl)phenyl]-4-trifluoromethyl-1H-imidazole (step 4)

To a stirred solution of 2-(4-bromophenyl)-1-[3-fluoro-4-(methylsulfonyl)phenyl]-4-trifluoromethyl-1H-imidazole (0.361 g, 0.78 mmol) in 1,4-dioxane (12 mL) was added 4-(tributylstannyl)thiazole (0.35 g, 0.94 mmol ), lithium chloride (0.083 g, 1.95 mmol), and tetrakis(triphenylphosphine)palladium(0) (0.090 g, 0.078 mmol) at room temperature under nitrogen. The mixture was heated at reflux temperature for 3 hours. After cooling, volatiles were removed by evaporation. The residue was redissolved in ethyl acetate (30 mL) and the whole washed with water and brine. After dried over $MgSO_4$ and concentration in vacuo. The crude mixture was purified by flash chromatography eluting with hexane/ethyl acetate (3/1). The resulting solid was recrystallized from ethyl acetate-hexane to give the title compound (0.319 g, 87.6% yield).

mp: 112.5–115.0° C.

$^1$H-NMR (CDCl$_3$) δ: 8.89 (d, J=2 Hz, 1H), 8.06 (dd, J=8, 9 Hz, 1H), 7.94 (d, J=8 Hz, 2H), 7.63 (d, J=2 Hz, 1H), 7.54 (d, J=1 Hz, 1H), 7.47 (d, J=8 Hz, 2H), 7.27–7.19 (m, 2H), 3.28 (s, 3H).

Anal. Calcd. for. $C_{20}H_{13}F_4N_3O_2S_2$, 0.7$H_2O$: C, 50.04; H, 3.02; N, 8.75. Found: C, 49.95; H, 3.00; N, 8.38.

MS (EI): m/z 467(M$^+$)

Example 154

2-Fluoro-4-[2-[4-(4-thiazolyl)phenyl]-4-(trifluoromethyl)-1H-imidazol-1-yl]benzenesulfonamide N-(3-Fluoro-4-sulfamoylphenyl)-4-(bromophenyl)benzenecarboximidamide (step 1)

The subtitle compound was prepared according to the procedure of Example 153 (step 1) using 4-amino-2- fluorobenzenesulfonamide, instead of 3-fluoro-4-(methylsulfonyl)aniline.

MS (EI): m/z 370 (M$^+$−1)

4-[2-(4-Bromophenyl)-4-hydroxy-4-trifluoromethyl-4,5-dihydro-1H-imidazol-1-yl]-2-fluorobenzenesulfonamide (step 2)

The subtitle compound was prepared according to the procedure of Example 153 (step 2) using N-(3-fluoro-4-sulfamoylphenyl)-4-(bromophenyl)benzenecarboximidamide, instead of N-[3-fluoro-4-(methylsulfonyl)phenyl]-4-(bromophenyl)benzenecarboximidamide.

MS (EI): m/z 483(M$^+$+2)

4-[2-(4-Bromophenyl)-4-hydroxy-4-trifluoromethyl-1H-imidazol-1-yl]-2-fluorobenzene sulfonamide (step 3)

The subtitle compound was prepared according to the procedure of Example 153 (step 3) using 4-[2-(4-bromophenyl)-4-hydroxy-4-trifluoromethyl-4,5-dihydro-1H-imidazol-1yl]-2-fluorobenzenesulfonamide instead of 2-(4-bromophenyl)-1-[3-fluoro-4-(methylsulfonyl)phenyl]-4-hydroxy-4-trifluoromethyl-4,5-dihydro-1H-imidazole.

$^1$H-NMR (CDCl$_3$) δ: 7.99 (dd, J=8, 9 Hz, 1H), 7.55 (d, J=1 Hz, 1H), 7.50 (d, J=9 Hz, 2H), 7.28 (d, J=9 Hz, 2H), 7.16–7.11 (m, 2H), 6.69 (s, 2H).

MS (EI): m/z 463 (M$^+$)

2-Fluoro-4-[2-[4-(4-thiazolyl)phenyl]-4-(trifluoromethyl)-1H-imidazol-1-yl]benzene sulfonamide (step 4)

The title compound was prepared according to the procedure of Example 153 (step 4) using 4-[2-(4-bromophenyl)-4-hydroxy-4-trifluoromethyl-1H-imidazol-1-yl]-2-fluorobenzenesulfonamide instead of 2-(4-bromophenyl)-1-[3-fluoro-4-(methylsulfonyl)phenyl]-4-trifluoromethyl-1H-imidazole.

mp: 130.0–133.0° C.

$^1$H-NMR (CDCl$_3$) δ: 8.88 (d, J=2 Hz, 1H), 7.99 (t, J=8 Hz, 1H), 7.92 (d, J=9 Hz, 2H), 7.62 (d, J=2 Hz, 1H), 7.53 (d, J=1 Hz, 1H), 7.46 (d, J=9 Hz, 2H), 7.22–7.15 (m, 2H), 5.28 (brs, 2H).

Anal. Calcd. for. C$_{19}$H$_{12}$F$_4$N$_4$O$_2$S$_2$, 0.3 hexane, 0.5 H$_2$O: C, 49.02; H, 3.26; N, 11.32. Found: C, 48.73; H, 3.13; N, 10.99.

MS (EI): m/z 468(M$^+$)

Example 155

1-[3-Chloro-4-(methylsulfonyl)phenyl]-5-[4-(2-furyl)phenyl]-3-(trifluoromethyl)-1H-pyrazole 3-Chloro-4-(methylsulfonyl)phenylhydrazine hydrochloride (step 1)

To a stirred suspension of 3-chloro-4-(methylsulfonyl)aniline (3.0 g, 15.0 mmol, Ish. K. Khanna et al., J. Med. Chem. 40. 1619 (1997)) in 20% aqueous HCl (20 mL) was added dropwise a solution of sodium nitrite (1.1 g, 16.0 mmol) in water (20 mL) below −5° C. After stirring for 1 hour at that temperature, tin(II) chloride dihydrate in 20% aqueous HCl (20 mL) was added dropwise below −5° C. The resulting suspension was stirred for 1 h at room temperature. The mixture was basified with aqueous NaOH (pH=14) and extracted with CHCl$_3$ (200 mL×2), dried over MgSO$_4$, and concentarted in vacuo. The solid (5 g) was dissolved in 10% methanolic HCl (30 mL), and volatiles were removed by evaporation. The residue was washed with ethanol to give the title compound (1.3 g, 34%).

$^1$H-NMR (DMSO-d$_6$) δ: 9.32 (br 1H), 7.89 (d, J=8.7 Hz, 1H), 7.20 (d, J=2.1 Hz, 1H), 7.02 (dd, J=8.7, 2.1 Hz, 1H), 3.29 (s, 3H).

1-[3-Chloro-4-(methylsulfonyl)phenyl]-5-[4-(2-furyl)phenyl]-3-(trifluoromethyl)-1H-pyrazole (step 2)

The title compound was prepared according to the procedure of Example 60 using [3-chloro-4-(methylsulfonyl)phenyl]hydrazine hydrochloride from step 1 instead of [3-fluoro-4-(methylsulfonyl)phenyl]hydrazine hydrochloride.

mp:139–142° C.

$^1$H-NMR (CDCl$_3$) δ: 8.05 (d, J=8.6 Hz, 1H), 7.76 (d, J=2.0 Hz, 1H), 7.71 (d, J=8.2 Hz, 2H), 7.52 (s, 1H), 7.34–7.24 (m, 3H), 6.81 (s, 1H), 6.75 (d, J=3.3 Hz, 1H), 6.52 (dd, J=3.3, 1.8 Hz, 1H), 3.28 (s, 3H).

Anal. Calcd. for C$_{21}$H$_{14}$N$_2$O$_3$F$_3$ClS: C, 54.03; H, 3.02; N, 6.00. Found: C, 53.79; H, 3.14; N, 5.92.

Example 156

5-[5-[4-(2-Furyl)phenyl-3-(trifluoromethyl)-1H-pyrazol-1-yl]-2-(methylsulfonyl)phenyl]methanol 3-Hydroxymethyl-4-(methylthio)nitrobenzene (step 1)

To a solution of 4-chloro-3-(hydroxymethyl)nitrobenzene (20 g, 0.10 mol) in DMSO (160 mL) and MeOH (80 mL), MeSNa (8.2 g, 0.12 mol) was added portionwise at 0° C., and the mixture was stirrred for 2 h at room temperature. The mixture was poured into ice water (300 mL) and the yellow precipitate was collected by filtration and washed with ether (150 mL) gave the title compound (21 g, quantitative).

$^1$H-NMR (DMSO-d$_6$) δ: 8.25 (d, J=2.5 Hz, 1H), 8.12 (dd, J=2.5, 8.7 Hz, 1H), 7.46 (d, J=8.7 Hz, 1H), 5.70 (br, 1H), 4.51 (s, 2H), 2.60 (s, 3H).

3-Hydroxymethyl-4-(methylsulfonyl)nitrobenzene (step 2)

To a solution of 3-hydroxymethyl-4-(methylthio)nitrobenzene from step 1 (20 g, 0.10 mol) in CH$_2$Cl$_2$ (500 mL) and MeOH (100 mL), m-CPBA (74 g, 0.30 mol) was added portionwise at 0° C., and the mixture was stirrred for 16 h at room temperature. The mixture was added aqueous Na$_2$SO$_3$ (20 g in 200 mL of water) at 0° C. Organic layer was separated and washed with saturated aqueous NaHCO$_3$ (300 mL), dried over MgSO$_4$, and concentarted in vacuo gave the title compound (15.6 g, 65%).

$^1$H-NMR (DMSO-d$_6$) δ: 8.57 (d, J=2.5 Hz, 1H), 8.34 (dd, J=2.5, 8.6 Hz, 1H), 8.16 (d, J=8.6 Hz, 1H), 5.88 (t, J=5.4 Hz, 1H), 5.00 (d, J=5.4 Hz, 1H), 3.35 (s, 3H).

3-Hydroxymethyl-4-(methylsulfonyl)aniline (step 3)

The title compound was prepared according to the procedure of Example 60 using 3-hydroxymethyl-4-(methylsulfonyl)nitrobenzene from step2 instead of 1-[3-fluoro-4-(methylsulfonyl)phenyl]hydradine hydrochloride.

$^1$H-NMR (DMSO-d$_6$) δ: 7.50 (d, J=8.6 Hz, 1H), 6.87 (d, J=2.1 Hz, 1H), 6.50 (dd, J=2.1, 8.6 Hz, 1H), 6.08 (br, 2H), 5.26 (t, J=5.6 Hz, 1H), 4.73 (d, J=5.6 Hz, 2H), 3.06 (s, 3H).

3-Hydroxymethyl-4-(methylsulfonyl)phenylhydrazine hydrochloride (step 4)

The title compound was prepared according to the procedure of step 1 of Example 155 using 3-hydroxymethyl-4-(methylsulfonyl)aniline from step3 instead of 3-chloro-4-(methylsulfonyl)aniline.

$^1$H-NMR (DMSO-d$_6$) δ: 10.50 (br, 1H), 9.05 (br, 1H), 7.78 (d, J=8.7 Hz, 1H), 7.29 (d, J=2.3 Hz, 1H), 6.95 (dd, J=2.3, 8.7 Hz, 1H), 4.84 (s, 2H), 3.17 (s, 3H).

5-[5-[4-(2-Furyl)phenyl-3-(trifluoromethyl)-1H-pyrazol-1-yl]-2-(methylsulfonyl)phenyl (step 5)

The title compound was prepared according to the procedure of Example 60 using 3-hydroxymethyl-4-(methylsulfonyl)phenylhydrazine hydrochloride from step4 instead of [3-fluoro-4-(methylsulfonyl)phenyl]hydrazine hydrochloride.

mp:135–150° C.

$^1$H-NMR (CDCl$_3$) δ: 7.99 (d, J=8.6 Hz, 1H), 7.76 (d, J=2.3 Hz, 1H), 7.69 (d, J=8.6 Hz, 2H), 7.51 (d, J=1.8 Hz, 1H), 7.35 (dd, J=2.3, 8.6 Hz, 1H), 7.25 (d, J=8.6 Hz, 2H), 6.81 (s, 1H), 6.74 (d, J=3.5 Hz, 1H), 6.51 (dd, J=1.8, 3.3 Hz, 1H), 4.95 (d, J=6.4 Hz, 2H), 3.17 (s, 3H).

Anal. Calcd. for C$_{22}$H$_{17}$N$_2$O$_4$F$_3$S: C, 57.14; H, 3.71; N, 6.06. Found: C, 56.47; H, 3.76; N, 5.91.

Example 157

5-[4-(2-Furyl)phenyl]-1-[3-methyl-4-(methylsulfonyl)phenyl]-3-(trifluoromethyl]-1H-pyrazole 3-Methyl-4-(methylsulfonyl)phenylhydrazine hydrochloride (step 1)

The title compound was prepared according to the procedure of Example 155 using 3-methyl-4-(methylsulfonyl)aniline (Kugita H. et al., *Chem. Pharm. Bull.* 10, 1001 (1962)) instead of 3-chloro-4-(methylsulfonyl)aniline.

$^1$H-NMR (DMSO-d$_6$) δ: 10.59 (br, 2H), 8.96 (br, 1H), 7.78 (d, J=7.9 Hz, 1H), 7.00–6.90 (m, 2H), 3.14 (s, 3H), 2.57 (s, 3H).

5-[4-(2-Furyl)phenyl]-1-[3-methyl-4-(methylsulfonyl)phenyl]-3-(trifluoromethyl)-1H-pyrazole (step 2)

The title compound was prepared according to the procedure of Example 60 using 3-methyl-4-(methylsulfonyl)phenylhydrazine hydrochloride from step1 instead of [3-fluoro-4-(methylsulfonyl)phenyl]hydrazine hydrochloride.

mp:135–139° C.

$^1$H-NMR (CDCl$_3$) δ: 7.99 (d, J=8.6 Hz, 1H), 7.68 (d, J=8.6 Hz, 2H), 7.51 (m, 2H), 7.27–7.21 (m, 3H), 6.80 (s, 1H), 6.73 (d, J=3.5 Hz, 1H), 6.50 (dd, J=1.8, 3.5 Hz, 1H), 3.09 (s, 3H), 2.71 (s, 3H).

Anal. Calcd. for C$_{22}$H$_{17}$N$_2$O$_3$F$_3$S: C, 59.19; H, 3.84; N, 6.27. Found: C, 59.20; H, 4.04; N, 6.18.

Example 158

1-[3-Chloro-4-(methylsulfonyl)phenyl]-5-4-(4-thiazolyl)phenyl]-3-trifluoromethyl-1H-pyrazole 1-[3-Chloro-4-(methylsulfonyl)phenyl]-5-4-(4-thiazolyl)phenyl]-3-trifluoromethyl-1H-pyrazole The title compound was prepared according to the procedure of Example 60 using [3-chloro-4-(methylsulfonyl)phenyl]hydrazine hydrochloride from step1of Example 155 instead of [3-fluoro-4-(methylsulfonyl)phenyl]hydrazine hydrochloride, 4,4,4-trifluoro-1-[4-(1,3-thiazol-4-yl)phenyl]-1,3-butanedione from step 3 of Example 82 instead of 4,4,4-trifluorro-1-[4-(2-fryl)phenyl]-1,3-butanedione.

mp:103–107° C.

$^1$H-NMR (CDCl$_3$) δ: 8.90 (d, J=1.8 Hz, 1H), 8.08 (d, J=8.6 Hz, 1H), 8.02–7.95 (m, 2H), 7.77 (d, J=2.1 Hz, 1H), 7.64 (d, J=2.0 Hz, 1H), 7.36–7.29 (m, 3H), 6.84 (s, 1H), 3.28 (s, 3H).

Anal. Calcd. for C$_{20}$H$_{13}$N$_3$O$_2$F$_3$ClS$_2$: C, 49.64; H, 2.71; N, 8.68. Found: C, 50.05; H, 3.15; N, 8.35.

Example 159

5-[4-(2-Furyl)phenyl]-1-[3-(methoxymetyl)-4-(methylsulfonyl)phenyl]-3-(trifluoromethyl)-1H-pyrazole 5-[4-(2-Furyl)phenyl]-1-[3-(methoxymetyl)-4-(methylsulfonyl)phenyl]-3-(trifluoromethyl)-1H-pyrazole To a solution of 5-[5-[4-(2-furyl)phenyl]-3-(trifluoromethyl)-1H-pyrazol-1-yl]-2-(methylsulfonyl) phenyl]methanol from Example 156 (260 mg, 0.56 mmol) in THF (10 mL). NaH (27 mg, 0.67 mmol) was added at 0° C., and the mixture was stirred for 0.5 h at room temperature, Iodomethane (0.050 mL, 0.67 mmol) was added at 0° C. and the mixture was stirred for 4 h at room temperature. The mixture was poured into water (30 mL), aqueous 2N HCl (5 mL) was added and extracted with ethyl acetate (30 mL×2), dried over MgSO$_4$, and concentarted in vacuo. The reaction mixture was purified by flash chromatography eluting with ethyl acetate/hexane (1/4). The resulting solid was crystallized from diisopropyl ether-hexane to give title compound (0.150 g, 56%).

mp:142–143° C.

$^1$H-NMR (CDCl$_3$) δ: 8.03 (d, J=8.6 Hz, 1H), 7.73–7.65 (m, 3H), 7.51 (s, 1H), 7.39 (dd, J=2.3, 8.6 Hz, 1H), 7.25 (d, J=8.2 Hz, 2H), 6.80 (s, 1H), 6.73 (d, J=3.3 Hz, 1H), 6.50 (dd, J=1.8, 3.3 Hz, 1H), 4.80 (s, 2H), 3.38 (s, 3H), 3.16 (s, 3H).

Anal. Calcd. for C$_{23}$H$_{19}$N$_2$O$_4$F$_3$S: C, 57.98; H, 4.02, N, 5.88. Found: C, 57.92; H, 4.13; N, 5.78.

Example 160

N-[5-[5-[4-(2-Furyl)phenyl]-3-(trifluoromethyl)-1H-pyrazol-1-yl]-2-(methylsulfonyl)benzyl]-N-methylamine hydrochloride step 1

1-[3-Chloromethyl-4-(methylsulfonyl)phenyl]-5-[4-(2-furyl)phenyl]-3-(trifluoromethyl)-1H-pyrazole A mixture of 5-[5-[4-(2-furyl)phenyl]-3-(trifluoromethyl)-1H-pyrazol-1-yl]-2-(methylsulfonyl) phenyl]methanol (170 mg, 0.37 mmol; Example 156) and triphenylphosphine (100 mg, 0.44 mmol) in CCl$_4$ (10 mL) was refluxed for 16 h. After cooled to room temperature, the precipitate was separated by celite filteration and washed with ether. The filtrate was purified by flash chromatography eluting with ethyl acetate/hexane (1/4) to give title compound (0.073 g, 41%).

MS(EI): m/z=480 (M$^+$)

step2

N-[5-[5-[4-(2-Furyl)phenyl]-3-(trifluoromethyl)-1H-pyrazol-1-yl]-2-(methylsulfonyl)benzyl]-N-methylamine hydrochloride To a solution of 1-[3-chloromethyl-4-(methylsulfonyl) phenyl]-5-[4-(2-furyl)phenyl]-3-(trifluoromethyl)-1H-pyrazole from step1 (70 mg, 0.15 mmol) in THF (3.0 mL), methylamine (5.0 ml, 10 mmol, 2.0 M in THF) and K$_2$CO$_3$ (200 mg, 1.5 mmol) was added at room temperature and stirred for 1 hour. The mixture was concentrated and ethyl acetate (30 mL) was added, dried over MgSO$_4$, and concentarted in vacuo. The solid was dissolved in 10% methanolic HCl (10 mL), and volatiles were removed by evaporation. The residual solid was recrystallized from ethanol to give the title compound (45 mg, 59%).

mp:270–272° C.

$^1$H-NMR (DMSO-d$_6$) δ: 9.20–8.90 (br 1H), 8.10–8.00 (m, 2H), 7.80 (s, 1H), 7.74 (d, J=8.2 Hz, 2H), 7.58 (d, J=8.1 Hz, 1H), 7.45–7.35 (m, 3H), 7.07 (d, J=3.3 Hz, 1H), 6.64 (s, 1H), 4.52 (s, 2H), 3.42 (s, 3H), 2.55 (s, 3H).

Anal. Calcd. for C$_{23}$H$_{22}$N$_3$O$_3$F$_3$ClS: C, 53.96; H, 4.13 ; N, 8.21. Found: C, 53.39; H, 4.25; N, 8.01.

Example 161

[5-[5-[4-(2-Furyl)phenyl]-3-(trifluoromethyl)-1H-pyrazol-1-yl]-2-(methylsulfonyl)phenyl] methanamine hydrochloride 2-[5-[5-[4-(2-Furyl)phenyl]-3-(trifluoromethyl)-1H-pyrazol-1-yl]-2-(methylsulfonyl)benzyl]1H-isoindole-1,3 (2H)-dione (step 1)

A mixture of 1-[3-chloromethyl-4-(methylsulfonyl) phenyl]-5-[4-(2-furyl)phenyl]-3-(trifluoromethyl)-1H-pyrazole from step1 of Example 160 (280 mg, 0.58 mmol) and potassium phthalimide (10 mg, 0.054 mmol) in DMF was heated at 90° C. for 1 hour. After cooled to room temperature, the mixture was poured into water (30 mL), and extracted with ether (30 mL×2), washed with water (30 mL) and brine (30 mL), dried over $MgSO_4$, and concentarted in vacuo to give the title compound (240 mg, 70%).

MS(EI): m/z 591(M$^+$)

[5-[5-[4-(2-Furyl)phenyl]-3-(trifluoromethyl)-1H-pyrazol-1-yl]-2-(methylsulfonyl)phenyl]methanamine hydrochloride (step 2)

A mixture of 2-[5-[5-[4-(2-furyl)phenyl]-3-(trifluoromethyl)-1H-pyrazol-1-yl]-2-methylsulfonyl) benzyl]-1H-isoindole-1,3(2H)-dione form step1 (240 mg, 0.41 mmol) and hydradine monohydrate (110 mg, 2.2 mmol) in EtOH (10 mL) was refluxed for 4 h. After cooled to room temperature, concentrated and water (20 mL) was added and extracted with ethyl acetate (30 mL×2) and washed with saturated aqueous $NaHCO_3$ (20 mL), dried over $MgSO_4$, and concentarted in vacuo. The reaction mixture was purified by flash chromatography eluting with $CH_2Cl_2$/MeOH (13/1). The resulting solid was dissolved in 10% methanolic HCl (10 mL), and volatiles were removed by evaporation. The residual solid was recrystallized from ethanol-isopropyl ether to give the title compound (12 mg, 6%).

mp:238–241° C.

$^1$H-NMR (CDCl$_3$) δ: 8.01 (d, J=8.6 Hz, 1H), 7.72–7.65 (m, 3H), 7.51 (d, J=1.3 Hz, 1H), 7.32 (dd, J=2.1, 8.6 Hz, 1H), 7.27–7.24 (m, 2H), 6.81 (s, 1H), 6.73 (d, J=3.5 Hz, 1H), 6.51 (dd, J=1.8, 3.5 Hz, 1H), 4.20 (s, 2H), 3.23 (s, 3H).

Anal. Calcd. for $C_{22}H_{19}N_3O_3F_3ClS$: C, 53.07; H, 3.85 N, 8.44. Found: C, 50.58; H, 4.68: N, 7.46.

Example 162

1-[3-Fluoro-4-(methylsulfonyl)phenyl]-5-[4-(2-furyl)phenyl]-1H-pyrazole 5-(4-Bromophenyl)-1-[3-fluoro-4-(methylsulfonyl)phenyl]-1H-pyrazole (step 1)

The title compound was prepared according to the procedure of Example 60 using (Z)-1-[4-bromophenyl)-3-(dimethylamino)-2-propen-1-one (John T. Gupton et al., *J Org. Chem.* 22, 4522 (1980)) instead of 4,4,4-trifluoro-1-[4-(2-furyl)phenyl]butane-1,3-dione.

$^1$H-NMR (CDCl$_3$) δ: 7.88 (t, J=7.7 Hz, 1H), 7.77 (d. J=1.8 Hz, 1H), 7.54 (d, J=8.6 Hz, 2H), 7.35 (dd, J=1.8, 10.7 Hz, 1H), 7.20–7.11 (m, 3H), 6.54 (d, J=1.8 Hz, 1H), 3.24 (s, 3H).

1-[3-Fluoro-4-(methylsulfonyl)phenyl)]-5-[4-(2-furyl) phenyl]-1H-pyrazole (step 2)

The title compound was prepared according to the procedure of Example 5 using 5-(4-bromophenyl)-1-[3-fluoro-4-(methylsulfonyl)phenyl]-1H-pyrazole instead of 4-[5-(4-bromophenyl)-3-(trifluoromethyl)-1H-pyrazol-1yl]-1-phenylsulfonamide, 2-furanboronic acid instead of 3-thienylboronic acid.

mp:155–156° C.

$^1$H-NMR (CDCl$_3$) δ: 7.87 (t, J=7.7 Hz, 1H), 7.78 (d. J=1.6 Hz, 1H), 7.70 (d, J=8.6 Hz, 2H), 7.51 (d, J=1.8 Hz, 1H), 7.38 (dd, J=2.0, 10.9 Hz, 1H), 7.30–7.20 (m, 3H), 6.73 (d, J=3.3 Hz, 1H), 6.56 (d, J=1.8 Hz, 1H), 6.51 (dd, J=1.8, 3.3 Hz, 1H), 3.23 (s, 3H),

Anal. Calcd. for $C_{20}H_{15}N_2O_3FS$: C, 62.82; H, 3.95: N, 7.33. Found: C, 62.26; H, 4.16; N, 7.12.

Example 163

4-Cyano-1-[3-fluoro-4-(methylsulfonyl)phenyl]-5-[4-(2-furyl)phenyl]-1H-pyrazole 5-(4-Bromophenyl)-4-cyano-1-[3-fluoro-4-(methylsulfonyl)phenyl]-1H-pyrazole (step 1)

The title compound was prepared according to the procedure of Example 60 using 2-(4-bromobenzoyl)-3-(dimethylmino)acrylonitrile (Field, George F. et al., DE 2330913) instead of 4,4,4-trifluorro-1-[4-(2-fryl)phenyl]-1, 3-butanedione.

$^1$H-NMR (CDCl$_3$) δ: 8.32 (s, 1H), 7.95 (dd, J=7.7, 8.6 Hz, 1H), 7.73 (d, J=8.7 Hz, 2H), 7.55 (dd, J=2.0, 10.7 Hz, 1H), 7.45 (d, J=8.7 Hz, 2H), 7.43–7.37 (m, 1H), 3.30 (s, 3H),

4-Cyano-1-[3-fluoro-4-(methylsulfonyl)phenyl]-5-[4-(2-furyl)phenyl]-1H-pyrazole (step 2)

The title compound was prepared according to the procedure of Example 5 using 5-(4-bromophenyl)-4-cyano-1-[3-fluoro-4-(methylsulfonyl)phenyl]-1H-pyrazole instead of 4-[5-(4-bromophenyl)-3-(trifluoromethyl)-1H-pyrazol-1-yl]-1-phenylsulfonamide, 2-furanboronic acid instead of 3-thienylboronic acid.

mp:153–157° C.

$^1$H-NMR (CDCl$_3$) δ: 8.07 (s, 1H), 7.93 (t, J=8.0 Hz, 1H), 7.77 (d. J=8.4 Hz, 2H), 7.54 (s, 1H), 7.42–7.34 (m, 3H), 7.22 (d, J=8.4 Hz, 1H), 6.79 (d, J=3.3 Hz, 1H), 6.52 (s, 1H), 3.24 (s, 3H).

Anal. Calcd. for $C_{21}H_{14}N_3O_3FS$: C, 61.91; H, 3.46 ; N, 10.31. Found: C, 61.75; H, 3.69; N, 10.15.

Example 164

N-[1-[3-Fluoro-4-(methylsulfonyl)phenyl]-5-[4-(1,3-thiazol-4-yl)phenyl]-1H-pyrazol-4-yl]acetamide (E)-1-(4-Bromophenyl)-3-(dimethylamino)-2-nitro-2-propen-1-one (step 1)

A mixture of 1-(4-bromophenyl)-2-nitroethanone (5.38 g, 0.022 mol, Seter J. et al., *Isr. J. Chem.*, 4, 7 (1966)) and N,N-dimethylfornamide dimethylacetal (2.9 g, 0.024 mol) and catalitic amount of p-TsOH in THF (100 mL) was refluxed for 10 h. The mixture was cooled to room temperature and concentrated in vacuo. The reaction mixture was purified by flash chromatography eluting with ethyl acetate/ hexane (1/1) to give title compound (2.8 g, 43%).

$^1$H-NMR (CDCl$_3$) δ: 8.35 (s, 1H), 7.68 (d, J=8.6 Hz, 2H), 7.58 (d, J=8.6 Hz, 2H), 3.38 (s, 3H), 2.77 (s, 3H).

5-(4-Bromophenyl)-1-[3-Fluoro-4-(methylsulfonyl) phenyl]-4-nitro-1H-pyrazole (step 2)

The title compound was prepared according to the procedure of Example 60 using (E)-1-(4-bromophenyl)-3-(dimethylamino)-2-nitro-2-propen-1-one from step1 instead of 4,4,4-trifluorro-1-[4-(2-fryl)phenyl]-1,3-butanedione.

$^1$H-NMR (CDCl$_3$) δ: 8.77 (s, 1H), 7.91 (t, J=8.2 Hz, 1H), 7.70 (d, J=8.6 Hz, 2H), 7.58 (dd, J=2.0, 10.7 Hz, 1H), 7.47 (d, J=8.6 Hz, 2H), 7.32 (dd, J=1.5, 8.1 Hz, 1H), 3.33 (s, 3H).

4-Amino-5-(4-bromophenyl)-1-[3-Fluoro-4-(methylsulfonyl)phenyl]-1H-pyrazole (step 3)

A mixture of 5-(4-bromophenyl)-1-[3-fluoro-4-(methylsulfonyl)phenyl]-4-nitro-1H-pyrazole from step2 (2.5 g, 5.7 mmol), iron powder (1.6 g, 28.4 mmol) and $NH_4Cl$ (30 mg, 0.57 mmol) in EtOH:$H_2O$ (40 mL: 10 mL) was refluxed for 1 h. After cooled to room temperature, the mixture was filtered by celite and washed with ethyl acetate and the filtrate was concentrated. Wataer (50 mL) was added to the resiual oil and extracted with ethyl acetate (80 mL),dried over $MgSO_4$, and concentarted in vacuo gave the title-compound (1.9 g, 82%).

$^1$H-NMR (CDCl$_3$) δ: 7.81 (t, J=8.2 Hz, 1H), 7.60 (d, J=8.2 Hz, 2H), 7.52 (s, 1H), 7.27 (dd, J=2.1, 11.4 Hz, 1H), 7.13 (d. J=8.2 Hz, 2H), 7.08 (dd, J=2.1, 8.6 Hz, 1H), 3.21 (s, 3H).

4-Amino-1-[3-fluoro-4-(methylsulfonyl)phenyl]-5-[4-(1,3-thiazol-4-yl)phenyl-1H-pyrazole (step 4)

The title compound was prepared according to the procedure of Example 151 using 4-amino-5-(4-bromophenyl)-1-[3-Fluoro-4-(methyl sulfonyl)phenyl]-1H-pyrazole from step3 instead of 1-(4-bromophenyl)-2-[3-fluoro-4-(methylsulfonyl)phenyl]-5-methyl-1H-pyrrole.

MS(EI): m/z 414 (M$^+$)

4-Amino-1-[3-fluoro-4-(methylsulfonyl)phenyl]-5-[4-(1,3-thiazol-4-yl)phenyl-1H-pyrazole (step 5)

To a solution of 4-amino-1-[3-fluoro-4-(methylsulfonyl)phenyl]-5-[4-(1,3-thiazol-4-yl) from step5 (240 mg, 0.58 mmol) and pyridine (0.15 mL, 1.7 mmol) in $CH_2Cl_2$ (20 mL), acetylchloride (0.050 mL, 0.69 mmol) was added at 0° C., and stirred for 1 h at room temperature. The mixture was washed with aqueous 2N HCl (20 mL), aqueous saturated $NaHCO_3$ (20 mL) and brine (20 mL), dried over $MgSO_4$, and concentarted in vacuo. The reaction mixture was purified by flash chromatography eluting with ethyl acetate/hexane (5/1). The resulting solid was recrystallized from ethyl acetate-hexane to give title compound (0.140 g, 53%).

mp: 225.2° C.

$^1$H-NMR (DMSO-d$_6$) d: 9.43 (s, 1H), 9.21 (d, J=1.8 Hz, 1H), 8.29 (d, J=1.8 Hz, 1H), 8.10 (s, 1H), 8.07 (d, J=8.6 Hz, 2H), 7.80 (m, 1H), 7.40–7.30 (m, 3H), 7.25–7.20 (m, 1H), 3.25 (s, 3H), 1.97 (s, 3H).

Anal. Calcd. for $C_{21}H_{17}N_4O_3FS_2$: C, 55.25; H, 3.75; N, 12.27. Found: C, 55.22; H, 3.98; N, 11.96.

Example 165

4-[3-Fluoro-4-(methylsulfonyl)phenyl]-3-[4-(1 3-thiazol-4-yl)phenyl]-2(5H)-furanone 3-(4-Bromophenyl)-4-[3-fluoro-4-(methylsulfonyl)phenyl]-2(5H)-furanone (step 1)

The title compound was prepared according to the procedure of Example 32 using 2-bromo-1-[3-fluoro-4-(methylsulfonyl)phenyl]ethanone (Lalezari, Iradj et al., J. Chem. Eng. Data, 11, 619 (1966)) instead of 2-bromo-1-[4-(methylsulfonyl)phenyl]ethanone, 4-bromophenylacetic acid instead of 4-(3-thienyl)phenylacetic acid.

$^1$H-NMR (CDCl$_3$) δ: 7.99 (t, J=7.2 Hz, 1H), 7.57 (d, J=8.6 Hz, 2H), 7.32–7.25 (m, 3H), 7.19 (d, J=1.5, 10.2 Hz, 1H), 5.16 (s, 2H), 3.25 (s, 3H).

4-[3-Fluoro-4-(methylsulfonyl)phenyl]1-3-[4-(1,3-thiazol-4-yl)phenyl]-2(5H)-furanone (step 2)

The title compound was prepared according to the procedure of Example 151 using 3-(4-bromophenyl)-4-[3-fluoro-4-(methylsulfonyl)phenyl]-2(5H)-furanone instead of 1-(4-bromophenyl)-2-[3-fluoro-4-(methylsulfonxyl)phenyl]-5-methyl-1H-pyrrole.

mp: 217.8° C.

$^1$H-NMR (CDCl$_3$) δ: 8.90 (d, J=2.0 Hz, 1H), 8.02–7.94 (m, 3H), 7.63 (d, J=2.0 Hz, 1H), 7.50 (d, J=8.6 Hz, 2H), 7.33 (dd, J=1.5, 8.2 Hz, 1H), 7.24 (dd, J=1.6, 10.5 Hz, 1H), 5.19 (s, 2H), 3.25 (s, 3H).

Anal. Calcd. for $C_{20}H_{14}NO_4FS_2$: C, 57.82; H, 3.40; N, 3.37. Found: C, 58.07; H, 3.63; N, 3.39.

Example 166

5,5-Dimethyl-4-[4-(methylsulfonyl)phenyl]-3-[4-(1,3-thiazol-4-yl)phenyl]-2(5H)-furanone (step 1)

3-(4-Bromophenyl)-5,5-dimethyl-4-[4-(methylsulfonyl)phenyl]-2(5H)-furanone

A mixture of [2-hydroxy-2-methyl-4-(methylsulfonyl)phenyl]propanone (1.5 g, 6.2 mmol, B. Cameron et al., WO 9619469), 4-bromophenylacetic acid (1.8 g, 8.1 mmol), 1-cyclohexyl-3-(2-morphorynoethyl)carbodiimide metho-p-toluenesulfonate (3.4 g, 8.1 mmol) and 4-(dimethylamino)pyridine (30 mg, 0.25 mmol) was stirred for 18 h at room temperature. 1,8-Diazabicyclo[5.4.0]undec-7-ene (1.9 mL, 12.7 mmol) was added and the mixture was refluxed for 3 h. After cooled to room temperature, $H_2O$ (50 mL) was added and extracted with $CH_2Cl_2$ (50 mL×2), washed with 2N aqueous HCl (50 mL), dried over $MgSO_4$, and concentarted in vacuo. The reaction mixture was purified by flash chromatography eluting with ethyl acetate/hexane (1/1) to give title compound (1.7 g, 65%).

$^1$H-NMR (CDCl$_3$) δ: 8.02 (d, J=8.6 Hz, 2H), 7.45–7.38 (m, 4H), 7.19 (d, J=8.7 Hz, 2H), 3.12 (s, 3H), 1.61 (s, 6H).

step 2

5,5-Dimethyl-4-[4-(methylsulfonyl)phenyl]-3-[4-(1,3-thiazol-4-yl)phenyl]-2(5H)-furanone The title compound was prepared according to the procedure of Example 151 using 3-(4-bromophenyl)-5,5-dimethyl-4-[4-(methylsulfonyl)phenyl]-2(5H)-furanone from step 1 instead of 1-(4-bromophenyl)-2-[3-fluoro-4-(methylsulfonyl)phenyl]-5-methyl-1H-pyrrole.

mp:215.8° C.

$^1$H-NMR (CDCl$_3$) δ: 8.85 (d, J=2.0 Hz, 1H), 8.01 (d, J=8.7 Hz, 2H), 7.83 (d, J=8.7 Hz, 2H), 7.55 (d, J=2.0 Hz, 1H), 7.47 (d, J=8.7 Hz, 2H), 7.41 (d, J=8.7 Hz, 2H), 3.12 (s, 3H), 1.63 (s, 6H).

Anal. Calcd. for $C_{22}H_{19}NO_4S_2$: C, 62.10; H, 4.50, N, 3.29. Found: C, 61.81; H, 4.68; N, 3.26.

Example 167

2-Fluoro-4-[5-oxo-4-[4-(1,3-thiazol-4-yl)phenyl]-2,5-dihydro-3-furanyl]benzenesulfonamide 4-Acetyl-2-(fluoro)benzenesulfonamide (step 1)

To a solution of 4-acetyl-2-fluoroaniline (5.0 g, 32.6 mmol, Krueger, G et al., Arzneim Forsch, 34, 11a, 1612 (1984)) in conc-HCl (24.0 mL), sodium nitrate (2.9 g, 42.4 mmol) in water (10 mL) was added at 0° C. After stirring for 1 h, the resultant yellow solution was added slowly to the suspension of copper (II) chloride dihydrate (1.7 g, 9.8 mmol) and sulfur dioxide (10 g, 156 mmol) in acetic acid (25 mL) at 0° C. The mixture was stirred for 30 min at 0° C. and poured into ice water (200 mL) and extracted with $CH_2Cl_2$ (80 mL×2). The extracts was cooled to 0°0 C. and 25% aqueous ammonia (70 mL) was added slowly and stirred for 1 h at room temperature. The mixture was concentrated and the residual solid was suspended with ether and collectted by filteration to give the title compound (3.3 g, 46%).

$^1$H-NMR (DMSO-d$_6$) δ: 7.97–7.87 (m, 3H), 7.79 (br s, 2H), 2.63 (s, 3H).

4-Bromoacetyl-2-(fluoro)benzenesulfonamide (step 2)

To a suspension of 4-acetyl-2-(fluoro)benzenesulfonamide from step1 (4.0 g, 18 mmol) in acetic acid (90 mL) was added dropwise a solution of bromine (2.9 g, 18 mmol) in acetic acid (10 mL) at 40° C. The mixture was heated at 70° C. for 4 h. After cooled to room temperature, the mixture was concentrated and the residual brown solid was rrecrystallized from ethyl acetate-hexane to give the title compound (3.2 g, 60%).

$^1$H-NMR (DMSO-d$_6$) δ: 8.20–7.92 (m, 3H), 7.90 (br s, 2H), 5.00 (s, 2H).

4-[4-(4-bromophenyl)-5-oxo-2,5-dihydro-3-furanyl]-2-(fluoro)benzenesulfonamide (step3)

The title compound was prepared according to the procedure of Example 32 using 4-bromoacetyl-2-(fluoro)

benzenesulfonamide from step 2 instead of [2-bromo-1-[4-methylsulfonyl) phenyl]ethanone, 4-bromophenylacetic acid instead of 4-(3-thienyl)phenylacetic acid.

MS (EI): m/z 411 (M⁺)

2-Fluoro-4-[5-oxo-4-[4-(1,3-thiazol-4-yl)phenyl-1-2,5-dihydro-3-furanyl]benzenesulfonamide (step4)

The title compound was prepared according to the procedure of Example 151 using 4-[4-(4-bromophenyl)-5-oxo-2,5-dihydro-3-furanyl]-2-(fluoro)benzenesulfonamide instead of 1-(4-bromophenyl)-2-[3-fluoro-4-(methylsulfonyl)phenyl]-5-methyl-1H-pyrrole.

mp: 194.2° C.

$^1$H-NMR (DMSO-d$_6$) δ: 9.22 (d, J=1.5 Hz, 1H), 8.26 (d, J=1.6 Hz, 1H), 8.06 (d, J=8.2 Hz, 2H), 7.83–7.72 (m, 3H), 7.52–7.42 (m, 3H), 7.35 (dd, J=1.6, 8.2 Hz, 1H), 5.41 (s, 2H).

Anal. Calcd. for C$_{19}$H$_{13}$N$_2$O$_4$FS$_2$: C, 54.80; H, 3.15; N, 6.73. Found: C, 54.79; H, 3.34; N, 6.62.

Example 168

4-[3-Fluoro-4-(methylsulfonyl)phenyl]-5-methyl-3-[4-(1,3-thiazol-4-yl) phenyl]isoxazole 3-(4-Bromophenyl)4-(3-fluoro-4-methylthiophenyl)-5-methyl-4,5-dihydro-5-isoxazolol (step 1)

To a solution of 1-(4-bromophenyl)-2-(3-fluoro-4-methylthiophenyl)ethanone (1.50 g, 4,42 mmol) in a mixture of ethanol (12 ml) and water (6 ml) were added hydroxylamine hydrochloride (615 mg, 8.84 mmol) and anhydrous sodium acetate (715 mg, 8.84 mmol) at room temperature. The mixture was heated for 2 h at 75° C. and then diluted with diethyl ether (200 ml), washed with water (50 ml×2) and saturated sodium bicarbonate (50 ml×2), and dried over magnesium sulfate. Removal of solvent gave 1.56 g (~100%) of 1-(4-bromophenyl)-2-(3-fluoro-4-methylthiophenyl)ethanone oxime as an orange solid.

To a solution of 1-(4-bromophenyl)-2-(3-fluoro-4-methylthiophenyl)ethanone oxime (1.56 g, 4,42 mmol) in tetrahydrofuran (10 ml) was added dropwise 9.7 ml (9.70 mmol) of 1 M lithium N,N-diisopropylamide in tetrahydrofuran and hexane, which was prepared from N,N-diisopropylamine and 1.6 M n-butyl lithium in hexane, over 0.5 h at −78~−50° C. After 1 h, a solution of N-acetyl imidazole (584 mg, 5.31 mmol) in tetrahydrofuran (10 ml) was added to the mixture at the same temperature. The resulting mixture was allowed to warm up to room temperature and stirred for further 1 h. Then, the mixture was acidified with 2M hydrochloric acid (~30 ml) and extracted with diethyl ether (150 ml). The separated organic layer was washed with saturated sodium bicarbonate (50 ml×2) and water (50 ml), dried over magnesium sulfate, and evaporated. The obtained oily residue was chromatographed on a column of silica gel (80 g) as eluting with ethyl acetate/hexane (1/4) to afford 632 mg (36%) of the title compound as a colorless oil.

$^1$H-NMR (CDCl$_3$) δ: 7.50–7.40 (4 H, m), 7.23–7.16 (1H, m), 6.94–6.79 (2 H, m), 4.43 (1H, s), 3.29 (1H, br s), 2.45 (3 H, s), 1.31 (3 H, s).

MS; 395 and 397 (M⁺).

3-(4-Bromophenyl)-4-(3-fluoro-4-methylthiophenyl)-5-methylisoxazole (Step 2)

A mixture of 3-(4-bromophenyl)-4-(3-fluoro-4-methylthiophenyl)-5-methyl-4,5-dihydro-5-isoxazolol (630 mg, 1.59 mmol) and p-toluenesulfonic acid monohydrate (274 mg, 1.59 mmol) in methanol (10 ml) was refluxed for 2 h. The mixture was evaporated, dissolved in ethyl acetate (100 ml), washed with saturated sodium bicarbonate (50 ml×2), and dried over anhydrous sodium sulfate. Removal of solvent gave 583 mg (97%) of the title compound as a pale yellow oil.

$^1$H-NMR (CDCl$_3$) δ: 7.51–7.45 (2 H, m), 7.34–7.20 (3 H, m), 6.92–6.82 (2 H, m), 2.50 (3H, s), 2.45 (3 H, s).

MS; 377 and 379 (M⁺).

3-(4-Bromophenyl)-4-[3-fluoro-4-(methylsulfonyl)phenyl]-5-methylisoxazole (step 3)

To a solution of 3-(4-bromophenyl)-4-(3-fluoro-4-methylthiophenyl)-5-methylisoxazole (580 mg, 1.53 mmol) in dichloromethane (20 ml) was added m-chloroperbenzoic acid (70% purity, 1.13 g, 4.60 mmol) at 0° C. The mixture was allowed to warm to room temperature and stirred for 2 h. The excess peracid was quenched with saturated sodium sulfite (~2 ml) until the color of KI-starch paper did not change. The mixture was diluted with diethyl ether (100 ml), washed with saturated sodium bicarbonate (50 ml×2), and dried over magnesium sulfate. Removal of solvent gave a colorless oily residue, which was chromatographed on a column of silica gel (60 g) as eluting with ethyl acetate/hexane (1/2) to afford 634 mg (~100%) of the title compound as a colorless foam.

$^1$H-NMR (CDCl$_3$) δ: 7.98 (1H, t, J=7.7 Hz), 7.56–7.50 (2 H, m), 7.30–7.24 (2 H, m), 7.15–7.04 (2 H, m), 3.29 (3 H, s), 2.52 (3 H, s).

MS; 409 and 411 (M⁺).

4-[3-Fluoro-4-(methylsulfonyl)phenyl]-5-methyl-3-[4-(1 3-thiazol-4-yl)phenyl]isoxazole (step 4)

A mixture of 3-(4-bromophenyl)4-[3-fluoro-4-(methylsulfonyl)phenyl]-5-methylisoxazole (219 mg, 0.53 mmol), tributyl(1,3-thiazol-4-yl)tin (200 mg, 0.53 mmol) and tetrakis(triphenylphosphine)palladium (62 mg, 0.053 mmol) in toluene (5 ml) was refluxed for 26 h. The mixture was evaporated and the obtained residue was chromatographed on a column of silica gel (40 g) as eluting with ethyl acetate/hexane (1/2) to give 198 mg of a white solid which was recrystallized from ethyl acetate/hexane to afford 128 mg (58%) of the title compound.

m.p.: 130° C.

$^1$H-NMR (CDCl$_3$) δ: 8.90 (1H, d, J=2.0 Hz), 8.01–7.93 (3 H, m), 7.62 (1H, d, J=1.8 Hz), 7.49–7.43 (2 H, m), 7.17 (1H, dd, J=1.5 and 8.1Hz), 7.09 (1H, dd, J=1.5 and 10.5 Hz), 3.27 (3 H, s), 2.53 (3 H, s).

MS; 414 (M⁺).

Example 169

5-[3-Fluoro-4-(methylsulfonyl)phenyl]-2-methyl-4-[4-(1,3-thiazol-4-yl)phenyl]-1,3-oxazole

[3-Fluoro-4-(methylsulfanyl)phenyl]methanol (Step 1)

The mixture of 3-fluoro-4-(methylsulfanyl)benzaldehyde (19.44 g, 114.2 mmol) and sodium borohydride (2.1 g, 55.46 mmol) in methanol (200 mL) was stirred at room temperature for 2 hour. Water was added to the mixture, and the mixture was evaporated, diluted with ethyl acetate (300 mL), washed with water (100 mL), dried over MgSO$_4$, and concentrated in vacuo. The residue was purified by flash chromatography on silica gel eluting with ethyl acetate/hexane (1/4) to provide the subtitle compound (19.91 g, 100% yield) as an oil.

$^1$H-NMR (CDCl$_3$) δ: 7.26–7.29 (m, 1H), 7.06–7.23 (m, 2H), 4.67 (br s, 2H), 2.47 (s, 3H).

4-(Bromomethyl)-2-fluoro-1-(methylsulfanyl)benzene (Step 2)

The mixture of [3-fluoro-4-(methylsulfanyl)phenyl] methanol (9.00 g, 52.26 mmol) and carbon tetrabromide (19.06 g, 57.49 mmol) in CH$_2$Cl$_2$ (200 mL) was added triphenylphosphine (15.08 g, 57.49 mmol) at 0° C. After 1 hour, the mixture was concentrated in vacuo. The residue was purified by flash chromatography on silica gel eluting with ethyl acetate/hexane (1/10) to provide the subtitle compound (12.16 g, 94% yield) as an oil.

$^1$H-NMR (CDCl$_3$) δ: 7.06–7.24 (m, 3H), 4.44 (s, 2H), 2.47 (s, 3H).

1-(4-Bromophenyl)-2-[3-fluoro-4-(methylsulfanyl)phenyl]-1-ethanone (Step 3)

To the mixture of 4-bromobenzoyl chloride (10.81 g, 49.26 mmol), zinc (4,40 g, 67.24 mmol) and tetrakis(triphenylphosphine)palladium(0) (2.99 g, 2.586 mmol) in DME (250 mL) was added dropwise the solution of 4-(bromomethyl)-2-fluoro-1-(methylsulfanyl)benzene (12.16 g, 51.72 mmol) in DME (120 mL) at room temperature. After 2.5 hour, the mixture was filtered through celite, the filtrate was evaporated, diluted with ethyl acetate (300 mL), washed with water (100 mL), brine (100 mL), dried over sodium sulfate, and concentrated in vacuo. The residue was washed with ethyl acetate-isopropylether, to give the subtitle compound (12.16 g, 73% yield) as a solid.

$^1$H-NMR (CDCl$_3$) δ: 7.85 (d, J=8.6 Hz, 2H), 7.61 (d, J=8.4 Hz, 2H), 7.21 (d, J=7.9 Hz, 1H), 6.93–7.01 (m, 2H), 4.21 (s, 2H), 2.45 (s, 3H).

1-(4-Bromophenyl)-2-[3-fluoro-4-(methylsulfonyl)phenyl]-1-ethanone (Step 4)

To a stirred solution of 1-(4-bromophenyl)-2-[3-fluoro-4-(methylsulfanyl)phenyl]-1-ethanone (1.91 g, 5.636 mmol) in acetic acid (20 mL) was added lead tetraacetate (2.75 g, 6.200 mmol) at room temperature. The mixture was heated at reflux temperature for 2 hours, and cooled down to room temperature. The mixture was evaporated, diluted with ethyl acetate (200 mL), washed with saturated NaHCO$_3$ solution (100 mL), water (100 mL), dried over MgSO$_4$, and concentrated in vacuo. To a stirred solution of the residue (1.81 g,) in CH$_2$Cl$_2$ (10 mL) was added 3-chloroperoxybenzoic acid (1.88 g, 7.643 mmol) at 0° C. The mixture was allowed to warm to room temperature and stirred for 1.5 hour. The mixture was poured into saturated NaHCO$_3$ solution (50 mL), extracted with ethyl acetate (150 mL). The organic layer was washed with saturated NaHCO$_3$ solution (50 mL), water (50 mL), dried over MgSO$_4$ and concentrated in vacuo. The residue was purified by flash chromatography on silica gel eluting with ethyl acetate/hexane (1/2) to provide the subtitle compound (1.02 g, 49% yield) as a solid.

$^1$H-NMR (CDCl$_3$) δ: 7.93 (t, J=7.6 Hz, 1H), 7.86 (d, J=8.9 Hz, 2H), 7.66 (d, J=8.7 Hz, 2H), 7.15–7.23 (m, 2H), 4.35 (s, 2H), 3.22 (s, 3H).

2-Acetoxy-1-(4-bromophenyl)-2-[3-fluoro-4-(methylsulfonyl)phenyl]-1-ethanone (Step 5)

The mixture of 1-(4-bromophenyl)-2-[3-fluoro-4-(methylsulfonyl)phenyl]-1-ethanone (1.02 g, 2.748 mmol) and lead tetraacetate (1.34 g, 3.023 mmol) in acetic acid (15 mL) was heated at reflux temperature for 8 hours, and cooled down to room temperature. The mixture was evaporated, poured in to ethyl acetate (50 mL) and saturated NaHCO$_3$ solution (50 mL). The formed precipitate was removed by filtration. The filtrate was extracted with ethyl acetate (100 mL), washed with water (50 mL), brine (50 mL), dried over MgSO$_4$, and concentrated in vacuo. The residue was purified by flash chromatography on silica gel eluting with ethyl acetate/hexane (1/2) to provide the subtitle compound (743.7 mg, 63% yield) as a solid.

$^1$H-NMR (CDCl$_3$) δ: 7.97 (t, J=7.3 Hz, 1H), 7.79 (d, J=8.7 Hz, 2H), 7.62 (d, J=8.7 Hz, 2H), 7.36–7.43 (m, 2H), 6.81 (s, 1H), 3.20 (s, 3H), 2.23 (s, 3H).

4-(4-Bromophenyl)-5-[3-fluoro-4-(methylsulfonyl)phenyl]-2-methyl-1,3-oxazole (Step 6)

The mixture of 2-acetoxy-1-(4-bromophenyl)-2-[3-fluoro-4-(methylsulfonyl)phenyl]-1-ethanone (743.7 mg, 1.733 mmol) and ammonium acetate (333.9 mg, 4.333 mmol) in acetic acid (15 mL) was heated at reflux temperature for 2.5 hours, and cooled down to room temperature. The mixture was evaporated, diluted with ethyl acetate (100 mL), washed with saturated NaHCO$_3$ solution (100 mL×2), water (50 mL), brine (50 mL), dried over MgSO$_4$, and concentrated in vacuo. The residue was purified by flash chromatography on silica gel eluting with ethyl acetate/hexane (1/2) to provide the subtitle compound (447.1 mg, 63% yield) as a solid.

$^1$H-NMR (CDCl$_3$) δ: 7.92 (t, J=7.2 Hz, 1H), 7.43–7.59 (m, 6H), 3.25 (s, 3H), 2.59 (s, 3H).

5-[3-Fluoro-4-(methylsulfonyl)phenyl]-2-methyl-4-[4-(1,3-thiazol-4-yl)phenyl]-1,3-oxazole (step 7)

The title compound was prepared according to the procedure of Example 168 (step 4) using 4-(4-bromophenyl)-5-[3-fluoro-4-(methylsulfonyl)phenyl]-2-methyl-1,3-oxazole instead of 3-(4-bromophenyl)-4-[3-fluoro-4-(methylsulfonyl)phenyl]-5-methylisoxazole.

mp: 196–197° C.

$^1$H-NMR (CDCl$_3$) δ: 8.91 (d, J=2.0 Hz, 1H), 8.02 (d, J=8.2 Hz, 2H), 7.91 (t, J=8.2 Hz, 1H), 7.69 (d, J=8.2 Hz, 2H), 7.63 (d, J=1.8 Hz, 1H), 7.58 (dd, J=1.5, 8.2 Hz, 1H), 7.50 (dd, J=1.5, 11.2 Hz, 2H), 3.24 (s, 3H), 2.61 (s, 3H).

Anal. Calcd. for C$_{20}$H$_{15}$N$_2$O$_3$F$_1$S$_2$: C, 57.96; H, 3.65; N, 6.76. Found: C, 57.83; H, 3.76; N, 6.65.

Example 170

4-[3-Fluoro-4-(methylsulfonyl)phenyl]-5-methyl-3-[3-methyl-4-(1,3-thiazol-4-yl(phenyl]isoxazole 1-(4-Bromo-3-methylphenyl)-2-(3-fluoro-4-methylthiophenyl)ethanone. (step 1)

The title compound was prepared according to the procedure of step 1 in the Example 169 using 4-bromo-3-methylbenzoyl chloride, which was prepared according to the literature (G. Cignarella et al., J. Pharmaco. Ed. Sci., 1983, 38, 187–198.), instead of 4-bromobenzoyl chloride.

$^1$H-NMR (CDCl$_3$) δ: 7.84 (1 H, s), 7.64–7.62 (2 H, m), 7.23 (1 H, t, J=7.9 Hz), 7.01–6.92 (2 H, m), 4.21 (2 H, s), 2.46 (3 H, s), 2.45 (3 H, s).

3-(4-Bromo-3-methylphenyl)-4-(3-fluoro-4-methylthiophenyl)-5-methyl-4,5-dihydro-5-isoxazolol. (step 2)

The title compound was prepared according to the procedure of step 1in the Example 168 using 1-(4-bromo-3-methylphenyl)-2-(3-fluoro-4-methylthiophenyl)ethanone, instead of 1-(4-bromophenyl)-2-(3-fluoro-4-methylthiophenyl)ethanone.

$^1$H-NMR (CDCl$_3$) δ: 7.54 (1 H, d, J=2.1 Hz), 7.44 (1 H, d, J=8.4 Hz), 7.22–7.15 (2 H), m), 6.93–6.79 (2 H, m), 4.43 (1 H, s), 3.49 (1 H, br s), 2.44 (3 H, s), 2.34 (3 H, s), 1.30 (3 H, s).

3-(4-Bromo-3-methylphenyl)-4-(3-fluoro-4-methylthiophenyl)-5-methylisoxazole. (step 3)

The title compound was prepared according to the procedure of step 2 in the Example 168 using 3-(4-bromo-3-methylphenyl)-4-(3-fluoro-4-methylthiophenyl)-5-methyl-4,5-dihydros-5-isoxazolol, instead of 3-(4-bromophenyl)-4-(3-fluoro-4-methylthiophenyl)-5-methyl-4,5-dihydro-5-isoxazolol.

$^1$H-NMR (CDCl$_3$) δ: 7.47 (1 H, d, J=8.2 Hz), 7.42 (1 H, d, J=2.0 Hz), 7.22 (1 H, d, J=7.7 Hz), 6.98 (1 H, dd, J=2.1 and 8.2 Hz), 6.92–6.84 (2 H, m), 2.50 (3 H, s), 2.45 (3 H, s), 2.36 (3 H, s).

3-(4-Bromo-3-methylphenyl)-4-[3-fluoro-4-(methylsulfonyl)phenyl]-5-methylisoxazole. (step 4)

The title compound was prepared according to the procedure of step 3 in the Example 168 using 3-(4-bromo-3- methylphenyl)-4-(3-fluoro-4-methylthiophenyl)-5-methylisoxazole, instead of 3-(4-bromophenyl)-4-(3-fluoro-4-methylthiophenyl)-5-methylisoxazole.

$^1$H-NMR (CDCl$_3$) δ: 7.97 (1 H, t, J=7.7 Hz), 7.51 (1 H, d, J=8.2 Hz), 7.40 (1 H, d, J=1.8 Hz), 7.13 (1 H, dd, J=1.5 and 8.1 Hz), 7.07 (1 H, dd, J=1.3 and 10.4 Hz), 6.92 (1 H, dd, J=1.6 and 8.2 Hz), 3.27 (3 H, s), 2.52 (3 H, s), 2.39 (3 H, s).

4-[3-Fluoro-4-(methylsulfonyl)phenyl]-5-methyl-3-[3-methyl-4-(1,3-thiazol-4-yl)phenyl]isoxazole. (step 5)

The title compound was prepared according to the procedure of step 4 in the Example 168 using 3-(4-bromo-3-methylphenyl)-4-[3-fluoro-4-(methylsulfonyl)phenyl]-5-methylisoxazole, instead of 3-(4-bromophenyl)-4-[3-fluoro-4-(methylsulfonyl)phenyl]-5-methylisoxazole.

m.p.: 99.5° C. (from dichloromethane/diisopropyl ether/hexane)

$^1$H-NMR (CDCl$_3$) δ: 8.90 (1 H, d, J=2.0 Hz), 7.96 (1 H, t, J=7.6 Hz), 7.60 (1 H, d, J=8.1 Hz), 7.46 (1 H, br s), 7.40 (1 H, d, J=2.0 Hz), 7.20–7.08 (3 H, m), 3.28 (3 H, s), 2.53 (3 H, s), 2.45 (3 H, s).

MS; 428 (M$^+$).

Example 171

4-{5-Methyl-3-[4-(1,3-thiazol-4-yl)phenyl]-4-isoxazoly}benzenesulfonamide 1-(4-Bromophenyl)-2-phenylethanone. (step 1)

The title compound was prepared according to the procedure of step 1 in the Example 169 using benzyl bromide and 4-bromo-3-methylbenzoyl chloride, instead of 4-bromobenzoyl chloride.

$^1$H-NMR (CDCl$_3$) δ: 7.90–7.83 (2 H, m), 7.62–7.56 (2 H, m), 7.38–7.22 (5 H, m), 4.25 (2 H, s).

3-(4-Bromophenyl)-5-methyl-4-phenyl-4,5-dihydro-5-isoxazolol. (step 2)

The title compound was prepared according to the procedure of step 1 in the Example 168 using 1-(4-bromophenyl)-2-phenylethanone, instead of 1-(4-bromophenyl)-2-(3-fluoro-4-methylthiophenyl)ethanone.

m.p.; 153° C. (from ethyl acetate/hexane)

$^1$H-NMR (CDCl$_3$) δ: 7.51–7.27 (7 H, m), 7.17–7.08 (2 H, m), 4.47 (1 H, s), 3.12 (1 H, s), 1.28 (3 H, s).

3-(4-Bromophenyl)-5-methyl-4-phenylisoxazole. (step 3)

The title compound was prepared according to the procedure of step 2 in the Example 168 using 3-(4-bromophenyl)-5-methyl-4-phenyl-4,5-dihydro-5-isoxazolol, instead of 3-(4-bromophenyl)-4-(3-fluoro-4-methylthiophenyl)-5-methyl-4,5-dihydro-5-isoxazolol.

$^1$H-NMR (CDCl$_3$) δ: 7.52–7.13 (9 H, m), 2.45 (3 H, s).

4-[3-(4-Bromophenyl)-5-methyl-4-isoxazolyl]benzenesulfonamide. (step 4)

To stirred chlorosulfonic acid (5 ml) was added 3-(4-bromophenyl)-5-methyl-4-phenylisoxazole (469 mg, 1.49 mmol) at −78° C. The mixture was allowed to warm up to room temperature and stirred for further 1 h. The resulting black mixture was poured into ice-conc. ammonia water (200 ml) carefully and extracted with ethyl acetate (150 ml). The organic layer was washed with water (50 ml×2), dried over anhydrous sodium sulfate, and evaporated. The obtained residue was chromatographed on a column of silica gel (60 g) as eluting with ethyl acetate/hexane (1/1) to afford 512 mg (87%) of the title compound as a foam.

$^1$H-NMR (CDCl$_3$) δ: 7.98–7.91 (2 H, m), 7.52–7.46 (2 H, m), 7.34–7.24 (4 H, m), 4.97 (2 H, br s), 2.49 (3 H, s).

4-{5-Methyl-3-[4-(1,3-thiazol-4-yl)phenyl]-4-isoxazolyl}benzenesulfonamide. (step 5)

The title compound was prepared according to the procedure of step 4 in the Example 168 using 4-[3-(4-bromophenyl)-5-methyl-4-isoxazolyl]benzenesulfonamide, instead of 3-(4-bromophenyl)-4-[3-fluoro-4-(methylsulfonyl)phenyl]-5-methylisoxazole.

m.p.: 112–115° C. (from ethyl acetate/hexane)

$^1$H-NMR (CDCl$_3$) δ: 8.88 (1 H, d, J=2.0 Hz), 7.97–7.88 (4 H, m), 7.59 (1 H, d, J=2.0 Hz), 7.50–7.43 (2 H, m), 7.39–7.32 (2 H, m), 4.89 (2 H, br s), 2.50 (3 H, s).

MS; 397 (M$^+$).

Example 172

2-Fluoro-4-{5-methyl-3-[4-(1,3-thiazol-4-yl)phenyl]-4-isoxazolyl}benzenesulfonamide 1-(4-Bromophenyl)-2-(3-fluorophenyl)ethanone. (step 1)

The title compound was prepared according to the procedure of step 1 in the Example 169 using 3-fluorobenzyl bromide and 4-bromobenzoyl chloride.

$^1$H-NMR (CDCl$_3$) δ: 7.89–7.83 (2 H, m), 7.65–7.59 (2 H, m), 7.34–7.25 (1 H, m), 7.06–6.92 (3 H, m), 4.25 (2 H, s).

3-(4-Bromophenyl)-4-(3-fluorophenyl)-5-methyl-4,5-dihydro-5-isoxazolol. (step 2)

The title compound was prepared according to the procedure of step 1in the Example 168 using 1-(4-bromophenyl)-2-(3-fluorophenyl)ethanone, instead of 1-(4-bromophenyl)-2-(3-fluoro-4-methylthiophenyl)ethanone.

$^1$H-NMR (CDCl$_3$) δ: 7.50–7.26 (5 H, m), 7.05–6.82 (3 H, m), 4.46 (1 H, s), 3.16 (1 H, br s), 1.30 (3 H, s).

3-(4-Bromophenyl)-4-(3-fluorophenyl)-5-methylisoxazole. (step 3)

The title compound was prepared according to the procedure of step 2 in the Example 168 using 3-(4-bromophenyl)-4-(3-fluorophenyl)-5-methyl-4,5-dihydro-5-isoxazolol, instead of 3-(4-bromophenyl)-4-(3-fluoro-4-methylthiophenyl)-5-methyl-4,5-dihydro-5-isoxazolol.

$^1$H-NMR (CDCl$_3$) δ: 7.50–7.26 (5 H, m), 7.11–6.85 (3 H, m), 2.46 (3 H, s).

2-[3-(4-Bromophenyl)-5-methyl-4-isoxazolyl]-4-fluorobenzenesulfonamide and 4-[3-(4-Bromophenyl)-5-methyl-4-isoxazolyl]-2-flourobenzenesulfonamide. (step 4)

To stirred chlorosulfonic acid (5 ml) was added 3-(4-bromophenyl)-4-(3-fluorophenyl)-5-methylisoxazole (618 mg, 1.86 mmol) at −78° C. The mixture was allowed to warm up to 70° C., and stirred for further 1 h. The resulting black mixture was poured into ice-conc. ammonia water (200 ml) carefully and extracted with ethyl acetate (150 ml). The organic layer was washed with water (50 ml×2), dried over anhydrous sodium sulfate, and evaporated. The obtained residue was chromatographed on a column of silica gel (60 g) as eluting with ethyl acetate/hexane (1/1) to afford, first, 307 mg (40%) of 2-[3-(4-bromophenyl)-5-methyl-4-isoxazolyl]-4-flourobenzenesulfonamide as a pale yellow solid.

$^1$H-NMR (CDCl$_3$) δ: 8.23 (1 H, dd, J=5.4 and 8.9 Hz), 7.46–7.40 (2 H, m), 7.33–7.25 (3 H, m), 7.04 (1 H, dd, J=2.6 and 8.4 Hz), 4.52 (2 H, br s), 2.33 (3 H, s).

The second fractions gave 304 mg (40%) of 4-[3-(4-bromophenyl)-5-methyl-4-isoxazolyl]-2-fluorobenzenesulfonamide as a colorless oil.

$^1$H-NMR (CDCl$_3$) δ: 7.91 (1 H, dd, J=7.6 and 8.4 Hz), 7.55–7.48 (2 H, m), 7.29–7.23 (2 H, m), 7.09–7.00 (2 H, m), 5.30 (2 H, br s), 2.50 (3 H, s).

2-Fluoro-4-{5-methyl-3-[4-(1,3-thiazol-4-yl)phenyl]-4-isoxazolyl}benzenesulfonamide. (step 5)

The title compound was prepared according to the procedure of step 4 in the Example 168 using 4-[3-(4-bromophenyl)-5-methyl-4-isoxazolyl]-2-fluorobenzenesulfonamide, instead of 3-(4-bromophenyl)-4-[3-fluoro-4-(methylsulfonyl)phenyl]-5-methylisoxazole.

m.p.: 216° C. (from ethyl acetate/hexane)

$^1$H-NMR (DMSO-d$_6$) δ: 9.11 (1 H, d, J=1.8 Hz), 8.16 (1 H, d, J=1.8 Hz), 7.98–7.92 (2 H, m), 7.70 (1 H, t, J=7.9 Hz), 7.62 (2 H, br s), 7.37–7.31 (2 H, m), 7.28 (1 H, dd, J=1.5 and 11.2 Hz), 7.10 (1 H, dd, J=1.6 and 8.1 Hz), 2.40 (3 H, s). MS; 415 (M$^+$).

Example 173

5-[3-Fluoro-4-(methylsulfonyl)phenyl]-2-methyl-4-[3-methyl-4-(1,3-thiazol-4-yl)phenyl]-1,3-oxazole 1-(4-Bromo-3-methylphenyl)-2-[3-fluoro-4-(methylsulfonyl)phenyl]-1-ethanone (Step 1)

To a stirred solution of 1-(4-bromo-3-methylphenyl)-2-[3-fluoro-4-(methylsulfanyl)phenyl]-1-ethanone (1.50 g, 4.246 mmol) in CH$_2$Cl$_2$ (50 mL) was added 3-chloroperoxybenzoic acid (2.62 g, 10.62 mmol) at 0° C. The mixture was allowed to warm to room temperature and stirred for 1.5 hour. The mixture was poured into saturated NaHCO$_3$ solution (50 mL), extracted with ethyl acetate (100 mL). The organic layer was washed with water (50 mL), brine (50 mL), dried over MgSO$_4$ and concentrated in vacuo. The residue was purified by flash chromatography on silica gel eluting with ethyl acetate/hexane (1/2) to provide the subtitle compound (1.21 g, 74% yield) as a solid.

$^1$H-NMR (CDCl$_3$) δ: 7.93 (t, J=7.6 Hz, 1H), 7.85 (s, 1H), 7.67 (s, 2H), 7.15–7.22 (m, 2H), 4.34 (s, 2H), 3.22 (s, 3H), 2.48 (s, 3H).

2-Acetoxy-1-(4-bromo-3-methylphenyl)-2-[3-fluoro-4-(methylsulfonyl)phenyl]-1-ethanone (Step 2)

The title compound was prepared according to the procedure of Example 169 (step 5).

$^1$H-NMR (CDCl$_3$) δ: 7.96 (t, J=7.7 Hz, 1H), 7.78 (s, 2H), 7.59–7.65 (m, 2H), 7.35–7.43 (m, 2H), 6.82 (s, 1H), 3.20 (s, 3H), 2.44 (s, 3H), 2.23 (s, 3H).

4-(4-Bromo-3-methylphenyl)-5-[3-fluoro-4-(methylsulfonyl)phenyl]-2-methyl-1,3-oxazole (Step 3)

The title compound was prepared according to the procedure of Example 169 (step 6).

$^1$H-NMR (CDCl$_3$) δ: 7.91 (t, J=7.6 Hz, 1H), 7.39–7.79 (m, 5H), 3.25 (s, 3H), 2.59 (s, 3H), 2.43 (s, 3H).

5-[3-Fluoro-4-(methylsulfonyl)phenyl]-2-methyl-4-[3-methyl-4-(1,3-thiazol-4-yl)phenyl]-1,3-oxazole (step 4)

The title compound was prepared according to the procedure of Example 168 mp: 177–178° C.

$^1$H-NMR (CDCl$_3$) δ: 8.92 (d, J=2.0 Hz, 1H), 7.91 (t, J=7.4 Hz, 1H), 7.69 (d, J=7.9 Hz, 1H), 7.46–7.61 (m, 4H), 7.42 (d, J=2.0 Hz, 1H), 3.25 (s, 3H), 2.61 (s, 3H), 2.50 (s, 3H).

Anal. Calcd. for C$_{21}$H$_{27}$N$_2$O$_3$F$_1$S$_2$: C, 58.86; H, 4.00; N, 6.54. Found: C, 58.51; H, 4.15; N, 6.43.

Example 174

2-Fluoro-4-[5-[3-hydroxy-4-(1,3-thiazol-4-yl)phenyl]-3-(trifluoromethyl)-1H-pyrazole-1-yl]benzenesulfonamide 4,4,4-Trifluoro-1-[3-hydroxy-4-(1,3-thiazol-4-yl)phenyl]-1,3-butanedione (step 1)

To a stirred solution of 4,4,4-trifluoro-1-[3-methoxy-4-(1,3-thiazol-4-yl)phenyl]-1,3-butanedione (395 mg, 1.2 mmol) in DMF (6 ml) was added sodium thiomethoxide (420 mg, 6.0 mmol) and the mixture was heated at 120° C. for 3 hours. The mixture was cooled down to room temperature, and poured into water. The whole was extracted with ethyl acetate. The organic layer was washed with brine, dried over MgSO$_4$, and concentrated in vacuo to give title compound (378 mg, 99% yield).

$^1$H-NMR (DMSO-d$_6$) δ: 10.92 (s, 1H), 9.24 (d, J=2 Hz, 1H), 8.36 (d, J=2 Hz, 1H), 8.16 (d, J=8 Hz, 1H), 7.53–7.45 (m, 2H), 6.27 (s, 1H).

2-Fluoro-4-[5-[3-hydroxy-4-(1,3-thiazol-4-yl)phenyl]-3-(trifluoromethyl)-1H-pyrazol-1-yl]benzenesulfonamide (step 2)

The title compound was prepared according to the procedure of Example 60 using 4,4,4-trifluoro-1-[3-hydroxy-4-(1,3-thiazol-4-yl)phenyl]-1,3-butanedione instead of 4,4,4-trifluoro-1-[4-(2-furyl)phenyl]-1,3-butanedione, and using (2-fluoro-4-sulfamoylphenyl)hydrazine hydrochloride instead of (2-fluoro-4-methylsulfonylphenyl)hydrazine hydrochloride.

mp: 224–226° C.

$^1$H-NMR (CDCl$_3$) δ: 8.97 (d, J=2 Hz, 1H), 7.85–7.79 (m, 1H), 7.69 (d, J=2 Hz, 1H), 7.65 (d, J=8 Hz, 1H), 7.37 (dd, J=11, 2 Hz, 1H), 7.19 (dd, J=8, 2 Hz, 1H), 6.98 (d, J=2 Hz, 1H), 6.80 (s, 1H), 6.71 (dd, J=8, 2 Hz, 1H), 5.35 (s, 2H).

Anal. Calcd. for C$_{19}$H$_{12}$F$_4$N$_4$O$_3$S$_2$ 1/10 Hexane+1/10 H$_2$O: C, 47.57; H, 2.77; N, 11.32 Found: C, 47.61; H, 2.91; N, 10.93.

Example 175

2-Fluoro-4-[5-[3-methoxy-4-(1,3-thiazol-4-yl)phenyl]-3-(trifluoromethyl)-1H-pyrazol-1-yl]benzenesulfonamide The title compound was prepared according to the procedure of Example 107 using (2-fluoro-4-sulfamoylphenyl)hydrazine hydrochloride instead of (2-fluoro-4-methylsulfonylphenyl)hydrazine hydrochloride.

mp: 97–99° C.

$^1$H-NMR (CDCl$_3$) δ: 8.84 (d, J=2 Hz, 1H), 8.29 (d, J=8 Hz, 1H), 8.07 (d, J=2 Hz, 1H), 7.87–7.81 (m, 1H), 7.38 (dd, J=11.2 Hz, 1H), 7.20 (dd, J=9, 1 Hz, 1H), 6.93–6.89 (m, 2H), 6.84 (s, 1H), 5.31 (s, 2H), 3.88 (s, 3H).

Anal. Calcd. for C$_{20}$H$_{14}$F$_4$N$_4$O$_3$S$_2$ Ethyl Acetate: C, 49.14; H, 3.78; N, 9.55. Found: C, 48.84; H, 3.63; N, 9.81.

Example 176

2-Fluoro-4-[5-[4-(1,3-thiazol-4-yl)-3-(trifluoromethyl)phenyl]-3-(trifluoromethyl)-1H-pyrazol-1-yl]benzenesulfonamide 4,4,4-Trifluoro-1-[4-bromo-3-(trifluoromethyl)phenyl]-1,3-butanedione (step 1)

The title compound was prepared according to the procedure of Example 94 (step 3) using 1-[4-bromo-3-(trifluoromethyl)phenyl]-1-ethanone instead of 1-[4-(1,3-oxazol-4-yl)phenyl]-1-ethanone. The compound was used for next reaction without purification.

2-Fluoro-4-[5-[4-bromo-3-(trifluoromethyl)phenyl]-3-(trifluoromethyl)-1H-pyrazol-1-yl]benzenesulfonamide (step 2)

The title compound was prepared according to the procedure of Example 60 using 4,4,4-trifluoro-1-[4-bromo-3-(trifluoromethyl)phenyl]-1,3-butanedione instead of 4,4,4-trifluoro-1-[4-(2-furyl)phenyl]-1,3-butanedione, and using (2-fluoro-4-sulfamoylphenyl)hydrazine hydrochloride instead of (2-fluoro-4-methylsulfonylphenyl)hydrazine hydrochloride.

$^1$H-NMR (DMSO-d$_6$) δ: 7.96–7.86 (m, 5H), 7.63 (dd, J=11, 2 Hz, 1H), 7.49–7.36 (m, 3H).

2-Fluoro-4-[5-[4-(1,3-thiazol-4-yl)-3-(trifluoromethyl)phenyl]-3-(trifluoromethyl)-1H-pyrazol-1-yl]benzenesulfonamide (step 3)

To a stirred solution of 2-fluoro-4-[5-[4-bromo-3-(trifluoromethyl)phenyl]-3-(trifluoromethyl)-1H-pyrazol-1- yl]benzenesulfonamide (308 mg, 0.58 mmol) in dioxane (5 ml) was added 4-(tributylstannyl)thiazole (260 mg, 0.70 mmol), tetrakis(triphenylphosphine)palladium (67 mg, 0.058 mmol), lithium chloride (61 mg, 1.45 mmol), and the mixture was heated at reflux temperature for 16 hours. The reaction mixture was cooled down to room temperature, and diluted with ethyl acetate. The whole was washed with saturated potassium fluoride aqueous solution, and the precipitate was removed by filteration through celite. The resulting solution was extracted with ethyl acetate. The organic layer was washed with brine, dried over MgSO$_4$, and concentrated in vacuo. The residue was purified by flash chromatography eluting with ethyl acetate-hexane (1:2) to give title compound (56 mg, 18% yield).

mp: 140–142° C.

$^1$H-NMR (CDCl$_3$) δ: 8.90 (d, J=2 Hz, 1H), 7.90–7.84 (m, 1H), 7.78 (d, J=2 Hz, 1H), 7.72 (d, J=8 Hz, 1H), 7.56 (d, J=2 Hz, 1H), 7.42–7.40 (m, 1H), 7.37 (d, J=2 Hz, 1H), 7.14 (dd, J=9, 2 Hz, 1H), 6.90 (s, 1H), 5.57 (s, 2H).

Anal. Calcd. for C$_{20}$H$_{11}$F$_7$N$_4$O$_2$S$_2$ 1/10 Hexane: C, 45.39; H, 2.29; N, 10.28. Found: C, 45.25; H, 2.28; N, 10.17.

Example 177

4-{2-Ethyl-4-[1-[3-Fluoro-4-(methylsulfonyl) phenyl]-3-(trifluoromethyl)-1H-pyrazol-5-yl] phenyl}-1,3-thiazole 1-(3-Ethyl-4-hydroxyphenyl)-1-ethanone (step 1)

To a stirred solution of 2-ethylphenol (13 g, 106.4 mmol) in carbon disulfide (30 ml) was added aluminum chloride (30 g, 225 mmol) portionwise at 0° C. Then, acetyl chloride (8.4 ml, 118.1 mmol) was added, and the mixture was heated at reflux temperature for 16 hours. The reaction mixture was cooled down to room temperature, and poured into ice. The whole was extracted with diethyl ether. The organic layer was washed with brine, dried over MgSO$_4$, and concentrated in vacuo. The residue was recystallized with hexane-toluene to give title compound (9.24 g, 53% yield).

$^1$H-NMR (CDCl$_3$) δ: 7.82 (s, 1H), 7.74 (dd, J=8, 2 Hz, 1H), 6.88 (dd, J=8, 5 Hz, 1H), 2.70 (q, J=8 Hz, 2H), 2.58 (d, J=2 Hz, 3H), 1.26 (t, J=8 Hz, 3H).

1-(4-[[tert-Butyl(dimethyl)silyl]oxy]-3-ethylphenyl)-1-ethanone (step 2)

To a stirred solution of 1-(3-ethyl-4-hydroxyphenyl)-1-ethanone (9.24 g, 56.27 mmol) in DMF (60 ml) was added tert-butyldimethylsilyl chloride (9.33 g, 61.9 mmol), imidazole (4.6 g, 67.52 mmol), and the mixture was stirred at room temperature for 3 hours. The reaction mixture was poured into water. The whole was extracted with ethyl acetate. The organic layer was washed with brine, dried over MgSO$_4$, and concentrated in vacuo. The residue was fractionally distilled under reduced pressure (180° C., 0.5 mmHg) to give title compound (12.3 g, 78% yield).

$^1$H-NMR (CDCl$_3$) δ: 7.80 (d, J=2 Hz, 1H), 7.71 (dd, J=8, 3 Hz, 1H), 6.80 (d, J=8 Hz, 1H), 2.65 (q, J=8 Hz, 2H), 2.55 (s, 3H), 1.21 (t, J=8 Hz, 3H), 1.02 (s, 9H), 0.27 (s, 6H).

1-(4-[[tert-Butyl(dimethyl)silyl]oxy]-3-ethylphenyl)-4,4,4-trifluoro-1,3-butanedione (step 3)

To a stirred solution of 1,1,1,3,3,3-hexamethyldisilazane (1.79 g, 11.1 mmol) in THF (37 ml) was added n-butyl lithium (1.52 M solution in hexane; 7.3 ml, 11.1 mmol) dropwise at 0° C., and the mixture was stirred at 0° C. for 30 minutes, then cooled at −78° C. A solution of 1-(4-[[tert-butyl(dimethyl)silyl]oxy]-3-ethylphenyl)-1-ethanone (2.57 g, 9.23 mmol) in THF (40 ml) was added dropwise, and the mixture was stirred at −78° C. for 1 hour. 1-(Trifluoroacetyl) imidazole (2.0 g, 12.2 mmol) was added, and the mixture was stirred at −78° C. for 3 hours, and quenched with water. The reaction mixture was warmed up to room temperature, and diluted with ethyl acetate. The whole was extracted with ethyl acetate. The organic layer was washed with brine, dried over MgSO$_4$, and concentrated in vacuo. The residue was used for next reaction without further purification. (3.45 g, 99% yield).

2-Ethyl-4-[1-[3-fluoro-4-(methylsulfonyl)phenyl]-3-(trifluoromethyl)-1H-pyrazol-5-yl]phenol (step 4)

To a stirred solution of 1-(4-[[tert-butyl(dimethyl)silyl] oxy]-3-ethylphenyl)-4,4,4-trifluoro-1,3-butanedione (749 mg, 2.0 mmol) in ethanol (25 ml) was added (2-fluoro-4-methylsulfonylphenyl)hydrazine hydrochloride (530 mg, 2.2 mmol), and the mixture was heated at reflux temperature for 16 hours. The reaction mixture was cooled down to room temperature, and poured into water. The whole was extracted with ethyl acetate. The organic layer was washed with brine, dried over MgSO$_4$, and concentrated in vacuo. The residue was dissolved in THF (5 ml). Tetrabutylammonium fluoride (1.0 M solution in THF; 2.5 ml, 2.5 mmol) was added, and the mixture was stirred for 1 hour. Then, the reaction mixture was poured into water. The whole was extracted with ethyl acetate. The organic layer was washed with brine, dried over MgSO$_4$, and concentrated in vacuo. The residue was purified by flash chromatography eluting with ethyl acetate-hexane (1:2) to give title compound (140 mg, 16% yield).

$^1$H-NMR (DMSO-d$_6$) δ: 9.83 (s, 1H), 7.96–7.90 (m, 1H), 7.57 (dd, J=11, 2 Hz, 1H), 7.41 (dd, J=8, 2 Hz, 1H), 7.13 (s, 1H), 7.02–6.97 (m, 2H), 6.81 (d, J=8 Hz, 1H), 3.56 (s, 3H), 2.48 (q, J=8 Hz, 2H), 1.01 (t, J=8 Hz, 3H).

2-Ethyl-4-[1-[3-fluoro-4-(methylsulfonyl)phenyl]-3-(trifluoromethyl)-1H-pyrazol-5-yl]phenyl trifluoromethanesulfonate (step 5)

To a stirred solution of 2-ethyl-4-[1-[3-fluoro-4-(methylsulfonyl)phenyl]-3-(trifluoromethyl)-1H-pyrazol-5-yl]phenol (140 mg, 0.327 mmol) in CH$_2$Cl$_2$ (10 ml) was added triethylamine (40 mg, 0.392 mmol), trifluoromethane-sulfonic anhydride (100 mg, 0.358 mmol), and the mixture was stirred for 3 hours. The reaction mixture was poured into water. The whole was extracted with CH$_2$Cl$_2$. The organic layer was washed with brine, dried over MgSO$_4$, and concentrated in vacuo. The compound was used for next reaction without purification.

4-[2-Ethyl-4-[1-[3-Fluoro-4-(methylsulfonyl)phenyl]-3-(trifluoromethyl)-1H-pyrazol-5-yl]phenyl]-1,3-thiazole (step 6)

To a stirred solution of 2-ethyl-4-[1-[3-fluoro-4-(methylsulfonyl)phenyl]-3-(trifluoromethyl)-1H-pyrazol-5-yl]phenyl trifluoromethanesulfonate (183 mg, 0.33 mmol) in dioxane (5 ml) was added 4-(tributylstannyl)thiazole (135 mg, 0.36 mmol), tetrakis(triphenylphosphine)palladium (38 mg, 0.033 mmol), lithium chloride (35 mg, 0.82 mmol), and the mixture was heated at reflux temperature for 16 hours. The reaction mixture was cooled down to room temperature, and diluted with ethyl acetate. The whole was washed with saturated potassium fluoride aqueous solution, and the precipitate was removed by filteration through celite. The resulting solution was extracted with ethyl acetate. The organic layer was washed with brine, dried over MgSO$_4$, and concentrated in vacuo. The residue was purified by flash chromatography eluting with ethyl acetate-hexane (1:2) to give title compound (25 mg, 15% yield).

mp: not detected.

$^1$H-NMR (CDCl$_3$) δ: 8.92 (d, J=2 Hz, 1H), 7.96–7.90 (m, 1H), 7.55 (d, J=8 Hz, 1H), 7.45 (d, J=12 Hz, 1H), 7.40 (d, J=2 Hz, 1H), 7.29–7.23 (m, 2H), 7.13 (d, J=8 Hz, 1H), 6.84 (s, 1H), 3.23 (s, 3H), 2.79 (q, J=8 Hz, 2H), 1.08 (t, J=8 Hz, 3H).

Anal. Calcd. for $C_{22}H_{17}F_4N_3O_2S_2$ 1/10 Hexane: C, 53.84; H, 3.68; N, 8.33. Found: C, 53.82; H, 3.92; N, 8.00.

Example 178

1-[3-Fluoro-4-(methylsulfonyl)phenyl]-2-[3-methyl-4-(4-thiazolyl)phenyl]-4-trifluoromethyl-1H-imidazole N-[3-Fluoro-4-(methylsulfonyl)phenyl]-4-bromo-3-methylbenzenecarboximidamide. (step 1)

The subtitle compound was prepared according to the procedure of Example 153 (step 1) using 4-bromo-3-methylbenzonitrile, instead of 4-bromobenzonitrile.

2-(4-Bromo-3-methylphenyl)-1-[3-fluoro-4-(methylsulfonyl)phenyl]-4-hydroxy-4-trifluoromethyl-4,5-dihydro-1H-imidazole. (step 2)

The subtitle compound was prepared according to the procedure of Example 153 (step 2) using N-[3-fluoro-4-(methylsulfonyl)phenyl]-4-bromo-3-methylbenzenecarboximidamide instead of N-[3-fluoro-4-(methylsulfonyl)phenyl]-4-bromobenzenecarboximnidamide.

$^1$H-NMR (DMSO-$d_6$) δ: 7.69–7.60 (m, 3H), 7.49 (s, 1H), 7.19–7.08 (m, 2H), 6.71 (dd, J=2, 9 Hz, 1H), 4.51 (d, J=12 Hz, 1H), 3.99 (d, J=12 Hz, 1H), 3.27 (s, 3H), 2.38 (s, 3H).

2-(4-Bromo-3-methylphenyl)-1-[3-fluoro-4-(methylsulfonyl)phenyl]-4-trifluoromethyl-1H-imidazole. (step 3)

The subtitle compound was prepared according to the procedure of Example 153 (step 3) using 2-(4-bromo-3-methylphenyl)-1-[3-fluoro-4-(methylsulfonyl)phenyl]-4-hydroxy-4-tifluoromethyl-4,5-dihydro-1H-imidazole instead of 2-(4-bromophenyl)-1-[3-fluoro-4-(methylsulfonyl)phenyl]-4-hydroxy-4-trifluoromethyl-4,5-dihydro-1H-imidazole.

$^1$H-NMR (CDCl$_3$) δ: 8.06 (dd, J=8, 8 Hz, 1H), 7.53–7.49 (m, 2H), 7.46 (d, J=8 Hz, 1H), 7.24–7.15 (m, 2H), 6.82 (dd, J=2, 8 Hz, 1H), 3.28 (s, 3H), 2.39 (s, 3H).

1-[3-Fluoro-4-(methylsulfonyl)phenyl]-2-[3-methyl-4-(4-thiazolyl)phenyl]-4-trifluoromethyl-1H-imidazole. (step 4)

The title compound was prepared according to the procedure of Example 153 (step 4) using 2-(4-bromo-3-methylphenyl)-1-[3-fluoro-4-(methylsulfonyl)phenyl]-4-trifluoromethyl-1H-imidazole instead of 2-(4-bromophenyl)-1-[3-fluoro-4-(methylsulfonyl)phenyl]-4-trifluoromethyl-1H-imidazole.

mp: 197.0–198.0° C.

$^1$H-NMR (CDCl$_3$) δ: 8.90 (d, J=2 Hz, 1H), 8.06 (dd, J=8, 8 Hz, 1H), 7.59–7.53 (m, 3H), 7.41 (d, J=2 Hz, 1H), 7.29–7.19 (m, 2H), 7.05 (dd, J=2, 8 Hz, 1H), 3.28 (s, 3H), 2.46 (s, 3H).

Anal.Calcd.for.$C_{21}H_{15}F_4N_3O_2S_2$,0.1hexane,0.5H$_2$O: C,51.79; H, 3.45; N, 8.47. Found: C, 51.66; H, 3.30; N, 8.12.

MS (EI): m/z 481 (M$^+$)

Example 179

2-Fluoro-4-[4-methyl-2-[4-(4-thiazolyl)phenyl]-1H-imidazol-1-yl]benzenesulfonamide 4-[2-(4-Bromophenyl)-4-hydroxy-4-methyl-4,5-dihydro-1H-imidazol-1-yl]-2-fluorobenzenesulfonamide. (step 1)

The subtitle compound was prepared according to the procedure of Example 154 (step 2) using bromoacetone instead of 3-bromo-1,1,1-trifluoroacetone.

4-[2-(4-Bromophenyl)-4-hydroxy-4-methyl-1H-imidazol-1-yl]-2-fluorobenzene sulfonamide. (step 2)

The subtitle compound was prepared according to the procedure of Example 153 (step 3) using 4-[2-(4-bromophenyl)-4-hydroxy-4-methyl-4,5-dihydro-1H-imidazol-1-yl]-2-fluorobenzenesulfonamide instead of 2-(4-bromophenyl)-1-[3-fluoro-4-(methylsulfonyl)phenyl]-4-hydroxy-4-trifluoromethyl-4,5-dihydro-1H-imidazole.

$^1$H-NMR (CDCl$_3$) δ: 7.92 (dd, J=8, 8 Hz, 1H), 7.45 (d, J=9 Hz, 2H), 7.23 (d, J=9 Hz, 2H), 7.09 (s, 1H), 7.06–7.04 (m, 1H), 6.91 (d, J=1 Hz, 1H), 5.33 (brs, 2H), 2.05 (s, 3H).

2-Fluoro-4-[4-methyl-2-[4-(2-trimethylsilylthiazol-4-yl)phenyl]-1H-imidazol-1-yl]benzenesulfonamide. (step 3)

The title compound was prepared according to the procedure of Example 153 (step 4) using 4-[2-(4-bromophenyl)-4-hydroxy-4-methyl-1H-imidazol-1-yl]-2-fluorobenzenesulfonamide instead of 2-(4-bromophenyl)-1-[3-fluoro-4-(methylsulfonyl)phenyl]-4-trifluoromethyl-1H-imidazole and using 4-(tributylstannyl)-2-trimethylsilylthiazole instead of 4-(tributylstannyl)thiazole. The crude product was used next reaction without further purification.

MS (EI): m/z 486 (M$^+$)

2-Fluoro-4-[4-methyl-2-[4-(4-thiazolyl)phenyl]-1H-imidazol-1-yl]benzenesulfonamide. (step 4)

To a stirred solution of 2-fluoro-4-[4-methyl-2-[4-(2-trimethylsilylthiazol-4-yl)phenyl]-1H-imidazol-1-yl]benzenesulfonamide (crude, 0.634 mmol) in THF (3 mL) was added tetrabutylammonium fluoride (0.95 mL, 1.0 M solution in THF, 0.95 mmol) at 0° C. The reaction mixture was warmed to room temperature and stirred for 30 minutes. The reaction mixture was added water (20 mL) and extracted with ethyl acetate (20 mL×3). The organic layer was washed with water and brine. After dried over MgSO$_4$ and concentration in vacuo. The crude mixture was purified by flash chromatography eluting with hexane/ethyl acetate (1/3). The resulting solid was recrystallized from ethyl acetate-hexane to give the title compound (0.116 g, 44.1% yield, via 2 steps).

mp: 145.0–147.0° C.

$^1$H-NMR (CDCl$_3$) δ: 8.87 (d, J=2 Hz, 1H), 8.00–7.94 (m, 1H), 7.89 (d, J=8 Hz, 2H), 7.58 (d, J=2 Hz, 1H), 7.43 (d, J=8 Hz, 2H), 7.13–7.07 (m, 2H), 6.92 (s, 1H), 5.30 (brs, 2H), 2.34 (s, 3H).

Anal.Calcd.for.$C_{19}H_{15}FN_4O_2S_2$,0.5H$_2$O: C,53.89; H, 3.81; N, 13.23. Found: C, 53.66; H, 3.93; N, 12.88.

MS (E): m/z 414 (M$^+$)

Example 180

5-[3-Chloro-5-methyl-4-(4-thiazolyl)phenyl]-1-[3-fluoro-4-(methylsulfonyl)phenyl]-3-trifluoromethyl-1H-pyrazole 1-(4-[tert-Butyl(dimethyl)silyl]oxy]-3-methylphenyl)-1-ethanone (step 1)

The subtitle compound was prepared according to the procedure of Example 177 (step 2) using 4'-hydroxy-3'-methylacetophenone instead of 1-(3-ethyl-4-hydroxyphenyl)-1-ethanone.

$^1$H-NMR (CDCl$_3$) δ: 7.69 (d, J=2 Hz, 1H), 7.62 (dd, J=2, 8 Hz, 1H), 6.70 (d, J=8 Hz, 1H), 2.45 (s, 3H), 2.15 (s, 3H), 0.93 (s, 9H), 0.16 (s, 6H).

1-(4-[[tert-Butyl(dimethyl)silyl]oxy]-3-methylphenyl)-4,4,4-trifluoro-1,3-butanedione (step 2)

The subtitle compound was prepared according to the procedure of Example 177 (step 3) using 1-(4-][tert-butyl(dimethyl)silyl]oxy]-3-methylphenyl)-1-ethanone instead of 1-(4-[[tert-butyl(dimethyl)silyl]oxy]-3-ethylphenyl)-1-ethanone.

MS (EI): m/z 360 (M$^+$)

2-Methyl-4-[1-[3-fluoro-4-(methylsulfonyl)phenyl]-3-(trifluoromethyl)-1H-pyrazol-5-yl]phenol (step 3)

The subtitle compound was prepared according to the procedure of Example 177 (step 4) using 1-(4-[[tert-butyl(dimethyl)silyl]oxy]-3-methylphenyl)-4,4,4-trifluoro-1,3-butanedione instead of 1-(4-[[tert-butyl(dimethyl)silyl]oxy]-3-ethylphenyl)-4,4,4-trifluoro-1,3-butanedione.

$^1$H-NMR (CDCl$_3$) d: 7.90 (dd, J=8, 8 Hz, 1H), 7.41 (dd, J=2, 11 Hz, 1H), 7.23 (dd, J=2, 9 Hz, 1H), 7.09 (d, J=2 Hz, 1H), 6.88 (dd, J=2, 8 Hz, 1H), 6.78 (d, J=8 Hz, 1H), 6.70 (s, 1H), 5.46 (brs, 1H), 3.24 (s, 3H), 2.25 (s, 3H).

2-Chloro-6-methyl-4-[1-[3-fluoro-4-(methylsulfonyl)phenyl]-3-(trifluoromethyl)-1H-pyrazol-5-yl]phenol (step 4)

To a stirred solution of 2-methyl-4-[1-[3-fluoro-4-(methylsulfonyl)phenyl]-3-(trifluoromethyl)-1H-pyrazol-5-yl]phenol (0.332 g, 0.8 mmol) in CH$_2$Cl$_2$ (10 ml) was added sulfryl chloride (0.113 g, 0.84 mmol) at room temperature, and the mixture was stirred for 30 minutes. The reaction mixture was poured into water, and the whole was extracted with CH$_2$Cl$_2$. The organic layer was washed with brine, dried over MgSO$_4$, and concentrated in vacuo. The residue was recystallized with CH$_2$Cl$_2$-hexane to give the subtitle compound (0.318 g, 88.6% yield).

$^1$H-NMR (CDCl$_3$) d: 7.93 (dd, J=8, 8 Hz, 1H), 7.44 (dd, J=2, 10 Hz, 1H), 7.21 (dd, J=2, 9 Hz, 1H), 7.09 (d, J=2 Hz, 1H), 6.94 (s, 1H), 6.71 (s, 1H), 5.86 (s, 1H), 3.24 (s, 3H), 2.27 (s, 3H).

2-Chloro-6-methyl-4-[1-[3-fluoro-4-(methylsulfonyl)phenyl]-3-(trifluoromethyl)-1H-pyrazol-5-yl]phenyl trifluoromethanesulfonate (step 5)

The subtitle compound was prepared according to the procedure of Example 177 (step 5) using 2-chloro-6-methyl-4-[1-[3-fluoro-4-(methylsulfonyl)phenyl]-3-(trifluoromethyl)-1H-pyrazol-5-yl]phenol instead of 2-ethyl-4-[1-[3-fluoro-4-(methylsulfonyl)phenyl]-3-(trifluoromethyl)-1H-pyrazol-5-yl]phenol.

$^1$H-NMR (CDCl$_3$) d: 7.97 (dd, J=8, 8 Hz, 1H), 7.46 (dd, J=2, 10 Hz, 1H), 7.29 (d, J=2 Hz, 1H), 7.18 (dd, J=2, 8 Hz, 1H), 7.12 (d, J=2 Hz, 1H), 6.83 (s, 1H), 3.25 (s, 3H), 2.44 (s, 3H).

MS (EI): m/z 580 (M$^+$)

5-[3-Chloro-5-methyl-4-(4-thiazolyl)phenyl]-1-[3-fluoro-4-(methylsulfonyl)phenyl]-3-trifluoromethyl-1H-pyrazole. (step 6)

The subtitle compound was prepared according to the procedure of Example 177 (step 6) using 2-chloro-6-methyl-4-[1-[3-fluoro-4-(methylsulfonyl)phenyl]-3-(trifluoromethyl)-1H-pyrazol-5-yl]phenyl trifluoromethanesulfonate instead of 2-ethyl-4-[1-[3-fluoro-4-(methylsulfonyl)phenyl]-3-(trifluoromethyl)-1H-pyrazol-5-yl]phenyl trifluoromethanesulfonate.

$^1$H-NMR (CDCl$_3$) d: 8.97 (d, J=2 Hz, 1H), 7.98 (dd, J=8, 8 Hz, 1H), 7.50 (d, J=10 Hz, 1H), 7.40 (d, J=2 Hz, 1H), 7.28–7.25 (m, 2H), 7.09 (s, 1H), 6.83 (s, 1H), 3.25 (s, 3H), 2.14 (s, 3H).

Anal.Calcd.for.C$_{21}$H$_{14}$ClF$_4$N$_3$O$_2$S$_2$: C,48.89; H, 2.74; N, 8.14. Found: C, 48.95; H, 2.86; N, 7.77.

MS (EI): mz 515 (M$^+$)

Example 181

4-Chloro-1-[3-fluoro-4-(methylsulfonyl)phenyl]-5-[3-methyl-4-(4-thiazolyl)phenyl]-3-trifluoromethyl-1H-pyrazole 2-Methyl-4-[1-[3-fluoro-4-(methylsulfonyl)phenyl]-3-(trifluoromethyl)-1H-pyrazol-5-yl]phenyl trifluoromethanesulfonate (step 1)

The subtitle compound was prepared according to the procedure of Example 177 (step 5) using 2-methyl-4-[1-[3-fluoro-4-(methylsulfonyl)phenyl]-3-(trifluoromethyl)-1H-pyrazol-5-yl]phenol instead of 2-ethyl-4-[1-[3-fluoro-4-(methylsulfonyl)phenyl]-3-(trifluoromethyl)-1H-pyrazol-5-yl]phenol.

$^1$H-NMR (CDCl$_3$) d: 7.94 (dd, J=7, 8 Hz, 1H), 7.41 (dd, J=2, 10 Hz, 1H), 7.33–7.29 (m, 2H), 7.18 (dd, J=1, 8 Hz, 1H), 7.11 (dd, J=2, 9 Hz, 1H), 6.81 (s, 1H), 3.24 (s, 3H), 2.41(s, 3H).

MS (EI): m/z 546 (M$^+$)

2-Methyl-4-[4-chloro-1-[3-fluoro-4-(methylsulfonyl)phenyl]-3-(trifluoromethyl)-1H-pyrazol-5-yl]phenyl trifluoromethanesulfonate (step 2)

To a stirred solution of 2-methyl-4-[1-[3-fluoro-4-(methylsulfonyl)phenyl]-3-(trifluoromethyl)-1H-pyrazole-5-yl]phenyl trifluoromethanesulfonate (0.185 g, 0.339 mmol) in DMF (2 mL) was added N-chlorosuccinimide (0.227 g, 1.70 mmol) at 0° C. The reaction mixture was warmed to room temperature and stirred for 72 hours. The reaction mixture was added water (20 mL) and extracted with ethyl acetate/hexane/ether=2/1/1 (20 mL×2). The organic layer was washed with water and brine. After dried over MgSO$_4$ and concentration in vacuo. The crude mixture was purified by flash chromatography eluting with hexane/ethyl acetate (4/1) to give the subtitle compound (0.117 g, 59.7% yield).

$^1$H-NMR (CDCl$_3$) d: 7.92 (dd, J=8, 9 Hz, 1H), 7.40–7.32 (m, 3H), 7.19–7.08 (m, 2H), 3.23 (s, 3H), 2.43(s, 3H).

MS (EI): m/z 580 (M$^+$)

4-Chloro-1-[3-fluoro-4-(methylsulfonyl)phenyl]-5-[3-methyl-4-(4-thiazolyl)phenyl]-3-trifluoromethyl-1H-pyrazole. (step 3)

The subtitle compound was prepared according to the procedure of Example 177 (step 6) using 2-methyl-4-[4-chloro-1-[3-fluoro-4-(methylsulfonyl)phenyl]-3-(trifluoromethyl)-1H-pyrazol-5-yl]phenyl trifluoromethanesulfonate instead of 2-ethyl-4-[1-[3-fluoro-4-(methylsulfonyl)phenyl]-3-(trifluoromethyl)-1H-pyrazol-5-yl]phenyl trifluoromethanesulfonate.

$^1$H-NMR (CDCl$_3$) d: 8.93 (s, 1H), 7.91 (t, J=8 Hz, 1H), 7.73 (d, J=8 Hz, 1H), 7.47–7.39 (m, 2H), 7.30–7.27 (m, 1H), 7.21–7.13 (m, 2H), 3.22 (s, 3H), 2.50 (s, 3H).

Anal.Calcd.for.C$_{21}$H$_{14}$ClF$_4$N$_3$O$_2$S$_2$,0.2hexane: C,49.63; H, 3.06; N, 7.96. Found: C, 49.99; H, 3.18; N, 7.82.

MS (EI): m/z 515 (M$^+$)

Example 182

4-[4-(Methylsulfonyl)phenyl]-3-[4-(1,3-thiazol-4-yl)phenyl]-2(5H)-furanone

The title compound was prepared according to the procedure of Example 151 using 3-(4-bromophenyl)-4-[4-(methylsulfonyl)phenyl]-2(5H)-furanone (WO 9500501) instead of 1-(4-bromophenyl)-2-[3-fluoro-4-(methylsulfonyl)phenyl]-5-methyl-1H-pyrrole.

mp: 236.8° C.

$^1$H-NMR (CDCl$_3$) δ: 9.22 (d, J=2.0 Hz, 1H), 8.25 (d, J=1.8 Hz, 1H), 8.05 (d, J=8.6 Hz, 2H), 7.97 (d, J=8.7 Hz, 2H), 7.67 (d, J=8.6 Hz, 2H), 7.43 (d, J=8.7 Hz, 2H), 5.44 (s, 2H), 3.25 (s, 3H).

Anal. Calcd. for C$_{20}$H$_{15}$NO$_4$S$_2$: C, 60.44; H, 3.80; N, 3.52. Found: C, 59.52; H, 3.96; N, 3.30.

Example 183

4-[5-Oxo-4-[4-(1,3-thiazol-4-yl)phenyl]-2,5-dihydro-3-franyl]benzenesulfonamide step 1

4-[4-(4-Bromophenyl)-5-oxo-2,5-dihydro-3-franyl]benzenesulfonamide

The title compound was prepared according to the procedure of Example 32 using 4-(bromoacetyl)benzensulfonamide (GB 1071180) instead of 2-bromo-1-[4-(methylsulfonyl)phenyl]ethanone, 4-bromophenylacetic acid instead of 4-(3-thienyl)phenylacetic acid.

$^1$H-NMR (DMSO-d$_6$) δ: (CDCl3) δ: 7.93 (d, J=8.2 Hz, 1H), 7.53 (d, J=8.2 Hz, 2H), 7.42 (d, J=8.2 Hz, 2H), 7.29 (d, J 8.2 Hz, 2H), 6.23 (brs, 2H), 5.18 (5, 2H) step 2

4-[5-Oxo-4-[4-(1,3-thiazol-4-yl)phenyl]-2,5-dihydro-3-franyl]benzenesulfonamide

The title compound was prepared according to the procedure of Example 151 susing 4-[4-(4-Bromophenyl)-5-oxo-2,5-dihydro-3-franyl]benzenesulfonamide (from step 1) instead of 1-(4-bromophenyl)-2-[3-fluoro-4-(methylsulfonyl)phenyl]-5-methyl-1H-pyrrole.

mp: amorphous $^1$H-NMR (CDCl$_3$) δ: (DMSO-d$_6$) δ: 9.23 (d, J=1.8 Hz, 1H), 8.25 (d, J=1.8 Hz, 1H), 8.05 (d, J=8.6 Hz, 2H), 7.84 (d, J=8.6 Hz, 2H), 7.60 (d, J=8.6 Hz, 2H), 7.44 (d, J=8.6 Hz, 2H), 5.42 (s, 2H).

Anal. Calcd. for $C_{19}H_{14}N_2O_4S_2$: C, 57.27; H, 3.54; N, 7.03. Found: C, 50.67; H, 3.73; N, 6.24.

Example 184

5,5-Dimethyl-3-[3-methyl-4-(1,3-thiazol-4-yl)phenyl]-4-[4-(methylsulfonyl)phenyl]-2(5H)-furanone (step 1)
5,5-Dimethyl-3-(3-methyl-4-methoxy)phenyl-4-[4-(methylsulfonyl)phenyl]-2(5H)-furanone The title compound was prepared according to the procedure of Example 166 step 1 using 4-methoxy-3-methylphenylacetic acid instead of 4-bromophenylacetic acid.

$^1$H-NMR (DMSO-d$_6$) δ: 8.01 (d, J=8.6 Hz, 2H), 7.60 (d, J=8.6 Hz, 2H), 7.13 (d, J=2.1 Hz, 1H), 7.03 (dd, J=2.1, 8.6 Hz, 1H), 6.83 (d, J=8.6 Hz, 1H), 3.73 (s, 3H), 3.27 (s, 3H), 2.02 (s, 3H), 1.53 (s, 6H).

step 2
5,5-Dimethyl-3-(3-methyl-4-hydroxy)phenyl-4-[4-(methylsulfonyl)phenyl]-2(5H)-furanone To a solution of 5,5-dimethyl-3-(3-methyl-4-methoxy)phenyl-4-[4-(methylsulfonyl)phenyl]-2(5H)-furanone (from step1, 2.0 g, 5.2 mmol) in CH$_2$Cl$_2$ (50 mL), boron tribromide (1.0 M solution in CH$_2$Cl$_2$, 26 mL, 26 mmol) was added slowly at −78° C. and the mixture was sirred for 0.5 h at that temperature. The mixture was stirred for further 2 h at 0° C. The mixture was poured into saturated aqueous NaHCO$_3$ (80 mL) and extracted with CH$_2$Cl$_2$ (70 mL×2), dried over MgSO$_4$, and concentrated in vacuo gave the title compound (1.9 g, 100%)

$^1$H-NMR (CDCl$_3$) δ: 8.00 (d, J=8.2 Hz, 2H), 7.44 (d, J=8.2 Hz, 2H), 7.23 (s, 1H), 6.93 (d, J=8.4 Hz, 1H), 6.60 (d, J=8.4 Hz, 1H), 4.98 (br s, 1H), 3.11 (s, 3H), 2.14 (s, 3H), 1.59 (s, 6H).

step 3
4-[5,5-Dimethyl-4-[4-(methylsulfonyl)phenyl]-2-oxo-2,5-dihydro-3-furanyl]-2-methylphenyl trifluoromethanesulfonate To a solution of 5,5-dimethyl-3-(3-methyl-4-hydroxy)phenyl-4-[4-(methylsulfonyl)phenyl]-2(5H)-furanone (from step2, 2.0 g, 5.3 mmol) and triethylamine (0.88 mL, 6.3 mmol) in CH$_2$Cl$_2$ (50 mL), trifluoromethanesulfonic anhydride (0.97 mL, 5.8 mmol) was added at room temperature and stirred for 1.5 h. The mixture was poued into H$_2$O and extacted with CH$_2$Cl$_2$ (50 mL×2), dried over MgSO$_4$, and concentarted in vacuo gave the title compound (2.5 g, 95%)

$^1$H-NMR (CDCl$_3$) δ: 8.04 (d, J=8.6 Hz, 2H), 7.44 (d, J=8.6 Hz, 2H), 7.09 (s, 1H), 7.46 (s, 1H), 7.26 (s, 1H), 3.12 (s, 3H), 2.30 (s, 3H), 1.61 (s, 6H).

step 4
5,5-Dimethyl-3-[3-methyl-4-(1,3-thiazol-4-yl)phenyl]-4-[4-(methylsulfonyl)phenyl]-2(5H)-furanone The title compound was prepared according to the procedure of Example 151 using 4-[5,5-dimethyl-4-[4-(methylsulfonyl)phenyl]-2-oxo-2,5-dihydro-3-furanyl]-2-methylphenyl trifluoromethanesulfonate from step 3 instead of 1-(4-bromophenyl)-2-[3-fluoro-4-(methylsulfonyl)phenyl]-5-methyl-1H-pyrrole.

mp: 180.3° C.

$^1$H-NMR (DMSO-d$_6$) δ: 9.18 (d, J=1.8 Hz, 1h), 8.02 (d, J=8.4 Hz, 2H), 7.85 (d, J=1.8 Hz, 1H), 7.64 (d, J=8.4 Hz, 2H), 7.52 (d, J=7.9 Hz, 1H), 7.29 (s, 1H), 7.11 (d, J=8.4 Hz, 1H), 3.27 (s, 3H), 2.33 (s, 3H), 1.57 (s, 6H).

Anal. Calcd. for $C_{23}H_{21}NO_4S_2$: C, 62.85; H, 4.82; N, 3.19. Found: C, 62.58; H, 5.10; N, 3.22.

Example 185

2-Methyl-4-[4-(methylsulfonyl)phenyl]-5-[4-(1,3-thiazol-4-yl)pbenyl]-1,3-thiazole step 1
2-(4-Bromophenyl)-1-(4-methylthiophenyl)ethanone 4-Bromophenylacetic acid (10.8 g, 0.050 mol) was disolved in thionyl chloride (50 mL) and stirred for 30 min at 90° C. The mixture was concentrated and the residual oil was disolved in carbon disulfide (100 mL) and thioanisole (12.5 g, 0.10 mol) was added and the mixture was cooled to 0° C., and AlCl$_3$ (14.7 g, 0.11 mol) was added portionwise. The mixture was stirred at room temperature for 16 h. The resultant dark green suspension was poured into ice water (150 mL) and extracted with CH$_2$Cl$_2$ (150 mL×2), washed with aqueous saturated NaHCO$_3$ (50 mL), dried over MgSO$_4$, and concentarted in vacuo gave the solid. The solid was suspended in ether and collected by filtration to give the title compound (8.4 g, 46%).

$^1$H-NMR (DMSO-d$_6$) δ: 7.96 (d, J=8.6 Hz, 2H), 7.50 (d, J=8.4 Hz, 2H), 7.38 (d, J=8.6 Hz, 2H), 7.22 (d, J=8.4 Hz, 2H), 4.35 (s, 2H), 2.54 (s, 3H).

step 2
2-Bromo-2-(4-bromophenyl)-1-(4-methylthiophenyl)ethanone

To a stirred suspension of 2-(4-bromophenyl)-1-(4-methylthiophenyl)ethanone from step1 (8.4 g, 0.024 mol) in acetic acid (130 mL), bromine (3.8 g, 0.024 mol) in 25% hydrogen bromide-acetic acid solution (50 mL) was added dropwise at room temperature. After stirring for 4 h at room temperature, concentrated gave the yellow solid. The solid was suspended in ether and collected by filtration, washed with ether to give the title compound (7.5 g, 73%).

$^1$H-NMR (DMSO-d$_6$) δ: 7.98 (d, J=8.7 Hz, 2H), 7.59 (d, J=8.6 Hz, 2H), 7.50 (d, J=8.6 Hz, 2H), 7.37 (d, J=8.7 Hz, 2H), 7.14 (s, 1H), 2.53 (s, 3H)

step 3
5-(4-Bromophenyl)-2-methyl-4-[4-(methylthio)phenyl]-1,3-thiazole

A mixture of 2-bromo-2-(4-bromophenyl)-1-(4-methylthiophenyl)ethanone (7.6 g, 0.018 mol) and thioacetamide 1.4 g, 0.018 mol) in ethanol (150 mL) was refluxed for 1 day. The mixture was concentrated and the solid was purified by flash chromatography eluting with $CH_2Cl_2$/hexane (2/1) to give title compound (3.8 g, 56%).

$^1$H-NMR (CDCl$_3$) δ: 7.44 (d, J=8.6 Hz, 2H), 7.40 (d, J=8.7 Hz, H), 7.18 (d, J=8.7 Hz, 2H), 7.16 (d, J=8.7 Hz, 2H), 2.74 (s, 3H), 2.48 (s, 3H).

step 4

5-(4-Bromophenyl)-2-methyl-4-[4-(methylsulfonyl)phenyl]-1,3-thiazole

To a solution of 5-(4-bromophenyl)-2-methyl-4-[4-(methylthio)phenyl]-1,3-thiazole from step 3 (3.8 g, 0.010 mol) in $CH_2Cl_2$ (40 mL), m-CPBA (6.2 g, 0.025 mol) was added at 0° C. The mixture was allowed to warm to room temperrature and stirred for 12 hours. The mixture was poured into aqueous saturated $Na_2SO_3$ (40 mL) and diluted with $CH_2Cl_2$ (50 mL). Organic later was separated and washed with aqueous saturated NaHCO$_3$ (50 mL), dried over MgSO$_4$, and concentarted in vacuo. The mixture was purified by flash chromatography eluting with ethyl acetate/hexane (1/1) to give title compound (3.1 g, 76%).

$^1$H-NMR (CDCl$_3$) δ: 7.85 (d, J=8.4 Hz, 2H), 7.69 (d, J=8.4 Hz, 2H), 7.48 (d, J=8.4 Hz, 2H), 7.17 (d, J=8.4 Hz, 2H), 3.05 (s, 3H), 2.76 (s, 3H).

step 5

2-Methyl-4-[4-(methylsulfonyl)phenyl]-5-[4-(1,3-thiazol-4-yl)phenyl]-1,3-thiazole The title compound was prepared according to the procedure of Example 151 using 5-(4-bromophenyl)-2-methyl-4-[4-(methylsulfonyl)phenyl]-1,3-thiazole from step 1 instead of 1-(4-bromophenyl)-2-[3-fluoro-4-(methylsulfonyl)phenyl]-5-methyl-1H-pyrrole.

mp: 193.9° C.

$^1$H-NMR (CDCl$_3$) δ: 8.90 (d, J=1.6 Hz, 1H), 7.92 (d, J=8.2 Hz, 2H), 7.84 (d, J=8.6 Hz, 2H), 7.74 (d, J=8.6 Hz, 2H), 7.59 (d, J=1.6 Hz, 1H), 7.38 (d, J=8.2 Hz, 2H), 3.04 (s, 3H), 2.78 (s, 3H).

Anal. Calcd. for $C_{20}H_{16}N_2O_2S_3$: C, 58.23; H, 3.91; N, 6.79. Found: C, 58.07; H, 3.99; N, 6.64.

Example 186

1-[4-(Methylsulfonyl)phenyl]-5-[2-methyl-4-(4-thiazolyl)phenyl]-3-trifluoromethyl-1H-pyrazole 1-[4-(tert-Butyldimethylsilyl)oxy]-2-methylphenyl]ethanone (step 1)

To a stirred solution of 1-[4-Hydroxy-2-methylphenyl]ethanone (10 g) in DMF (150 mL) was added imidazol (6.8 g) and tert-Butyldimethylsilyl chloride (12.04 g) the mixturecwas stirred continued for 3 hours. water (300 mL) was added to the reaction mixture. The whole was extracted with diethyl ether (200 mL×2). The combined diethyl ether extracts was washed with saturated NaHCO$_3$ solution, dried over sodium sulfate, and concentrated in vacuo. The resulting oil was distilled under reduced pressuer (b.p.=120–123° C. at 0.8 mmHg) to give title compound (16.34 g).

$^1$H-NMR (CDCl$_3$) δ: 7.70–7.66 (m, 1H), 6.71–6.68 (m, 2H), 2.54 (s, 3H), 2.53 (s, 3H), 0.99 (s, 9H), 0.23 (s, 6H).

1-[4-[(tert-Butyl(dimethylsilyl)oxy]-2-methylphenyl]-4,4,4-trifluoro-1,3-butadione (step 2)

The title compound was prepared according to the procedure of Example 27 (step 1) using 1-[4-(tert-Butyl(dimethylsilyl)oxy)2-methylphenyl]ethanone, instead of 4-(2,5-dimethylpyrrol-1-yl)acetophenone.

$^1$H-NMR (CDCl$_3$) δ: 7.4 (br, 1H), 6.7–6.6 (br m, 2H), 2.32 (br, 3H), 0.97 (s, 9H), 0.19 (s, 6H).

MS (EI): m/z 360 (M$^+$), 303

3-Methyl-4-[1-[4-(methylsulfonyl)phenyl]-3-(trifluoromethyl)-1H-pyrazol-5-yl]phenol (step 3)

[4-(methylsulfonyl)phenyl]hydrazine hydrochloride (0.37 g, 1.6 mmol) was added to a solution of 1-[4-[(tert-Butyl (dimethylsilyl]oxy]-2-methylphenyl]-4,4,4-trifluoro-1,3-butadione (0.6 g, 1.6 mmol) in EtOH (5 mL). The mixture was heated at reflux temperature for 15 hours and cooled down to room temperature. The reaction mixture was concentrated in vacuo, and the residue was taken up in ethyl acetate, washed with water and brine, dried over magnesium sulfate, and concentrated in vacuo. The residue and tetrabutylammonium fluoride (1.0M solution in THF; 2 mL) were added to THF (3 mL). Resulting mixture was stirred for 1 hour and taken up in ethyl acetate, washed with water and brine, dried over miagnesium sulfate, and concentrated in vacuo. The residue was purified by flash chromatography eluting with hexane/ethyl acetate (2/1) to give the title compound (0.56 g, 58.0% yield).

$^1$H-NMR (CDCl$_3$) δ: 7.88 (dt, J=9, 2 Hz, 2H), 7.49 (dt, J=9, 2 Hz, 2H), 7.09–7.05 (m, 1H), 6.73–6.70 (m, 2H), 6.67 (s, 1H), 3.05 (s, 3H).

3-Methyl-4-[1-[4-(methylsulfonyl)phenyl]-3-(trifluoromethyl)-1H-pyrazol-5-yl]phenyl trifluoromethanesulfonate (step 4)

To a stirred solution of 3-methyl-4-[1-[4-(methylsulfonyl)phenyl]-3-(trifluoromethyl)-1H-pyrazol-5-yl]phenol (10.3 g, 0.76 mmol) in dichloromethane (5 ml) was added triethylamine (0.101 g, 1.0 mmol), trifluoromethanesulfonic anhydride (0.226 g, 0.8 mmol), and the mixture was stirred for 2 hours. The reaction mixture was poured into water. The whole was extracted with dichloromethane. The organic layer was washed with brine, dried over MgSO$_4$, and concentrated in vacuo. The residue was purified by flash chromatography eluting with ethyl acetate-hexane (1:2) to give title compound (0.37 g).

$^1$H-NMR (CDCl$_3$) δ: 7.91 (dt, J=9, 2 Hz, 2H), 7.45 (dt, J=9, 2 Hz, 2H), 7.36–7.32 (m, 1H), 7.23–7.19 (m, 2H), 6.65 (s, 1H), 3.05 (s, 3H), 2.08 (s, 3H).

1-[4-(Methylsulfonyl)phenyl]-5-[2-methyl-4-(4-thiazolyl)phenyl]-3-trifluoromethyl-1H-pyrazole. (step 5)

The title compound was prepared according to the procedure of Example 177 (step 6) using 3-methyl-4-[1-[4-(methylsulfonyl)phenyl]-3-(trifluoromethyl)-1H-pyrazol-5-yl]phenyl trifluoromethanesulfonate, instead of 2-ethyl-4-[1-[3-fluoro-4-(methylsulfonyl)phenyl]-3-(trifluoromethyl)-1H-pyrazol-5-yl]phenyl trifluoromethanesulfonate.

mp:174.7° C.

$^1$H-NMR (CDCl$_3$) δ: 8.91 (d, J=2 Hz, 1H), 7.90–7.84 (m, 3H), 7.82 (br d, J=2 Hz, 1H), 7.63 (d, J=2 Hz, 1H), 7.52 (dt, J=9, 2 Hz, 2H), 7.29 (d, J=8 Hz, 1H), 6.75 (s, 1H), 3.04 (s, 3H), 2.08 (s, 3H).

Anal. Calcd. for: $C_{21}H_{16}N_3O_2F_3S_2$: C, 54,42; H, 3.48; N, 9.07. Found: C, 54.20; H, 3.60; N, 9.00.

Example 187

1-[3-Fluoro-4-(methylsulfonyl)phenyl]-5-[2-methyl-4-(4-thiazolyl)phenyl]-3-trifluoromethyl-1H-pyrazole 4-[1-[3-Fluoro-4-(methylsulfonyl)phenyl]-3-(trifluoromethyl)-1H-pyrazol-5-yl]-3-methyl-phenyl trifluoromethanesulfonate (step 1)

[3-Fluoro-4-(methylsulfonyl)phenyl]hydrazine hydrochloride (0.265 g, 1.1 mmol) was added to a solution of 1-[4-[(tert-Butyl(dimethylsilyl]oxy]-2-methylphenyl]-4,4,4-trifluoro-1,3-butadione (0.4 g, 1.1 mmol) in EtOH (5 mL). The mixture was heated at reflux temperature for 15 hours and cooled down to room temperature. The reaction mixture was concentrated in vacuo, and the residue was taken up in ethyl acetate, washed with water and brine, dried over magnesium sulfate, and concentrated in vacuo. The residue and tetrabutylammonium fluoride (1.0M solution in THF; 2 mL) were added to THF (3 mL). The resulting mixture was stirred for 1 hour and taken up in ethyl acetate, washed with water and brine, dried ove rmagnesium sulfate, and concentrated in vacuo. The residue was used for next reaction without purification. To a stirred solution of the crude product in $CH_2Cl_2$ (5 ml) was added triethylamine (0.202 g), trifluoromethanesulfonic anhydride (0.423 g), and the mixture was stirred for 3 hours. The reaction mixture was poured into water. The whole was extracted with dichloromethane. The organic layer was washed with brine, dried over $MgSO_4$, and concentrated in vacuo. The residue was purified by flash chromatography eluting with ethyl acetate-hexane (1:2) to give title compound (0.4 g).

$^1$H-NMR (CDCl$_3$) δ: 7.78 (dd, J=9, 8 Hz, 1H), 7.25–7.13 (m, 4H), 7.00 (dd, J=1 Hz, 1H), 6.65 (s, 1H), 3.12 (s, 3H), 2.00 (s, 3H).

1-[3-Fluoro-4-(methylsulfonyl)phenyl]-5-[2-methyl-4-(4-thiazolyl)phenyl]-3-trifluoromethyl-1H-pyrazole. (step 2)

The title compound was prepared according to the procedure of Example 177 (step 6) using 4-[1-[3-Fluoro-4-(methylsulfonyl)phenyl]-3-(trifluoromethyl)-1H-pyrazol-5-yl]-3-methyl-phenyl trifluoromethanesulfonate, instead of 2-ethyl-4-[1-[3-fluoro-4-(methylsulfonyl)phenyl]-3-(trifluoromethyl)-1H-pyrazol-5-yl]phenyl trifluoromethanesulfonate.

mp:131.9° C.

$^1$H-NMR (CDCl$_3$) δ: 8.92 (d, J 2 Hz, 1H), 7.90 (br, 1H), 7.85 (dd, J=8, 2 Hz, 1H), 7.84 (dd, J=9, 8 Hz, 1H), 7.65 (d, J=2 Hz, 1H), 7.39 (dd, J=11, 2 Hz, 1H), 7.30 (d, J=2 Hz, 1H), 7.19 (dd, J=9, 2 Hz, 1H), 6.75 (s, 1H), 3.20 (s, 3H), 2.11 (s, 3H).

Anal. Calcd. for: $C_{21}H_{15}N_3O_2F_4S_2$: C, 52.39; H, 3.14; N, 8.73. Found: C, 52.56; H, 3.20; N, 8.68.

Example 188

2-Fluoro-4-[5-methyl-3-[3-methyl-4-(1,3-thiazol-4-yl)phenyl]-4-isoxazolyl]benzenesulfonamide 1-(4-Bromo-3-methylphenyl)-2-(3-fluorophenyl)ethanone. (step 1)

The title compound was prepared according to the procedure of step 3 in the Example 169 using 3-fluorobenzyl bromide and 4-bromo-3-methylbenzoyl chloride (Cignarella, G.; Curzu, M. M.; Grella, G.; Loriga, M.; Anania, V.; Desole, M. S.; *J. Farmaco. Ed. Sci.*, 1983, 38, 187–198.).

$^1$H-NMR (CDCl$_3$) δ: 7.85 (1 H, br s), 7.68–7.60 (2 H, m), 7.34–7.25 (1 H, m), 705–6.92 (3 H, m), 4.24 (2 H, s), 2.46 (3 H, s).

3-(4-Bromo-3-methylphenyl)-4-(3-fluorophenyl)-5-methyl-4,5-dihydro-5-isoxazolol. (step 2)

The title compound was prepared according to the procedure of step 1in the Example 168 using 1-(4-bromo-3-methylphenyl)-2-(3-fluorophenyl)ethanone, instead of 1-(4-bromophenyl)-2-(3-fluoro-4-methylthiophenyl)ethanone.

$^1$H-NMR (CDCl$_3$) δ: 7.55 (1 H, d, J=1.8 Hz), 7.45 (1 H, d, J=8.2 Hz), 7.37–7.26 (1 H, m), 7.19 (1 H, dd, J=2.3 and 8.4 Hz), 7.05–6.81 (3 H, m), 4.46 (1 H, s), 3.00 (1 H, br s), 2.35 (3 H, s), 1.30 (3 H, s).

3-(4-Bromop-3-methylhenyl)-4-(3-fluorophenyl)-5-methylisoxazole. (step 3)

The title compound was prepared according to the procedure of step 2 in the Example 168 using 3-(4-bromo-3-methylphenyl)-4-(3-fluorophenyl)-5-methyl-4,5-dihydro-5-isoxazolol, instead of 3-(4-bromophenyl)-4-(3-fluoro-4-methylthiophenyl)-5-methyl-4,5-dihydro-5-isoxazolol.

$^1$H-NMR (CDCl$_3$) δ: 7.45 (1 H, d, J=8.2 Hz), 7.39 (1 H, d, J=1.8 Hz), 7.38–7.30 (1 H, m), 7.10–6.86 (4 H, m), 2.45 (3 H, s), 2.34 (3 H, s).

4-[3-(4-Bromo-3-methylphenyl)-5-methyl-4-isoxazolyl]-2-fluorobenzenesulfonamide and 2-[3-(4-Bromophenyl)-5-methyl-4-isoxazolyl]-4-fluorobenzenesulfonamide. (step 4)

The title compounds were prepared according to the procedure of step 4 in the Example 172 using 3-(4-bromo-3-methylphenyl)-4-(3-fluorophenyl)-5-methylisoxazole, instead of 3-(4-bromophenyl)-4-(3-fluorophenyl)-5-methylisoxazole.

First, 42% of 2-[3-(4-bromophenyl)-5-methyl-4-isoxazolyl]-4-fluorobenzenesulfonamide was obtained as a pale yellow foam.

$^1$H-NMR (CDCl$_3$) δ: 8.20 (1 H, dd, J=5.8 and 8.7 Hz), 7.42 (1 H, br s), 7.38 (1 H, d, J=8.4 Hz), 7.31–7.22 (1 H, m), 7.01 (1 H, dd, J=2.1 and 8.4 Hz), 6.93 (1 H, dd, J=2.1 and 8.4 Hz), 4.89 (2 H, br s), 2.30 (6 H, s).

The second fractions gave 37% of 4-[3-(4-bromo-3-methylphenyl)-5-methyl-4-isoxazolyl]-2-fluorobenzenesulfonamide as a colorless foam.

$^1$H-NMR (CDCl$_3$) δ: 7.91 (1 H, t, J=8.2 Hz), 7.50 (1 H, d, J=8.2 Hz), 7.41 (1 H, d, J=1.5 Hz), 7.09–7.01 (2 H, m), 6.92 (1 H, dd, J=2.1 and 8.6 Hz), 5.16 (2 H, br s), 2.50 (3 H, s), 2.39 (3 H, s).

2-Fluoro-4-[5-methyl-3-[3-methyl-4-(1,3-thiazol-4-yl)phenyl]-4-isoxazolyl]benzenesulfonamide. (step 5)

The title compound was prepared according to the procedure of step 4 in the Example 168 using 4-[3-(4-bromo-3-methylphenyl)-5-methyl-4-isoxazolyl]-2-fluorobenzenesulfonamide, instead of 3-(4-bromophenyl)-4-[3-fluoro-4-(methylsulfonyl)phenyl]-5-methylisoxazole.

m.p.: 114–116° C. (from ethyl acetate/diisopropyl ether/hexane)

$^1$H-NMR (CDCl$_3$) δ: 8.91 (1 H, d, J=2.0 Hz), 7.92 (1 H, dd, J=6.9 and 8.1 Hz), 7.60 (1 H, d, J=7.7 Hz), 7.47 (1 H, br s), 7.40 (1 H, d, J=1.8 Hz), 7.17–7.05 (3 H, m), 5.09 (2 H, br s), 2.52 (3 H, s), 2.45 (3 H, s).

MS; 429 (M$^+$).

Example 189

5-Methyl-3-[4-(methylsulfonyl)phenyl]-4-[4-(1,3-thiazol-4-yl)phenyl]isoxazole 2-(4-Bromophenyl)-1-(4-methylthiophenyl)ethanone. (step 1)

The title compound was prepared according to the procedure of step 3 in the Example 169 using 4-bromobenzyl bromide and 4-methylthiobenzoyl chloride.

$^1$H-NMR (CDCl$_3$) δ: 7.92–7.86 (2 H, m), 7.47–7.41 (2 H, m), 7.29–7.22 (2 H, m), 7.16–7.10 (2 H, m), 4.19(2 H, s), 2.52 (3 H, s).

4-(4-Bromophenyl)-3-(4-methylthiophenyl)-5-methyl-4,5-dihydro-5-isoxazoiol. (step 2)

The title compound was prepared according to the procedure of step 1 in the Example 168 using 2-(4-bromophenyl)-1-(4-methylthiophenyl)ethanone, instead of 1-(4-bromophenyl)-2-(3-fluoro-4-methylthiophenyl)ethanone.

$^1$H-NMR (CDCl$_3$) δ: 7.53–7.44 (4 H, m), 7.19–7.00 (4 H, m), 4.45 (1 H, s), 2.45 (3 H, s), 1.28 (3 H, s). One signal due to OH group was not observed.

4-(4-Bromophenyl)-3-(4-methylthiophenyl)-5-methylisoxazole. (step 3)

The title compound was prepared according to the procedure of step 2 in the Example 168 using 4-(4- bromophenyl)-3-(4-methylthiophenyl)-5-methyl-4,5-dihydro-5-isoxazolol, instead of 3-(4-bromophenyl)-4-(3-fluoro-4-methylthiophenyl)-5-methyl-4,5-dihydro-5-isoxazolol.

$^1$H-NMR (CDCl$_3$) δ: 7.54–7.48 (2 H, m), 7.35–7.30 (2 H, m), 7.21–7.16 (2 H, m), 7.08–7.02 (2 H, m), 2.48 (3 H, s), 2.43 (3 H, s).

4-(4-Bromophenyl)-5-methyl-3-(4-methylsulfonylphenyl)isoxazole. (step 4)

The title compounds were prepared according to the procedure of step 3 in the Example 168 using 4-(4-bromophenyl)-3-(4-methylthiophenyl)-5-methylisoxazole, instead of 3-(4-bromophenyl)-4-(3-fluoro-4-methylthiophenyl)-5-methylisoxazole.

$^1$H-NMR (CDCl$_3$) δ: 7.96–7.90 (2 H, m), 7.66–7.60 (2 H, m), 7.58–7.52 (2 H, m), 7.17–7.11 (2 H, m), 3.07 (3 H, s), 2.47 (3 H, s).

2-Fluoro-4-[5-methyl-3-[3-methyl-4-(1,3-thiazol-4-yl)phenyl]-4-isoxazolyl]benzenesulfonamide. (step 5)

A mixture of 4-(4-bromophenyl)-5-methyl-3-(4-methylsulfonylphenyl)isoxazole (300 mg, 0.765 mmol) and tributyl(2-trimethylsilylthiazol-4-yl)tin in toluene (5 ml) in the presence of tetrakis(triphenylphosphine)palladium (88 mg, 0.0765 mmol) was refluxed for 17 hours. After filtration through a pad of Celite, the filtrate was concentrated to give a black oil. This was dissolved in tetrahydrofuran (8 ml) and 2M hydrochloric acid (4 ml) was added there at room ttemperature. The mixture was stirred for 1 hour at the same temperature, diluted with ethyl acetate (150 ml), washed with water (50 ml) and saturated aqueous sodium bicarbonate (50 ml×2), and dried over anhydrous magnesium sulfate. Removal of solvent gave a yellow residue, which was chromatographed on a column of silica gel (60 g) as eluting with ethyl acetate/hexane (1:2) to afford 158 mg (52%) of the title compound as a white solid.

m.p.: 159° C. (from ethyl acetate/diisopropyl ether/exane)

$^1$H-NMR (CDCl$_3$) δ: 8.91 (1 H, d, J=1.8 Hz), 8.01–7.87 (4 H, m), 7.72–7.66 (2 H, m), 7.61 (1 H, d, J=2.0 Hz), 7.29–7.22 (2 H, m), 3.06 (3 H, s), 2.52 (3 H, s).

MS; 396 (M$^+$).

Example 190

4-[3-Methyl-5-[4-(1,3-thiazol-4-yl)phenyl]-4-isoxazolyl]benzenesulfonamide 4-(4-Bromophenyl)-3-phenyl-3-buten-2-one. (step 1)

A mixture of phenylacetone (4.92 g, 36.7 mmol) and 4-bromobenzaldehyde (6.78 g, 36.7 mmol) in benzene (40 ml) in the presence of piperidine (0.11 ml, 1.47 mmol) was refluxed for 48 hours. After evaporation, the obtained residue was chromatographed on a column of silica gel (300 g) as eluting with ethyl acetate/hexane (1:20 to 1:2) to afford a yellow solid, which was washed with ethyl acetate/hexane to give 4.22 g (38%) of the title compound as a pale yellow solid.

$^1$H-NMR (CDCl$_3$) δ: 7.56 (1 H, s), 7.46–7.37 (3 H, m), 7.32–7.26 (2 H, m), 7.19–7.12 (2 H, m), 6.92–6.86 (2 H, m), 2.29 (3 H, s).

4-(4-Bromophenyl)-3-phenyl-3-buten-2-one oxime. (step 2)

A mixture of 4-(4-bromophenyl)-3-phenyl-3-buten-2-one (2.00 g, 6.64 mmol), hydroxylamine hydrochloride (923 mg, 13.3 mmol) and sodium acetate (1.09 g, 13.3 mmol) in ethanol was refluxed for 2 hours. After evaporation, the residue was diluted with diethyl ether (200 ml), washed with water (50 ml), 2M hydrochloric acid (50 ml), and saturated aqueous sodium bicarbonate (50 ml×2), and dried over anhydrous magnesium sulfate. Removal of solvent gave 2.06 g (98%) of the title compounds.

TLC: Rf=0.26 and 0.15 (ethyl acetate/hexane=1/5).

5-(4-Bromophenyl)-3-methyl-4-phenylisoxazole. (step 3)

To a stirred mixture of 4-(4-bromophenyl)-3-phenyl-3-buten-2-one oxime (2.06 g, 6.52 mmol) and sodium bicarbonate (2.46 g, 29.3 mmol) in a mixture of tetrahydrofuran (30 ml) and water (20 ml) was added a solution of potassium iodide (4.09 g, 24.7 mmol) and iodine (1.98 g, 7.82 mmol) in water (30 ml) at room temperature. Then, the resulting mixture was refluxed for 5 hours in the dark. After cooling down to room temperature, 50 ml of saturated aqueous sodium sulfite was added. The organic layer was separated and the water layer was extracted with ethyl acetate (100 ml×2). The combined organic layers were dried over anhydrous magnesium sulfate and evaporated. The obtained residue was chromatographed on a column of silica gel (120 g) as eluting with ethyl acetate/hexane (1:15) to afford 1.64 g (80%) of the title compound as a pale brown oil.

$^1$H-NMR (CDCl$_3$) δ: 7.49–7.37 (7 H, m), 7.30–7.26 (2 H, m), 2.24 (3 H, s).

4-[5-(4-Bromophenyl)-3-methyl-4-isoxazolyl]benzenesulfonamide. (step 4)

To stirred chlorosulfonic acid (5 ml) was added 5-(4-bromophenyl)-3-methyl-4-phenylisoxazole (628 mg, 2.00 mmol) at −78° C. The mixture was allowed to warm up to room temperature and stirred for 1 hour. The resulting black mixture was poured into ice-conc. ammonia water (200 ml) carefully and extracted with ethyl acetate (150 ml). The separated organic layer was washed with water (50 ml×2), dried over anhydrous sodium sulfate, and evaporated. The obtained residue was chromatographed on a column of silica gel (60 g) as eluting with ethyl acetate/hexane (1/1) to afford 512 mg (87%) of the title compound as a pale brown solid.

$^1$H-NMR (CDCl$_3$) δ: 7.82–7.76 (2 H, m), 7.59–7.53 (2 H, m), 7.50–7.44 (2 H, m), 7.36 (2 H, br s), 7.32–7.26 (2 H, m), 2.11 (3 H, s).

4-[3-Methyl-5-[4-(1,3-thiazol-4-yl)phenyl]-4-isoxazolyl]benzenesulfonamide. (step 5)

The title compound was prepared according to the procedure of step 4 in the Example 168 using 4-[5-(4-bromophenyl)-3-methyl-4-isoxazolyl]benzenesulfonamide, instead of 3-(4-bromophenyl)-4-[3-fluoro-4-(methylsulfonyl)phenyl]-5-methylisoxazole.

m.p.: 236° C. (from ethyl acetate)

$^1$H-NMR (DMSO-d$_6$) δ: 9.10 (1 H, d, J=2.0 Hz), 8.16 (1 H, d, J=2.0 Hz), 7.95 (2 H, d, J=8.6 Hz), 7.81 (2 H, d, J=8.6 Hz), 7.51 (2 H, d, J=8.6 Hz), 7.43 (2 H, d, J=8.7 Hz), 7.36 (2 H, br s), 2.12 (3 H, s).

MS; 397 (M$^+$).

Example 191

3-Methyl-5-[4-(methylsulfonyl)phenyl]-4-[4-(1,3-thiazol-4-yl)phenyl]isoxazole 3-(4-Bromophenyl)-4-(4-methylthiophenyl)-3-buten-2-one. (step 1)

The title compound was prepared according to the procedure of step 1 in the Example 190 using (4-bromophenyl)acetone and 4-methylthiobenzaldehyde, instead of phenylacetone and 4-bromobenzaldehyde.

$^1$H-NMR (CDCl$_3$) δ: 7.60 (1 H, s), 7.58–7.52 (2 H, m), 7.08–7.01 (4 H, m), 6.98–6.92 (2 H, m), 2.44 (3 H, s), 2.34 (3 H, s).

3-(4-Bromophenyl)-4-(4-methylthiophenyl)-3-buten-2-one oxime. (step 2)

The title compound was prepared according to the procedure of step 2 in the Example 190 using 3-(4-bromophenyl)-4-(4-methylthiophenyl)-3-buten-2-one, instead of 4-(4-bromophenyl)-3-phenyl-3-buten-2-one.

TLC: Rf=0.12 (ethyl acetate/hexane=1/5).

4-(4-Bromophenyl)-3-methyl-5-(4-methylthiophenyl) isoxazole. (step 3)

The title compound was prepared according to the procedure of step 3 in the Example 190 using 3-(4-bromophenyl)-4-(4-methylthiophenyl)-3-buten-2-one oxime, instead of 4-(4-bromophenyl)-3-phenyl-3-buten-2-one oxime.

$^1$H-NMR (CDCl$_3$) δ: 7.57 (2 H, d, J=8.2 Hz), 7.42 (2 H, d, J=8.4 Hz), 7.17 (2 H, d, J=8.9 Hz), 7.16(2 H, d, J=8.2 Hz), 2.48 (3 H, s), 2.23 (3 H, s).

4-(4-Bromophenyl)-3-methyl-5-[4-(methylsulfonyl)phenyl] isoxazole. (step 4)

The title compound was prepared according to the procedure of step 3 in the Example 168 using 4-(4-bromophenyl)-3-methyl-5-(4-methylthiophenyl)isoxazole, instead of 3-(4-bromophenyl)-4-(3-fluoro-4-methylthiophenyl)-5-methylisoxazole.

$^1$H-NMR (CDCl$_3$) δ: 7.95–7.89 (2 H, m), 7.74–7.69 (2 H, m), 7.65–7.58 (2 H, m), 7.19–7.14 (2 H, m), 3.06 (3 H, s), 2.26 (3 H, s).

3-Methyl-5-[4-(methylsulfonyl)phenyl]-4-[4-(1,3-thiazol-4-yl)phenyl]isoxazole. (step 5)

The title compound was prepared according to the procedure of step 4 in the Example 168 using 4-(4-bromophenyl)-3-methyl-5-[4-(methylsulfonyl)phenyl] isoxazole, instead of 3-(4-bromophenyl)-4-[3-fluoro-4-(methylsulfonyl)phenyl]-5-methylisoxazole.

m.p.: 119° C. (from ethyl acetate/hexane)

$^1$H-NMR (CDCl3) δ: 8.93 (1 H, d, J=2.0 Hz), 8.05 (2 H, br d, J=7.9 Hz), 7.90 (2 H, br d, J=8.1 Hz), 7.77 (2 H, br d, J=8.0 Hz), 7.65 (1 H, d, J=2.0 Hz), 7.37 (2 H, br d, J=7.9 Hz), 3.05 (3 H, s), 2.30 (3 H, s).

MS; 396 (M$^+$).

Example 192

2-Fluoro-4-[2-methyl-5-[4-(1,3-thiazol-4-yl)phenyl]-1,3-oxazol-4-yl]benzenesulfonamide 2-Acetoxy-1-(4-bromophenyl)-2-(3-fluorophenyl)-1-ethanone. (step 1)

The title compound was prepared according to the procedure of Example 169 (step 5) using 1-(4-bromophenyl)-2-(3-fluorophenyl)-1-ethanone, instead of 1-(4-bromophenyl)-2-[3-fluoro-4-(methylsulfonyl)phenyl]-1-ethanone.

$^1$H-NMR (CDCl$_3$) δ7.78 (d, J=8.9 Hz, 2H), 7.57 (d, J=8.7 Hz, 2H), 7.31–7.39 (m, 1H), 7.14–7.23 (m, 2H), 7.01–7.09 (m, 1H), 6.76 (s, 1H), 2.21 (s, 3H)

4-(4-Bromophenyl)-5-(3-fluorophenyl)-2-methyl-1,3-oxazole. (step 2)

The title compound was prepared according to the procedure of Example 169 step 6 using 2-acetoxy-1-(4-bromophenyl)-2-(3-fluorophenyl)-1-ethanone, instead of 2-acetoxy-1-(4-bromophenyl)-2-[3-fluoro-4-(methylsulfonyl)phenyl]-1-ethanone.

$^1$H-NMR (CDCl$_3$) δ7.51 (s, 4H), 7.24–7.34 (m, 3H), 6.98–7.06 (m, 1H), 2.55 (s, 3H).

4-[4-(4-Bromophenyl)-2-methyl-1,3-oxazol-5-yl]-2-fluorobenzenesulfonamide. (step 3)

The title compound was prepared according to the procedure of Example 172 step 4 using 4-(4-bromophenyl)-5-(3-fluorophenyl)-2-methyl-1,3-oxazole, instead of 3-(4-bromophenyl)-5-methyl-4-phenylisoxazole.

$^1$H-NMR (CDCl$_3$) δ7.87 (t, J=7.7 Hz, 1H), 7.56 (d, J=8.7 Hz, 2H), 7.40–7.49 (m, 4H), 5.11 (br s, 2H), 2.58 (s, 3H).

2-Fluoro-4-[2-methyl-4-[4-(1,3-thiazol-4-yl)phenyl]-1,3-oxazol-5-yl]benzenesulfonamide. (step 4)

The title compound was prepared according to the procedure of Example 168 (step 4) using 4-[4-(4-bromophenyl)-2-methyl-1,3-oxazol-5-yl]-2-fluorobenzenesulfonamide instead of 3-(4-bromophenyl)-4-[3-fluoro-4-(methylsulfonyl)phenyl]-5-methylisoxazole.

mp: 116–118° C.

$^1$H-NMR (CDCl$_3$) δ: 8.91 (d, J=2.0 Hz, 1H), 8.00 (d, J=8.6 Hz, 2H), 7.86 (t, J=7.7 Hz, 1H), 7.68 (d, J=8.6 Hz, 2H), 7.62 (d, J=1.8 Hz), 7.45–7.54 (m, 2H), 5.12 (br s, 2H), 2.60 (s, 3H).

Anal. Calcd. for C$_{19}$H$_{14}$N$_3$O$_3$F$_1$S$_2$.0.7EtOH: C, 54.73; H, 4.10; N, 9.39. Found: C, 54,46; H, 4,42; N, 9.09.

Example 193

2-fluoro-4-[2-methyl-5-[4-(1,3-thiazol-4-yl)phenyl]-1,3-oxazol-4-yl]benzenesulfonamide 2-(4-Bromophenyl)-1-(3-fluorophenyl)-1-ethanone. (step 1)

The title compound was prepared according to the procedure of Example 169 step 3 using 3-fluorobenzoyl chloride and 4-bromobenzylbromide, instead of 4-bromobenzoyl chloride and 4-(bromomethyl)-2-fluoro-1-(methylsulfanyl) benzene.

$^1$H-NMR (CDCl$_3$) δ7.82 (dt, J=1.5, 7.6 Hz, 1H), 7.64–7.69 (m, 1H), 7.26–7.32 (m, 1H), 7.44–7.50 (m, 3H), 7.13 (d, J=8.2 Hz, 2H), 4.22 (s, 2H).

2-Acetoxy-1-(4-bromophenyl)-2-(3-fluorophenyl)-1-ethanone. (step 2)

The title compound was prepared according to the procedure of Example 169 step 5 using 2-(4-bromophenyl)-1-(3-fluorophenyl)-1-ethanone, instead of 1-(4-bromophenyl)-2-[3-fluoro-4-(methylsulfonyl)phenyl]-1-ethanone.

$^1$H-NMR (CDCl$_3$) δ7.68 (d, J=7.7 Hz, 1H), 7.57–7.62 (m, 1H), 7.51 (d, J=8.4 Hz, 2H), 7.20–7.44 (m, 4H), 6.73 (s, 1H), 2.20 (s, 3H).

5-(4-Bromophenyl)-4-(3-fluorophenyl)-2-methyl-1,3-oxazole. (step 3)

The title compound was prepared according to the procedure of Example 169 step 6 using 2-acetoxy-1-(4-bromophenyl)-2-(3-fluorophenyl)-1-ethanone, instead of 2-acetoxy-1-(4-bromophenyl)-2-[3-fluoro-4-(methylsulfonyl)phenyl]-1-ethone.

$^1$H-NMR (CDCl$_3$) δ7.26–7.52 (m, 7H), 7.02–7.06 (m, 1H), 2.54 (s, 3H).

4-[5-(4-Bromophenyl)-2-methyl-1,3-oxazol-4-yl]-2-fluorobenzenesulfonamide. (step 4)

The title compound was prepared according to the procedure of Example 172 step 4 using 5-(4-bromophenyl)-4-(3-fluorophenyl)-2-methyl-1,3-oxazole, instead of 3-(4-bromophenyl)-5-methyl-4-phenylisoxazole.

$^1$H-NMR (CDCl$_3$) δ7.87 (t, J=7.6 Hz, 1H), 7.55 (t, J=8.6 Hz, 4H), 7.42 (d, J=8.6 Hz, 2H), 5.07 (br s, 2H), 2.56 (s, 3H).

2-Fluoro-4-[2-methyl-5-[4-(2-trimethylsilyl-1,3-thiazol-4-yl)phenyl]-1,3-oxazol-4-yl]benzenesulfonamide. (step 5)

The title compound was prepared according to the procedure of Example 153 (step 4) using 4-[5-(4-Bromophenyl)-2-methyl-1,3-oxazol-4-yl]-2-fluorobenzenesulfonamide instead of 2-(4-bromophenyl)-1-[3-fluoro-4-(methylsulfonyl)phenyl]-4-trifluoromethyl-1H-imidazole and using 4-(tributylstannyl)-2-trimethylsilylthiazole instead of 4-(tributylstannyl)thiazole. The crude product was used next reaction without further purification.

2-Fluoro-4-[2-methyl-5-[4-(1,3-thiazol-4-yl)phenyl]-1,3-oxazol-4-yl]benzenesulfonamide. (step 6)

The title compound was prepared according to the procedure of Example 179 (step 4) using 2-fluoro-4-[2-methyl-5-[4-(2-trimethylsilyl-1,3-thiazol-4-yl)phenyl]-1,3-oxazol- 4-yl]benzenesulfonamide instead of 2-fluoro-4-[4-methyl-2-[4-(2-trimethylsilylthiazol-4-yl)phenyl]-1H-imidazol-1-yl]benzenesulfonamide.

mp: 192–194° C.

$^1$H-NMR (CDCl$_3$) δ: 8.92 (d, J=2.0 Hz, 1H), 8.00 (d, J=8.4 Hz, 2H), 7.87 (t, J=8.4 Hz, 1H), 7.57–7.66 (m, 5H), 5.07 (br s, 2H), 2.58 (s, 3H).

Anal. Calcd. for C$_{19}$H$_{14}$N$_3$O$_3$F$_1$S$_2$.0.2H$_2$O.0.4AcOEt: C, 54.46; H, 3.90; N, 9.25. Found: C, 54.27; H, 4.02; N, 9.03.

Example 194

4-[4-[3-(Difluoromethyl)-1-[3-Fluoro-4-(methylsulfonyl)phenyl]-1H-pyrazol-5-yl]-2-methylphenyl]-1,3-thiazole 4,4-Diifluoro-1-[3-methyl-4-(1,3-thiazol-4-yl)phenyl]-1,3-butanedione (step 1)

The title compound was prepared according to the procedure of Example 106 (step 5) using ethyl difluoroacetate instead of ethyl trifluoroacetate.

$^1$H-NMR (CDCl$_3$) δ: 8.96 (d, J=2 Hz, 1H), 7.88–7.75 (m, 3H), 7.48 (d, J=2 Hz, 1H), 6.60 (s, 1H), 6.02 (t, J=54 Hz, 1H), 2.55 (s, 3H).

4-[4-[3-(Difluoromethyl)-1-[3-Fluoro-4-(methylsulfonyl)phenyl]-1H-pyrazol-5-yl]-2-methylphenyl]-1,3-thiazole (step 2)

The title compound was prepared according to the procedure of Example 106 (step 6) using 4,4-Diifluoro-1-[3-methyl-4-(1,3-thiazol-4-yl)phenyl]-1,3-butanedione instead of 4,4,4-trifluoro-1-[3-methyl-4-(1,3-thiazol-4-yl)phenyl]-1,3-butanedione.

mp: 122.9° C.

$^1$H-NMR (CDCl$_3$) δ: 8.92 (d, J=2 Hz, 1H), 7.91 (dd, J=9, 7 Hz, 1H), 7.65 (d, J=8 Hz, 1H), 7.43 (d, J=2 Hz, 1H), 7.43 (dd, J=11, 2 Hz, 1H), 7.28–7.24 (m, 2H), 7.09 (brd, J=8 Hz, 1H), 6.78 (s, 1H), 6.77 (t, J=55 Hz 1H), 3.23 (s, 3H), 2.47 (s, 3H).

Anal. Calcd. for C$_{21}$H$_{16}$F$_3$N$_3$O$_2$S$_2$: C, 54,42; H, 3.48; N, 9.07. Found: C, 54.27; H, 3.57; N, 8.99.

Example 195

3-(Difluoromethyl)-2-fluoro-4-[5-[3-methyl-4-(1,3-thiazol-4-yl)phenyl]-1H-pyrazol-1-yl]benzenesulfonamide The title compound was prepared according to the procedure of Example 106 (step 6) using 4,4-Diifluoro-1-[3-methyl-4-(1,3-thiazol-4-yl)phenyl]-1,3-butanedione (example 194, step 1) instead of 4,4,4-trifluoro-1-[3-methyl-4-(1,3-thiazol-4-yl)phenyl]-1,3butanedione and (2-fluoro-4-sulfamoylphenyl)hydrazine hydrochloride instead of (2-fluoro-4-methylsulfonylphenyl)hydrazine hydrochloride.

mp: 204.3° C.

$^1$H-NMR (CDCl$_3$) δ: 8.92 (d, J=2 Hz, 1H), 7.86 (dd, J=8, 8 Hz, 1H), 7.64 (d, J=8 Hz, 1H), 7.43 (d, J=2 Hz, 1H), 7.39 (dd, J=11, 2 Hz, 1H), 7.18 (dd, J=9, 2 Hz, 1H), 7.09 (dd, J=8, 2 Hz, 1H), 6.78 (s, 1H), 6.77 (t, J=55 Hz 1H), 5.09 (br, 2H), 3.73 (s, 3H).

MS (EI): m/z 464 (M$^+$)

Anal. Calcd. for C$_{20}$H$_{15}$F$_3$N$_4$O$_2$S$_2$ 0.25H$_2$O: C, 51.22; H, 3.33; N, 11.95. Found: C, 51.14; H, 3.45; N, 11.77.

Example 196

2-Fluoro-4-[5-[2-fluoro-4-(1,3-thiazol-4-yl)phenyl]-3-(trifluoromethyl)-1H-pyrazol-1-yl]benzenesulfonamide 2-Bromo-1-(3-fluoro-4-hydroxyphenyl)-1-ethanone (step 1)

To a stirred solution of 1-(3-fluoro-4-hydroxyphenyl)-1-ethanone (2.0 g, 12.98 mmol) in dioxane (3 ml) was added a solution of bromine (2.09 g, 13.1 mmol) in dioxane (12 ml), and the mixture was stirred for 16 hours. The mixture was concentrated in vacuo to give title compound (3.02 g, 99% yield). The compound was used for next reaction without purification.

$^1$H-NMR (DMSO-d$_6$) δ: 7.85–7.75 (m, 2H), 7.14–7.08 (m, 1H), 4.85 (s, 2H).

2-Fluoro-4-(1,3-thiazol-4-yl)phenol (step 2)

To a stirred solution of phosphorus pentasulfide (8.6 g, 19.3 mmol) in dioxane (53 ml) was added formamide (5.2 g, 115.5 mmol), and the mixture was heated at reflux temperature for 2 hours. The mixture was cooled down to room temperature, and the solution was decanted away from solids. To a stirred solution of 2-bromo-1-(3-fluoro-4-hydroxyphenyl)-1-ethanone (3.02 g, 12.98 mmol) in dioxane (50 ml) was added the thioformamide solution, and the mixture was heated at reflux temperature for 6 hours. The mixture was cooled down to room temperature, and made basic by addition of 0.5M NaOH aqueous solution. The whole was extracted with ethyl acetate. The organic layer was washed with brine, dried over MgSO$_4$, and concentrated in vacuo. The residue was purified by flash chromatography eluting with ethyl acetate-hexane (1:3) to give title compound (2.11 g, 83% yield).

$^1$H-NMR (CDCl$_3$) δ: 8.87 (d, J=2 Hz, 1H), 7.67 (d, J=12 Hz, 1H), 7.57 (d, J=8 Hz, 1H), 7.41 (d, J=2 Hz, 1H), 7.07–7.01 (m, 1H), 6.18 (s, 1H).

2-Fluoro-4-(1,3-thiazol-4-yl)phenyl trifluoromethanesulfonate (step 3)

To a stirred solution of 2-fluoro-4-(1,3-thiazol-4-yl)phenol (2.11 g, 10.81 mmol), triethylamine (1.31 g, 12.97 mmol) in CH$_2$Cl$_2$ (65 ml) was added trifluoromethanesulfonic anhydride (3.35 g, 11.89 mmol) at 0° C., and the mixture was stirred for 1 hour. The mixture was diluted with water, and the whole was extracted with CH$_2$Cl$_2$. The organic layer was washed with brine, dried over MgSO$_4$, and concentrated in vacuo. The residue was purified by flash chromatography eluting with ethyl acetate-hexane (1:4) to give title compound (3.47 g, 98% yield).

$^1$H-NMR (CDCl$_3$) δ: 8.89 (d, J=2 Hz, 1H), 7.87 (dd, J=11, 2 Hz, 1H), 7.76 (ddd, J=9, 2, 1 Hz, 1H), 7.62 (d, J=2 Hz, 1H), 7.43–7.37 (m, 1H).

1-[2-Fluoro-4-(1,3-thiazol-4-yl)phenyl]-1-ethanone (step 4)

To a stirred solution of 2-fluoro-4-(1,3-thiazol-4-yl)phenyl trifluoromethanesulfonate (3.47 g, 10.6 mmol) in DMF (11.7 ml) was added triethylamine (1.29 g, 12.72 mmol), butyl vinyl ether (5.31 g, 53 mmol), 1,3-bis(diphenylphosphino)propane (240 mg, 0.583 mmol), palladium acetate (120 mg, 0.53 mmol) successively, and the mixture was heated at 80° C. for 5 hours. The mixture was cooled down to room temperature. 2N HCl aqueous solution (30 ml) was added, and the mixture was stirred for 1 hour. The mixture was made neutral by addition of NaHCO$_3$, and extracted with ethyl acetate. The organic layer was washed with water, brine, dried over MgSO$_4$, and concentrated in vacuo. The residue was purified by flash chromatography eluting with ethyl acetate-hexane (1:4) to give title compound (2.03 g, 87% yield).

$^1$H-NMR (CDCl$_3$) δ: 8.90 (d, J=2 Hz, 1H), 7.98–7.92 (m, 1H), 7.78–7.76 (m, 1H), 7.73 (d, J=1 Hz, 1H), 7.71 (d, J=2 Hz, 1H), 2.67 (d, J=5 Hz, 3H).

4,4,4-Trifluoro-1-[2-fluoro-4-(1,3-thiazol-4-yl)phenyl]-1,3-butanedione (step 5)

To a stirred solution of 1-[2-fluoro-4-(1,3-thiazol-4-yl)phenyl]-1-ethanone (2.03 g, 9.18 mmol) in t-butylmethylether (60 ml) was added ethyl trifluoroacetate (1.56 g, 11.01 mmol), sodium methoxide (28 wt. % solution in methanol; 2.49 ml, 11.01 mmol) at 0° C., and the mixture was stirred for 3 hours. The mixture was extracted with ethyl acetate. The organic layer was washed with brine, dried over $MgSO_4$, and concentrated in vacuo to give title compound (2.92 g, 99% yield). The compound was used for next reaction without purification.

$^1$H-NMR (DMSO-$d_6$) δ: 9.23–9.21 (m, 1H), 8.44–8.27 (m, 1H), 7.96–7.81 (m, 3H), 6.23–6.17 (m, 1H).

2-Fluoro-4-[5-[2-fluoro-4-(1,3-thiazol-4-yl)phenyl]-3-(trifluoromethyl)-1H-pyrazol-1-yl]benzenesulfonamide (step 6)

To a stirred solution of 4,4,4-trifluoro-1-[2-fluoro-4-(1,3-thiazol-4-yl)phenyl]-1,3-butanedione (349 mg, 1.1 mmol) in ethanol (13.8 ml) was added 2-fluoro-4-hydradinobenzenesulfonaride hydrochloride (292 mg, 1.21 mmol), and the mixture was heated at reflux temperature for 16 hours. The mixture was cooled down to room temperature, and concentrated in vacuo. The residue was dissolved in ethyl acetate, washed with brine, dried over $MgSO_4$, and concentrated in vacuo. The residue was purified by flash chromatography eluting with ethyl acetate/hexane (1/3–1/2). The resulting solid was recrystallized with diisopropyl ether-hexane to give title compound (326 mg, 61% yield).

$^1$H-NMR (DMSO-$d_6$) δ: 9.13 (d, J=2 Hz, 1H), 8.30 (d, J=2 Hz, 1H), 7.88–7.71 (m, 5H), 7.52–7.45 (m, 2H), 7.27–7.25 (m, 2H).

MS (EI): m/z 486 ($M^+$)

Example 197

2-Fluoro-4-[5-[2-chloro-4-(1,3-thiazol-4-yl)phenyl]-3-(trifluoromethyl)-1H-pyrazol-1-yl]benzenesulfonamide 2-Bromo-1-(3-chloro-4-hydroxyphenyl)-1-ethanone (step 1)

The title compound was prepared according to the procedure of Example 196 (step 1) using 1-(3-chloro-4-hydroxyphenyl)-1-ethanone instead of 1-(3-fluoro-4-hydroxyphenyl)-1-ethanone.

$^1$H-NMR (DMSO-$d_6$) δ: 7.99–7.67 (m, 2H), 7.00–6.94 (m, 1H), 4.71 (s, 2H).

2-Chloro-4-(1,3-thiazol-4-yl)phenol (step 2)

The title compound was prepared according to the procedure of Example 196 (step 2) using 2-bromo-1-(3-chloro-4-hydroxyphenyl)-1-ethanone instead of 2-bromo-1-(3-fluoro-4-hydroxyphenyl)-1-ethanone.

$^1$H-NMR (CDCl$_3$) δ: 8.86 (d, J=2 Hz, 1H), 7.93 (d, J=2 Hz, 1H), 7.70 (dd, J=8, 2 Hz, 1H), 7.41 (d, J=2 Hz, 1H), 7.05 (d, J=8 Hz, 1H), 6.22 (s, 1H).

2-Chloro-4-(1,3-thiazol-4-yl)phenyl trifluoromethanesulfonate (step 3)

The title compound was prepared according to the procedure of Example 196 (step 3) using 2-chloro-4-(1,3-thiazol-4-yl)phenol instead of 2-fluoro-4-(1,3-thiazol-4-yl)phenol.

$^1$H-NMR (CDCl$_3$) δ: 8.90 (d, J=2 Hz, 1H), 8.13 (d, J=2 Hz, 1H), 7.89 (dd, J=9, 2 Hz, 1H), 7.62 (d, J=2 Hz, 1H), 7.42 (d, J=9 Hz, 1H).

1-[2-Chloro-4-(1,3-thiazol-4-yl)phenyl]-1-ethanone (step 4)

The title compound was prepared according to the procedure of Example 196 (step 4) using 2-chloro-4-(1,3-thiazol-4-yl)phenyl trifluoromethanesulfonate instead of 2-fluoro-4-(1,3-thiazol-4-yl)phenyl trifluoromethanesulfonate.

$^1$H-NMR (CDCl$_3$) δ: 8.90 (d, J=2 Hz, 1H), 8.03 (d, J=2 Hz, 1H), 7.86 (dd, J=8, 2 Hz, 1H), 7.67 (d, J=2 Hz, 1H), 7.66 (d, J=8 Hz, 1H), 2.69 (s, 3H).

4,4,4-Trifluoro-1-[2-chloro-4-(1,3-thiazol-4-yl)phenyl]-1,3-butanedione (step 5)

The title compound was prepared according to the procedure of Example 196 (step 5) using 1-[2-chloro-4-(1,3-thiazol-4-yl)phenyl]-1-ethanone instead of 1-[2-fluoro-4-(1,3-thiazol-4-yl)phenyl]-1-ethanone.

$^1$H-NMR (CDCl$_3$) δ: 8.92 (s, 1H), 8.11 (s, 1H), 7.93 (d, J=9 Hz, 1H), 7.79 (d, J=8 Hz, 1H), 7.72 (s, 1H), 6.67 (s, 1H).

2-Fluoro-4-[5-[2-chloro-4-(1,3-thiazol-4-yl)phenyl]-3-(trifluoromethyl)-1H-pyrazol-1-yl]benzenesulfonamide (step 6)

The title compound was prepared according to the procedure of Example 196 (step 6) using 4,4,4-trifluoro-1-[2-chloro-4-(1,3-thiazol-4-yl)phenyl]-1,3-butanedione instead of 4,4,4-trifluoro-1-[2-fluoro-4-(1,3-thiazol-4-yl)phenyl]-1,3-butanedione.

$^1$H-NMR (CDCl$_3$) δ: 8.92 (d, J=2 Hz, 1H), 8.07 (d, J=2 Hz, 1H), 7.93 (dd, J=8, 2 Hz, 1H), 7.84–7.78 (m, 1H), 7.70 (d, J=2 Hz, 1H), 7.41 (d, J=8 Hz, 1H), 7.36 (dd, J=11, 2 Hz, 1H), 7.13 (d, J=9 Hz, 1H), 6.84 (s, 1H), 5.12 (s, 2H).

MS (EI): m/z 502 ($M^+$)

Example 198

2-Fluoro-4-[5-[3-ethyl-4-(1,3-thiazol-4-yl)phenyl]-3-(trifluoromethyl)-1H-pyrazol-1-yl]benzenesulfonamide 4-Bromo-2-ethylphenol (step 1)

To a stirred solution of 2-ethylphenol (8.97 g, 73.4 nunol) in acetic acid (100 ml) was added hydrobromic acid (48 wt. % solution in water; 50 ml, 442 mmol), DMSO (50 ml, 705 mmol) dropwise, and the mixture was stirred for 1 hour. The mixture was diluted with water, and the whole was extracted with diethylether. The organic layer was washed with saturated $NaHCO_3$ aqueous solution, brine, dried over $MgSO_4$, and concentrated in vacuo to give title compound (15.2 g, 99% yield). The compound was used for next reaction without purification.

$^1$H-NMR (CDCl$_3$) δ: 7.24 (d, J=3 Hz, 1H), 7.16 (dd, J=9, 3 Hz, 1H), 6.64 (d, J=8 Hz, 1H), 2.60 (q, J=8 Hz, 2H), 1.22 (t, J=8 Hz, 3H).

4-Bromo-2-ethylphenyl trifluoromethanesulfonate (step 2)

The title compound was prepared according to the procedure of Example 196 (step 3) using 4-bromo-2-ethylphenol instead of 2-fluoro-4-(1,3-thiazol-4-yl)phenol.

$^1$H-NMR (CDCl$_3$) δ: 7.48 (d, J=2 Hz, 1H), 7.39 (dd, J=9, 3 Hz, 1H), 7.12 (d, J=9 Hz, 1H), 2.72 (q, J=8 Hz, 2H), 1.27 (t, J=8 Hz, 3H).

1-(4-Bromo-2-ethylphenyl)-1-ethanone (step 3)

The title compound was prepared according to the procedure of Example 196 (step 4) using 4-bromo-2-ethylphenyl trifluoromethanesulfonate instead of 2-fluoro-4-(1,3-thiazol-4-yl)phenyl trifluoromethanesulfonate.

$^1$H-NMR (CDCl$_3$) δ: 7.50 (d, J=8 Hz, 1H), 7.44 (d, J=2 Hz, 1H), 7.39 (dd, J=8, 2 Hz, 1H), 2.85 (q, J=7 Hz, 2H), 2.56 (s, 3H), 1.21 (t, J=7 Hz, 3H).

2-Bromo-1-(4-bromo-2-ethylphenyl)-1-ethanone (step 4)

The title compound was prepared according to the procedure of Example 196 (step 1) using 1-(4-bromo-2-ethylphenyl)-1-ethanone instead of 1-(3-fluoro-4-hydroxyphenyl)-1-ethanone.

$^1$H-NMR (CDCl$_3$) δ: 7.50–7.47 (m, 2H), 7.43 (dd, J=8, 2 Hz, 1H), 4.36 (s, 2H), 2.83 (q, J=7 Hz, 2H), 1.23 (t, J=7 Hz, 3H).

4-(4-Bromo-2-ethylphenyl)-1,3-thiazole (step 5)

The title compound was prepared according to the procedure of Example 196 (step 2) using 2-bromo-1-(4-bromo-2-ethylphenyl)-1-ethanone instead of 2-bromo-1-(3-fluoro-4-hydroxyphenyl)-1-ethanone.

¹H-NMR (CDCl₃) δ: 8.88 (d, J=2 Hz, 1H), 7.47–7.36 (m, 3H), 7.31 (d, J=2 Hz, 1H), 2.76 (q, J=8 Hz, 2H), 1.15 (t, J=7 Hz, 3H).

1-[3-Ethyl-4-(1,3-thiazol-4-yl)phenyl]-1-ethanone (step 6)

To a stirred solution of 4-(4-bromo-2-ethylphenyl)-1,3-thiazole (2.35 g, 8.76 mmol) in dioxane (45 ml) was added tributyl(1-ethoxyvinyl)tin (3.48 g, 9.64 mmol), tetrakis(triphenylphosphine)palladium (1010 mg, 0.876 mmol), lithium chloride (928 mg, 21.9 mmol), and the mixture was heated at reflux temperature for 16 hours. The reaction mixture was cooled down to room temperature, and diluted with ethyl acetate. The whole was washed with saturated potassium fluoride aqueous solution, and the precipitate was removed by filteration through celite. The resulting solution was extracted with ethyl acetate. The organic layer was concentrated in vacuo. To the residue was added THF (15 ml), 2N HCl aqueous solution (15 ml), and the mixture was heated at reflux temperature for 8 hours. The reaction mixture was cooled down to room temperature, made neutral by addition of NaHCO₃, and extracted with ethyl acetate. The organic layer was washed with brine, dried over MgSO₄, and concentrated in vacuo. The residue was purified by flash chromatography eluting with ethyl acetate-hexane (1:5) to give title compound (1.51 g, 74% yield).

¹H-NMR (CDCl₃) δ: 8.92 (d, J=2 Hz, 1H), 7.93 (d, J=2 Hz, 1H), 7.83 (dd, J=8, 2 Hz, 1H), 7.61 (d, J=8 Hz, 1H), 7.40 (d, J=2 Hz, 1H), 2.87 (q, J=8 Hz, 2H), 2.64 (s, 3H), 1.91 (t, J=8 Hz, 3H).

1-[3-Ethyl-4-(1,3-thiazol-4-yl)phenyl]-4,4,4-trifluoro-1,3-butanedione (step 7)

The title compound was prepared according to the procedure of Example 196 (step 5) using 1-[3-ethyl-4-(1,3-thiazol-4-yl)phenyl]-1-ethanone instead of 1-[2-fluoro-4-(1,3-thiazol-4-yl)phenyl]-1-ethanone.

¹H-NMR (CDCl₃) δ: 9.05 (d, J=2 Hz, 1H), 7.92 (d, J=2 Hz, 1H), 7.83 (dd, J=8, 2 Hz, 1H), 7.63 (d, J=8 Hz, 1H), 7.46 (d, J=2 Hz, 1H), 6.61 (s, 1H), 2.86 (q, J=7 Hz, 2H), 1.20 (t, J=8 Hz, 3H).

2-Fluoro-4-[5-[3-ethyl-4-(1,3-thiazol-4-yl)phenyl]-3-(trifluoromethyl)-1H-pyrazol-1-yl]benezenesulfonamide (step 8)

The title compound was prepared according to the procedure of Example 196 (step 6) using 1-[3-ethyl-4-(1,3-thiazol-4-yl)phenyl]-4,4,4-trifluoro-1,3-butanedione instead of 4,4,4-trifluoro-1-[2-fluoro-4-(1,3-thiazol-4-yl)phenyl]-1,3-butanedione.

¹H-NMR (CDCl₃) δ: 8.89 (d, J=2 Hz, 1H), 7.85–7.79 (m, 1H), 7.50 (d, J=8 Hz, 1H), 7.38 (d, J=2 Hz, 1H), 7.35 (dd, J=11, 2 Hz, 1H), 7.23 (d, J=2 Hz, 1H), 7.17 (dd, J=9, 2 Hz, 1H), 7.09 (d, J=8, 2 Hz, 1H), 6.82 (s, 1H), 5.71 (d, J=5 Hz, 2H), 2.76 (q, J=7 Hz, 2H), 1.06 (t, J=8 Hz, 3H).

MS (EI): m/z 496 (M⁺)

The chemical structures of the compounds prepared in the Examples 1 to 198 are summarized in the following tables.

TABLE

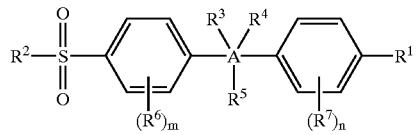

(I)

| Ex.# | A | R¹ | R² | R³ | R⁴ | R⁵ | R⁶ | R⁷ |
|---|---|---|---|---|---|---|---|---|
| 1 | pyrazole | 2-thienyl | methyl | 3-CF₃ | H | — | H | H |
| 2 | pyrazole | 3-thienyl | methyl | 3-CF₃ | H | — | H | H |
| 3 | pyrazole | 2-furyl | methyl | 3-CF₃ | H | — | H | H |
| 4 | pyrazole | 4-benzo[b]-furan-2-yl | methyl | 3-CF₃ | H | — | H | H |
| 5 | pyrazole | 3-thienyl | amino | 3-CF₃ | H | — | H | H |
| 6 | pyrazole | 3-thienyl | amino | 4-cyano | H | — | H | H |
| 7 | pyrazole | 4-pyridyl | amino | 3-CF₃ | H | — | H | H |
| 8 | pyrazole | 3-pyridyl | amino | 3-CF₃ | H | — | H | H |
| 9 | pyrazole | 5-methyl-2-thienyl | amino | 3-CF₃ | H | — | H | H |
| 10 | pyrazole | 3-fliryl | amino | 3-CF₃ | H | — | H | H |
| 11 | pyrazole | 5-pyrimidinyl | amino | 3-CF₃ | H | — | H | H |
| 12 | pyrazole | 2-pyrrolyl | amino | 3-CF₃ | H | — | H | H |
| 13 | pyrazole | 2-benzothienyl | amino | 3-CF₃ | H | — | H | H |
| 14 | pyrazole | 5-acetyl-thiohene-2-yl | amino | 3-CF₃ | H | — | H | H |
| 15 | pyrazole | 3-pyrrolyl | amino | 3-CF₃ | H | — | H | H |
| 16 | pyrazole | 3-methyl-2-thienyl | amino | 3-CF₃ | H | — | H | H |
| 17 | pyrazole | 3-thienyl | amino | 3-CO₂CH₃ | H | — | H | H |
| 18 | pyrazole | 5-thienyl | amino | 3-CH₂CN | H | — | H | H |
| 19 | pyrazole | 3-thienyl | amino | 3-CH₂OH | H | — | H | H |
| 20 | pyrazole | 3-furyl | methyl | 3-CF₃ | H | — | H | H |
| 21 | pyrazole | 2-thiazolyl | amino | 3-CF₃ | H | — | H | H |
| 22 | pyrazole | 2-thiazolyl | methyl | 3-CF₃ | H | — | H | H |
| 23 | pyrazole | 5-thiazolyl | amino | 3-CF₃ | H | — | H | H |
| 24 | pyrazole | 5-thiazolyl | methyl | 3-CF₃ | H | — | H | H |
| 25 | pyrazole | 5-Cl-2-thienyl | amino | 3-CF₃ | H | — | H | H |
| 26 | pyrazole | imidazolyl | amino | 3-CF₃ | H | — | H | H |

TABLE-continued (I)

| Ex.# | A | R¹ | R² | R³ | R⁴ | R⁵ | R⁶ | R⁷ |
|---|---|---|---|---|---|---|---|---|
| 27 | pyrazole | 2,5-dimethyl-pyrrol-1-yl | amino | 3-$CF_3$ | H | — | H | H |
| 28 | pyrazole | 2-thienyl | amino | 3-$CF_3$ | H | — | H | H |
| 29 | pyrazole | 2-furyl | amino | 3-$CF_3$ | H | — | H | H |
| 30 | pyrazole | 2-furyl | amino | 3-$CF_3$ | H | — | H | 3-methyl |
| 31 | pyrazole | 2-furyl | methyl | 3-$CF_3$ | H | — | H | 3-methyl |
| 32 | 2-furanone | 3-thienyl | methyl | H | H | — | H | H |
| 33 | 2-furanone | 2-thienyl | methyl | H | H | — | H | H |
| 34 | 2-furanone | 3-furyl | methyl | H | H | — | H | H |
| 35 | pyrrole | 2-furyl | methyl | 2-methyl | H | H | 3-F | H |
| 36 | pyrrole | 3-furyl | methyl | 2-methyl | H | H | 3-F | H |
| 37 | pyrrole | 3-furyl | methyl | 2-methyl | 3-methyl | H | H | H |
| 38 | pyrrole | 3-furyl | methyl | 2-methyl | H | H | H | H |
| 39 | pyrrole | 3-furyl | methyl | 2-methyl | H | H | H | 3-methyl |
| 40 | pyrrole | 2-furyl | methyl | 2-methyl | H | H | H | 3-methyl |
| 41 | pyrrole | 3-furyl | methyl | 2-methyl | H | H | H | 3-Cl |
| 42 | pyrrole | 2-furyl | methyl | 2-methyl | H | H | H | 3-Cl |
| 43 | pyrrole | phenyl | methyl | 2-methyl | H | H | H | H |
| 44 | pyrrole | 2-furyl | methyl | 2-methyl | H | H | H | H |
| 45 | pyrrole | 2-thienyl | methyl | 2-methyl | H | H | H | H |
| 46 | pyrrole | 3-thienyl | methyl | 2-methyl | H | H | H | H |
| 47 | pyrrole | 2-pyrrolyl | methyl | 2-methyl | H | H | H | H |
| 48 | pyrrole | 1-$(CH_3)_3$C-OC(O)-2-pyrrolyl | methyl | 2-methyl | H | H | H | H |
| 49 | pyrrole | 2-thiazolyl | methyl | 2-methyl | H | H | H | H |
| 50 | oxazole | 2-thienyl | methyl | 2-methyl | — | — | H | H |
| 51 | oxazole | 2-furyl | methyl | 2-methyl | — | — | H | H |
| 52 | imidazole | 2-thienyl | methyl | 4-$CF_3$ | H | — | H | H |
| 53 | imidazole | 2-furyl | methyl | 4-$CF_3$ | H | — | H | H |
| 54 | pyrrole | 2-furyl | amino | 4-methyl | H | H | H | H |
| 55 | pyrrole | 3-furyl | methyl | 4-methyl | H | H | H | H |
| 56 | pyrrole | 3-furyl | methyl | 4-methyl | H | H | H | H |
| 57 | pyrrole | phenyl | methyl | 4-methyl | H | H | H | H |
| 58 | pyrrole | 2-furyl | methyl | 4-methyl | H | H | H | H |
| 59 | pyrrole | 2-furyl | methyl | 4-methyl | H | H | H | H |
| 60 | pyrazole | 2-furyl | methyl | 3-$CF_3$ | H | — | 3-F | H |
| 61 | pyrazole | 2-furyl | $CFH_2$ | 3-$CF_3$ | H | — | H | H |
| 62 | pyrazole | 2-furyl | methyl | 4-cyano | H | — | H | H |
| 63 | pyrazole | 2-furyl | methyl | 3-$CH_2OH$ | H | — | H | H |
| 64 | pyrazole | 2-furyl | methyl | 3-$CH_2CN$ | H | — | H | H |
| 65 | pyrazole | 2-furyl | methyl | 3-$CO_2C_2H_5$ | H | — | H | H |
| 66 | pyrazole | 1-imidazolyl | methyl | 3-$CF_3$ | H | — | H | H |
| 67 | pyrazole | 2-furyl | methyl | 3-COOH | H | — | H | H |
| 68 | thiophene | 2-furyl | methyl | H | H | — | H | H |
| 69 | thiophene | 3-furyl | methyl | H | H | — | H | H |
| 70 | pyrazole | 2-furyl | amino | 3-$CF_3$ | H | — | H | 3-Cl |
| 71 | pyrazole | 2-furyl | methyl | 3-$CF_3$ | H | — | H | 3-Cl |
| 72 | pyrazole | 2-furyl | amino | 3-$CF_3$ | H | — | H | 3-methoxy |
| 73 | pyrazole | 2-furyl | amino | 3-$CF_3$ | H | — | H | 3-F |
| 74 | pyrazole | 2-furyl | methyl | 3-$CF_3$ | H | — | H | 3-F |
| 75 | pyrazole | 5-oxazolyl | amino | 3-$CF_3$ | H | — | H | H |
| 76 | pyrazole | 5-oxazolyl | methyl | 3-$CF_3$ | H | — | H | H |
| 77 | pyrazole | 2-furyl | amino | 3-$CF_3$ | H | — | H | 2-methyl |
| 78 | pyrazole | 2-furyl | methyl | 3-$CF_3$ | H | — | H | 2-methyl |
| 79 | pyrazole | 2-furyl | amino | 3-$CF_3$ | H | — | H | 2-F |
| 80 | pyrazole | 2-furyl | methyl | 3-$CF_3$ | H | — | H | 2-F |
| 81 | pyrazole | 2-furyl | methyl | 3-$CF_3$ | H | — | H | 3-methoxy |
| 82 | pyrazole | 4-thiazolyl | methyl | 3-$CF_3$ | H | — | H | H |
| 83 | pyrazole | 2-furyl | methyl | 3-$CF_3$ | H | — | 3-F | 3-methyl |
| 84 | pyrazole | 5-oxazolyl | methyl | 3-$CF_3$ | H | — | 3-F | H |
| 85 | pyrazole | 3-furyl | methyl | 3-$CF_3$ | H | — | 3-F | H |
| 86 | pyrazole | 2-thienyl | methyl | 3-$CF_3$ | H | — | 3-F | H |
| 87 | pyrazole | 3-thienyl | methyl | 3-$CF_3$ | H | — | 3-F | H |
| 88 | pyrazole | 2-thiazolyl | amino | 3-$CO_2CH_3$ | H | — | H | H |
| 89 | pyrazole | 2-thiazolyl | amino | 4-cyano | H | — | H | H |
| 90 | pyrazole | 2-thiazolyl | amino | 3-$CF_3$ | 4-Cl | — | H | H |

TABLE-continued $$\text{(I)}$$

Structure (I): R²-S(O)₂- attached to phenyl ring bearing (R⁶)ₘ, connected to central atom A (bearing R³, R⁴, R⁵) which is connected to second phenyl ring bearing R¹ and (R⁷)ₙ.

| Ex.# | A | R¹ | R² | R³ | R⁴ | R⁵ | R⁶ | R⁷ |
|---|---|---|---|---|---|---|---|---|
| 91 | pyrazole | 2-furyl | methyl | 3-CF₃ | H | — | 3-F | 2-F |
| 92 | pyrazole | 2-furyl | methyl | 3-CF₃ | H | — | 3-F | 2-CH₃ |
| 93 | pyrazole | 2-furyl | methyl | 3-CF₃ | H | — | 3-F | 3-Cl |
| 94 | pyrazole | 1,3-oxazol-4-yl | methyl | 3-CF₃ | H | — | 3-F | H |
| 95 | pyrazole | 1,3-oxazol-4-yl | methyl | 3-CF₃ | H | — | H | H |
| 96 | pyrazole | 1,3-oxazol-2-yl | methyl | 3-CF₃ | H | — | 3-F | H |
| 97 | pyrazole | 1,3-oxazol-2-yl | methyl | 3-CF₃ | H | — | H | H |
| 98 | pyrazole | 1,3-oxazol-2-yl | amino | 3-CF₃ | H | — | H | H |
| 99 | pyrazole | 1,3-thiazol-4-yl | methyl | 3-CF₃ | H | — | 3-F | H |
| 100 | pyrazole | 1,3-thiazol-4-yl | amino | 3-CF₃ | H | — | H | H |
| 101 | pyrazole | 1,3-thiazol-4-yl | amino | 3-CF₃ | H | — | 3-CH₃ | H |
| 102 | pyrazole | 2-methyl-1,3-thiazol-4-yl | methyl | 3-CF₃ | H | — | 3-F | H |
| 103 | pyrazole | 1,3-thiazol-4-yl | amino | 3-CF₃ | H | — | 3-F | H |
| 104 | pyrazole | 5-methyl-1,3-thiazol-4-yl | methyl | 3-CF₃ | H | — | 3-F | H |
| 105 | pyrazole | 1,3-thiazol-4-yl | methyl | 3-CF₃ | H | — | 3-F | 3-F |
| 106 | pyrazole | 1,3-thiazol-4-yl | methyl | 3-CF₃ | H | — | 3-F | 3-CH₃ |
| 107 | pyrazole | 1,3-thiazol-4-yl | methyl | 3-CF₃ | H | — | 3-F | 3-CH₃O |
| 108 | pyrazole | 1,3-oxazol-4-yl | methyl | 3-CF₃ | H | — | 3-F | 3-CH₃O |
| 109 | pyrazole | 1,3-thiazol-4-yl | methyl | 3-CF₃ | H | — | 3-F | 3-Cl |
| 110 | pyrazole | 1,3-oxazol-4-yl | methyl | 3-CF₃ | H | — | 3-F | 3-CH₃ |
| 111 | pyrazole | 1,3-oxazol-4-yl | methyl | 3-CF₃ | H | — | H | 3-CH₃O |
| 112 | pyrazole | 1,3-oxazol-4-yl | methyl | 3-CF₃ | H | — | H | 3-CH₃ |
| 113 | pyrazole | 1,3-thiazol-4-yl | amino | 3-CF₃ | H | — | 3-F | 3-CH₃ |
| 114 | pyrazole | 1,3-thiazol-4-yl | amino | 3-CF₃ | H | — | 3-F | 3-F |
| 115 | pyrazole | 1,3-thiazol-4-yl | methyl | 3-CF₃ | H | — | 3-HOCH₂ | H |
| 116 | pyrazole | 1,3-oxazol-4-yl | amino | 3-CF₃ | H | — | H | 3-CH₃ |
| 117 | pyrazole | 1,3-oxazol-4-yl | amino | 3-CF₃ | H | — | H | 3-CH₃O |
| 118 | pyrazole | 1,3-oxazol-4-yl | amino | 3-CF₃ | H | — | H | H |
| 119 | pyrazole | 1,3-thiazol-4-yl | methyl | 3-CF₃ | H | — | H | 3-Cl |
| 120 | pyrazole | 1,3-thiazol-4-yl | methyl | 3-CF₃ | H | — | H | 3-CH₃O |
| 121 | pyrazole | 1,3-oxazol-4-yl | amino | 3-CF₃ | H | — | 3-F | H |
| 122 | pyrazole | 1,3-thiazol-4-yl | amino | 3-CF₃ | H | — | 3-F | 3-Cl |
| 123 | pyrazole | 1,3-oxazol-4-yl | amino | 3-CF₃ | H | — | 3-F | 3-CH₃ |
| 124 | pyrazole | 1,3-thiazol-4-yl | methyl | 3-CF₃ | H | — | H | 3-F |
| 125 | pyrazole | 1,3-thiazol-4-yl | methyl | 3-CF₃ | H | — | H | 3-CH₃ |
| 126 | pyrazole | 2-furyl | methyl | 3-C₂H₅OC(O)— | H | — | 3-F | H |
| 127 | pyrazole | 2-furyl | methyl | 3-COOH | H | — | 3-ethoxy | H |
| 128 | pyrazole | 2-furyl | methyl | 3-COOH | H | — | 3-F | H |
| 129 | pyrazole | 2-furyl | methyl | 3-HOCH₂— | H | — | 3-F | H |
| 130 | pyrazole | 2-furyl | methyl | 3-morpholino-carbonyl | H | — | 3-F | H |
| 131 | pyrazole | 2-furyl | methyl | 3-CH₃NHC(O)— | H | — | 3-F | H |
| 132 | pyrazole | 2-furyl | methyl | 3-NH₂C(O)— | H | — | 3-F | H |
| 133 | pyrazole | 2-furyl | methyl | 3-(CH₃)₂NC(O)— | H | — | 3-F | H |
| 134 | pyrazole | 2-furyl | methyl | 3-CH₃ONHC(O)— | H | — | 3-F | H |
| 135 | pyrazole | 2-furyl | methyl | 3-CF₃ | H | — | 3-CF₃ | H |
| 136 | pyrazole | 2-furyl | methyl | 3-CF₃ | H | — | 3-CH₃O | H |
| 137 | pyrazole | 2-furyl | amino | 3-CF₃ | H | — | 3-F | H |
| 138 | pyrazole | 2-furyl | amino | 3-CF₃ | H | — | 3-F | 3-Cl |
| 139 | pyrazole | 2-furyl | amino | 3-CF₃ | H | — | 3-F | 3-CH₃ |
| 140 | pyrazole | 2-furyl | amino | 3-CF₃ | H | — | 2-Cl | H |
| 141 | pyrazole | 2-furyl | amino | 3-CF₃ | H | — | 2-F | H |
| 142 | pyrazole | 2-furyl | methyl | 3-CF₃ | H | — | 2-CH₃ | H |
| 143 | pyrazole | 2-furyl | amino | 3-CF₃ | H | — | 3-CH₃ | H |
| 144 | pyrazole | 2-furyl | amino | 3-CF₃ | H | — | 3-Cl | H |
| 145 | pyrazole | 2-furyl | amino | 3-CF₃ | H | — | 2-CH₃ | H |
| 146 | pyrazole | 2-furyl | methyl | 3-CF₃ | H | — | 3-CH₃O | H |
| 147 | pyrazole | 2-furyl | methyl | 3-CF₃ | H | — | 2-CF₃ | H |
| 148 | pyrazole | 2-furyl | amino | 3-CF₃ | H | — | 3-CH₃O | H |
| 149 | pyrazole | 1,3-thiazol-4-yl | amino | 3-CF₃ | H | — | 3-Cl | 3-CH₃ |
| 150 | pyrazole | 1,3-thiazol-4-yl | amino | 3-CF₃ | H | — | 2-F | 3-CH₃ |
| 151 | pyrrole | 1,3-thiazol-4-yl | methyl | 5-CH₃ | H | H | 3-F | H |
| 152 | pyrrole | 1,3-thiazol-4-yl | methyl | 5-CH₃ | H | H | 3-F | 3-CH₃ |
| 153 | pyrazole | 1,3-thiazol-4-yl | methyl | 2-CF₃ | H | — | 3-F | H |

TABLE-continued (I)

| Ex.# | A | $R^1$ | $R^2$ | $R^3$ | $R^4$ | $R^5$ | $R^6$ | $R^7$ |
|---|---|---|---|---|---|---|---|---|
| 154 | pyrazole | 1,3-thiazol-4-yl | amino | 3-$CF_3$ | H | — | 3-F | H |
| 155 | pyrazole | 2-furyl | methyl | 3-$CF_3$ | H | — | 3-Cl | H |
| 156 | pyrazole | 2-furyl | methyl | 3-$CF_3$ | H | — | 3-$HOCH_2$ | H |
| 157 | pyrazole | 2-furyl | methyl | 3-$CF_3$ | H | — | 3-$CH_3$ | H |
| 158 | pyrazole | 1,3-thiazol-4-yl | methyl | 3-$CF_3$ | H | — | 3-Cl | H |
| 159 | pyrazole | 2-furyl | methyl | 3-$CF_3$ | H | — | 3-$CH_3OCH_2$ | H |
| 160 | pyrazole | 2-furyl | methyl | 3-$CF_3$ | H | — | 3-$CH_3NH$—$CH_2$— | H |
| 161 | pyrazole | 2-furyl | methyl | 3-$CF_3$ | H | — | 3-$NH_2CH_2$ | H |
| 162 | pyrazole | 2-furyl | methyl | H | H | — | 3-F | H |
| 163 | pyrazole | 2-furyl | methyl | 4-cyano | H | — | 3-F | H |
| 164 | pyrazole | 1,3-thiazol-4-yl | methyl | 4-$CH_3C(O)NH$ | H | — | 3-F | H |
| 165 | 2-furanone | 1,3-thiazol-4-yl | methyl | H | H | — | 3-F | H |
| 166 | 2-furanone | 1,3-thiazol-4-yl | methyl | 5-$CH_3$ | 5-$CH_3$ | — | H | H |
| 167 | 2-furanone | 1,3-thiazol-4-yl | amino | H | H | — | 3-F | H |
| 168 | isoxazole | 1,3-thiazol-4-yl | methyl | 5-$CH_3$ | — | — | 3-F | H |
| 169 | 1,3-oxazole | 1,3-thiazol-4-yl | methyl | 2-$CH_3$ | — | — | 3-F | H |
| 170 | isoxazole | 1,3-thiazol-4-yl | methyl | 5-$CH_3$ | — | — | 3-F | 3-$CH_3$ |
| 171 | isoxazole | 1,3-thiazol-4-yl | amino | 5-$CH_3$ | — | — | H | H |
| 172 | isoxazole | 1,3-thiazol-4-yl | amino | 5-$CH_3$ | — | — | 2-F | H |
| 173 | 1,3-oxazole | 1,3-thiazol-4-yl | methyl | 5-$CH_3$ | — | — | 3-F | 3-$CH_3$ |
| 174 | pyrazole | 1,3-thiazol-4-yl | amino | 3-$CF_3$ | H | — | 3-OH | 3-F |
| 175 | pyrazole | 1,3-thiazol-4-yl | amino | 3-$CF_3$ | H | — | 3-$CH_3O$ | 3-F |
| 176 | pyrazole | 1,3-thiazol-4-yl | amino | 3-$CF_3$ | 4-Cl | — | 3-$CF_3$ | 3-F |
| 177 | pyrazole | 1,3-thiazol-4-yl | methyl | 3-$CF_3$ | H | — | 3-$C_2H_5$ | 3-F |
| 178 | pyrazole | 1,3-thiazol-4-yl | methyl | 3-$CF_3$ | H | — | 3-F | 3-$CH_3$ |
| 179 | pyrazole | imidazolyl | amino | 4-$CH_3$ | H | — | 3-F | H |
| 180 | pyrazole | 1,3-thiazol-4-yl | methyl | 3-$CF_3$ | H | — | 3-Cl,5-$CH_3$ | 3-F |
| 181 | pyrazole | 1,3-thiazol-4-yl | methyl | 3-$CF_3$ | 4-Cl | — | 3-$CH_3$ | 3-F |
| 182 | 2-furanone | 1,3-thiazol-4-yl | methyl | H | H | — | H | H |
| 183 | 2-furanone | 1,3-thiazol-4-yl | amino | H | H | — | H | H |
| 184 | 2-furanone | 1,3-thiazol-4-yl | methyl | 5-$CH_3$ | 5-$CH_3$ | — | 3-$CH_3$ | H |
| 185 | 1,3-thiazole | 1,3-thiazol-4-yl | methyl | 2-$CH_3$ | — | — | H | H |
| 186 | pyrazole | 1,3-thiazol-4-yl | methyl | 3-$CF_3$ | H | H | 2-$CH_3$ | H |
| 187 | pyrazole | 1,3-thiazol-4-yl | methyl | 3-$CF_3$ | H | H | 3-F | 2-$CH_3$ |
| 188 | isoxazole | 1,3-thiazol-4-yl | amino | 5-$CH_3$ | — | — | 3-F | 3-$CH_3$ |
| 189 | isoxazole | 1,3-thiazol-4-yl | methyl | 5-$CH_3$ | — | — | H | H |
| 190 | isoxazole | 1,3-thiazol-4-yl | amino | 5-$CH_3$ | — | — | H | H |
| 191 | isoxazole | 1,3-thiazol-4-yl | methyl | 3-$CH_3$ | — | — | H | H |
| 192 | 1,3-oxazole | 1,3-thiazol-4-yl | amino | 2-$CH_3$ | — | — | 3-F | H |
| 193 | isoxazole | 1,3-thiazol-4-yl | amino | 2-$CH_3$ | — | — | 3-F | H |
| 194 | pyrazole | 1,3-thiazol-4-yl | methyl | 3-$CHF_2$ | — | — | 3-F | 3-$CH_3$ |
| 195 | pyrazole | 1,3-thiazoly-4-yl | amino | 3-$CF_2H$ | H | — | 3-F | 3-$CH_3$ |
| 196 | pyrazole | 1,3-thiazoly-4-yl | amino | 3-$CF_3$ | H | — | 3-F | 2-F |
| 197 | pyrazole | 1,3-thiazoly-4-yl | amino | 3-$CF_3$ | H | — | 3-F | 2-Cl |
| 198 | pyrazole | 1,3-thiazoly-4-yl | amino | 3-$CF_3$ | H | — | 3-F | 3-$C_2H_5$ |

What is claimed is:

1. A compound of the formula:

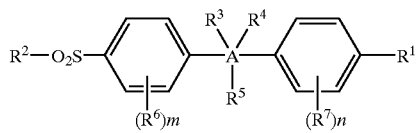

or its pharmaceutically acceptable salt thereof, wherein

A is partially unsaturated or unsaturated five membered heterocyclic, or partially unsaturated or unsaturated five membered carbocyclic, wherein the 4-(sulfonyl) phenyl and the 4-substituted phenyl in the formula (I) are attached to ring atoms of Ring A adjacent to each other;

$R^1$ is aryl and the aryl being optionally substituted by one to four substituents selected from halo, $C_{1-4}$ alkyl, halo-substituted $C_{1-4}$ alkyl, $C_{1-4}$ alkoxy, $C_{1-4}$ alkyl carbonyl, hydroxy, nitro, cyano and amino;

$R^2$ is $C_{1-4}$ alkyl, halo-substituted $C_{1-4}$ alkyl, $C_{1-4}$ alkylamino, $C_{1-4}$ dialkylamino or amino;

$R^3$, $R^4$ and $R^5$ are independently hydrogen, halo, $C_{1-4}$ alkyl, halo-substituted $C_{1-4}$ alkyl, $C_{2-5}$ alkenyl, $C_{2-5}$ alkynyl, $C_{1-4}$ alkoxy, hydroxy-$C_{1-4}$ alkyl, $C_{1-4}$ alkoxy $C_{1-4}$ alkyl, $C_{1-4}$ alkanoyl, cyano, nitro, cyano $C_{1-4}$ alkyl, carboxy, $C_{1-4}$ alkoxycarbonyl, aminocarbonyl, N—$C_{1-4}$ alkylaminocarbonyl, N,N-di $C_{1-4}$ alkylaminocarbonyl, N-arylaminocarbonyl, N,N-diarylaminocarbonyl, N—$C_{1-4}$ alkyl-N-arylaminocarbonyl, aryl, aryloxy, aryloxy-$C_{1-4}$ alkyl, heteroaryl, heteroaryloxy, heteroaryloxy-$C_{1-4}$ alkyl, morpholino-carbonyl, $C_{1-4}$ alkoxyaminocarbonyl or $C_{1-4}$ alkyl-carbonylamino; or two or $R^3$, $R^4$ and $R^5$ are taken together with atoms to which they are attached and form a 4–7 membered ring;

$R^6$ and $R^7$ are independently hydrogen, halo, $C_{1-4}$ alkyl, halo-substituted $C_{1-4}$ alkyl, $C_{1-4}$ alkoxy, $C_{1-4}$ alkylthio, $C_{1-4}$ alkylamino, N,N-di $C_{1-4}$ alkylamino, hydroxyl-$C_{1-4}$ alkyl, $C_{1-4}$ alkoxy-$C_{1-4}$ alkyl, $C_{1-4}$ alkyl-$C_{1-4}$ alkoxy, $C_{1-4}$ alkylamino-$C_{1-4}$ alkyl, hydroxy, amino $C_{1-4}$ alkyl and N,N-di $C_{1-4}$ alkylamino-$C_{1-4}$ alkyl; and m and n are independently 1, 2, 3, or 4;

with the proviso that if A is pyrazolyl, $R^2$ is amino, $R^3$ and $R^4$ are hydrogen, and $R^5$ is halo-substituted $C_{1-4}$ alkyl, $R^1$ is not unsubstituted phenyl.

2. A compound according to claim 1, wherein A is thienyl, oxazolyl, furyl, pyrrolyl, thiazolyl, imidazolyl, isoxazolyl, isothiazolyl, pyrazolyl, oxolinyl, thiolinyl, pyrazolinyl, imidazolinyl, pyrrolinyl or furanone.

3. A compound according to claim 2, wherein

A is thienyl, oxazolyl, furyl, pyrrolyl, thiazolyl, imidazolyl, isoxazolyl, isothiazolyl, pyrazolyl or furanone; and $R^3$, $R^4$ and $R^5$ are independently hydrogen, halo, $C_{1-4}$ alkyl, halo-substituted $C_{1-4}$ alkyl, $C_{2-5}$ alkenyl, $C_{2-5}$ alkynyl, $C_{1-4}$ alkoxy, hydroxy-$C_{1-4}$ alkyl, $C_{1-4}$ alkoxy $C_{1-4}$ alkyl, $C_{1-4}$ alkanoyl, cyano, nitro, cyano $C_{1-4}$ alkyl, carboxyl, $C_{1-4}$ alkoxycarbonyl, aminocarbonyl, N—$C_{1-4}$ alkylaminocarbonyl, N,N-di-$C_{1-4}$ alkylaminocarbonyl, morpholino-carbonyl, $C_{1-4}$ alkoxyaminocarbonyl or $C_{1-4}$ alkyl-carbonylamino.

4. A compound of claim 3, wherein

A is thienyl, oxazolyl, furyl, pyrrolyl, thiazolyl, imidazolyl, isoxazolyl, pyrazolyl, or furanone;

$R^1$ is phenyl, and the phenyl being optionally substituted by one to three substituents selected from halo, $C_{1-4}$ alkyl, halo-substituted $C_{1-4}$ alkyl, $C_{1-4}$ alkoxy, $C_{1-4}$ alkyl carbonyl, hydroxy, nitro, cyano and amino; p1 $R^3$, $R^4$ and $R^5$ are independently hydrogen, halo, $C_{1-4}$ alkyl, halo-substituted $C_{1-4}$ alkyl, $C_{2-5}$ alkenyl, $C_{1-4}$ alkoxy, hydroxy-$C_{1-4}$ alkyl, $C_{1-4}$ alkoxy $C_{1-4}$ alkyl, $C_{1-4}$ alkanoyl, cyano, nitro, cyano $C_{1-4}$ alkyl, carboxy, $C_{1-4}$ alkoxycarbonyl, aminocarbonyl, morpholino-carbonyl, $C_{1-4}$ alkoxyaminocarbonyl or $C_{1-4}$ alkyl-carbonylamino; and $R^6$ and $R^7$ are independently hydrogen, halo, $C_{1-4}$ alkyl, halo-substituted $C_{1-4}$ alkyl, $C_{1-4}$ alkoxy, $C_{1-4}$ alkylthio, hydroxyl-$C_{1-4}$ alkyl, $C_{1-4}$ alkoxy-$C_{1-4}$ alkyl, $C_{1-4}$ alkyl-$C_{1-4}$ alkoxy, $C_{1-4}$ alkylamino-$C_{1-4}$ alkyl, or hydroxy; and m and n are independently 1 or 2.

5. A compound according to claim 4, wherein

A is thienyl, oxazolyl, furyl, pyrrolyl, thiazolyl, imidazolyl, isooxazolyl, pyrazolyl or furanone;

$R^1$ is phenyl, and the phenyl being optionally substituted by halo, $C_{1-4}$ alkyl, $C_{1-4}$ alkyl carbonyl or $C_{1-4}$ alkoxy carbonyl;

$R^2$ is methyl, ethyl, fluoromethyl, difluoromethyl or amino;

$R^3$, $R^4$ and $R^5$ are independently hydrogen, halo, $C_{1-4}$ alkyl, fluoro-substituted $C_{1-4}$ alkyl, $C_{1-4}$ alkoxy, hydroxy-$C_{1-4}$ alkyl, $C_{1-4}$ alkanoyl, cyano, nitro, cyano $C_{1-4}$ alkyl, carboxy, $C_{1-4}$ alkoxycarbonyl, morpholino-carbonyl, $C_{1-4}$ alkoxyaminocarbonyl or $C_{1-4}$ alkyl-carbonylamino; and $R^6$ and $R^7$ are independently hydrogen, halo, $C_{1-4}$ alkyl, halo-substituted $C_{1-4}$ alkyl, $C_{1-4}$ alkoxy, hydroxyl-$C_{1-4}$ alkyl, $C_{1-4}$ alkoxy-$C_{1-4}$ alkyl, $C_{1-4}$ alkyl-$C_{1-4}$ alkoxy, $C_{1-4}$ alkylamino-$C_{1-4}$ alkyl or hydroxy.

6. A compound according to claim 5, wherein

A is thienyl, oxazolyl, furyl, pyrrolyl, thiazolyl, imidazolyl, isooxazolyl, pyrazolyl or furanone;

$R^1$ is phenyl, and the phenyl or heteroaryl being optionally substituted by one to three substituents selected from fluoro, chloro, methyl, ethyl, propyl, fluoromethyl, difluoromethyl, trifluoromethyl, chloromethyl, methoxyl, acetyl, ethylcarbonyl, methoxycarbonyl, ethoxycarbonyl and butoxycarbonyl;

$R^2$ is methyl, fluoromethyl or amino;

$R^3$, $R^4$ and $R^5$ are independently hydrogen, fluoro, chloro, methyl, ethyl, propyl, fluoromethyl, difluoromethyl, trifluoromethyl, methoxy, ethoxyl, hydroxymethyl, hydroxyethyl, methylcarbonyl, cyano, nitro, cyanomethyl, cyanoethyl, carboxy, methoxylcarbonyl, ethoxycarbonyl, morpholinocarbonyl, methoxyaminocarbonyl or methylcarbonylamino; and $R^6$ and $R^7$ are independently hydrogen, fluoro, chloro, methyl, ethyl, propyl, fluoromethyl, difluoromethyl, trifluoromethyl, methoxy, ethoxy, hydroxymethyl, hydroxyethyl, methoxymethyl, methoxyethyl, ethoxymethyl, methylaminomethyl, methylaminoethyl, ethylaminomethyl, aminomethyl, aminoethyl or hydroxy.

7. A compound according to claim 6, wherein

A is oxazolyl, pyrrolyl, imidazolyl, isoxazolyl, pyrazolyl or furanone;

$R^1$ is phenyl;

$R^2$ is methyl, fluoromethyl or amino;

$R^3$, $R^4$ and $R^5$ are independently hydrogen, methyl, trifluoromethyl, hydroxymethyl, cyano, cyanomethyl, carboxy, ethoxycarbonyl, morpholinocarbonyl, methoxyaminocarbonyl or methylcarbonylamino; and $R^6$ and $R^7$ are independently hydrogen, fluoro, chloro, methyl, methoxy, hydroxymethyl, ethoxy, trifluoromethyl, methoxymethyl, methylaminomethyl, aminomethyl or hydroxy.

8. A compound of claim 1, wherein said compound is selected from the group consisting of 1-(4-biphenyl)-2-methyl-5-[4-(2-methylsulfonyl)phenyl]-1H-pyrrole; and 2-(biphenyl)-4-methyl-1-[4-(methylsulfonyl)phenyl]-1H-pyrrole; or a pharmaceutically acceptable salt thereof.

9. A pharmaceutical composition useful for the treatment of a medical condition in which prostaglandins are implicated as pathogens, said condition is selected from the group consisting of pain, arthritis including rheumatoid arthritis, osteoarthritis, gout, ankylosing spondylitis, systemic lupus erythematosus, and juvenile arthritis, bursitis, burns, injuries following surgical and dental procedures, fever, inflammation, dysmenorrhea, headache, toothache, sprains and strains, which composition comprises a compound of the formula (I) of claim 1, and a pharmaceutically inert carrier.

10. A method for the treatment of a medical condition in which prostaglandins are implicated as pathogens, in a mammalian subject, which comgrises administering to said subject a pharmaceutical composition according to claim 9.

* * * * *